US010662482B2

(12) United States Patent
Viguie et al.

(10) Patent No.: US 10,662,482 B2
(45) Date of Patent: May 26, 2020

(54) TET2 AS A DIAGNOSTIC AND PROGNOSTIC MARKER IN HEMATOPOIETIC NEOPLASMS

(71) Applicants:INSTITUT NATIONAL DE LA SANTE ET DE LA RECHERCHE MEDICALE (INSERM), Paris (FR); INSTITUT GUSTAVE-ROUSSY, Villejuif (FR); ASSISTANCE PUBLIQUE-HOPITAUX DE PARIS, Paris (FR); CENTRE HENRI BECQUEREL, Rouen (FR); UNIVERSITE PARIS DESCARTES, Paris (FR); UNIVERSITE PIERRE ET MARIE CURIE (PARIS 6), Paris (FR); UNIVERSITE PARIS-SUD, Orsay (FR)

(72) Inventors: Franck Viguie, Deuil la Barre (FR); Olivier Bernard, Vanves (FR); Michaela Fontenay, Paris (FR); Christian Bastard, Ardouval (FR); Francois Delhommeau, Antony (FR); William Vainchenker, Paris (FR)

(73) Assignees: INSTITUT NATIONAL DE LA SANTE ET DE LA RECHERCHE MEDICALE (INSERM), Paris (FR); INSTITUT GUSTAVE-ROUSSY, Villejuil (FR); ASSISTANCE PUBLIQUE-HOPITAUX DE PARIS, Paris (FR); CENTRE HENRI BECQUEREL, Rouen (FR); UNIVERSITE PARIS DESCARTES, Paris (FR); UNIVERSITY PIERRE ET MARIE CURIE (PARIS 6), Paris (FR); UNIVERSITE PARIS-SUD, Orsay (FR)

( * ) Notice: Subject to any disclaimer, the term of this patent is extended or adjusted under 35 U.S.C. 154(b) by 276 days.

(21) Appl. No.: 15/177,055

(22) Filed: Jun. 8, 2016

(65) Prior Publication Data

US 2016/0319370 A1    Nov. 3, 2016

Related U.S. Application Data

(63) Continuation of application No. 12/997,203, filed as application No. PCT/EP2009/057295 on Jun. 12, 2009, now Pat. No. 9,389,233.

(30) Foreign Application Priority Data

Jun. 12, 2008  (EP) ...................................... 08305255
Mar. 13, 2009  (EP) ...................................... 09155169

(51) Int. Cl.
*C12Q 1/6886* (2018.01)
*G01N 33/574* (2006.01)
*A61K 31/7068* (2006.01)

(52) U.S. Cl.
CPC ........ *C12Q 1/6886* (2013.01); *A61K 31/7068* (2013.01); *G01N 33/57426* (2013.01);
(Continued)

(58) Field of Classification Search
CPC ............ C12Q 1/6886; C12Q 2600/156; G01N 33/57426
See application file for complete search history.

(56) References Cited

U.S. PATENT DOCUMENTS 4,683,202 A    7/1987  Mullis
5,854,033 A   12/1998  Lizardi
(Continued)

OTHER PUBLICATIONS

Gaiger, A. et al. Blood 86(6):2371 (Sep. 1995).*
(Continued)

*Primary Examiner* — Diana B Johannsen
(74) *Attorney, Agent, or Firm* — Potomac Law Group, PLLC

(57) ABSTRACT

The present invention concerns an in vitro method for diagnosing a myeloid tumour or a lymphoid tumour in a subject, which comprises the step of analyzing a biological sample from said subject by (i) detecting the presence of a mutation in the Ten Eleven Translocation protein family member 2 gene (TET2) coding for the polypeptide having the sequence SEQ ID NO: 2, and/or (ii) analyzing the expression of the TET2 gene; wherein the detection of such
(Continued)

a TET2 mutation, of the absence of expression of TET2 or of the expression of a truncated TET2 is indicative of a subject developing or predisposed to develop a myeloid tumour or a lymphoid tumour.

13 Claims, 10 Drawing Sheets

Specification includes a Sequence Listing.

(52) U.S. Cl.
CPC .. *C12Q 2600/106* (2013.01); *C12Q 2600/118* (2013.01); *C12Q 2600/154* (2013.01); *C12Q 2600/156* (2013.01); *C12Q 2600/158* (2013.01); *C12Q 2600/16* (2013.01)

(56) References Cited

U.S. PATENT DOCUMENTS

| | | |
|---|---|---|
| 9,389,233 B2 * | 7/2016 | Viguie ................ C12Q 1/6886 |
| 2007/0059717 A1 | 3/2007 | Pascual et al. |
| 2012/0302517 A1 | 11/2012 | Viguie et al. |

OTHER PUBLICATIONS

International Search Report issued in application No. PCT/EP2009/057295 dated Oct. 5, 2009.
Barany, Genetic disease detection and DNA amplification using cloned thermostable ligase, Proc. Natl. Acad. Sci. USA, Jan. 1991, vol. 88, pp. 189-193.
Baxter et al., "Acquired mutation of the tyrosine kinase JAK2 in human myeloproliferative disorders" Lancet, Mar. 2005, vol. 365, pp. 1054-1061.
Bellanné-Chantelot et al., "Genetic and clinical implications of the Val617Phe JAK2 mutation in 72 families with myeloproliferative disorders," Blood, 2006, vol. 108, No. 1, pp. 346-352.
Braun et al., "NF-kB constitutes a potential therapeutic target in high-risk myelodysplastic syndrome," Blood, 2006, vol. 107(3), pp. 1156-1165.
Campbell et al., "The Myeloproliferactive Disorders," N. Engl. J. Med., 2006, vol. 355(23), pp. 2452-2466.
Chalignéet al., "New mutations of MPL in primitive myelofibrosis: only the MPL W515 mutations promote a $G_1$/S-phase transition," Leukemia, 2008, vol. 22, pp. 1557-1566.
Charbonnier et al., "Detection of Exon Deletions and Duplications of the Mismatch Repair Genes in Hereditary Nonpolyposis Colorectal Cancer Families Using Multiplex Polymerase Chain Reaction of Short Fluorescent Fragments," Cancer Res., Jun. 2000, vol. 60, pp. 2760-2763.
Claessens et al., "In vitro proliferation and differentiation of erythroid progenitors from patients with myelodysplastic syndromes: evidence for Fas-dependent apoptosis," Blood, Mar. 2002, vol. 99, No. 5, pp. 1594-1601.
Clasessens et al., "Rescue of early-stage myelodysplastic syndrome-deriving erythroid precursors by the ectopic expression of a dominant-negative form of FADD," *Blood*, May 2005, vol. 105, No. 10, pp. 4035-4042.
Cole et al., "The EBV-Hybridoma Technique and its Application to Human Lung Cancer," Monoclonal Antibodies and Cancer Therapy, Alan R. Liss, Inc., 1985, pp. 77-96.
Daser A, et al., "The versatile mixed lineage leukaemia gene *MLL* and its many associations in leukaemogenesis", Seminars Cancer Biol., 2005, vol. 15(3), pp. 175-188.
Database Genbank [Online], Apr. 2, 1996, XP002502623 (2 pages).
Database UniProt [online], Jun. 10, 2008 (Jun. 10, 2008), XP002502624, Database Accession No. Q6N021, http://www.uniprot.org:uniprot.q6n021.txt? (4 pages).
Database UniProt [online], Jun. 10, 2008 (Jun. 10, 2008), XP002502625, Database Accession No. Q8NFU7, http://www.uniprot.org:uniprot.q8nfu7.txt? (3 pages).
Database UniProt [Online], Jun. 10, 2008, XP002502625, Database Accession No. Q8NFU7 <URL: http://www.uniprot.org:uniprot.Q8NFU7.txt?> (3 pages).
Delhommeau et al., "LBA-3 TET2 is Novel Tumor Suppressor Gene Inactivated in Myeloproliferative Neoplasm: Identification of a Pre-JAK2 V617F event", Annu Meet Abstr, 2008 (2 pages).
Delhommeau et al., "Oncogenic mechanisms in myeloproliferative disorders," Cell Mol. Life Sci., 2006, vol. 63(24), pp. 2939-2953.
Dupont et al., "The JAK2 617V>F mutation triggers erythropoietin hypersensitivity and terminal erythroid amplification in primary cells from patients with polycythemia vera," Blood, Aug. 2007, vol. 110(3), pp. 1013-1021.
Ebert et al., "Identification of RPS14 as a 5q⁻ syndrome gene by RNA interference screen," Nature, Jan. 2008, vol. 451, No. 17, pp. 335-339.
Fenaux et al., "A multicenter phase 2 study of the farnesyltransferase inhibitor tipifarnib in intermediate- to high-risk myelodysplastic syndrome," Blood, May 2007, vol. 109, No. 10, pp. 4158-4163.
Finazzi et al., "Essential Thrombocythemia," Semin. Hematol., 2005, vol. 42, pp. 230-238.
Gilbert H.S., "Familial Myeloproliferative disease," *Baillieres Clin. Haematol.*, Dec. 1998, vol. 11, No. 4, pp. 849-858.
Guatelli et al., "Isothermal, in vitro amplification of nucleic acids by a multienzyme reaction modeled after retroviral replication," Proc. Natl. Acad. Sci. USA, Mar. 1990, vol. 87, pp. 1874-1878.
Haase D., "Cytogenetic features in myelodysplastic syndromes," Annals of Hematology, 2008, vol. 87, No. 7, pp. 515-526.
Harper, et al., "Chromosomal Rearrangements Leading to MLL Gene Fusions: Clinical and Biological Aspects," Cancer Res, Dec. 2008, vol. 68(24), pp. 10024-10027.
Itzykson et al., "Optimal sequencing of treatments for patients with myelodysplastic syndromes," Current Opinion in Hematology, 2009, vol. 16, pp. 77-83.
Jabbour et al., "Evolution of Decitabine Development: Accomplishments, Ongoing Investigations, and Future Strategies," Cancer, Jun. 2008, vol. 112, No. 11, pp. 2341-2351.
James et al., "The hematopoietic stem cell compartment of JAK2V617F-positive myeloproliferative disorders is a reflection of disease heterogeneity," Blood, Sep. 2008, vol. 112, No. 6, pp. 2429-2438.
James et al., "A unique clonal JAK2 mutation leading to constitutive signalling causes polycythaemia vera," Nature, Apr. 2005, vol. 434, pp. 1144-1148.
Kiladjian et al., "Pegylated interferon-alfa-2a induces complete hematologic and molecular responses with low toxicity in polycythemia vera," Blood, Oct. 2008, vol. 112, No. 8, pp. 3065-3072.
Köhler et al., "Continuous cultures of fused cells secreting antibody of predefined specificity," Nature, Aug. 1975, vol. 256, pp. 495-497.
Kojima et al., "FLJ10849, a septin family gene, fuses MLL in a novel leukemia cell line CNLBC1 derived from chronic neutrophilic leukemia in transformation with t(4;11)(q21;q23)," Leukemia, 2004, vol. 18, No. 5, pp. 998-1005.
Kozbor et al., "The production of monoclonal antibodies from human lymphocytes," Immunol. Today, 1983, vol. 4, No. 3, pp. 72-79.
Kralovics et al., "A Gain-of-Function Mutation of JAK2 in Myeloproliferative Disorders," N. Engl. J. Med., Apr. 2005, vol. 352, pp. 1779-1790.
Kralovics et al., "Clonal hematopoiesis in familial polycythemia vera suggests the involvement of multiple mutational events in the early pathogenesis of the disease," Blood, Nov. 2003, vol. 102, No. 10, pp. 3793-3796.
Kuendgen et al., "Current status of epigenetic treatment in myelodysplastic syndromes," Ann. Hematol., vol. 87, pp. 601-611, 2008.
Kwoh et al., "Transcription-based amplification system and detection of amplified human immunodeficiency virus type 1 with a bead-based sandwich hybridization format," Proc. Natl. Acad. Sci. USA, Feb. 1989, vol. 86, pp. 1173-1177.
Levine et al., "The JAK2V617F activating mutation occurs in chronic myelomonocytic leukemia and acute myeloid leukemia, but

(56) References Cited

OTHER PUBLICATIONS not in acute lymphoblastic leukemia or chronic lymphocytic leukemia," Blood, Nov. 2005, vol. 106, No. 10, pp. 3377-3379.
Lizardi et al., "Exponential Amplification of Recombinant-RNA Hybridization Probes," Bio/Technology, Oct. 1988, vol. 6, pp. 1197-1202.
Lorsbach et al., "TET1, a Member of a Novel Protein Family, is Fused to MLL in Acute Myeloid Leukemia Containing the t(10;11)(q22;q23)," Leukemia, 2003, vol. 17(3), pp. 637-641.
Morgan et al., "A Role for JAK2 Mutations in Myeloproliferactive Diseases," Annu. Rev. Med., 2008, vol. 59, pp. 213-222.
Ono et al., "LCX, Leukemia-associated Protein with a CXXC Domain, Is Fused to MLL in Acute Myeloid Leukemia with Trilineage Dysplasia Having t(10;11)(q22;q23)," Cancer Research, Jul. 2002, vol. 62(14), pp. 4075-4080.
Passamonti et al., "A dynamic prognostic model to predict survival in post-polycythemia vera myelofibrosis," Blood, Apr. 2008, vol. 111, No. 7, pp. 3383-3387.
Passamonti et al., "Prognostic factors for thrombosis, myelofibrosis, and leukemia in essential thrombocythemia: a study of 605 patients," Haematologica, 2008, vol. 93, No. 11, pp. 1645-1651.
Pikman et al., "MPLW515L Is a Novel Somatic Activating Mutation in Myelofibrosis with Myeloid Metaplasia," PLoS Med, Jul. 2006, vol. 3, No. 7 (e270), pp. 1140-1151.
Robert-Richard et al., "Human cell engraftment after busulfan or irradiation conditioning of NOD/SCID mice," Haematologica, The Hematology Journal, 2006, vol. 91(10), pp. 1384-1387.
Rumi et al., "JAK2 (V617F) As an Acquired Somatic Mutation and a Secondary Genetic Event Associated With Disease Progression in Familial Myeloproliferative Disorders," Cancer, Nov. 2006, vol. 107, No. 9, pp. 2206-2211.
Sheils et al., "Nucleic acid microarray: an overview," Current Diagnostic Pathology, 2003, vol. 9, pp. 155-158.
Tahiliani et al., "Conversion of 5-Methylcytosine to 5-Hydroxymethylcytosine in Mammalian DNA by MLL Partner TET1," NIH Public Access Author Manuscript, Science, available in PMC Jul. 2009, pp. 1-11.
Tefferi et al.,"Classification and diagnosis of myeloproliferative neoplasms: The 2008 World Health Organization criteria and point-of-care diagnostic algorithms," Leukemia, 2008, vol. 22, pp. 14-22.
Tiu et al., "Clonality of the stem cell compartment during evolution of myelodysplastic syndromes and other bone marrow failure syndromes," *Leukemia*, 2007, vol. 21, pp. 1648-1657.
"Diagnosis"—The Leukemia & Lymphoma Society, www.lls.org, Jun. 24, 2014, 2 pgs.
"Signs and Symptoms" (acute AML), Someday is today—The Leukemia & Lymphoma Society, www.lls.org, Jun. 24, 2014, 1 pg.
"Signs and Symptoms" (early sign of non-Hodgkin lymphoma)—The Leukemia & Lymphoma Society, (Jun. 24, 2014) 1 pg.
"Signs and Symptoms" (no MDS symptoms)—Someday is today—The Leukemia & Lymphoma Society (Jun. 24, 2014), 1 pg.
Acute Myeloid Leukemia—NCCN Clinical Practice Guidelines in Oncology (NCCN Guidelines ), Version 2.2014, (Mar. 28, 2014), 89 pages.
Acute Myeloid Leukemia, Practice Guidelines in Oncology—v1.1. 2008 (Dec. 30, 2007), National Comprehensive Cancer Network, Inc., 36 pages.
Buckstein, et al. "Myelodysplastic Syndromes (MDS)",(May 2008), 20 pgs.
Fabre, et al. "Treatment of AML with Azacytidine (AZA): Current Results of the French ATU Program", Blood (ASH Annual Meeting Abstracts) (2007), vol. 110, Abstract 1849 (printed online Jun. 24, 2014), 1 pg.
Fenaux, et al. "Azacitidine prolongs overall survival and reduces infections and hospitalizations in patients with WHO-defined acute myeloid leukaemia compared with conventional care regimens: an update", ecancermedicalscience (2008), vol. 2, No. 121, pp. 1-3.
Garcia-Manero, "Demethylating Agents in Myeloid Malignancies", Curr Opin Oncol. (Nov. 2008), vol. 20, No. 6, pp. 1-11.
Is Lymphoma on Your Radar?, Leukaemia Foundation, downloaded on Jun. 13, 2014, 2 pgs.
Leone, et al. "DNA methylation and demethylating drugs in myelodysplastic syndromes and secondary leukemias", Haematologica (2002), vol. 87, pp. 1324-1341.
Myelodysplastic Syndromes—NCCN Clinical Practice Guidelines in Oncology (NCCN Guidelines ), Version 2.2014 (May 21, 2013), 65 pages.
NCBI dbSNP entry for submission ss81446742 of cluster rs949681, Build 129, Apr. 2008 (9 pages).
Langemeijer, et al., "Acquired mutations in TET2 are common in myelodysplastic syndromes," Nature Genetics 41(7):pp. 838-843 (Jul. 2009; published online May 31, 2009).
Tefferi, et al., "TET2 mutations and their clinical correlates in polycythemia vera, essential thrombocythemia and myelofibrosis," Leukemia 23: pp. 905-911 (Mar. 5, 2009).
Tefferi, et al., Detection of mutant TET2 in myeloid malignancies other than myeloproliferative neoplasms: CMML, MDS, MDS/MPN and AML, Leukemia 23: pp. 1343-1345 (Mar. 19, 2009).
Thomas, et al., "The rationale and use of hypomethylation agents in adult acute myeloid leukemia," Expert Opin. Drug Discov. 4(2): pp. 195-205 (Feb. 2009).

\* cited by examiner

MEQDRTNHVEGNRLSPFLIPSPPICQTEPLATKLQNGSPLPERAHPEVNGDTKWHSFKSYYGIPCM
KGSQNSRVSPDFTQESRGYSKCLQNGGIKRTVSEPSLSGLLQIKKLKQDQKANGERRNFGVSQERN
PGESSQPNVSDLSDKKESVSSVAQENAVKDFTSFSTHNCSGPENPELQILNEQEGKSANYHDKNIV
LLKNKAVLMPNGATVSASSVEHTHGELLEKTLSQYYPDCVSIAVQKTTSHINAINSQATNELSCEI
THPSHTSGQINSAQTSNSELPPKPAAVVSEACDADDADNASKLAAMLNTCSFQKPEQLQQQKSVFE
ICPSPAENNIQGTTKLASGEEFCSGSSSNLQAPGGSSERYLKQNEMNGAYFKQSSVFTKDSFSATT
TPPPPSQLLLSPPPPLPQVPQLPSEGKSTLNGGVLEEHHHYPNQSNTTLLREVKIEGKPEAPPSQS
PNPSTHVCSPSPMLSERPQNNCVNRNDIQTAGTMTVPLCSEKTRPMSEHLKHNPPIFGSSGELQDN
CQQLMRNKEQEILKGRDKEQTRDLVPPTQHYLKPGWIELKAPRFHQAESHLKRNEASLPSILQYQP
NLSNQMTSKQYTGNSNMPGGLPRQAYTQKTTQLEHKSQMYQVEMNQGQSQGTVDQHLQFQKPSHQV
HFSKTDHLPKAHVQSLCGTRFHFQQRADSQTEKLMSPVLKQHLNQQASETEPFSNSHLLQHKPHKQ
AAQTQPSQSSHLPQNQQQQQKLQIKNKEEILQTFPHPQSNNDQQREGSFFGQTKVEECFHGENQYS
KSSEFETHNVQMGLEEVQNINRRNSPYSQTMKSSACKIQVSCSNNTHLVSENKEQTTHPELFAGNK
TQNLHHMQYFPNNVIPKQDLLHRCFQEQEQKSQQASVLQGYKNRNQDMSGQQAAQLAQQRYLIHNH
ANVFPVPDQGGSHTQTPPQKDTQKHAALRWHLLQKQEQQQTQQPQTESCHSQMHRPIKVEPGCKPH
ACMHTAPPENKTWKKVTKQENPPASCDNVQQKSIIETMEQHLKQFHAKSLFDHKALTLKSQKQVKV
EMSGPVTVLTRQTTAAELDSHTPALEQQTTSSEKTPTKRTAASVLNNFIESPSKLLDTPIKNLLDT
PVKTQYDFPSCRCVEQIIEKDEGPFYTHLGAGPNVAAIREIMEERFGQKGKAIRIERVIYTGKEGK
SSQGCPIAKWVVRRSSSEEKLLCLVRERAGHTCEAAVIVILILVWEGIPLSLADKLYSELTETLRK
YGTLTNRRCALNEERTCACQGLDPETCGASFSFGCSWSMYYNGCKFARSKIPRKFKLLGDDPKEEE
KLESHLQNLSTLMAPTYKKLAPDAYNNQIEYEHRAPECRLGLKEGRPFSGVTACLDFCAHAHRDLH
NMQNGSTLVCTLTREDNREFGGKPEDEQLHVLPLYKVSDVDEFGSVEAQEEKKRSGAIQVLSSFRR
KVRMLAEPVKTCRQRKLEAKKAAAEKLSSLENSSNKNEKEKSAPSRTKQTENASQAKQLAELLRLS
GPVMQQSQQPQPLQKQPPQPQQQQRPQQQQPHHPQTESVNSYSASGSTNPYMRRPNPVSPYPNSSH
TSDIYGSTSPMNFYSTSSQAAGSYLNSSNPMNPYPGLLNQNTQYPSYQCNGNLSVDNCSPYLGSYS
PQSQPMDLYRYPSQDPLSKLSLPPIHTLYQPRFGNSQSFTSKYLGYGNQNMQGDGFSSCTIRPNVH
HVGKLPPYPTHEMDGHFMGATSRLPPNLSNPNMDYKNGEHHSPSHIIHNYSAAPGMFNSSLHALHL
QNKENDMLSHTANGLSKMLPALNHDRTACVQGGLHKLSDANGQEKQPLALVQGVASGAEDNDEVWS
DSEQSFLDPDIGGVAVAPTHGSILIECAKRELHATTPLKNPNRNHPTRISLVFYQHKSMNEPKHGL
ALWEAKMAEKAREKEEECEKYGPDYVPQKSHGKKVKREPAEPHETSEPTYLRFIKSLAERTMSVTT
DSTVTTSPYAFTRVTGPYNRYI-2002

Figure 1

PATIENT nAML2          PATIENT MDS03
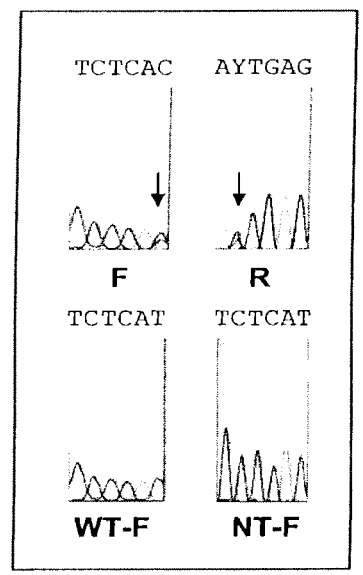
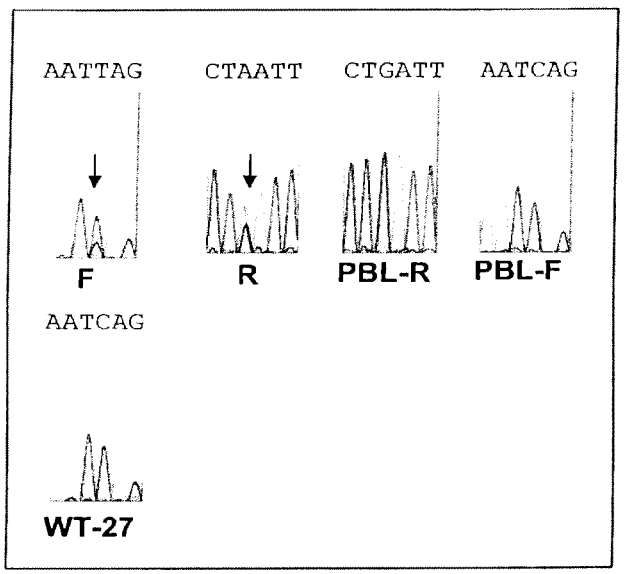
Figure 2

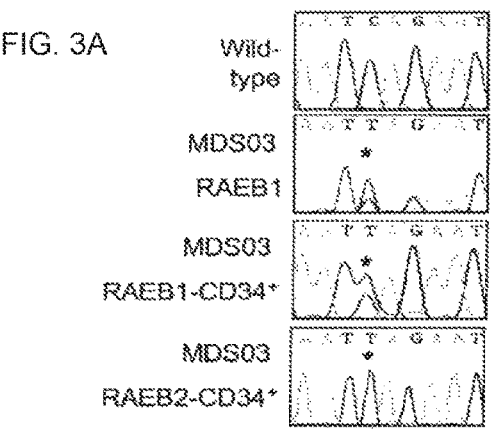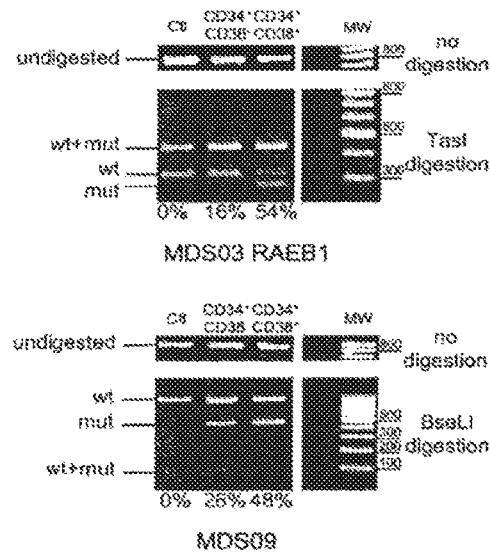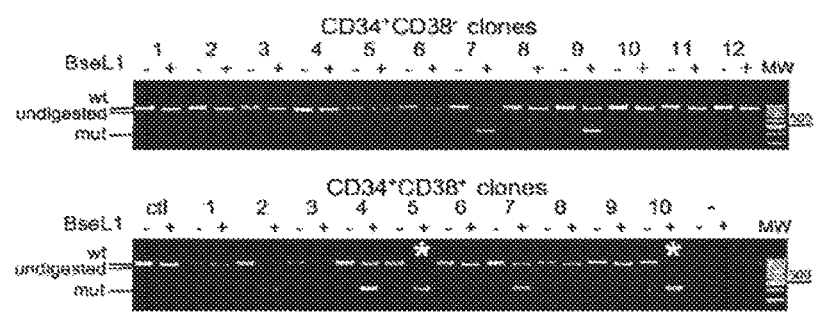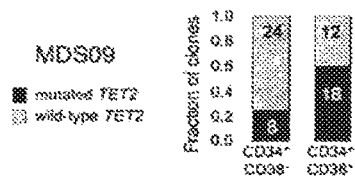
FIG. 3D

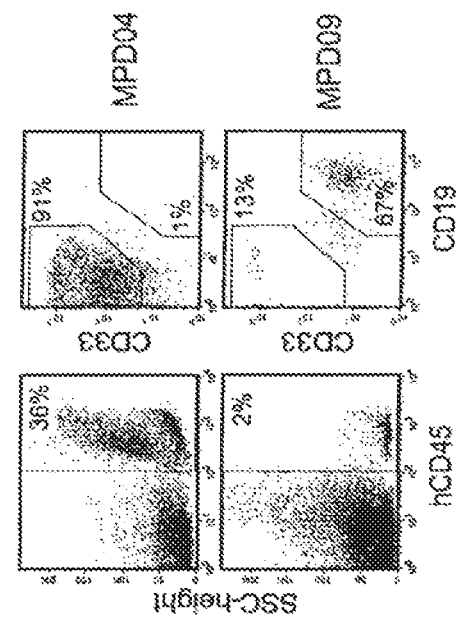
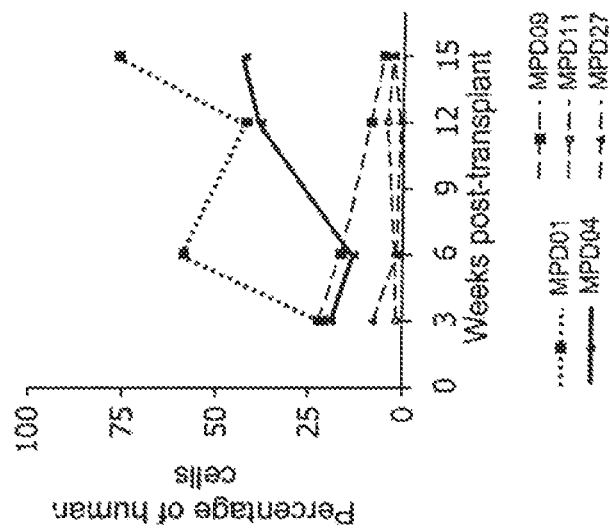
FIG. 4A
FIG. 4B

TET2 AS A DIAGNOSTIC AND PROGNOSTIC MARKER IN HEMATOPOIETIC NEOPLASMS

CROSS-REFERENCE TO RELATED APPLICATION(S)

This application is a continuation of U.S. patent application Ser. No. 12/997,203, filed Dec. 9, 2010, which is the National Stage of International Patent Application No. PCT/EP2009/057295, filed Jun. 12, 2009, which claims priority from European Patent Application Nos. 08305255.5, filed Jun. 12, 2008, and European Patent Application No. 09155169.7, filed Mar. 13, 2009. The contents of these applications are incorporated herein by reference in their entirety.

FIELD OF THE INVENTION

The present invention relates to genetic markers to diagnose myeloid neoplasms, more particularly to a new identified tumour suppressor gene, the Ten Eleven Translocation protein family member 2 gene (TET2). Genetic alterations of TET2 are useful to diagnose myeloid tumours, such as myelodysplastic/myeloproliferative syndromes, MDS, AML or MPD, and lymphoid tumours.

BACKGROUND OF THE INVENTION

Hematopoiesis is maintained by a hierarchical system where hematopoietic stem cells (HSCs) give rise to multipotent progenitors, which in turn differentiate into all types of mature blood cells. The molecular mechanisms controlling multipotentiality, self-renewal, quiescence and HSC commitment have been extensively studied. However, numerous issues remain to be addressed and important genes regulating these processes remain to be identified.

Myeloid malignancies include Acute Myeloid leukaemia (AML), Myeloproliferative disorders (MPDs), myelodysplastic syndromes (MDS) and myelodysplastic/myeloproliferative syndromes that are all clonal stem-cell (HSC) or progenitor malignant disorders (TIU et al., Leukemia, vol. 21(8), p: 1648-57, 2007).

Several genetic mutations have been correlated to AML, and four groups are recognized: (i) the AML with recurrent genetic abnormalities AML t(8;21)(q22;q22) with RUNX1-ETO fusion gene; AML with abnormal bone marrow eosinophils and inv(16)(p13;q22) or t(16;16)(p13;q22) with CBFB/MYH11 rearrangement; acute promyelocytic leukaemia APL with t(15;17)(q22;q12) PML/RARA; AML with 11q23 (MLL) abnormalities); (ii) AML with multilineage dysplasia following MDS or MDS/MPD or without antecedent of MDS or MPD; (iii) AML or MDS therapy related and (iv) other unclassified AML among that comprises the group of AML with normal karyotype which prognosis is based on molecular analysis of oncogenes such as mutations of FLT3-ITD or NPM1.

Myelodysplastic/myeloproliferative syndromes include four myeloid diseases grouped in 1999 by the WHO: chronic myelomonocytic leukemia (CMML), juvenile myelomonocytic leukemia (JMML), atypical chronic myeloid leukemia (aCML) and unclassified myelodysplastic/myeloproliferative syndromes (U-MDS/MPS).

MDS include refractory anemia (RA), and refractory cytopenia with multilineage dysplasia (RCMD). MDS are characterized by ineffective hematopoiesis in one or more of the lineage of the bone marrow. Early MDS mostly demonstrate excessive apoptosis and hematopoietic cell dysplasia (CLAESSENS et al., Blood, vol. 99, p: 1594-601, 2002; CLASESSENS et al., Blood, vol. 105, p: 4035-42, 2005). In about a third of MDS patients, this ineffective hematopoiesis precedes progression to secondary AML (sAML). Although some molecular events associated with specific MDS subtypes (ELBERT et al., Nature, vol. 451(7176), p: 335-9, 2008) or disease transformation (BRAUN et al., Blood, vol. 107(3), p: 1156-65, 2006) have been identified, the underlying molecular defects are still poorly understood. No biological markers, except morphological features, are currently available for early diagnosis and prognosis.

MPDs, referred now as myeloproliferative neoplasms (MPN; TEFFERI & VARDIMAN, Leukemia, vol. 22, p: 14-22, 2008), are chronic myeloid diseases including chronic myelogenous leukaemia (CML), polycythemia vera (PV), essential thrombocythemia (ET), primary myelofibrosis (PMF) and idiopathic myelofibrosis (IMF). MPDs are characterized by an increased proliferation of one or several myeloid lineages. If most MPDs are sporadic diseases, familial cases of MPDs, for which the exact prevalence is unknown, have been reported (GILBERT, Baillieres Clin. Haematol., vol. 11, p: 849-858, 1998; KRALOVICS et al., Blood, vol. 102, p: 3793-3796, 2003; BELLANNE-CHANTELOT et al., Blood, vol. 108, p: 346-352, 2006). The clinical analysis of these familial cases has shown that they are phenotypically identical to sporadic cases. Nevertheless, MPD families are characterized by a clinical and genetic heterogeneity. First, MPD cases from a single family can either display the same subtype or different types of MPD (GILBERT, abovementioned, 1998; BELLANNE-CHANTELOT et al., abovementioned, 2006; RUMI et al., Cancer, vol. 107, p: 2206-2211, 2006). Second, about 6-15% of patients with PV and 3-5% of patients with ET are at risk of developing hematological complication after 15 years of evolution (FINAZZI & HARRISON, Semin. Hernatol., vol. 42, p: 230-238, 2005; KILADJIAN et al., Blood, vol. 112, p: 1746, 2008; PASSAMONTI et al., Blood, vol. 111, p: 3383-3387, 2008; PASSAMONTI et al., Haematologica, vol. 93, p: 1645-1651, 2008).

MPDs, in both sporadic and familial cases, are commonly associated with an acquired constitutive kinase activity, as exemplified by the JAK2$^{V617F}$ mutation in Polycythemia Vera, in most PV cases and in half of ET and PMF cases (MORGAN & GILLIGAND, Annu. Rev. Med., vol. 59, p: 213-22, 2008; DELHOMMEAU et al., Cell Mol. Life Sci., vol. 63(24), p: 2939-53, 2006, CAMPBELL & GREEN, N. Engl. J. Med., vol. 355(23), p: 2452-66, 2006; BELLANNE-CHANTELOT et al., abovementioned, 2006; JAMES et al., Nature, vol. 434, p: 1144-1148, 2005; BAXTER et al., Lancet, vol. 365, p: 1054-1061, 2005; LEVINE et al., Blood, vol. 106, p: 3377-3379, 2005; KRALOVICS et al., N. Engl. J. Med., vol. 352, p: 1779-1790, 2005). MPDs frequently result from the expression of a constitutive tyrosine kinase protein:

Through a fusion like BCR-ABL in CML, FIPIL1-PDGFRA in HES, TEL-PDGFRB in CMML with hypereosinophilia, ZNF198-FGFR1 in rare MPD coupled to lymphoid proliferation and PCM1-JAK2 in rare MPDs, AML and T cell lymphomas A limited or single nucleotide mutation i.e. JAK2 V617F (1849G>T), which recent discovery of in PV (98%), ET (75%), IMF (50%) and a few percent of CMML, MDS/MPD and U-MPD allows for a new MPD classification and diagnosis criteria and perspectives for treatment. In addition, KIT mutations are recurrent in systemic mast cell proliferation.

Through activating mutations in the receptor for thrombopoietin receptor (MPL), especially of the tryptophan 515 (MPLW515$^{K/L/A}$) (PIKMAN et al., *PLoS Med*, vol. 3(e270), 2006; CHALIGNÉ et al., *Leukemia*, vol. 22, p1557-66, 2008).

Marginal cases of CML presented with BCR/JAK2 rearrangement due to t(9;22)(p24;q11).

The JAK2 gene on chromosome 9p encodes a tyrosine kinase that associates with type 1 cytokine receptors. The V617F mutation is predicted to disrupt the auto-inhibitory effect of the JH2 domain to constitutive activation of the kinase. Wild type JAK2 exerts a dominant negative effect on the activity of the mutated protein. Therefore the loss of WT JAK2 associated to the duplication of the mutated gene by mitotic recombination observed in most of MPD samples allows for a higher expression and activity of the mutated kinase.

However, several observations, such as the Polycythemia Vera co expressing the WT and mutated JAK2 and the characterization of secondary AML emerging from mutated MPD but lacking of JAK2 mutation in the blast phases indicate oncogenetic events earlier occurring before JAK2 mutation. Moreover, and as discussed previously, the MPD disease evolution is indeed highly variable within and between families. Thus, there is some evidence that there is at least one other mutation than JAK2 implicated in MPDs and, more specifically, their progression.

Lymphoid tumours consist of expansion of cells with lymphoid features. Acute lymphoblastic leukaemia/lymphoma are proliferation of cells blocked in lymphoid differentiation, from either T (T-cell acute lymphoblastic leukaemia; T-ALL) or B (B-cell precursor acute lymphoblastic leukaemia; BCP-ALL) origin. Some leukaemia lymphoma are from Natural Killer (NK) origin. Lymphoma involve expansion of more mature lymphoid cells (B or T). Some neoplasms are chronic, and can involve T cell (prolymphocytic leukaemia) or B cells (Chronic Lymphocytic Leukaemia). The classification of lymphoid neoplasm is based on anatomopathological analyses, differentiation markers and pathogenesis data (Swerdllow S. H., Campo E., Harris N. L., Jaffe E. S., Pileri S. A., Stein H., Thiele J. W., Vardiman J. W. (Eds): WHO classification of tumors of haematopoietc and lymphoid tissues. IARC: Lyon 2008). For example, Anaplasic large T-cell lymphoma are associated with NPM-ALK fusion oncogene (and variant thereof), follicular lymphoma are associated with BCL2 activation following t(14;18)(q32;q21) chromosomal translocation, mantle cell lymphoma are associated with CCND1 activation following t(11;14)(q13;q32) chromosomal translocation. Many lymphoma however lack any reliable molecular marker suggesting a pathophysiological mechanism. This is the case, In particular, for more than 50% of diffuse large B cell lymphomas (DLBCL), for most peripheral T-cell lymphomas (PTCL) and for a majority of non-follicular low grade lymphomas.

Therefore, there was an urgent need of a reliable diagnostic marker that allows to identify lymphoid and myeloid neoplasms, in particular MDS and MPD, and eventually to prognosticate their progression.

The Ten Eleven Translocation protein family contains three recently identified members, with unknown functions, characterized in that they share two highly conserved domains at their C-terminal end. As used herein, the expression "gene of the TET family" refers to members of the Ten Eleven Translocation family, TET1, TET2 or TET3, which have been recently identified (Lorsbach et al, *Leukemia* 2003).

Among them, TET1 is the only studied member, because it has been identified as a fusion partner with the protein mixed lineage leukemia (MLL) in two different and independent studies (ONO et al., *Cancer Research*, vol. 62(14), p: 4075-80, 2002 and LORSBACH et al., *Leukemia*, vol. 17(3), p: 637-41, 2003). This protein, also called LCX, or "leukemia associated protein with a CXXC domain in N-terminal region", contains an α-helical coiled-coil region in its C-terminal region, region which is retained in the fusion MLL-TET1. On the contrary, the N-terminus CXXC domain of TET1 is not present in this protein fusion (Ono R, Cancer Research 2002). The two highly conserved carboxy terminal regions are included in the MLL-TET1 fusion (Lorsbach et al, Leukemia 2003). One conserved region is disrupted by the translocation; the other one is fused to MLL. Despite its description as an MLL fusion partner 7 years ago, functional and sequence analysis of the TET1 gene have been reported recently, after the priority date of the present application.

The MLL gene is located at human chromosome 11q23 and is found to be rearranged in a heterogenous group of lymphoid, myeloid and mixed lineage human leukemias. More than 70 loci have been described to be rearranged with the 11q23 chromosomal band and at least 50 of these have been cloned and characterized on a molecular level. Most of the MLL rearrangements map to a 8.3 kb base of the genes. The partners genes are always fused in frame to the 5' part MLL and may include MLL itself. Amplifications of MLL have also been reported. The partner genes code for proteins with disparate functions. In the MLL fusion, they may provide transcriptional activation domains, chromatin modifier complex recruitment or dimerization/oligomerization motif. Indeed, the expression of an MLL-Beta-galactosidase (a bacterial protein able to tetramerize) or to dimerization domain is sufficient to induce leukemia in mouse models. Therefore, it is not possible to infer the function of a protein or its independent involvement in cellular transformation from its fusion to MLL (The versatile mixed lineage leukaemia gene MLL and its many associations in leukaemogenesis. Daser A, Rabbitts T H. Semin Cancer Biol. 2005 June; 15(3):175-88. Review. Chromosomal rearrangements leading to MLL gene fusions: clinical and biological aspects. Harper D P, Aplan P D. Cancer Res. 2008 Dec. 15; 68(24): 10024-7.)

On the contrary, little is known about the TET2 protein, which is encoded by a gene located on the 4q24 chromosomal region, and the TET3 protein, which is encoded by a gene located on the 2p12 chromosomal region.

More specifically, the Ten Eleven Translocation oncogene number 2 (TET2) has been designated recently (Lorsbach et al, *Leukemia* 2003). The TET2 gene located on the chromosomal region 4q24, comprises 11 exons spread over >130 Kb and is normally widely expressed. This gene is referenced with the accession number ID 57790, and its cDNA (Accession number NM_001127208, SEQ ID NO:1) is encoding a protein of 2002 amino acids (Accession number NP_001120680, SEQ ID NO:2).

The TET2 protein shares two highly conserved regions with a single orthologous *Drosophila* predicted protein. These regions are i) a 310 amino acid region located near the center of the protein TET2 (amino acids 1134 to amino acid 1444), and ii) a second 80 amino acid region located near the carboxyterminal end of the protein TET2 (corresponding to amino acid 1843 until amino acid 1922) (these regions are highlighted in FIG. 1). The predicted sequence of TET2 did not reveal any motif corresponding to an identified function.

Applicants report herein that one or both copies of the Ten Eleven Translocation 2 (TET2) gene are often inactivated/modified by acquired mutations in MPD, MDS and CMML but also in lymphoma. These events target the hematopoietic stem cell and indicate an important function for TET2 as a tumor suppressor gene in myeloid or lymphoid neoplasms.

SUMMARY OF THE INVENTION

In a first aspect, the present invention provides an in vitro method for diagnosing a myeloid tumour or a lymphoid tumour in a subject, which comprises the step of analyzing a biological sample from said subject by:
 (i) detecting the presence of a mutation in the Ten Eleven Translocation protein family member 2 gene (TET2) coding for the polypeptide having the sequence SEQ ID NO:2, and/or
 (ii) analyzing the expression of the TET 2 gene;
 wherein the detection of such a TET2 mutation, of the absence of expression of TET2 or of the expression of a truncated TET2 is indicative of a subject developing or predisposed to develop a myeloid tumour or a lymphoid tumour.

In a preferred embodiment, said subject is a mammal, preferably a human.

In another preferred embodiment, said myeloid cancer is selected in the group consisting of myelodysplastic syndrome (MDS), acute myeloid leukemia (AML), myeloproliferative disease (MPD) and myelodysplastic/myeloproliferative syndrome.

In still another preferred embodiment, said lymphoid tumour is selected in the group consisting of lymphoma and more preferentially of T cell lymphoma.

Preferably, said mutation is detected on each copy of the TET2 gene coding for the polypeptide having the sequence SEQ ID NO:2 (encoded by the cDNA having the sequence SEQ ID NO:39) and is included in the group consisting of deletions, insertions and point mutations such as mutations affecting splice sites, missense mutation and nonsense mutations, preferably missense mutation and nonsense mutations.

In a more preferred aspect of the invention, the mutation is a deletion or an insertion which results in the absence of expression of the TET2 protein or in the expression of a truncated TET2 protein.

Even more preferably, this truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4), preferably the 80 amino acid region located near the carboxyterminal end of the protein TET2 (corresponding to amino acid 1843 until amino acid 1922, SEQ ID NO:4).

For example, these deletions or insertions can be selected in the group comprising or consisting of those disclosed in Table I in reference to SEQ ID NO:39 for nucleic acid position and to SEQ ID NO:2 for amino acid position.

TABLE I

| Nucleotide Change | Consequence |
|---|---|
| del1264_1666 | p.Glu135 FS |
| delC 1642 | p.Ser261 FS |
| del1893_1896 | p.Lys345FS |

TABLE I-continued

| Nucleotide Change | Consequence |
|---|---|
| delC 2448 | p.Gln530 FS |
| delA 2505 | p.Thr549 FS |
| delC 2524 | p. Pro555 FS |
| Ins 2540_2544 | p.Leu560FS |
| delT 2685 | p.Ser609 FS |
| delA 2815 | p.Gln652FS |
| del 2834_2835 | p.His658 FS |
| delA 2935 | p.Glu692 FS |
| delT 2944 | p.Leu699 STOP |
| delG 2994 | p.Glu711 FS |
| delC 3009 | p.His717 FS |
| insA 3009 | p.His717 FS |
| del 3131_3137 | p. Leu757 FS |
| insC 3151 | p.Gln764 FS |
| delA 3166 | p.Gln769 FS |
| delT3215 | p.Phe785 FS |
| insA3350 | p.Gln831FS |
| insT3995 | p.Glu846 FS |
| delA3430 | p.Asn857FS |
| insT 3465 | p.Pro869 FS |
| insA 5757 | p.Gln891 STOP |
| insCT 3581 | pGly 908 FS |
| del CA 3756_3757 | p.Gln966 FS |
| dupT 3914 | p.Glu1026 STOP |
| delT 3998 | p.Leu1046FS |
| delA 4130 | p.Lys1090 FS |
| delG 4271 | p.Glu1137 FS |
| delA4327 | p.Asn1156 FS |
| delG 4527 | p.Ala1223 FS |
| — | p.del 1237-1239 |
| delG 4932 | p.Glu1357 FS |
| insG 5119 | p.Leu 1420 FS |
| delG 5133 | p.Asp 1425 FS |
| insA 5177 | p.Arg1440FS |
| dupA 5177 | p.Arg1440FS |
| delC 5222 | p.Leu1457 STOP |
| del5521_5524 | pThr1554 FS |
| insA 5540 | p.Tyr1560 FS |
| del 5583_5605 | p.Pro1575FS |
| delT 5570 | p.Leu1637 FS |
| del5828_5843 | p.Met1656 FS |
| del6049_6050 | p.Asp1830 FS |
| delC 6360 | p.Gln1834 FS |
| del6396_6531 | p.Val1846 FS |
| delA 6507 | p.Thr1883 FS |
| insC 6507 | p.Thr1883 FS |
| del6511_6512 | p.Pro1885FS |
| DelC 6555 | p.Leu1889FS |
| insC splice site | mutation of splice site exon 8 |

Del: deletion;
ins: insertion;
FS: frame shift

In another more preferred aspect of the invention, the mutation is a missense mutation, which is located in the open reading frame of the TET2 protein, preferably in at least one of the two highly conserved regions shared by the TET proteins and corresponding to i) the 310 amino acid region located near the center of the protein TET2 (amino acids 1134 to amino acid 1444, SEQ ID N0:3), and ii) the 80 amino acid region located near the carboxyterminal end of the protein TET2 (corresponding to amino acid 1843 until amino acid 1922, SEQ ID N0:4), and more preferably in the 80 amino acid region located near the carboxyterminal end of the protein TET2 (corresponding to amino acid 1843 until amino acid 1922, SEQ ID N0:4). For example, these missense mutations can be selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I1873T, R1896M, and S1898F, preferably can be selected in the group comprising or consisting of L1197N, H1219Y, E1235V, C1271W, K1299E, L1340P, R1302G, G1370E, A1344E, N1387S, H1868R, G1869W, L1872P, I1873T, R1896M, and S1898F, and more preferably in the group comprising or consisting of H1868R, G1869W, L1872P, I1873T, R1896M, and S1898F.

In another more preferred aspect of the invention, the mutation is a nonsense mutation, which is located in the open reading frame of the TET2 protein, preferably before or inside at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID N0:4), and more preferably before or inside the 80 amino acid region located near the carboxyterminal end of the protein TET2 (corresponding to amino acid 1843 until amino acid 1922, SEQ ID NO:4). For example, said nonsense mutations can be selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, Q1834Stop and W1847Stop.

In another aspect of the invention, the mutation in the TET2 gene induces absence of expression or under-expression of the polypeptide having the sequence SEQ ID NO:2 and more preferably the absence of expression or under-expression of at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), more preferably of the 80 amino acid region located near the carboxyterminal end of the protein TET2 (corresponding to amino acid 1843 until amino acid 1922, SEQ ID NO:4).

In a second aspect, the present invention provides a kit for diagnosing myeloid cancer in a subject comprising at least one nucleic acid probe or oligonucleotide or at least one antibody, which can be used in a method as defined previously for detecting the presence of a mutation in the TET2 gene and/or analysing the expression of the TET2 gene.

In a preferred embodiment of the invention, said oligonucleotide is at least one PCR primer, and preferably a set of PCR primers.

More preferably, said set of primers is selected in the group comprising SEQ ID NO: 5 to SEQ ID NO: 38 (see examples).

In a third aspect, the present invention provides the use of a hypomethylating agent for treating a patient suffering from a myeloid or a lymphoid tumour, for which tumour, a TET2 mutation, an absence of TET2 expression or an expression of a truncated TET2 has been detected.

In a final aspect, the present invention provides a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of a hypomethylating agent.

BRIEF DESCRIPTION OF THE DRAWINGS

The FIG. 1 shows the protein sequence of TET2 (SEQ ID NO: 2), highlighting the conserved regions between species (bold).

The FIG. 2 shows the sequence traces obtained by sequencing the PCR products obtained for samples obtained from two patients A and E, showing that the mutation only occurs in the tumoral and not in non-tumoral samples (NT), and Peripheral Blood Lymphocytes (PBL). R corresponds to the sequence obtained with the Reverse primer, and F corresponds to the one obtained with the Forward primer. WT corresponds to the sequence obtained in healthy individuals.

FIGS. 3A-3D show that in MDS samples, mutated TET2 is observed in immature CD34$^+$ cells and is associated with in vivo expansion of the mutated clone.

FIGS. 4A-4B show that JAK2$^{V617F}$-positive MPD hematopoietic stem cells with TET2 defects display enhanced NOD/SCID repopulating capacities.

Figure 5:
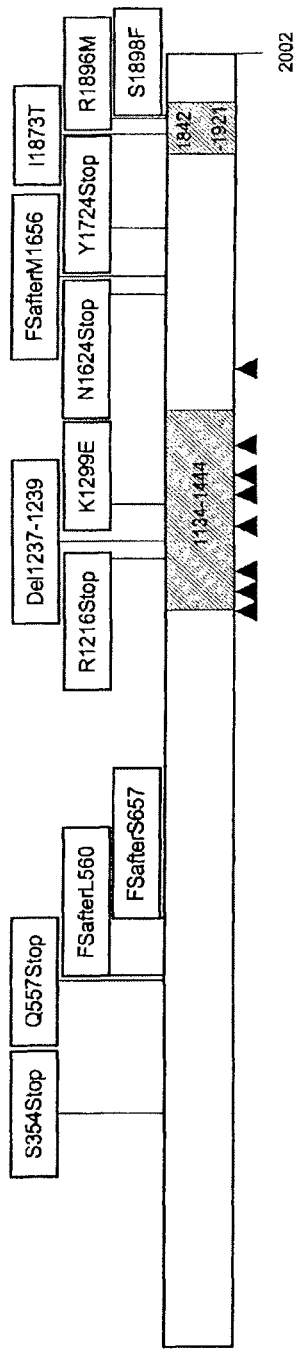

The FIG. 5 shows the locations of some of the identified mutations of the TET2 gene distributed along the protein sequence Conserved regions are marked with gray stripes. Arrowheads indicate the location of exon boundaries. FS: Frame shift.

Figure 6:
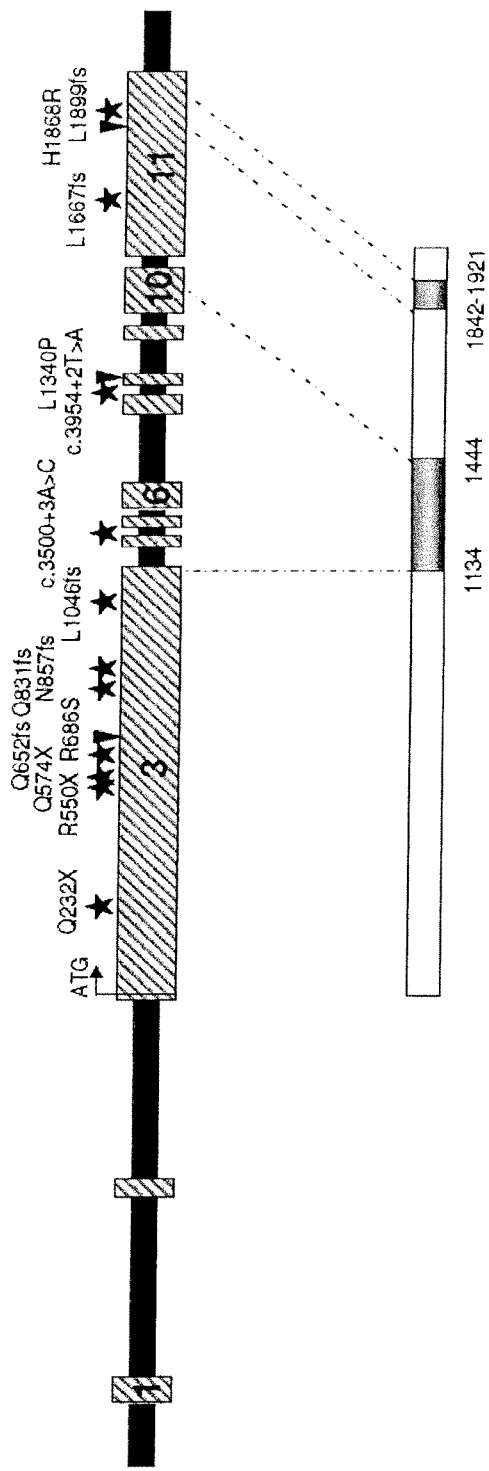

The FIG. 6 shows a schematic representation of the TET2 gene and protein showing the mutations identified in familial myeloproliferative neoplasms. Hatched boxes indicate exons. Truncating mutations are depicted as stars, missense mutations as inverted triangles. Conserved functional domains are depicted as boxes on the protein scheme. fs: frameshift.

Figure 7:
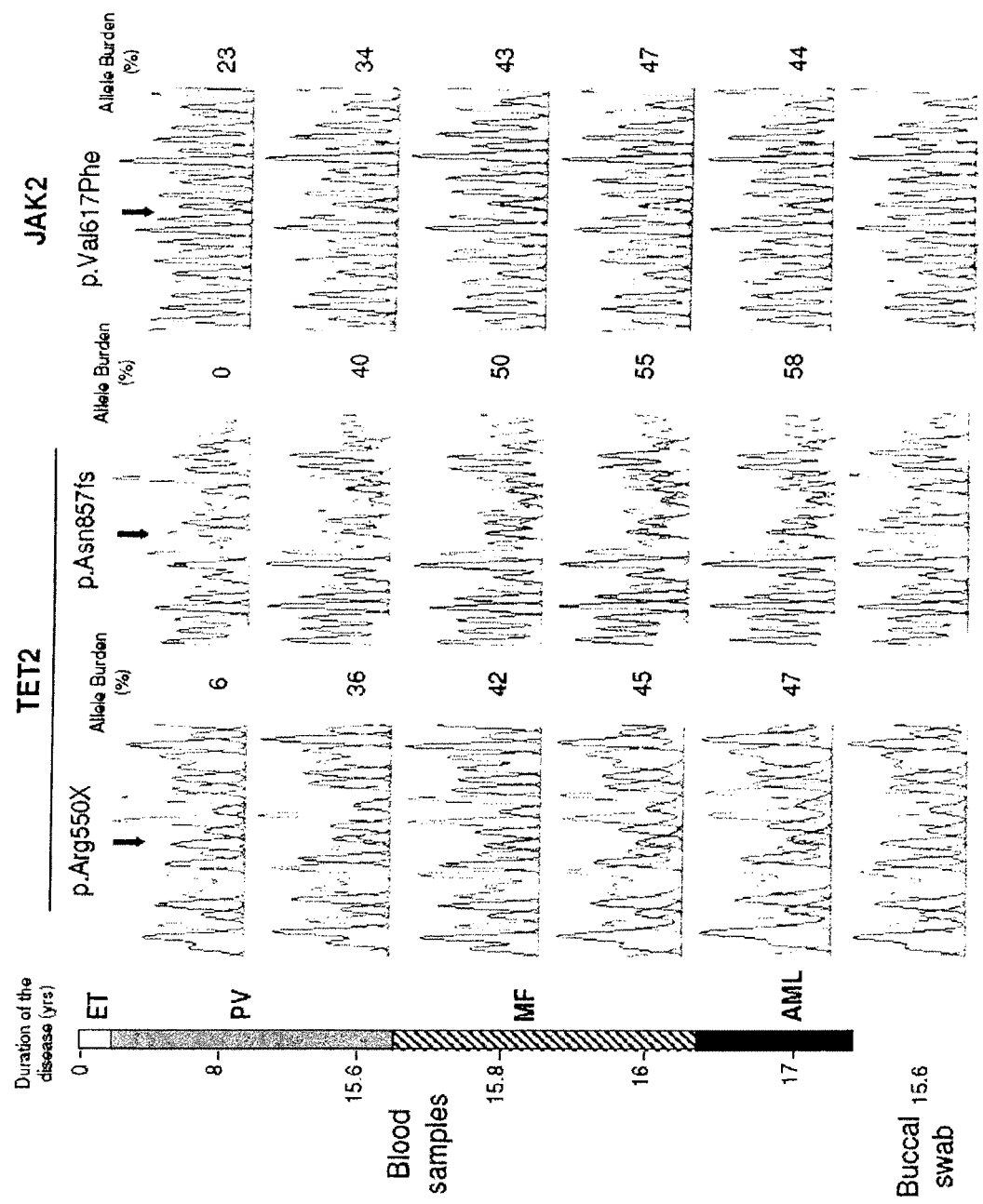

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding phenotype for each sample (white: ET; grey: PV; hatched: post-ET MF; black: AML).

Figure 8:
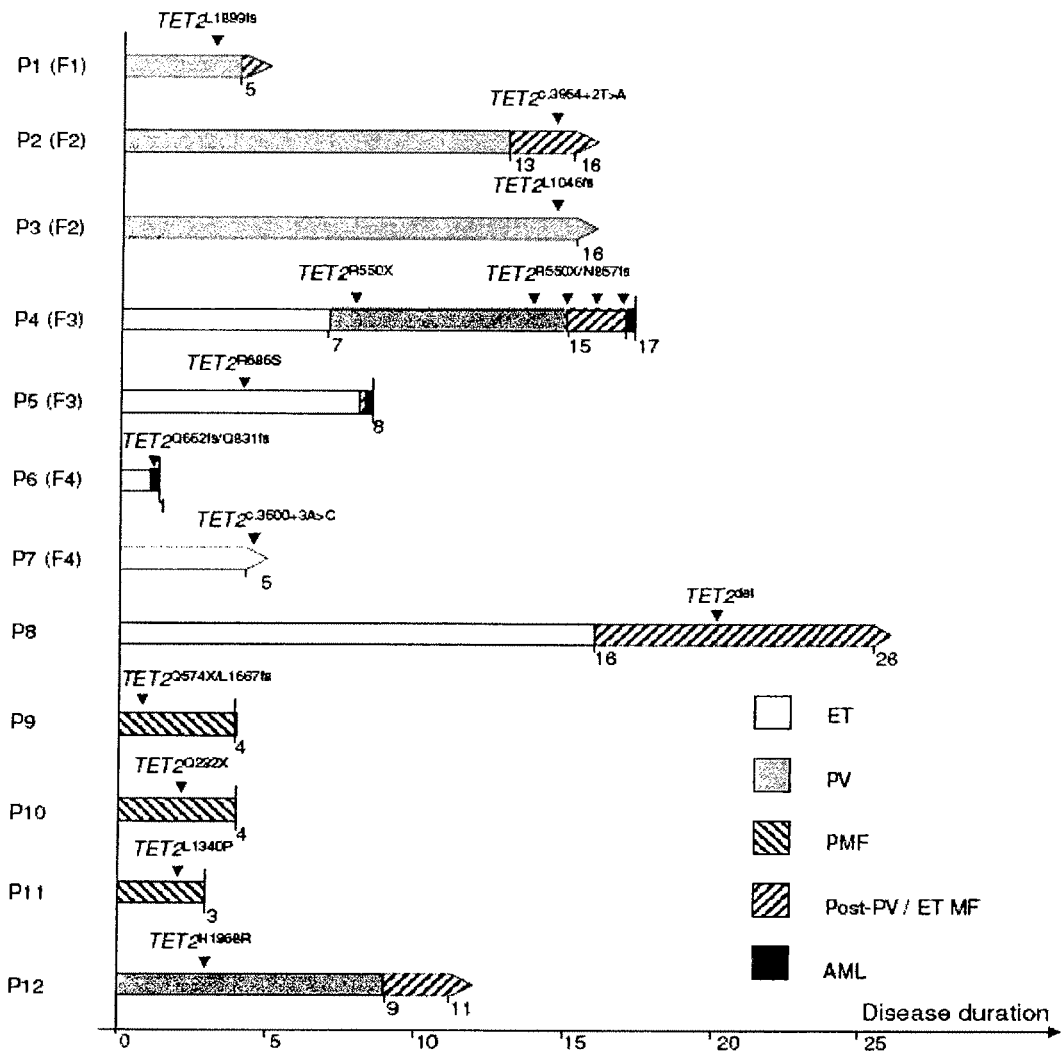

The FIG. 8 shows the schematic representation of the clinical status of the twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

Figure 9:
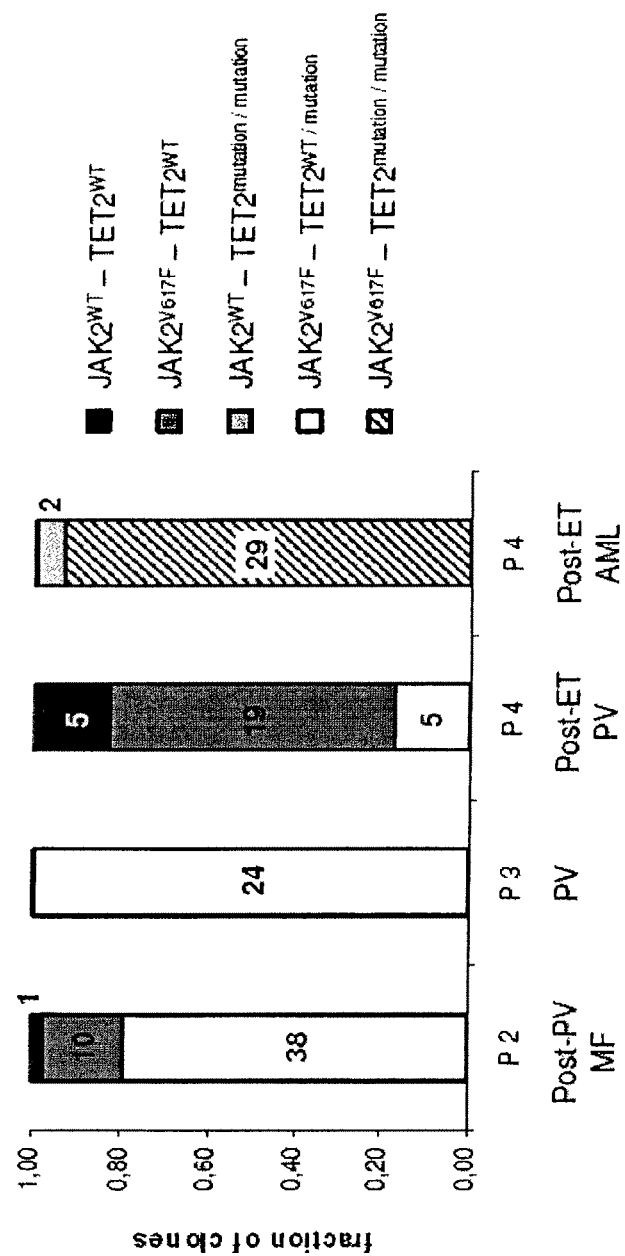

The FIG. 9 shows the TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

Figure 10:
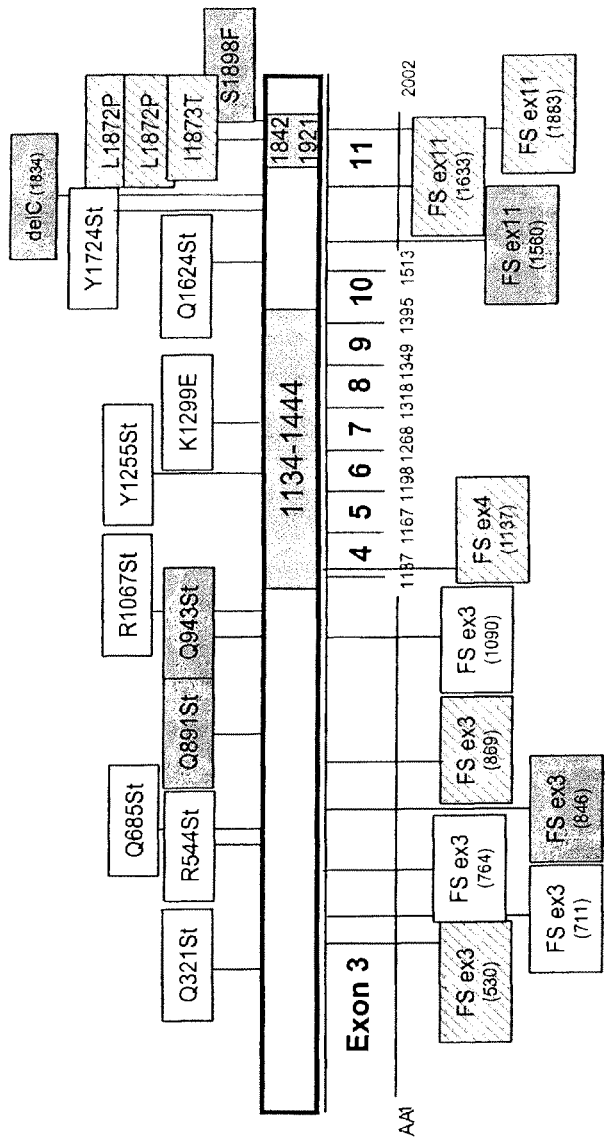

The FIG. 10 shows the clinical status and TET2 genotypes in MDS patients. Whites boxes represent low/int-1 grade MDS, hatched boxes represent int-2/high grade MDS and grey boxes represent secondary AML.

DETAILED DESCRIPTION OF THE INVENTION

The present invention is based on the discovery by the present inventors that the TET2 alleles are often genetically targeted by mutations and/or deletions in tumoral cells in patients suffering from lymphoid tumour or from myeloid tumour such as MPD, AML or MDS and can be considered as a bona fide tumor suppressor gene of human myeloid malignancies.

In a first aspect, the inventors report that, for sporadic cancer, the frequencies of TET2 mutation in unselected patient series were 12% in MPD, 18.5% in MDS, 24% in sAML until 50% in CMML patients. Also, applicants demonstrated that TET2 is a tumor suppressor gene in myeloid malignant disorders, because mutated hematopoietic stem cells are endowed with a growth advantage leading to enhanced proliferation.

In a second aspect, the inventors demonstrated by an analysis of 61 familial MPD cases (i.e. PV, ET, and PMF) that anomalies of TET2 gene are found in 20% of the three major MPD phenotypes (PV, ET and PMF) with a higher prevalence in PMF (42%).

Among the TET2-positive patients diagnosed with PV or ET, 77% developed myelofibrosis (MF) suggesting that the presence of acquired events of TET2 influence the evolution of the disease. In four patients (3 PV and 1 ET), we were able to show that the TET2 defect preceded from one to 7 years the hematological complication. The patients with a defect in TET2 are prone to progress to MF. This highly suggested a possible link between the TET2 acquired mutations and the severity of the disease, more specifically between TET2 and the development of MF.

In a third aspect, the inventors report that, for sporadic cancer, the frequencies of TET2 mutation in patients suffering from T-cell lymphoid tumour was ~20%. Finally, the TET2 rearrangements were observed in patients suffering from B-cell lymphoid tumour.

Thus, in a first aspect of the invention, there is provided an in vitro method for diagnosing a myeloid tumour or a lymphoid tumour in a subject, which comprises the step of analyzing a biological sample from said subject by:
  (i) detecting the presence of a mutation in the Ten Eleven Translocation protein family member 2 gene (TET2) coding for the polypeptide having the sequence SEQ ID NO:2, and/or
  (ii) analyzing the expression of the TET2 gene;
  wherein, the detection of a TET2 mutation, of the absence of expression of TET2 or of the expression of a truncated TET2 is indicative of a subject developing or predisposed to develop a myeloid tumour or a lymphoid tumour.

Recent evidence indicate that proteins of the TET family encode enzymes responsible for the conversion of 5-methylcytosine to 5-hydroxymethylcytosine (TAHILIANI et al., *Sciencexpress*, 2009), thus have potential roles in CpG demethylation and epigenetic regulation. Moreover, this reference established that the conserved TET domains, where most TET2 mutations are observed, are implicated in this activity.

Concomitantly, several works have established, in the last years, a role for hypomethylating agents in MDS (ITZYKSON & FENAUX, *Current Opinion in Hematology*, vol. 16, p: 77-83, 2009).

The results of the inventors now suggest that the observed efficiency of hypomethylating agent in some MDS potentially results from a demethylation defect in MDS with TET2 mutations.

Thus, the results of the inventors further suggest the use of hypomethylating agent on subjects suffering from lymphoid or myeloid tumour, such as MDS, for which tumour, a TET2 mutation, an absence of TET2 expression or an expression of a truncated TET2 has been detected.

Consequently and according to a preferred embodiment, the detection of a TET2 mutation, of the absence of expression of TET2 or of the expression of a truncated TET2 is indicative of a subject developing a myeloid tumour or a lymphoid tumour suffering from a demethylation defect, which subject can be advantageously treated with a hypomethylating agent, such as azacytidine (AZA).

Preferably, the method of the invention is dedicated to diagnose myeloid tumours.

In fact, the inventors have established that the frequency of TET2 mutations in patients suffering from myeloid tumor or from lymphoid tumour is greater than 10%.

The present invention furthermore provides a method for detection of the presence or absence of cells that have the potential to evolve to invasive myeloid neoplasms or to invasive lymphoid tumours, although those cells are not detectable as a lesion or precursor by conventional means.

As used herein, the term "subject" refers to a mammal, preferably a human.

Said subject may be a healthy, but the method of the invention is particularly useful for testing a subject thought to develop or to be predisposed to developing a myeloid cancer (i.e., myeloid tumour) or a lymphoid tumour. In that case, the method of the invention enables to confirm that said subject develops or is predisposed for developing a myeloid cancer (i.e., a myeloid tumour) or a lymphoid tumour.

More preferably, said lymphoid tumour is selected in the group consisting of lymphoma such as T- or B-cell lymphoma, and more preferentially of T cell lymphoma.

Still more preferably, said myeloid cancer (i.e., myeloid tumour) is selected in the group consisting of myelodysplastic syndrome (MDS), acute myeloid leukemia (AML), myeloproliferative disorders (MPD) and myelodysplatic/ myeloproliferative syndrome. Advantageously, said myeloid cancer is a myelodysplatic/myeloproliferative syndrome, and preferably a chronic myelomonocytic leukemia (CMML).

According to a preferred embodiment, the method of the invention is for diagnosing a myelofibrosis (MF) in a subject, wherein said subject is suffering from polycythemia vera (PV) or from thrombocythemia (ET), and wherein the detection of a TET2 mutation or TET2 under-expression is indicative of a subject developing or predisposed to develop a myelofibrosis (MF).

According to still another preferred embodiment, the subject is suffering from myelodysplastic syndrome (MDS), and the detection of a TET2 mutation or TET2 under-expression is indicative of a subject with a good prognosis.

As used herein a good prognosis corresponds to a patient suffering from MDS and having a reduced risk of developing an AML.

In fact, the inventors have established that five-year survival was significantly increased in TET2 mutated patients suffering from MDS compared to unmutated patients ($p<0.05$).

As used herein, the expression "biological sample" refers to solid tissues such as, for example, a lung biopsy; buccal swab, fluids and excretions such as for example, sputum, induced sputum, blood, serum, plasma, urine. Preferably, said biological sample is a bone marrow sample.

In this aspect of the invention, the method comprises the step of detecting the presence of a mutation in the TET2 gene coding for the polypeptide having the sequence SEQ ID NO:2.

As used herein, the term "mutations" correspond to any modification in the sequence of the original nucleic acid sequence. These mutations comprise small-scale mutations, or large scale mutations. Small scale mutations are those affecting a gene in one or a few nucleotides, including point mutations, insertions or deletions of one or more extra nucleotides in the DNA. Point mutations can be silent, missense and nonsense mutation. Large scale mutation in the genomic structure, such as gene duplications, deletions, or mutations whose effect is to juxtapose previously separate pieces of DNA, potentially bringing together separate genes to form functionally distinct fusion genes. These last mutations include chromosomal translocations, interstitial deletions, chromosomal inversions and loss of heterezygosity.

Preferably, only a biological sample containing cells including genomic DNA (or optionally RNA) from the subject to be tested is required.

Preferably, this detecting step is realized on each allele of the TET2 gene. In fact, the diagnosis is more reliable when the mutation is detected on each allele of the TET2 coding for the polypeptide having the sequence SEQ ID NO:2.

In a particular embodiment, the in vitro method of the invention aims to detect mutation included in the group consisting of deletions, insertions and point mutations such as mutations affecting splice sites, missense mutation and nonsense mutations, preferably missense mutation and nonsense mutations.

The inventors have established that the existence of such mutations is associated with myeloid or lymphoid cancer. Moreover, the inventors observed that the polypeptidic C-terminal domain of the TET2 protein is preferentially targeted by the deleterious mutations in the studied patients (see examples).

For deletion or insertion, said deletion or insertion preferably results in the absence of expression of the TET2 protein or in the expression of a truncated TET2 protein, which truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4). More preferably, said truncated TET2 protein does not comprise the 80 amino acid region located near the carboxyterminal end of the protein TET2 (corresponding to amino acid 1843 until amino acid 1922, SEQ ID NO:4).

For example, these deletions or insertions can be selected in those disclosed in table 1.

For missense mutation, said missense mutation is preferably located in the open reading frame of the TET2 protein, and preferably in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4).

As an example, said missense mutations are selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I1873T, R1896M, and S1898F; preferably in the group comprising or consisting of I1175V, L1197N, H1219Y, E1235V, C1271W, K1299E, L1340P, R1302G, G1370E, A1344E, N1387S, H1868R, G1869W, L1872P, I1873T, R1896M, and S1898F.

More preferably, said missense mutation is located in the 80 amino acid region located near the carboxyterminal end of the protein TET2 (corresponding to amino acid 1843 until amino acid 1922, SEQ ID NO:4). Even more preferably, said missense mutations are selected in the group comprising or consisting of H1868R, G1869W, L1872P, I1873T, R1896M, and S1898F, as an example I1873T, R1896M, and S1898F.

For non sense mutation, said nonsense mutation preferably results in the introduction of a stop mutation in the open reading frame of the TET2 protein, and preferably before at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

As an example, said nonsense mutations are selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, Q1834Stop and W1847Stop; preferably in the group comprising or consisting of Q321Stop, S354Stop, R544Stop, Q557Stop, R1216Stop, and Y1724Stop.

Also, said nonsense mutation can result in the introduction of a stop mutation inside at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

More preferably, said nonsense mutation results in the introduction of a stop mutation in the open reading frame of the TET2 protein before the 80 amino acid region located near the carboxyterminal end of the protein TET2 (corresponding to amino acid 1843 until amino acid 1922, SEQ ID NO:4). As an example, said nonsense mutation is selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, and Q1834Stop.

Also, said nonsense mutation can result in the introduction of a stop mutation in the open reading frame of the TET2 protein inside the 80 amino acid region located near the carboxyterminal end of the protein TET2 (corresponding to amino acid 1843 until amino acid 1922, SEQ ID NO:4). As an example, said nonsense mutation is W1847Stop.

Typical techniques for detecting the presence of a mutation may include restriction fragment length polymorphism, hybridization techniques, DNA sequencing, exonuclease resistance, microsequencing, solid phase extension using ddNTPs, extension in solution using ddNTPs, oligonucleotide ligation assays, methods for detecting single nucleotide polymorphisms such as dynamic allele-specific hybridization, ligation chain reaction, mini-sequencing, DNA "chips", allele-specific oligonucleotide hybridization with single or dual-labelled probes merged with PCR or with molecular beacons, and others.

Advantageously, the alteration is detected on the cDNA or DNA of the TET2 gene by either PCR and sequencing, SNP-array or CGH, all of them being well known for the skilled person.

In molecular biology and bioinformatics, a SNP array is a type of DNA microarray which is used to detect polymorphisms within a population. The basic principles of SNP array are the same as the DNA microarray. These are the convergence of DNA hybridization, fluorescence microscopy, and solid surface DNA capture. The three mandatory components of the SNP arrays are: i) the array that contains immobilized nucleic acid sequences or target; ii) one or more labeled Allele specific oligonucleotide (ASO) probes; and iii) a detection system that records and interprets the hybridization signal (see in Sheils, O., Finn, S. and O'Leary J. (2003) "Nucleic acid microarray: an overview." Current Diagnostic Pathology. 9:155-158).

Comparative genomic hybridization (CGH) is a molecular cytogenetic method of screening a tumor for genetic changes. The alterations are classified as DNA gains and losses and reveal a characteristic pattern that includes mutations at chromosomal and subchromosomal levels. The method is based on the hybridization of fluorescently labeled tumor DNA (frequently fluorescein (FITC)) and normal DNA (frequently rhodamine or Texas Red) to normal human metaphase preparations. Using epifluorescence microscopy and quantitative image analysis, regional differences in the fluorescence ratio of gains/losses vs. control DNA can be detected and used for identifying abnormal regions in the genome. CGH will detect only unbalanced chromosomes changes. Structural chromosome aberrations such as balanced reciprocal translocations or inversions can usually not be detected, as they do not systematically change the copy number (Emanuel B S, Saitta S C. From microscopes to microarrays: dissecting recurrent chromosomal rearrangements. *Nat Rev Genet.* 2007 November; 8(11):869-83. Review).

In another preferred embodiment of the invention, the method comprises the step of analyzing the expression of the TET family member 2 gene (TET2).

According to the results obtained by the inventors, the absence of expression or the under-expression of the TET2 protein or the expression of a truncated TET2 protein as disclosed previously is associated with myeloid cancer.

Methods for analyzing the expression of a gene are well known for the man skilled in the art.

In a particular embodiment of the invention, the expression of the TET2 gene is assessed by analyzing the expression of mRNA transcript or mRNA precursors, such as nascent RNA, of said gene.

Such analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TAQMAN), and probes arrays such as GENECHIP™ DNA Arrays (AFFYMETRIX).

Advantageously, the analysis of the expression level of mRNA transcribed from the TET2 gene involves the process of nucleic acid amplification, e. g., by RT-PCR (the experimental embodiment set forth in U.S. Pat. No. 4,683,202), ligase chain reaction (BARANY, Proc. *Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990), transcriptional amplification system (KWOH et al., 1989, *Proc. Natl. Acad. Sci. USA*, vol. 86, p: 1173-1177, 1989), Q-Beta Replicase (LIZARDI et al., *Biol. Technology*, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another particular embodiment, the expression of the TET2 gene is assessed by analyzing the expression of the TET2 protein translated from said gene.

Such analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the TET2 protein. Said analysis can be assessed by a variety of techniques well known by one of skill in the art including, but not limited to, enzyme immunoassay (EIA), radioimmunoassay (RIA), Western blot analysis and enzyme linked immunoabsorbant assay (ELISA).

Polyclonal antibodies can be prepared by immunizing a suitable animal, such as mouse, rabbit or goat, with the TET2 protein (SEQ ID NO:2) or a fragment thereof (e.g., at least 10 or 15 amino acids). The antibody titer in the immunized animal can be monitored over time by standard techniques, such as with an ELISA using immobilized polypeptide. At an appropriate time after immunization, e.g., when the specific antibody titers are highest, antibody producing cells can be obtained from the animal and used to prepare monoclonal antibodies (mAb) by standard techniques, such as the hybridoma technique originally described by KOHLER and MILSTEIN (*Nature*, vol. 256, p: 495-497, 1975), the human B cell hybridoma technique (KOZBOR et al., *Immunol.*, vol. 4, p: 72, 1983), the EBV-hybridoma technique (COLE et al., *In Monoclonal Antibodies and Cancer Therapy*, Alan R. Liss, Inc., p: 77-96, 1985) or trioma techniques. The technology for producing hybridomas is well known (see generally Current Protocols in Immunology, COLIGAN et al. ed., John Wiley & Sons, New York, 1994). Hybridoma cells producing the desired monoclonal antibody are detected by screening the hybridoma culture supernatants for antibodies that bind the polypeptide of interest, e.g., using a standard ELISA.

As previously mentioned, mutations in the TET2 gene may trigger the absence of expression or the under-expression of the TET2 protein.

As used herein, the "under-expression" of a polypeptide occurs when the transcription and/or the translation of the gene is affected by the mutation, leading to an expression level in a biological sample that is lower than the standard error of the assay employed to assess expression, and is preferably at least 20% inferior to the normal level of expression of said gene, preferably at least 50% inferior to the normal level of expression of said gene, and most preferably at least 100% inferior to the normal level of expression of said gene.

Therefore, the method of the invention may comprise comparing the level of expression of the TET2 gene in a biological sample from a subject with its expression level in a control (i.e., normal expression level). A significantly lower level of expression of said gene in the biological sample of a subject as compared to the normal expression level is an indication that the patient may develop a myeloid neoplasm.

As used herein, a "control" corresponds preferably to a control sample comprising non-tumoral cells. Preferably, said control corresponds to peripheral blood leukocytes (PBL), and most preferably to a peripheral blood leukocyte immortalized with Epstein Barr Virus.

Thus, the "normal" level of expression of the TET2 gene is the level of expression of said gene in a biological sample of non-tumoral cell. Preferably, said normal level of expression is assessed in a control sample and preferably, the average expression level of said gene in several control samples.

Analyzing the normal expression of the TET2 gene may be assessed by any of a wide variety of well-known methods for detecting expression of a transcribed nucleic acid or translated protein as previously described.

In a preferred embodiment of the invention, said mutation in the TET2 gene induces absence of expression or underexpression of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxy-terminal end of the protein TET2 (corresponding to amino acid 1843 until amino acid 1922, SEQ ID NO:4), and more preferably of the 80 amino acid region located near the carboxy-terminal end of the protein TET2 (corresponding to amino acid 1843 until amino acid 1922, SEQ ID NO:4).

In a second aspect, the present invention refers to a kit for diagnosing myeloid cancer or lymphoid cancer in a subject comprising at least one nucleic acid probe or oligonucleotide or at least one antibody, which can be used in a method as defined in the present in invention, for detecting the presence of a mutation in the TET2 gene and/or analysing the expression of the TET2 gene.

Preferably, the oligonucleotide is at least one PCR primer, preferably a set of PCR primers is provided, which allows to amplify the TET2 gene or a fragment thereof. The skilled person readily provides such an oligonucleotide or set of PCR primers which allows to amplify a region of the TET2 gene, provided that the nucleic acid sequence of TET2 is well known (Accession number NM 001127208, SEQ ID NO:1) (Current Protocols in Molecular Biology; edited by Fred M. Ausubel et al., supra).

In a preferred embodiment, the kit comprises at least one PCR primer selected in the group comprising SEQ ID NO:5 to SEQ ID NO: 38 (see examples and sequence listing) for detecting the presence of a mutation in the TET2 gene and/or analysing the expression of said gene.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The present kits can also include one or more reagents, buffers, hybridization media, nucleic acids, primers, nucleotides, probes, molecular weight markers, enzymes, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like.

In one embodiment, the kit is made up of instructions for carrying out the method described herein for diagnosing a myeloid cancer or a lymphoid cancer in a subject. The instructions can be provided in any intelligible form through a tangible medium, such as printed on paper, computer readable media, or the like.

Still a further aspect of the present invention refers to the use, for diagnosing myeloid or lymphoid cancer, of the abovementioned kit comprising at least one nucleic acid probe or oligonucleotide or at least one antibody, which can be used in a method as defined for detecting the presence of a mutation in the TET2 gene and/or analysing the expression of the TET2 gene.

Advantageously, myeloid cancer is selected in the group consisting of myelodysplastic syndrome, acute myeloid leukemia, myeloproliferative disease and myelodysplatic/myeloproliferative syndrome.

Still advantageously, said lymphoid cancer is selected in the group consisting of lymphoma such as T- or B-cell lymphoma, and more preferentially of T-cell lymphoma.

In still another aspect, the invention relates to the use of a hypomethylating agent for treating a patient suffering from a myeloid or a lymphoid tumour, for which tumour, a TET2 mutation, an absence of TET2 expression or an expression of a truncated TET2 has been detected.

Preferably, said myeloid tumour is not a MDS.

Hypomethylating agent are well known from the skilled person and include, as an example, azacytidine.

In a final aspect, the invention relates to a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of hypomethylating agent.

Preferably, said myeloid tumour is not a MDS.

Preferably said hypomethylating agent is azacytidine.

A therapeutically efficient amount of hypomethylating agent can be simply determined by the skilled person. As an example of therapeutically efficient amount of azacytidine for treating lymphoid or myeloid tumour, one can cite the regimen which is disclosed in FENAUX et al. (*Blood*, vol. 110, 817, 2007) which is incorporated herein by reference.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1. Identification of TET2 Gene Mutation in MDS, MPD and in AML

We identified 6 patients suffering from myeloid cancer (AML (nAML1, nAML2, nAML3) or MDS (MDS01, MDS02, and MDS03)) and harboring an acquired chromosomal translocation associated with a genomic deletion in the vicinity of the chromosome 4 breakpoint at 4q24. These deletions were homozygous in one instance and heterozygous in the other cases and could indicate the location of a tumor suppressor gene in that region.

FISH analyses first permit to narrow the commonly deleted region in these patients to a ~500 kb interval (data not shown). Computer and RT-PCR assisted analyses uncovered the structure of a single gene, Ten Eleven Translocation (TET2) lying in this region (FIG. 1).

TET2 gene comprises 11 exons spread over 150 Kb. The predicted TET2 protein, encoded by exons 3 to 11, belongs to a three-member family (TET family) in human and mouse. Proteins of the TET family share two highly conserved regions with a single orthologous *Drosophila* protein in their central and carboxy-terminal part (FIG. 1).

The FIG. 1 shows the protein sequence of TET2 (SEQ ID NO:2), highlighting the conserved regions between species (bold).

For TET2, a translational initiation codon situated at the 5' end of exon 3 (Nucleotides 862-864 of the cDNA or 27-29 of Exon 3) was predicted to allow for the synthesis of a 2002 amino acids protein (FIG. 1). An alternative ATG situated in exon 2 (nucleotides 798-800 of the cDNA or 111-113 of Exon 2) will direct the synthesis of 21 more amino acids. Additional starts are not excluded.

TET2 transcript is widely expressed (ONO et al., above-mentioned, 2002; LORSBACH et al., abovementioned, 2003), and as suggested by available data, the expression of TET2 was confirmed in human bone marrow and blood tissues by RT-PCR (data not shown). More specifically, TET2 transcripts were detected in umbilical cord blood CD34$^+$ cells, in granulocytes from healthy controls, and in hematopoietic cell lines.

Finally, of these six patients, five harbored a deletion on one chromosome 4 whereas both copies were deleted in MDS01.

The involvement of the same 4q24 region was also found by using a different approach in MPD. Analysis of CD34$^+$CD38$^-$ multipotent progenitors, CD34$^+$CD38$^+$ committed progenitors, and mature cells, led us to identify two subsets of JAK2 V617F MPD at diagnosis with distinct kinetics of hematopoietic expansion (DUPONT et al., *Blood*, vol. 110 (3), p: 1013-21, 2007). The first subset is characterized by a late expansion of the malignant clone; i.e. downstream of the committed progenitor. In contrast, the second subset of patients had an early expansion of the clone, upstream of the committed progenitor. We hypothesized that the second subset of patients had a molecular defect able to promote the early expansion of the malignant clone. Five patients from this second subset (MPD01 to MPD05) were analyzed using high-resolution CGH and SNP arrays to compare presumed clonal cells (granulocytes) versus polyclonal cells (peripheral blood mononuclear cells or lymphocytes) DNA. One primary myelofibrosis (PMF) patient (MPD01) and one polycythemia vera (PV) patient (MPD04) exhibited a large acquired loss-of-heterozygosity (LOH) without copy number modification (uniparental disomy; UPD (20)) ranging from q22 to qter of chromosome 4. The third patient (MPD05) demonstrated an acquired deletion located in the 4q24 region. This 325 kb deletion in MPD05 was included in the 4q24 LOH region of patients MPD01 and MPD04 and contained TET2 as a single candidate gene. This region was normal in the two other studied MPD samples (MPD02 and MPD03).

As the 4q24 region is affected in patients suffering from myeloid neoplasms, and as TET2 localized in this region, the integrity of the TET2 gene might be affected in these patients. Moreover, loss of the two copies of TET2 in patient MDS01 and recurrent loss of one copy in 8 other patients with MDS, MPD or AML designated TET2 as a candidate tumor suppressor gene.

PCR on the TET2 gene was thus performed in order to detect alterations of the TET2 gene in these patients. Importantly, both alleles were analysed in order to detect bi-allelic modifications.

2. Experimental Procedure to Detect Alterations of the TET2 Gene

2.1. Primers Used for the Identification of TET2 Mutations or Deletions (Table 2)

TABLE 2

| SEQ ID NO | Tm (° C.) | Sequences | Amplified region | Length of amplicon |
|---|---|---|---|---|
| 5 | 60.9 | TGAACTTCCCACATTAGCTGGT | 106374235-106375189 | 955 |
| 6 | 60.7 | GAAACTGTAGCACCATTAGGCATT | | |
| 7 | 62.0 | CAAAAGGCTAATGGAGAAAGACGTA | 106374894-106375729 | 836 |
| 8 | 62.0 | GCAGAAAAGGAATCCTTAGTGAACA | | |
| 9 | 63.0 | GCCAGTAAACTAGCTGCAATGCTAA | 106375458-106376300 | 843 |
| 10 | 62.3 | TGCCTCATTACGTTTTAGATGGG | | |
| 11 | 60.0 | GACCAATGTCAGAACACCTCAA | 106376065-106376931 | 867 |
| 12 | 60.9 | TTGATTTTGAATACTGATTTTCACCA | | |
| 13 | 60.5 | TTGCAACATAAGCCTCATAAACAG | 106376703-106377490 | 788 |
| 14 | 60.9 | ATTGGCCTGTGCATCTGACTAT | | |

TABLE 2-continued

| SEQ ID NO | Tm (° C.) | Sequences | Amplified region | Length of amplicon |
|---|---|---|---|---|
| 15 | 62.1 | GCAACTTGCTCAGC AAAGGTACT | 106377284-106378064 | 781 |
| 16 | 62.3 | TGCTGCCAGACTCA AGATTTAAAA | | |
| 17 | 60.1 | ATACTACATATAAT ACATTCTAATTCCC TCACTG | 106381631-106382125 | 495 |
| 18 | 61.5 | TGTTTACTGCTTTG TGTGTGAAGG | | |
| 19 | 61.7 | CATTTCTCAGGATG TGGTCATAGAAT | 106383324-106383609 | 286 |
| 20 | 61.5 | CCCAATTCTCAGGG TCAGATTTA | | |
| 21 | 60.1 | AGACTTATGTATCT TTCATCTAGCTCTG | 106383864-106384462 | 599 |
| 22 | 60.1 | ACTCTCTTCCTTTC AACCAAAGATT | | |
| 23 | 60.0 | ATGCCACAGCTTAA TACAGAGTTAGAT | 106400093-106400454 | 362 |
| 24 | 60.9 | TGTCATATTGTTCA CTTCATCTAAGCTA AT | | |
| 25 | 61.1 | GATGCTTTATTTAG TAATAAAGGCACCA | 106402226-106402579 | 354 |
| 26 | 61.5 | TTCAACAATTAAGA GGAAAAGTTAGAAT AATATTT | | |
| 27 | 61.7 | TGTCATTCCATTTT GTTTCTGGATA | 106410076-106410436 | 361 |
| 28 | 60.5 | AAATTACCCAGTCT TGCATATGTCTT | | |
| 29 | 63.0 | CTGGATCAACTAGG CCACCAAC | 106413052-106413825 | 774 |
| 30 | 63.0 | CCAAAATTAACAAT GTTCATTTTACAAT AAGAG | | |
| 31 | 61.1 | GCTCTTATCTTTGC TTAATGGGTGT | 106415516-106416263 | 748 |
| 32 | 60.5 | TGTACATTTGGTCT AATGGTACAACTG | | |
| 33 | 60.5 | AATGGAAACCTATC AGTGGACAAC | 106416016-106417122 | 1107 |
| 34 | 60.2 | TATATATCTGTTGT AAGGCCCTGTGA | | |
| 35 | 62.0 | CAGAGCTTTCTGGA TCCTGACAT | 106416670-106417204 | 535 |
| 36 | 60.3 | GCCCACGTCATGAG AACTATACTAC | | |
| 37 | 66 | TCTAAGCTCAGTCT ACCACCCATCCATA | 106416118-106416671 | 570 |
| 38 | 66.7 | TGCTCGCTGTCTGA CCAGACCTCAT | | |

2.2. PCR

PCR were performed in 20 μL starting from 25-50 ng of DNA on APPLIED BIOSYSTEM PCR 9700.

For each sample: 17 PCR were used to detect the mutations/deletions localized on the TET2 gene. The mix was prepared as below:

| | mix *1 |
|---|---|
| 10X | 2 |
| dNTP 25 mM | 0.15 |
| O1 100 pmol/μl | 0.1 |
| O2 100 pmol/μl | 0.1 |
| hot star (5 U/μl) | 0.2 |
| Water | 15.5-16.5 |
| DNA sample (25 ng/μl) | 1-2 |

We use the following PCR cycles conditions:

| | | |
|---|---|---|
| 15' | 94° C. | 1 cycle |
| 20 s | 94° C. | 2 cycles |
| 20 s | 56° C. | |
| 30 s | 72° C. | |
| 20 s | 94° C. | 2 cycles |
| 20 s | 54° C. | |
| 30 s | 72° C. | |
| 20 s | 94° C. | 2 cycles |
| 20 s | 52° C. | |
| 30 s | 72° C. | |
| 20 s | 94° C. | 37 cycles |
| 20 s | 50° C. | |
| 30 s | 72° C. | |
| 10' | 72° C. | 1 cycle |

2.3. Sequencing of the PCR Products

Finally, the PCR products sequencing was realized by EUROFINS MWG Biotech (France, 9, rue de la Laponie, 91967 Les Ulis cedex) or by "Département des services commun de l'Institut Cochin" (Plate forme transcriptomique, Hôpital Cochin/Bat G. Roussy/3ème étage, 27 rue du Fg St Jacques, 75014 Paris) with the kit Big Dye terminator V1.1 and 3130 XL sequencing machines (both from APPLIED BIOSYSTEMS).

3. Mutations of the TET2 Gene in Patients Suffering from MDS or AML with Heterozygous 4q24 Deletion

3.1. In Tumoral Cells

TET2 gene integrity was checked on the 4q24 "intact" copy of the 8 abovementioned patients harboring the heterozygous acquired chromosomal translocation associated with a genomic deletion in the vicinity of the chromosome 4 breakpoint at 4q24.

To identify potential mutations of the TET2 gene in these alleles, the sequence of the eight coding exons and of their splice sites in the DNA extracted from bone marrow samples of 8 patients having a 4q24 rearrangement was investigated by PCR as described previously.

Table 3 discloses the status of both alleles of the TET2 genes in patients suffering from MPD, MDS or AML and having a 4q24 deletion on one allele:

| Patient | Copy 1 | Copy 2 | Disease |
|---|---|---|---|
| nAML1 | R1896M | Deletion | AML |
| nAML2 | I1873T | Deletion | AML |
| nAML3 | Deletion | Unknown | AML |
| MDS01 | Deletion | Deletion | RA |
| MDS02 | FS after L560 (Exon 3) | Deletion | RA |
| MDS03 | N1624Stop (Exon 11) | Deletion | RA |
| MPD01 | Q557Stop | Q557Stop | PMF |

-continued

| Patient | Copy 1 | Copy 2 | Disease |
|---|---|---|---|
| MPD04 | Deletion (1237 to 1239) | Deletion (1237 to 1239) | PV |
| MPD05 | Deletion | Wild type | PV |

Comparison of the sequence obtained from the patients with the wild type counterpart identified nucleotide changes in 6 patients (Table 3). Changes were not attributable to identified polymorphisms. Patient nAML1 and nAML2 harbored single nucleotide changes, leading to an I1873T in patient nAML2 and to R1896M in patient nAML1. Patient MDS03 exhibited a CAG to TAG changes, introducing a stop codon instead of N1624. Patient MPD01 exhibited a single nucleotide change, introducing a stop codon instead of NQ557. Patient MDS02 had a 4 base pair insertion, leading to a stop codon 6 amino acids after L560. Patient MPD04 had an in frame 9-nucleotide deletion. No notable nucleotide changes were observed in DNA of patient nAML3. Patient MDS01 harbors a bi-allelic deletion of the TET2 gene.

3.2. In Non-Tumoral Cells of the Patients

To confirm that the observed changes were somatically acquired, we analyzed DNA from non-tumoral samples when available.

In patient nAML2, the T to C change was not observed in DNA from EBV-transformed B cell population (FIG. 2). In patient nAML1, the analyses of a sample obtained after auto-bone marrow transplantation demonstrated an inversed ratio between the wild type G and the mutated T, when compared to the diagnosis sample (data not shown). Similarly, the signal corresponding to the mutated T is almost absent in DNA extracted from stimulated PBL from patient MDS03 (FIG. 2). This analysis has also shown the absence of mutation for MPD04 or of deletion for MPD05 in non-tumoral cells (data not shown). This analysis has further shown that a small amount of residual wild-type sequence is detected in peripheral mononuclear cells from patient MPD01 (data not shown).

The FIG. 2 shows the sequence traces obtained by sequencing of PCR on samples obtained from the two patients nAML2 and MDS03, and showing that the mutation only occurs in the tumoral (R: reverse primer and F: forward primer) and in non-tumoral samples (NT or PBL).

Taken together, these results demonstrate that the two copies of the TET2 gene is targeted in patients suffering from diverse myeloid neoplasm, and this through two different events, a chromosomal translocation associated with a deletion and point mutations, establishing TET2 as a tumor suppressor gene.

4. Alteration of the TET2 Gene in Patients Suffering from MDS or AML without Cytogenetically Detectable 4q24 Deletion To establish whether mutation of TET2 could also occurs independently of a chromosomal abnormality, DNA from bone marrow samples of 309 additional patients with different subtypes of MDS (n=81), sAML (n=21), CMML (n=9), $JAK2^{V617F}$ positive MPD (n=181), and $JAK2^{V617F}$ negative MPD (n=17) without known 4q24 abnormality was analyzed by PCR as previously described.

Table 4 discloses the status of the identified TET2 defect in patients suffering from MDS or AML:

| Patient | TET2 defect | Disease |
|---|---|---|
| sAML2 | S1898F | sAMLII |
| sAML4 | FS (Exon 3) | sAMLII |
| sAML5 | FS (Exon 11) | sAMLII |
| sAML6 | FS (Exon 11)/Q891stop | sAMLII |
| sAML7 | Q943Stop | sAMLII |
| MDS04 | K1299E/R544Stop | RA |
| MDS07 | No amplification Ex11 | RA |
| MDS30 | FS (Exon 3) | RA |
| MDS09 | FS (Exon 3) | RARS |
| MDS35 | Y1225Stop Exon 6 | RARS |
| MDS10 | Y1724Stop/Q321Stop | RCMD-RS |
| MDS28 | FS (Exon 3) | RCMD-RS |
| MDS18 | FS (Exon 11) | RAEB1 |
| MDS27 | FS (Exon 3)/FS (Exon 3) | RAEB1 |
| MDS33 | FS (Exon 4) | RAEB1 |
| MDS39 | L1872P | RAEB1 |
| MDS40 | FS (Exon 11) | RAEB1 |
| MDS42 | L1872P/I1873T Mutation of splice acceptor | RAEB1 |
| MDS34 | Site Exon 5 | RAEB2 |
| MDS41 | FS (Exon 11) | RAEB2 |
| CMML01 | Q685Stop | CMML |
| CMML02 | FS (Exon 3)/R1067Stop | CMML |

RA, refractory anemia; RARS, refractory anemia with ringed sideroblasts; RARS-T, RARS with thrombocytosis; RAEB, refractory anemia with excess blasts; RAEB1: blasts 5-9%; RAEB2: blasts 10-19%; AML, acute myeloid leukemia; FAB, French American British classification; del, deletion; FS, frame shift; ND, not done. All MDS/AML tested (22/27) were negative for $JAK2^{V617F}$. MDS03 was studied at the RAEB1 and RAEB2 phases. Two successive samples of patient MDS34 were analyzed. Selected patients analyzed during the initial part of the study appear in bold.

Table 5 discloses the status of the identified TET2 defect in patients suffering from MPD:

| Patient | TET2 defect | Disease | JACK2 and MPL status |
|---|---|---|---|
| MPD18 | R1216stop | PV | $JAK2^{V617F}$ |
| MPD20 | FS Ex11 | PV | $JAK2^{V617F}$ |
| MPD35 | S354stop | ET | $JAK2^{V617F}$ |
| MPD43 | FS Ex3/R550stop | post ET MF | $JAK2^{V617F}$ |
| MPD45 | FS Ex3 | PV | $JAK2^{V617F}$ |
| MPD69 | FS Ex7/FS Ex11 | PV | $JAK2^{V617F}$ |
| MPD74 | FS Ex3 | PMF | WT |
| MPD81 | FS Ex6 | ET | $JAK2^{V617F}$ |
| MPD86 | FS Ex5/R1404stop | PV | $JAK2^{V617F}$ |
| MPD89 | FS Ex10 | PV | $JAK2^{V617F}$ |
| MPD92 | R1302G | PMF | $JAK2^{V617F}$ |
| MPD96 | W1847stop | ET | $JAK2^{V617F}$ |
| MPD99 | FS Ex3 | ET | $JAK2^{V617F}$ |
| MPD120 | FS Ex3 | PV | $JAK2^{V617F}$ |
| MPD130 | FS Ex3 | ET | $JAK2^{V617F}$ |
| MPD132 | FS Ex3 | PV | $JAK2^{V617F}$ |
| MPD133 | G1869W | ET | $JAK2^{V617F}$ |
| MPD142 | FS Ex3 | PV | $JAK2^{V617F}$ |
| MPD149 | FS Ex6 | ET | $JAK2^{V617F}$ |
| MPD158 | FS Ex3 | PV | $JAK2^{V617F}$ |
| MPD163 | Q1542stop | ET | $MPL^{W515L}$ |
| MPD164 | FS Ex3 | PMF | $JAK2^{V617F}$ |
| MPD183 | FS Ex7/Q635stop | PV | $JAK2^{V617F}$ |
| MPD200 | FS Ex3/FS Ex11 | ET | WT |

PMF, primary myelofibrosis, PV, polycythemia vera, ET, essential thrombocythemia. WT: negative for $JAK2^{V617F}$ and $MPL^{515}$ mutations. FS, frame shift.

Obvious abnormalities of TET2 coding sequence were observed in 45 patients, resulting in conserved amino acid substitution, generation of in frame stop codons, or frame shifts (Tables 4 and 5. In one additional patient (MDS07), amplification of the 5' part of exon 11 only resulted in trace amounts of PCR fragment despite the use of several conditions and primers pairs (data not shown), which was attributed to an uncharacterized structural genomic rearrangement affecting this region. Defects of TET2 were observed in all types of MDS (22/111) and BCR-ABL negative MPDs associated with JAK2 V617F (21/181), or MPL W515L/K (1/6) or devoid of these mutations (2/11).

The results demonstrate that TET2 defects can be identified in unselected diverse myeloid disorders with a high prevalence (46/309=17%). As an example, patient MDS04 showed two changes leading to K1299D and R544Stop. Patient MDS10 had two stop mutations, Y1724Stop and Q321Stop. Patient sAML2 had a point mutation leading to S1898F. These observed mutations may result in a partial or total loss of function of the TET2 protein. It can be anticipated that other defects such as deletions of the TET2 gene might have been missed and thus the estimated the frequency of TET2 defects in these malignancies would be underestimated.

Overall, in 19/55 of the patients with TET2 defects, two different mutations were detected, likely targeting both copies of TET2. This point was confirmed by sequencing individual molecules after subcloning of the PCR fragments obtained from patient MDS42. A single defect was observed in 35/55 samples suggesting that TET2 haploinsufficiency may play a role in these malignancies.

5. TET2 Mutations Target Early Progenitors in MDS

MDS are myeloid malignancies originating from a HSC. If the mutations observed in TET2 are causative, they should also be observed in the HSC. To investigate this, we first analyzed the presence of the TET2 defects in $CD34^+$ cells, which include HSC and hematopoietic progenitors, from 4 MDS patients (MDS03, MDS09, MDS28, MDS35).

The FIG. 3a shows the sequencing histograms of sorted $CD34^+$ cells from patient MDS03 at RAEB1 and RAEB2 phases. Sequences observed in unsorted bone marrow sample and of wild-type control are shown for comparison purposes. Asterisks indicate the mutated nucleotide.

The FIG. 3b shows the PCR-RFLP analysis of DNA isolated from sorted MDS03 $CD34^+CD38^-$ and $CD34^+CD38^+$ cells at RAEB1 phase. Amplified fragments were digested using Tas1 and size-fractionated by agarose migration. The proportion of mutated TET2 mutated was evaluated by measuring the intensities of the mutated (mut) or wild-type (wt) signals relative to that of the signal generated by both alleles (wt+mut). Undigested (−) and digested (+). (ctl) correspond to PCR products from control DNA. MW: molecular weight.

The FIG. 3c shows the PCR-RFLP analysis of TET2 directly performed from sorted $CD34^+CD38^-$ and $CD34^+CD38^+$ cells from MDS09 patient using BseLI endonuclease.

The FIG. 3d shows the genotyping by PCR-RFLP using BseLI of sorted $CD34^+CD38^-$ and $CD34^+CD38^+$ cells from patient MDS09 grown at one cell per well. Annotations are as in b. The histograms represent the fraction of clones with wild-type (gray) or mutated (black) TET2. Note the absence of wild-type fragment in $CD34^+CD38^+$ clones indicated by asterisks.

In all cases, the mutated TET2 sequence could be detected (FIG. 3). In one of these patients (MDS03), $CD34^+$ cells could be analyzed at refractory anemia with excess of blasts 1 (RAEB1) and RAEB2 phases. Interestingly, the wild-type sequence was detected at the RAEB1 phase, but not at the RAEB2 phase (FIG. 3a), suggesting expansion of TET2 mutated progenitors with the disease progression.

We next fractionated the $CD34^+$ from these four patients into $CD34^+CD38^-$ (corresponding to HSC and multipotent progenitors) and $CD34^+CD38^+$ (corresponding to more mature progenitors) cell populations using CD34-PcCy5 and CD38-FITC antibodies (IMMUNOTECH) using a FACSDiva cell sorter (BECTON DICKINSON). In two patients (MDS03 and MDS09), PCR-RFLP analysis was used to distinguish mutated and wild-type TET2 sequences. The mutated TET2 burden increased in both patients from $CD34^+CD38^-$ to $CD34^+CD38^+$ cells (16% to 54% in MDS03, and 26% to 48% in MDS09) (FIG. 3b, c). Further analysis was performed at the cellular level, by seeding single hematopoietic progenitors from MDS09.

Sorted $CD34^+CD38^-$ cells from MDS09 bone marrow were seeded at one cell per well on a confluent layer of the MS5 cell line in MEM alpha medium supplemented with 10% FBS (STEM CELL TECHNOLOGIES), and a cocktail of early cytokines (thrombopoietin (Tpo) interleukin-3 (IL3), FLT3-L, Stem Cell factor (SCF) and interleukin-6 (IL6)). $CD34^+CD38^+$ cells were also seeded at one cell per well using the same combination of "late" cytokines (SCF, 1L3, erythropoietin (Epo) and granulocyte-colony stimulating factor (G-CSF)) as used in methylcellulose cultures (DUPONT et al., abovementioned, 2007). After three weeks ($CD34^+CD38^-$) or 10 days ($CD34^+CD38^+$), individual clones were collected for further genotyping.

The results show that TET2 mutation was identified in 8 out of 32 (25%) and 18 out of 30 (60%) clones derived from $CD34^+CD38^-$ and $CD34^+CD38^+$ cells, respectively (FIG. 3d). Interestingly, the wild-type copy of TET2 was not always amplified from clones bearing a mutated TET2, suggesting its loss in a minority of the cells.

For the two other patients (MDS28, MDS35), the increase in TET2 mutation burden from $CD34^+CD38^-$ to $CD34^-CD38^+$ samples was evaluated with the sequence graphs. To be more accurate, the amplified fragments from MDS28 samples were subcloned and individual bacterial clones were sequenced. The mutated copy was barely detectable in the $CD34^+CD38^-$ population of MDS28 whereas it represented 32% of TET2 sequences in the $CD34^+CD38^+$ population (data not shown). These data indicate that TET2 mutations target a $CD34^+CD38^-$ cell and that in MDS TET2 mutated burden increases from immature to mature progenitors, suggesting a selective advantage of the mutated cells during early phases of hematopoietic differentiation.

In three sAML samples (sAML2, sAML4, sAML5), TET2 mutations were also found in $CD34^+$ cells (data not shown). When analyzed, in sAML4, sAML5 sorted cells, no marked changes in the mutated TET2 burden were observed between $CD34^+C38^-$ and $CD34^+CD38^+$ populations.

6. Prevalence and Prognosis Impact of TET2 Mutations in MDS

So as to establish the prevalence and prognosis impact of TET2 mutations in MDS, we retrospectively analyzed TET 2 mutations and their prognosis value, in 204 MDS and AML post MDS enrolled in GFM multicenter trials (41 RA/RCMD/MDS-U/5q-, 18 RCMD, 28 BARS/RCMD-RS/BARS-T, 43 RAEB1, 32 RAEB2, 44 AML post MDS). TET2 mutations analysis was realized as described previously and the results are presented in table 6.

Table 6 discloses the status of the identified TET2 defect in patients suffering from MDS or AML:

RARS/RARS-T/RCMD-RS, 34.9% in RAEB1, 15.6% in RAEB2, 19% in AML post MDS. Other anomalies of the 4q24 region were found including a deletion in 1/46 pts analyzed by CGH and 3 LOH in 3/22 patients analyzed by SNP arrays and 2 deletions in 5/23 pts analyzed SNP arrays. Thus, the overall prevalence of 4q24 anomalies was 21.6% patients (44/204). 20 patients had two anomalies of TET2

| Disease | Nucleotide change | Consequence |
| --- | --- | --- |
| MDS02 G04 | delA 3166 | p.Gln769 FS |
| MDS 04 | c.4755A > G + c.2490C > T | p.[Lys1299Glu] + [Arg544X] |
| MDS01 A08 | insT 3465 | p.Pro869 FS |
| MDS01 A11 | c.5071 C > T | p.Arg1404 STOP |
| MDS02 C01 | delT 2685 + insA 3009 | p.Ser609 FS + p.His717 FS |
| MDS01 B03 | insA 5540 | p.Tyr1560 FS |
| MDS01 B11 | c.2913 C > T | p.Gln685 STOP |
| sAML1 | | del/wt |
| MDS 07 | | No amplification of 5' Exon 11 |
| MDS01 C08 | delC 6360 | p.Gln1834 FS |
| MDS01 C09 | c.3532C > T + insA 5757 | p.Cys1633 FS + p.Gln891 STOP |
| MDS01 D01 | c.6475T > C | p.Leu1872Pro |
| MDS02 H02 | c.4384A > G + c.4625C > G | p.Ile1175Val + p.Tyr1255 STOP |
| sAML2 | | Ser1898Phe |
| MDS01 D06 | del 2834_2835 | p.His658 FS |
| MDS 10 | | p.Gln530 FS + p.Tyr1724 STOP |
| MDS02 C12 | delT 2685 + c.6316T > G | p.Ser609 FS + p.Leu1819 STOP |
| MDS02 D01 | delC 3009 | p.His717 FS |
| MDS 01 | | del/del |
| MDS 02 | | del/p.Arg581 FS |
| MDS01 E02 | c.5730C > T | del/Gln1624 STOP |
| MDS02 D04 | delT 2944 | p.Leu699 STOP |
| MDS01 E06 | insC 3151 + p.5406C > T | p.Gln764 FS + Arg1516 STOP |
| MDS01 E07 | c.6475T > C + c.6478T > C | p.Leu1872Pro + p.Ile1873Thr |
| MDS01 E08 | delC 2448 + delA 4130 | p.Gln530 FS + p.Lys1090 FS |
| MDS01 F02 | p.6360C > T | p.Gln1834 STOP |
| MDS01 F04 | delG 2994 | p.Glu711 FS |
| MDS02 E01 | c.6114T > G + insT splice site | p.Tyr1751 STOP + mutation of splice site exon 8 |
| MDS01 F06 | p.3688C > T + delA 6507 | p.Gln943 STOP + p.Thr1883 FS |
| MDS01 G01 | delG 4271 + c.6478T > C | p.Glu1137 FS + p.Ile1873Thr |
| MDS01 G03 | p.3688C > T | p.Gln943 STOP |
| nAML2 | c.6478T > C | del/p.Ile1873Thr |
| MDS01 G05 | delC 5222 | p.Leu1457 STOP |
| MDS02 F11 | dupT 3914 | p.Glu1026 STOP |
| MDS01 G06 | delA 2935 + del5828_5843 | p.Glu692 FS + p.Met1656 FS |
| MDS02 A12 | p.4969G > A + del6396_6531 | p.Gly 1370 Glu + p.Val1846 FS |
| MDS01 G7/8 | g.4366-1G > T | mutation of splice acceptor site exon5 |
| MDS02 E10 | insCT 3581 | pGly 908 FS |
| MDS02 H12 | delG 4932 + del5521_5524 | p.Glu1357 FS + pThr1554 FS |
| MDS02 G03 | insC 3151 + insC 6507 | p.Gln764 FS + p.Thr1883 FS |
| MDS02 G01 | delG 5133 + del6511_6512 | p.Asp 1425 FS + p.Pro1885FS |
| MDS02 G07 | p.5253C > T | p.Arg1465 STOP |
| MDS02 C07 | c.4561A > T | p.Glu1234Val |
| MDS02 B07 | c.2109C > T | p.Gln417 STOP |
| nAML1 | c.6547G > T | del/p.Arg1896Met |
| MDS02 E11 | c.2784C > T + p.5253C > T | p.Gln642 STOP + p.Arg1465 STOP |
| MDS01 H05 | c.4515C > T | p.His1219 Tyr |
| MDS02 H06 | del1264_1666 | p.Glu135 FS |
| MDS02 B08 | delA4327 + c.5020A > G | p.Asn1156 FS + Asn 1387Ser |
| MDS02 D10 | insC 3151 + c.4891C > A | p.Gln764 FS + p.Ala1344 Glu |
| MDS02 B02 | delT 5570 + insC splice site | p.Leu1637 FS + mutation of splice site exon 8 |
| MDS01 F01 | insT3995 + c.4059A > T | p.Glu846 FS + p.Arg1067 STOP |
| MDS02 B11 | c.4673C > G + Del6049_6050 | p.Cys1271 Trp + p.Asp1830 FS |
| MDS01 E09 | insG 5119 | p.Leu 1420 FS |
| MDS | c.5430C > T | p.Gln1524STOP |
| MDS | c.5177dupA | p.Arg1440FS |
| MDS | c.5583_5605 del | p.Pro1575FS |
| MDS | c.5310 A > G | p.Lys1197Arg |
| MDS | c.2375C > A | p.Ser792STOP |

We found 59 mutations of the TET2 gene by direct sequencing of exons 3 to 11 (27 frameshifts, 21 nonsense and 11 missense mutations in conserved domains) in 43/204 pts (Table 6). The frequencies according to the WHO subtypes were 21.8% in RA, 5.2% in RCMD, 21.4% in identified by direct sequencing (17 patients), or sequencing plus SNP array (3 patients), indicating that the two copies of the gene were targeted in 43.5% of mutated patients.

Then, univariate and multivariate survival analyses were conducted with Cox hazard proportional model so as to establish the prognosis impact of TET2 mutations. Comparison between the 43 patients with TET2 coding sequence mutations and unmutated patients found no significant differences in initial characteristics for sex, age, previous exposure to chemo or radiotherapy, Hb level, WBC count, ANC, plt count, % bone marrow blasts, multilineage dysplasia, WHO and FAB subtypes, karyotype and IPSS.

The analysis revealed that five-year survival (Kaplan-Meier curve) was significantly increased in TET2 mutated patients compared to unmutated patients ($p<0.05$).

7. Rearrangement of the TET2 Gene in Patients Suffering from MPD with 4q24 Abnormality Detected by SNP or CGH Arrays Analyses Among 35 MPD samples, 4 patients had a LOH by SNP arrays and were analyzed for mutations within TET2 gene on both alleles. In 3 of the 4 samples a clear mutation or deletion was observed.

Table 7 discloses the status of both alleles of the TET2 genes in patients suffering from MPD:

| Patient | Copy 1 | Copy 2 | Disease |
|---------|--------|--------|---------|
| IGR-1 | Q557Stop | LOH | PMF |
| IGR-2 | Deletion 1237-1239 | LOH | PV |
| IGR-3 | whole gene deletion | No abnormality | PV |
| IGR-4 | unknown | LOH | ET |

In table 7, "PMF" stands for Primitive Myelofibrosis, "PV" for polycythemia Vera, "EV" for Essential Thrombocytosis. All these diseases are Class II MPDs.

Patient IGR-2 harbored a 9 base pair in frame deletion lead to the loss of three amino acids, P1237, L1238, S1239. As shown by SNP analyses and by the analyses of the sequence traces, patients IGR-1 and IGR-2 had lost the other TET2 copy. None of the mutations were observed in non-tumoral cells of the patients. These data establish that inactivation TET2 participates to the development of MPD.

Systematic sequencing of TET2 genes in 17 other patients revealed two patients with a stop codon on one allele (IGR17: S354Stop, IGR-18:R1216Stop) and one patient with one nucleotide deletion leading to a frameshift in exon 11.

8. Analysis of the Acquisition of the TET2 Rearrangement

Recent evidence indicate that $JAK2^{V617F}$ may not be the initiating event in some MPDs. Therefore we used MPD samples to evaluate the relative roles of TET2 defects and $JAK2^{V617F}$ mutation in these diseases and to gain insight into the sequence of the acquisition of the mutations. We first analyzed hematopoietic progenitors from five MPD patients with mutations in both genes, like the patient IGR2.

For MPD samples, Immature $CD34^+CD38^-$ cells were seeded at one cell per well for four to six weeks in conditions permitting simultaneous B, NK and granulocytic differentiations (lympho-myeloid differentiation) as described (DUPONT et al., abovementioned, 2007), whereas more mature $CD34^+CD38^+$ cells were grown in erythroid/granulocytic methylcellulose assays. Individual clones were collected for analysis of B, NK, and granulocytic differentiation by flow cytometry, and genotyping. $CD34^+CD38^+$ cells were seeded at 1,500 to 3,000 cells per culture dish in 2% standard methylcellulose supplemented with 37% FBS (STEM CELL TECHNOLOGIES), and a cocktail of cytokines as described (DUPONT et al., abovementioned, 2007)). Individual colonies grown from burst-forming units-erythroid (BFU-E) and colony-forming units-granulocyte/macrophage (CFU-GM) were picked on day 14. The obtained clones were analyzed for the presence of both molecular defects.

The results have shown that in all patients tested, sequence analyses revealed that both TET2 and JAK2 defects were present in clones derived from lympho-myeloid progenitors (data not shown). Interestingly the $JAK2^{V617F}$ mutation was not observed in the absence of TET2 defect whereas TET2 mutation could be observed in the absence of $JAK2^{V617F}$. These results demonstrate that, as in MDS, the TET2 mutation is present in immature progenitors of MPD patients and indicate that TET2 defects precede JAK2 mutation during the evolution of the disease.

To further define the role of the TET2 mutations in the amplification of the malignant clone, we compared the genotype of colonies derived from immature ($CD34^+CD38^-$) progenitors to that of erythroid and granulocytic colonies derived from committed ($CD34^+CD38^+$) progenitors.

The results shown that in three MPD patients (MPD01, MPD04, MPD35), almost all the colonies at different stages of hematopoietic differentiation harbored a TET2 mutation, suggesting that the TET2 mutated clone expanded at early steps of hematopoiesis (data not shown). In 2 other patients (MPD05, MPD20), most immature progenitors were wild-type whereas most committed progenitors were mutated for TET2. Within JAK2 wild-type progenitors from these two patients, we observed an increase in the proportion of clones with TET2 defects from the immature (2/37 and 0/34, respectively) to the committed (10/23 and 9/54, respectively) progenitor stage. Taken together, our results indicate that the selective advantage of the TET2 mutated clone at early differentiation steps is independent of the $JAK2^{V617F}$ mutation.

Overall, these data from MPD samples demonstrate that TET2 defects (i) occur at early steps of hematopoietic differentiation and that (ii) they may precede the occurrence of the $JAK2^{V617F}$ mutation and (iii) they give a selective advantage to the clone as it proceeds to myeloid differentiation.

9. Engraftment and Proliferation of TET2 Mutated Cells In Vivo

We reasoned that loss of function of TET2 could confer a growth advantage to the hematopoietic stem cells. To demonstrate that the TET2 mutations occur in a HSCs with NOD-SCID repopulating capacity, we used a xenotransplantation assay by injecting, into NOD-SCID mice, $CD34^+$ cells isolated from $JAK2^{V617F}$ MPD patients with TET2 mutations.

$CD34^+$ cells (1 to $10 \times 10^5$ cells) from $JAK2^{V617F}$ MPD patients with TET2 mutations were injected intravenously into sub-lethally irradiated (3.5 Gy) NOD-SCID mice, previously treated with 200 µg of anti-CD122 antibody (JAMES et al., Blood, vol. 112(6), p: 2429-36, 2008). Bone marrow was obtained with heparinized syringue from the right femur at 3, 6 and 12 weeks after transplantation and mice were sacrificed at week 15. Human cell engraftment was evaluated by the sum of human leukocytes ($CD45^+$) and erythroid populations ($CD45^-CD36^+$ and $CD45^-CD36^-$ GlycophorinA$^+$), as assessed by flow cytometry. Bone marrow cells were seeded in culture dish and 96-well plates for methylcellulose and long-term culture-initiating cell (LTC-IC) assays, respectively allowing the selective growth of human cells as described in JAMES et al. (abovementioned, 2008). Individual colonies were subsequently picked and genotyped.

We first compared the kinetics of chimerism after transplantation of CD34+ cells from these JAK2$^{V617F}$ MPD patients with TET2 mutations and from three JAK2$^{V617F}$ MPD devoid of TET2 defects (MPD09, MPD11, MPD27).

The FIG. 4a shows the percentage of human CD45-positive cells in mouse bone marrow monitored at 3, 6, 12, and 15 weeks post-transplant. MPD01 and MPD04 are patients with TET2 defects whereas MPD09 MPD11, and MPD27 are control patients devoid of identified TET2 defect.

The FIG. 4b shows the flow cytometric analysis of human cells present in NOD-SCID bone marrow 15 weeks after transplantation with 3×10$^5$ CD34+ cells from patients MPD04 and MPD09. The percentages of human CD45 (hCD45)-positive myeloid and lymphoid cells were determined using anti-CD45-PC7, anti-CD33-APC, and anti-CD 19-PE antibodies.

The results show that human cells from the three patients devoid of TET2 mutation disappeared with time (FIG. 4a).

In contrast, the percentage of human cells in the bone marrow of mice engrafted with cells from the two TET2 mutated patients increased with time (FIG. 4a). In these mice, differentiation was skewed toward myeloid progenitor expansion, at the expense of lymphoid progenitors, as judged from CD33 and CD19 antigen flow cytometry analyses (FIG. 4b) unlike what is observed with normal HSCs wherein lymphoid differentiation is favored (ROBERT-RICHARD et al., *Haematologica*, vol. 17(3), p: 637-41, 2003).

Human cells present in the mouse bone marrow 15 weeks after transplantation (W15) were tested in in vitro progenitor and LTC-IC assays, and analyzed for the presence of TET2 and JAK2 mutations. The TET2 defects were found in pooled W15 CFU-derived colonies from both MPD01 and MPD04 samples, and in all individual human LTC-IC and progenitors present in the mice (data not shown). The results were compared with progenitor assays performed immediately before engraftment (D0). All colonies arising from patients' committed progenitor cells (D0 CFU) harbored TET2 mutation.

These results demonstrate that TET2 mutation occurs in a HSC. Interestingly, the results have further shown that the proportion of progenitor cells carrying only the TET2 mutation increased upon transplantation at the expense of cells carrying both TET2 and JAK2$^{V617F}$ mutations. These cells are thought to reflect the original HSC population. Therefore, these observations indicate that TET2 mutated HSCs with a wild-type JAK2 are more numerous than the TET2/JAK2 double mutant HSCs, further establishing the mutation of TET2 as a "pre-JAK2$^{V617F}$" event in these patients.

Therefore our data are compatible with the hypothesis that TET2 defects endow the HSC with a selective engraftment advantage independently of JAK2$^{V617F}$.

10. Positions of the Identified Mutations on the TET2 Gene

We report that the inactivation of TET2 is a common early event in human MDS, MPD and sAML and that the frequencies of TET2 mutation in unselected patient series were 15/81=18.5% in MDS, 2/9=22% in CMML, 24/198=12% in MPD and 5/21=24% in sAML. It must be noticed that in these analyses we did not consider amino acid changes occurring outside of the conserved domains. Sequencing of the TET2 gene using the couples of primers identified in table 1 permits to identify a number of mutations in the TET2 gene (FIG. 5).

The FIG. 5 shows the locations of some of the identified mutations of the TET2 gene distributed along the protein sequence.

Mapping of the identified TET2 mutations on the TET2 sequence suggest an essential role for the carboxy terminal conserved region (amino acids in position 1860 to the position 1950) in the function of the protein.

Finally, the detection of acquired genetic defects targeting the two TET2 copies in 19 of the 55 patients with TET2 alteration establishes this gene as a bona fide tumor suppressor gene of human myeloid malignancies. TET2 defects are observed in both MDS and MPD, which are two distinct myeloid diseases. It is therefore likely that their characteristic clinical and biological phenotypes require at least another additional cooperating event. In MPD samples with both TET2 and JAK2 mutations, TET2 mutations likely occur first in the natural history of the disease, preceding the occurrence of JAK2$^{V617F}$ mutation.

11. Identification of TET2 Gene Mutations in Familial MPD

Families with at least 2 affected patients with MPD were collected through a national network as previously described (BELANNE-CHANTELOT et al., abovementioned, 2006). The diagnoses of MPD were reviewed based on the 2008 World Health Organization criteria. 1 All participants gave their written informed consent.

In a first step, we analyzed 15 probands of families compatible with an autosomal dominant inheritance, in search for a constitutional event that would account for these familial cases. Elected probands mostly suffered from PV or ET. In a second step, the analysis was extended to patients with hematological complications and to relatives of patients with TET2 variants.

Altogether, we analyzed 61 patients for mutations in the 6009 by coding sequence of the TET2 gene from 42 MPD families (40 European, 2 African: families F3 and F4) including at least two available affected patients with MPDs. Thirty-four patients displayed a simple phenotype consisting of either PV (15), ET (12) or PMF (7) with no observed hematological evolution of the disease after a follow-up period of 12 years. Twenty-seven other patients had experienced an evolution in their MPD phenotype: PV evolving into myelofibrosis (post PV MF, 5) or into AML (12); ET evolving into MF (4) or AML (5), or PMF turning into AML (1).

The analysis was performed by polymerase chain reaction (PCR) on genomic DNA extracted from buccal swabs after heating at 95° C. for 10 minutes to release genomic DNA. Purified PCR products were sequenced using the BIGDYE TERMINATOR chemistry (APPLIED BIOSYSTEMS) and run on an APPLIED BIOSYSTEMS 3100 capillary sequencer.

The JAK2V617F mutational status was determined as previously reported in BELANNE-CHANTELOT et al. (abovementioned, 2006).

The whole coding region of the TET2 gene was sequenced as described previously. Two multiplex PCRs were set up to estimate the copy number of each TET2 exon using the quantitative multiplex PCR of short fluorescent fragments (QMPSF) method (CHARBONNIER et al., *Cancer Res.*, vol. 60, p: 2760-2763, 2000). Two additional primer pairs amplifying short sequences of either the F9 or the DSCR1 gene were used as internal controls. PCR products were separated by capillary electrophoresis using a DNA genetic analyzer (ABI 3100). The analysis is based on the comparison of the peak heights generated from the tested DNA sample and the control DNA. The quantitative estimation of the height of peaks was determined using commercially available analysis software (GENEMAPPER VERSION 4.0, APPLIED BIOSYSTEMS).

Table 8 shows the TET2 mutations identified in 12 MPD patients.

| Patients | Phenotype | Evolution | JAK2 | TET2 Location | Nucleotide change | Proteic change |
|---|---|---|---|---|---|---|
| P1 (F1) | PV | MF | 95 | Exon 11 | c.5695delC | p.Leu1899fs |
| P2 (F2) | PV | MF | 63 | Intron 7 | c.3954 + 2T > A | p.? |
| P3 (F2) | PV | | 49-82 | Exon 3 | c.3138delT | pLeu1046fs |
| P4 (F3) | ET | PV > MF > AML | 23-47 | Exon 3 | c.1648C > T | p.Arg550X |
| | | | | Exon 3 | c.2570delA | p.Asn857fs |
| P5 (F3) | ET | MF > AML | 0 | Exon 3 | C2058A > T | p.Arg686Ser |
| P6 (F4) | ET | AML | 0 | Exon 3 | C1955delA | p.Gln652fs |
| | | | | Exon 3 | c.2490dupA | p.Gln831fs |
| P7 (F4) | ET | | 39 | Intron 4 | c.3500 + 3A > C | p.? |
| P8 | ET | MF | 90 | All exons | c.1.4999_5014del16 | p.0 |
| P9 | PMF | | 36 | Exon 3 | c.694C < T | p.Gln574X |
| | | | | Exon 11 | | p.Leu1667fs |
| P10 | PMF | | 33 | Exon 3 | c.4019T < C | p.Gln232X |
| P11 | PMF | | 66 | Exon 8 | c.5603A < G | p.Leu1340Pro |
| P12 | PV | MF | 78-96 | Exon 11 | | p.His1868Arg |

Patients were initially diagnosed with the phenotype indicated in the second column and subsequently had a hematological evolution shown in the third column. When measured in several samples, the JAK2V617F allele burden is indicated as a range.

The FIG. 6 is a schematic representation of the TET2 gene and protein showing the mutations identified in this study. Hatched boxes indicate exons. Truncating mutations are depicted as stars, missense mutations as inverted triangles. Conserved functional domains are depicted as boxes on the protein scheme. fs: frameshift.

Following this analysis, we identified a complete deletion of TET2 in one patient and a total of 39 point variants. Examination of these variants showed that 15 of them, identified in 12 patients, were deleterious heterozygous mutations. They were distributed as one deletion of the entire gene, 11 truncating (3 nonsense mutations, 6 out-of-frame insertions/deletions and 2 splice site mutations) and 3 missense mutations (FIG. 6, Table 8).

Furthermore, all three missense mutations were absent from 165 control individuals of ethnically matched populations, thus confirming their deleterious effect. Two, p.Leu1340Pro and p.His1868Arg, were located in the highly conserved TET2 functional domains (1134-1444 and 1842-1921). Truncating mutations seemed to be randomly distributed along the coding sequence (FIG. 6).

In patients P4, P6 and P9 two TET2 mutations were identified. For the former, multiple allele specific amplifications of the two mutations located in exon 3 showed that these two molecular events occurred on different alleles leading to the biallelic inactivation of TET2 (data not shown). The observation of such a biallelic inactivation of TET2 in these patients meets the criteria of the classical two-hit recessive model of carcinogenesis and supports the hypothesis that TET2 acts as a tumor suppressor gene.

Twenty-five other variants identified on the coding sequence of TET2 and the short nearby intronic regions were polymorphisms. Seven were substitutions in non-coding regions (intronic or 3'UTR), one was a variation in an intronic short tandem repeat, 4 were silent variations in the coding sequence and 13 were missense polymorphisms. They were all classified as polymorphisms on the basis of their presence in public databases, the fact that they were found in asymptomatic family members, or their identification in control populations. It is of interest to note that none of the missense polymorphisms were located in either one of the functional domains.

12. TET2 Mutations were Sequentially Acquired in a Patient with Two Mutations

Seven blood samples were available for patient P4 from family F3, throughout the last three steps of her evolution: PV, MF and AML. Sequencing these samples allowed us to determine the temporality of the clinical and molecular events.

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding henotype for each sample (white: ET; grey: PV; hatched: post-ET MF; black: AML).

The results show that JAK2V617F and the TET2 p.Arg550X mutation were already present in the first sample, when the patient suffered from PV. The second mutation, p.Asn857fs was detectable in the second sample, 7 years later and 5 months before the diagnosis of MF. This sequential analysis has shown that the burden of each of these mutations grew in time, concomitantly with the development of the disease.

Finally, TET2 mutations were found in similar proportions in JAK2V617F positive and negative patients suggesting that molecular events in both genes may arise independently of each other.

13. TET2 Molecular Events were Mainly Observed in Patients with PMF or Patients with PV or ET Who Secondarily Evolved Towards a Hematological Transformation Altogether, 12 patients were found carrying at least one TET2 mutation. They account for 20% of all MPD patients tested.

The FIG. 8 shows the schematic representation of the clinical status of these twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

This analysis shows that these TET2 defects were identified in patients diagnosed with the three main MPD phenotypes: PV (4/32), ET (5/21) and PMF (3/8). No TET2 mutation was observed in relatives with rare hematological phenotypes, including de novo AML and systemic mastocytosis (data not shown). All patients with a TET2 defect but two were positive for the JAK2V617F mutation. The allele burden varied from 33 to 95% (Table 6). The negative cases were ET patients who developed very active AML and died rapidly (P5 and P6, data not shown). We should note that the two patients, P3 and P7, who had not developed post-PV or post-ET MF at the time of examination, were characterized by a high level of JAK2V617F allele burden (82 and 39% respectively, Table 6).

Altogether, our results established that 20% of the JAK2V617F positive patients were found mutated for TET2 (10/49) vs. 17% among the JAK2V617F negative patients (2/12).

All patients carrying a TET2 mutation but two had either a myelofibrosis that occurred at onset or was acquired secondarily after PV or ET, or a secondary AML. Hence 29% (10/34) of patients with PMF or hematological complication after PV or ET were found mutated in TET2 compared to 7.4% (2/27) of patients without any diagnosed haematological complications after a mean time of disease duration of 12 years. Both patients with TET2 mutations and presenting PV or ET without hematological transformations had nevertheless an active course of the disease.

No correlation can be done between the clinical presentation, the hematological data or even the course of the disease in patients and the type and location of mutations or between patients with a single heterozygous TET2 mutation and patients with two. As shown on FIG. 8, TET2 mutations were found at different times in the evolution of the disease for each patient from the time of diagnosis (P9) to 20 years later (P8); the time to progression was also variable [1-16 years].

14. TET2 Mutations were Present in Early Hematopoietic Progenitors and were Acquired Independently from JAK2V617F Three patients were available for analysis of their progenitor cells, patient P4 from family F3 and patients P2 and P3 from F2. Blood progenitor cells were available for the former at two different steps of her disease during the PV stage and the blast phase after MF.

The FIG. 9 disclosed TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

The results show that eight years after diagnosis, during the PV stage, endogenous erythroid colonies already carried the p.Arg550X mutation (5/29) but p.Asn857fs was never observed (0/29, FIG. 9).

Nine years later, after leukemic transformation, all genotyped Burst forming unit-erythroid (BFU-E) and all colony forming unit-granulocyte macrophage (CFU-GM), but 2, carried JAK2V617F and both TET2 mutations (FIG. 9). The progenitor analysis therefore confirmed the temporality of these events: in patient P4, p.Arg550X was first acquired in the earliest stages of the disease; and the latest stages were characterized by the presence of both p.Arg550X and p.Asn857fs. Interestingly, two CFU-GM carried both TET2 mutations in the absence of JAK2V617F. For patient P2, colonies were found with either both JAK2 and TET2 mutations, the sole JAK2V617F or none (FIG. 9). This was an indication that for this patient the TET2 mutation occurred in clones already mutated for JAK2. All BFU-E and CFU-GM from patient P3 diagnosed with PV carried both JAK2 and TET2 mutations and did not allow concluding on the temporality of JAK2 and TET2 events.

15. TET2 Molecular Events were Mainly Observed in Patients with CMML

The nature and frequency of somatic mutations in TET2 was also studied in bone-marrow or peripheral blood collected from 88 patients with CMML1 (n=70) or CMML2 (n=18) according to the WHO criteria and 14 acute blastic transformation of a previously identified CMML. Patients signed their informed consent according to current ethical regulations. Patients with CMML in chronic phase were newly diagnosed (n=43) or known for hematopoietic disease and followed up every 3 months for therapeutic abstention, supportive cares or cytotoxic treatment, in most cases with Hydroxyurea (n=45).

Blood and bone-marrow samples were collected on EDTA and mononuclear cells were selected by Fycoll Hypaque. DNA was extracted using commercial kits (QIAGEN). Polymerase chain reaction (PCR) and direct sequencing reaction were performed using standard conditions with gene-specific primers designed to amplify coding sequences spanning from exon 3 to exon 11 of TET2 gene as described previously. For each PCR reaction, 20 ng of genomic DNA was used for PCR amplification followed by magnetic bead purification and bidirectional sequencing using ABI 3300 capillary sequencers (AGENCOURT BIOSCIENCE). Mutation Surveyor (SOFTGENETICS) was used to detect nonsense and missense mutations located in conserved regions spanning from 1134-1444 and 1842-1921 and sequences were reviewed manually to detect frameshift mutations. TET2 abnormalities were numbered according to FM 992369 EMBL nucleotide sequence database.

The mutations identified in TET2 are listed in table 10.

TABLE 10

| Patient | WHO | Nucleotide change in TET2 | Exon | Consequence |
|---|---|---|---|---|
| 2 | CMML1 | c.4453G > A | 5 | W1198STOP |
| 4 | CMML1 | c.5214C > T; Ins 5537 (A) | 10 & 11 | R1452 STOP; |

TABLE 10-continued

| Patient | WHO | Nucleotide change in TET2 | Exon | Consequence |
|---|---|---|---|---|
| | | | | Y1560FS |
| 5 | CMML1 | c.4942G > A | 9 | G1361S |
| 15 | CMML1 | c.4500C > A; Del 5118__21 (TTAT) | 6 & 10 | R1214W; L1420FS |
| 18 | CMML1 | delT 4172; c.5011A > T | 3 & 9 | F1104FS, D1384V |
| 19 | CMML1 | del 5362__5365; c.6441G > A | 10 & 11 | G1501FS; G1860R |
| 20 | CMML1 | c.2631C > T | 3 | Q591 STOP |
| 21 | CMML1 | Del 6507 (A) | 11 | T1883FS |
| 22 | CMML1 | c.2961C > T | 3 | Q701 STOP |
| 23 | CMML1 | c.1818G > T; c.4936G > A | 3 & 9 | E320 STOP; R1359H |
| 24 | CMML1 | c.4515C > T | 6 | H1219Y |
| 25 | CMML1 | c.4663n + 1 G > A; Del 6424__33 | 6 & 11 | Mutation splice donor site exon 6 + L1855FS |
| 26 | CMML1 | ins 2468__9 (AA) | 3 | K536FS |
| 28 | CMML1 | c.1272C > A; c.4814n − 1 G > A | 3 & 8 | Q138 STOP, Mutation splice receptor site exon 8 |
| 31 | CMML1 | Ins 3151 (C); c.4390T > G | 3 & 5 | Q764FS; I1175S |
| 32 | CMML1 | c.3675C > T | 3 | Q939 STOP |
| 35 | CMML1 | delG 4754; dup 6569__6573 (GAGA) | 7 & 11 | K1298FS; M1570FS |
| 39 | CMML1 | delA 3874; del 4830__31 (TC) | 3 & 8 | K1008FS; S1324FS |
| 40 | CMML1 | c.2208A > T; del 4347 (A) | 3 & 4 | K450 STOP; I1163FS |
| 41 | CMML1 | c.6478T > C | 11 | I1873T |
| 42 | CMML1 | ins 1921 (A); ins 2703 (G) | 3 & 3 | S354FS; L615FS |
| 44 | CMML1 | ins 3995 (T); c.4059 A > T | 3 & 3 | E846FS; R1067 STOP |
| 17 | CMML2 | c.2814C > T | 3 | Q652 STOP |
| 30 | CMML2 | Ins 4293 (A); c.6510A > G | 4 & 11 | G1145FS; T1884A |
| 34 | CMML2 | delT 4277; c.6598G > T | 4 & 11 | I1139FS; G1913V |
| 38 | CMML2 | c.4936G > C | 9 | R1359S |
| 14 | TA | c.3235C > A | 3 | S792 STOP |
| 29 | TA | c.2490C > T; Del 5334 (G) | 3 & 10 | R544 STOP; E1492FS |
| 1 | CMML1 | c.5043n − 1G > A; Dup 6575__6579 (GAGCA) | 10 & 11 | Mutation splice receptor site exon ex10; M1907FS |
| 7 | CMML1 | c.4439T > G | 5 | C1193W |
| 8 | CMML1 | c.4726G > T | 7 | C1289F |
| 9 | CMML1 | c.5100C > T | 10 | Q1414 STOP |
| 11 | CMML1 | Del 6023 (G) | 11 | L1721FS |
| 12 | CMML1 | Del 1921 (C) | 3 | S354 STOP |
| 16 | CMML1 | c.4827G > T; Ins 5178 (A) | 8 & 10 | E1323 STOP; R1440FS |
| 27 | CMML1 | insG 2703; ins 5125__26 (AA) | 3 & 10 | L615FS; K1422FS |
| 33 | CMML1 | Ins of 2950__85 (dup) | 3 | L718FS |
| 36 | CMML1 | c.4638G > A; c.4825T > C | 5 & 8 | C1193Y; L1322P |
| 37 | CMML1 | c.6414C > T; c.6496A > C | 11 & 11 | Q1852 STOP; E1879A |
| 43 | CMML1 | del 3859 (A) | 3 | N1000FS |
| 46 | CMML1 | del 1264__66 (AAA) | 3 | E135FS |
| 3 | CMML2 | c.4431C > T | 5 | Q1191 STOP |
| 6 | CMML2 | c.5070C > T | 10 | R1404 STOP |
| 10 | CMML2 | Del 2655__2658 (CAAA) | 5 | N598FS |
| 13 | CMML2 | Ins 5602__5606 (TCCAA) | 11 | S1582FS |
| 45 | CMML2 | c.2784 C > T; c.5253 C > T | 3 & 10 | Q642 STOP; R1465 STOP |

The results revealed that a mutated status of TET2 gene was detected in 44 out of the 88 (50%) patients. Among the 43 patients studied at diagnostic, a mutated status of TET2 gene was identified in 18 cases (42%). Such a mutated status was identified in 26 of the 45 patients (58%) studies along the course of the disease. These results thus suggest that TET2 mutation prevalence is higher in CMML than in any other studied myeloid disease.

Moreover, it must be noticed that two distinct mutations in TET2 sequence, suggesting a bi-allelic alteration of the gene, were identified in 18 out of the 44 (40%) mutated patients with a chronic phase CMML, including 5 out of the 18 (27%) patients whose mutations was identified at diagnosis, and 13 out of the 26 (50%) mutated patients studied along the course of the disease. Altogether, 69 mutations in TET2 were identified, including 33 frameshift mutations, 19 nonsense mutations, 14 missense mutations and 3 mutations in a splice site. These mutations most frequently involved exon 3 (22 events), exon 10 (9 events) and exon 11(10 events).

An analysis of overall survival was performed in 40 of the 43 patients whose TET2 status was determined at diagnosis with an at least two months follow-up and indicated a lower 1-year overall survival in patients with the 16 patients of this cohort with TET2 mutation, but the difference did not reach significance. When overall survival analysis was limited to the 29 patients with a CMML1 according to the WHO classification and an at least two months follow-up, the difference was then significant (p<0.01). None of the other tested parameters includes age, sex and FAB classification did affect survival. Finally, the results established that TET2 mutation was associated in the 29 patients with CMML1 with a trend to significantly lower survival.

16. Alteration of the TET2 Gene in Patients Suffering from Lymphoid Cancer

CGH analyses of 157 patients suffering from B-cell lymphoma showed the loss of a whole chromosome 4 in 2 cases, a partial deletion of chromosome 4q sequences deleting the TET2 gene in 4 cases and loss of the upstream side of TET2 associated with duplication of the downstream side of TET2 in one case. These rearrangements were found in diffuse large B-cell lymphomas (107 cases), whereas no rearrangement could be found in follicular lymphomas (50 cases).

We have analyzed 93 patients for variation within the coding sequence of TET2. They were 33 T cell lymphoma and 60 B cell lymphoma.

14 mutations were observed in 10 samples from T-cell lymphomas, including 10 frame shifts and 2 non-sense and 2 missense mutations.

Table 9 shows the TET2 mutations identified in 10 T-cell lymphomas patients.

| disease | Nucleotide changes | Amino acid consequences |
|---|---|---|
| T-lymphoma | c.3215delT | p.Phe785FS |
| T-lymphoma | c.[1893_1896delAAGC] + [4527delG] | p.[Lys345FS] + [Ala1223FS] |
| T-lymphoma | c.[2505delA] + [2524delC] | p.[Thr549FS] + [Pro555FS] |
| T-lymphoma | c.6564C > T | p.Tyr1902 |
| T-lymphoma | c.6745C > T | p.Pro1962Leu |
| T-lymphoma | c.5523_5524insA | p.Glu1555fs |
| T-lymphoma | c.[3131_3137delCCAGACT] + [5109G > T] | p.[Leu757FS] + [Val1417Phe] |
| T-lymphoma | c.[3747C > T] + [5331A > T] | p.[Gln963STOP] + [Lys1491STOP] |
| T-lymphoma | c.3756_3757del CA | p.Gln966 FS |
| T-lymphoma (LAI) | c.1642delC | p.Ser261 FS |

Thus, these results established that the frequencies of TET2 mutation in patients suffering from T-cell lymphoid tumour is 30%.

The invention claimed is:

1. A method for detecting a mutated TET2 gene comprising:
   (i) obtaining a blood or bone marrow sample of a subject having a myeloid tumour or a lymphoid tumour; and
   (ii) detecting that Hematopoietic Stem Cells (HSC) or CD34+/CD38− progenitor cells in said blood or bone marrow sample have a missense mutation S1898F, H1868R, G1869W, or L1872P or a frameshift at Q1834 or L1889 (numbering of SEQ ID NO: 2) by:
   a. sequencing a region of the nucleic acid contained in said cells, wherein the region encodes S1898F H1868R, G1869W, or L1872P or a frameshift at Q1834 or L1889, or
   b. hybridizing the nucleic acid contained in said cells with at least one probe or primer comprising at least 10 consecutive nucleotides of the region encoding S1898F, H1868R, G1869W, or L1872P or a frameshift at Q1834 or L1889.

2. The method according to claim 1, wherein said tumour is a myeloid tumour selected from the group consisting of myelodysplastic syndrome (MDS), acute myeloid leukemia (AML), myeloproliferative disease (MPD) and myelodysplatic/myeloproliferative syndrome.

3. The method according to claim 1, wherein said myeloid tumour is a myelodysplatic/myeloproliferative syndrome.

4. The method according to claim 1, wherein said tumour is a lymphoid tumour selected from the group consisting of lymphoma.

5. The method according to claim 1, wherein said subject is suffering from polycythemia vera (PV) or from thrombocythemia (ET).

6. The method according to claim 1, wherein said subject is suffering from myelodysplastic syndrome (MDS).

7. The method according to claim 1, wherein said subject is a mammal.

8. The method according to claim 1, wherein said mutation is detected on both alleles of the mutated TET2 gene.

9. The method of claim 1, wherein mutation induces absence of expression or under-expression of TET2 polypeptide.

10. The method according to claim 1, wherein the detecting step al comprises using a kit comprising at least one nucleic acid probe or oligonucleotide or at least one antibody.

11. The method according to claim 10, wherein said oligonucleotide is at least one PCR primer, which allows amplifying a region of the TET2 gene.

12. The method according to claim 1, further comprising the step of administering to said subject a therapeutically efficient amount of hypomethylating agent after the detecting step.

13. The method according to claim 1, wherein said at least one primer is one of SEQ ID NO:5 to SEQ ID NO:38.

* * * * *

SEQUENCE LISTING

```
<160> NUMBER OF SEQ ID NOS: 39

<210> SEQ ID NO 1
<211> LENGTH: 132428
<212> TYPE: DNA
<213> ORGANISM: Homo sapiens
<220> FEATURE:
<221> NAME/KEY: Intron
<222> LOCATION: (1)..(100)
<220> FEATURE:
<221> NAME/KEY: exon
<222> LOCATION: (101)..(787)
<220> FEATURE:
<221> NAME/KEY: Intron
<222> LOCATION: (788)..(44167)
<220> FEATURE:
<221> NAME/KEY: exon
```

```
<222> LOCATION: (44168)..(44294)
<220> FEATURE:
<221> NAME/KEY: Intron
<222> LOCATION: (44295)..(87704)
<220> FEATURE:
<221> NAME/KEY: exon
<222> LOCATION: (87705)..(91159)
<220> FEATURE:
<221> NAME/KEY: Intron
<222> LOCATION: (91160)..(95146)
<220> FEATURE:
<221> NAME/KEY: exon
<222> LOCATION: (95147)..(95237)
<220> FEATURE:
<221> NAME/KEY: Intron
<222> LOCATION: (95238)..(96641)
<220> FEATURE:
<221> NAME/KEY: exon
<222> LOCATION: (96642)..(96735)
<220> FEATURE:
<221> NAME/KEY: Intron
<222> LOCATION: (96736)..(97377)
<220> FEATURE:
<221> NAME/KEY: exon
<222> LOCATION: (97378)..(97586)
<220> FEATURE:
<221> NAME/KEY: Intron
<222> LOCATION: (97587)..(113426)
<220> FEATURE:
<221> NAME/KEY: exon
<222> LOCATION: (113427)..(113577)
<220> FEATURE:
<221> NAME/KEY: Intron
<222> LOCATION: (113578)..(115566)
<220> FEATURE:
<221> NAME/KEY: exon
<222> LOCATION: (115567)..(115656)
<220> FEATURE:
<221> NAME/KEY: Intron
<222> LOCATION: (115657)..(123417)
<220> FEATURE:
<221> NAME/KEY: exon
<222> LOCATION: (123418)..(123555)
<220> FEATURE:
<221> NAME/KEY: Intron
<222> LOCATION: (123556)..(126371)
<220> FEATURE:
<221> NAME/KEY: exon
<222> LOCATION: (126372)..(126726)
<220> FEATURE:
<221> NAME/KEY: Intron
<222> LOCATION: (126727)..(128855)
<220> FEATURE:
<221> NAME/KEY: exon
<222> LOCATION: (128856)..(132328)
<220> FEATURE:
<221> NAME/KEY: Intron
<222> LOCATION: (132329)..(132428)

<400> SEQUENCE: 1 gcgcggggc gtgtgcgcgg gacctcgaag tggtggtgga gtgcagacca gcaaaaagtt    60
tcaaagggaa atcttagatg tcacgtctt gtccaggcac ccgtgccatc ccaacctccc   120
acctcgcccc caaccttcgc gcttgctctg cttcttctcc caggggtgga gacccgccga   180
ggtccccggg gttcccgagg gctgcaccct tccccgcgct cgccagccct ggcccctact   240
ccgcgctggt ccgggcgcac cactcccccc gcgccactgc acggcgtgag ggcagcccag   300
gtctccactg cgcgccccgc tgtacggccc caggtgccgc cggcctttgt gctggacgcc   360
cggtgcgggg ggctaattcc ctgggagccg gggctgaggg ccccagggcg gcggcgcagg   420
ccggggcgga gcgggaggag gccggggcgg agcaggagga ggcccgggcg gaggaggaga   480
gccggcggta gcggcagtgg cagcggcgag agcttgggcg gccgccgccg cctcctcgcg   540
```

```
agcgccgcgc gcccgggtcc cgctcgcatg caagtcacgt ccgcccccctc ggcgcggccg      600
ccccgagacg ccggcccgc tgagtgatga aacagacgct caaactgcct tatgaatatt       660
gatgcggagg ctaggctgct tcgtagaga agcagaagga agcaagatgg ctgccctttta      720
ggatttgtta aaaggagac ccgactgcaa ctgctggatt gctgcaaggc tgagggacga      780
gaacgaggtc agagcgcttc tcttatgccg cgaaactctc cctttcttct cccttcgct      840
ttttctcggg cttccaggga ctggggagca aaccctgtag tgtcacccac aaataccaag     900
agggaagagg gaagcttcac aaattactgg agcctcttca acatggctga caaatatagt     960
tttaattccc tctacccctt ttaaacctgt agttctgtgt tctcttctct cctcctaatg    1020
ctcgtcccct catctcccag aaaacttacc tttgtgcctc cgacgagccg gtttcccggc    1080
cttttttaat cctcagaaaa gtgatttta aatttgcttt cctttctaaa atagttcagc     1140
tttgggggca ctacttttcc ctttaatcct cttccctgt ttctttcgtg taagtgaaac     1200
gagtctcccg tttatcctga caacctcag agagaacact gatagggtgt ttttcgaccc    1260
ttttatcagc tgtagggtct gggtctgggt ttgtgtctgc ctcctcctac cttcttatcc    1320
ccctttaggg ggctgtacga agtgaatgtc acagggagtg gaattggagt acactgagtg    1380
ggttttttt ttccttaagt ccgcgcgttt tgttagcggc gctgagtgaa agaggaaaga    1440
atagtttctc tggttcccca aacaagacca gaactcactt ttctcaaggt acataagtca    1500
gcgctgggct gagccttcca gcctggggaa tgtatgtaag agaatttatg gacaaatctg    1560
tgtcccggct ttgtgcttct cccgaatcag cttcgtttgg ttccttggta agtgacaggc    1620
agacacaaag gcaggcgcag gcccggggag ggggcgggag gggtggggga gcgcagcgtt    1680
ggagttgcaa gactgcaagg tcaggggcgc ctaaagaaat gaaacccaat cccagcaaag    1740
aagtgaagag cagatttata acagtcccat ccaaatttct ctttggcttc tctctttggt    1800
ctttcatctc tctgcctttc tctctgtgtc tcctctctac tctttcttct ctctctctca    1860
tacacataca cacacacaca cacacacaca cctcactcgc atcttgctga atctttcac    1920
tgggactgct tgtctagttt tattaagcta ataggtttg tatggagagt tttctaccta    1980
tgacataatg aagtgtggcc tggatagact cctggaaagg ccgaaaatga aatataagtg    2040
ttatttgctg gttattcccc tcatgatata cttttaatta cattgaggga gttctcccctt    2100
cttcatctaa tgtttaagaa ttgagaaaag gcttattttc cagcggtaaa atttagtgca    2160
taaaatttag tgaaatattt atatatttac gtgtctaggg agtggaatac attcatgaat    2220
ttaatatctc aaatcacaca ttgtgctttt tcccccttcag tcaggagtta taatgggaaa    2280
cccaaattca aagatattca tcaacaaatg atccatcata ggaataagat tgtatcttaa    2340
gggaagttgg gattcacaga gaaaagacat tggtttggtt tggtgtgata ctgtgggtat    2400
tgttgcctgg ctaatgaaat cattacattt gcatttaat ggaaagttga aatactaagg    2460
ggagttatgt tcttttacat gtttgtatgt gtgcttaata atgtttggaa tagaatataa    2520
atttaaacac aataaatatt gatttttta aatgttaata agcagagaac ggttaatgaa    2580
gtgttggata atcaaactga agtttagaag acaatttata ggattaaaaa atggatagaa    2640
ggaaaaacac aataatagat atttctccat aagtcgaatt tccaaaacta tttgtcctcg    2700
atagttcact ttgtaacttt ctattttgat ctttgttaat ttaatgtagt ttgctttaat    2760
cattgatacg tggggttctt tcacatgatt acaagggaga agcattactc atctctgtgg    2820
aatagaaacg gttcattggt tagttcttat ttgccctaaa attaaaacaa aaattaggat    2880
tttaccatta atgctgttca tggtaaacta tcgagaaaac tatggttaat tattccagca    2940
```

```
attcagaatt aaaaacaatt ccttttgcta acaaactaat atttacttttt tggggacaac    3000 ttttcaaatg ttgtggtata tactgtcttc aggctactca actaataata gatacaacat    3060
tttccactca ataaataaga ataactacat tggttaataa ttttgaatac aactatgaag    3120
gcttgttttt tcctgtcatc aaatttagat tcttgttatt ttgtgcatcc tacttttata    3180
ctgaaaatag ctgctaatta atactgtata aagtatttca gtgattataa ggaagagatg    3240
tgtatgttag tcactttatc ctttgttgga aaagagaaat tattttaata agtatggggt    3300
agtttacaat aaaagacata acctcagttc tttctttacc atatatgtga tcatactacc    3360
taggtgctcc aaaaattcca taggactgtc ttgggttatt gaattttagg aacatgataa    3420
tggacaataa caagatagat agcttttctt aactatgaca ttgttttgct tatttttctta   3480 ttgaactaat catcaatgag aaattaagtt gcagtgagag aaatcccttg ctttgtttaa    3540
attgtcatat ttgccaaact cttcttaagg ctttaattag gtctgatgtg ccagtttatg    3600
ccagaagccg gaggaattga tatgattttg aggcagtggc acatggtcct actagacatt    3660
ggcaagtgaa tatcacttcc agaacaagtg aagtgcacct gccaaggagt tgttatgaaa    3720
gaattccaaa gtccttattg ggcactggtc ttgtattagg taacaacaac tggagttaat    3780
gttttagttt cacttgttga agttaaaagt tccctatcaa ttcttctaag actccacccc    3840
caaacaatgt tgtaagtcaa atgtcactat tgaaatgtat ttccttaatt actgacctca    3900
ttaagaagcc cttcttatga ttcataggca cacctcacag aaactctatt ttccatcctg    3960
cccaaagtct gagtaggtaa attcttatga attcttatga aattaccttg aaataaaata    4020
tcttcaaaag ttacggatgc tagacattgt ataatgtcaa tatttttagaa tatctaatat   4080 ttagaaaatc ttagatctac ttttttatgct ttaattgctt ctaatgcaag ttaaattgtt   4140
tttgttgtta ttgtttttaat agaatttcat agtcttatct agcaatttca aatcgctgga  4200
aagagtcatc tttgttatat aaataaccat gtagactgtt ttaatgttat tgtttcctac   4260
cttgggaaca ggctaaaact ttggaccagc tgtcagtatt tgttcatcag aataacactt   4320
tgtcaatgat tattctacca ttgcacagta gttcttaagg atagtaatgg taccaaagcc   4380
agcagcaata gaatatctcc caagccaact ttacaattgg agccttcact gtgggaaaga   4440
ccagttgcca agtagagctg gtggttatct gggaaactgt gctgaagaac acaaccacaa    4500
atgattttgc caaatataca gtatttactt ggtctagatc tccaatttct atttctactc    4560
actgccaaaa ctgagtgaat actgtgacat tattgaagga ggttatgcag tacatctgtt   4620
ggtttggtat atagtaggag agaagggttc caggagggaa aggggaaagt cagagcatgt   4680
gaatcactgt gactacaatc caaaagaat tatgtatgtc tgctatttcc agcattattt    4740
ttgtcctata ttgtacattg cagagacttg ctgacttaaa atagatatat aatcttttc    4800 tcaaaagaat agatatttgg ttgtccattc caaataacaa attttggatg ggcgtggtga   4860
ctcatgcctg taatcctagc actttgggag gccaaggtga gagatcactt gaggccagga   4920
gtttgaaacc accctgggca acacagtcag gccccagtct ctacaaaaaa tttaaaagt    4980 tagtggggca tggtggtaca ttcctgtagt cccagctact caggagactg atataggagg   5040
atggattgag ctcaagtgtt ctaacttata gtgagctctg atcacaccac tgcgctccag   5100
cccaggcaag agggagagac cctatctcaa acagcgacaa caacaaaacc aaacaaacaa   5160
aaaagcacat tctatcagct ttgatttatg ttttcttcat ttgtaatgac atgtagtaa    5220 atgtgtcata cttcaaaaag aagaaacaga tagtaggtgg attttcaata taatatatat   5280
```

```
tagatataga taatatatat tttcaatata taatatatgt aaaaataaat tcagtgataa    5340
tatcatccta cctgcagttt taagaattca gaactcaggc caggtgtggt ggctcattct    5400
gggaggggaa ggcaggagga tcacttgagg ccagaagttc tagaccagcc tgggcaacat    5460
agtgagatac ctgtctctat tcaataaaaa taaaaataaa aataattcag aactcaatgc    5520
tttatactca ctgaaagttg ttcctctaaa ctgacttgaa atcatgttcc aaataaactg    5580
agaattaaag taagagacga ggccggttgt ggtggctcat gcctgtaatc ccagcacttt    5640
gggacgacaa ggcaggtgga tgacctgagg tcaggagttt gagaccagcc tggccaacat    5700
ggtgaaaccc tgtctctact aaaaatacaa aaattagccg gcatggtgg cacacaccag    5760 taatcccagc tactcaggag gctgaggccc gagaatcact tgagcctggg catggtggct    5820
catacctata atcccagcac tttgggaggc cgaggcaggt ggatcacctg acgtcaggaa    5880
ttcgagacca gtctggccaa catggtgaaa ccccatctcc actaaacata caaaattagc    5940
tgggtgtggt ggcacatgcc tgtagtctca gctattctgg aggctgatac aggagaattg    6000
cttgaacccT cccgggaggc agaggctgcg gtgagccgag atggctctgc tgcactccag    6060
cctgggcgag gcagagagac tctgcctcaa aaaagaaaa ataataataa taaataggag    6120
atgaataaat tgggataaag tgttttttgaa ggacagtcta ggatataaaa tgaactggtt    6180
gtttgactaa aaatactaca aatgtttctt tcaaattaca tttctttttt gtctattgga    6240
aggtaggcac tgatttctat gtctttctat tccctaatag aacctactgt tgacctctca    6300
gtcaatattt aatggatgat atagaactag tgaaaaacca tgcaatttaa ctagaaaaaa    6360
aaagtataat ctattttctt ttccttttc tttcttcTT tctttctttt tttttttttt    6420
tttgagacgg tatcttgctc tgtcacctag gctggagtgc agtggtgtga tctcggctca    6480
ctgcaacctc tgccttccag gttcaagtga ttctctttct cagcccccag agtagctggg    6540
actaggagcg tgccccacca cacctggcta atttttctat ttttattaga gacagggttt    6600
caccatgttg gccaggctga tctcgtactc ctggtctcag gtgatctgcc tgcccgggtc    6660
tcccaaagtg ctgggattac aggcatgagc cactgcacct ggtctaatct attttcaatg    6720
tataagagaa aaatagtgtt aagtgtcttg gtgatggtga tgatggtagg agtaatggtg    6780
tgttttcctt acatttaatt tctacaggct atggcaattg ccctataaaa gccacccatt    6840
ttaagcacaa aagtgaatgg ttttagtaa acttatatgg gatcatatat ttttaattga    6900 aatattttt gagttaatta tagattcata tgccattgta tgaaataata cagagagatt    6960
ccacgtatac ttgctcaatt tcccccagtg gcaacacttt gcaaaactat aatatcatat    7020
cacatcacat gcaaaactat aatatcatat cacaaccatg atactgacat tgatgtggcc    7080
tactaatctt attcagatgt cctcagttta acttgtactc atttgtgtgt gttttgtttt    7140
ataccattta gtcacatgat cacatatttt taaaccttt tttctcaaaa cagagaagtt    7200
tagcacaaaa gtttagcaat ttatcaatct tgtgattgtg ctgttatgcc atattaaaat    7260
gtgtgtcaga atgtaagttt ttgttttctt aaaagtcctt tttttgatag aatggccttt    7320
atgttaaaaa tattttaagt tgttttgtga cagtgtaagt cgatgtcatt taattctcat    7380 cacaaccta gagataggta ttattcttat ccctatttat gagtgaggaa actgaagccc    7440
agtgaggtta ataacttcc ttaagttcat acagcctata catggcttag cttagccag    7500 catttgagtt aagcagtctg tctctagtgc caaatctttt aatcactata ttatacttca    7560
tcattatcat tgatagctgt aaaagtgtat aatgtggact atgtagagaa agtcataaaa    7620
ggagatttaa aatgcataca gttgttcaca tgaaaacttg tagccaaatg ttcattacag    7680
```

-continued

```
cattattaat aatggtaaaa aatggaaaca acccagatgt ctatcatgtc atgagtgaat   7740
aaacaaattg tggtatatcc atacagtgaa atattattaa gtagtataaa ggaatggatt   7800
attgataaat gctgtcacat aggtgaatct gagaggcaca agaaaggcca catatgatat   7860
gctttcaatt ttaagtaacg tccagaatag gcaaatctaa ggagacagaa agttggctag   7920
ttattactag gggctaggga tgggagggag gtgactccta ataagtatga gatttctttt   7980
ggtgatgatg aaaatgttct ataattagat agtaatgatt gcccaactct ttgaatatgc   8040
tgaaacccac tgaattatat gctttaaaag gatgaattta ttgtatgtga attatatttc   8100
aaaaagctgt tgttataaaa atgaatgtag ttgagttatt tggtttattt tatgtcagaa   8160
aatgtcttac atctcatgca aaagaaatgc aggaactatt tggattgaat gaggctaagc   8220
atatctttct aggaagatgg catcaaggag ttttattatg cctgtaatcc tggcactttg   8280
ggaggccaag gcgggagacc agaagtttga gattagtctg ggcaacatcc tcttatagat   8340
gagaaggata cttaatcact caaaagttgg cattgtgttt tgtgataaca atagccttta   8400
gagctcatat gggaagattc aatagatagt gataggttat atgacttggt aaagagggct   8460
taatgtatag gtgcaagaaa cttctctcaga tgtctttagt tacctagcca ttcagttcag   8520
gagatgtaac ccaagtgtta aaaggaatgt gactgggtgc ggtggctcac acctgtaatc   8580
ccagcacttt gcgaggcgga agtgggtggg tctcttgagc tcaggagttg gagacaagcc   8640
tgggcaacat ggcaaaaccc catccctaca aaaaatgcac aaattagctg gtgtggtgg   8700 cacatccctg tagttccagg tacttgtggg gctgaggcgg gaggatggct cgagcctggg   8760
aagttgaggc tgcagtgagc catgttggtg cccccacact tcagcctggg tgacaaaatg   8820
agaccctctc tctcaaaaaa aaactataaa aattgctgtt cttgtttaaa ttactacaaa   8880
gtgcagttta atctagaaat aataacaaat tactagattt gggggttat taatgtctta   8940 tctatgtgaa aacagaaggg caatgcaggg cagagaataa acttcaaaac tttgagtttg   9000
ttaactgttt atatctccac ttgtcatgtt tcagatttta aagttaaaat gacaaagtat   9060
ctcatagggt ttaaacaagt gactcttttc ctgttaactg atactgtggc atgttgaaga   9120
tgtaaaataa ggttgaaaag gaaattgctt tgcagcagtc ttcataatgc caggacaaag   9180
tgagaaacag ggtcagaatg atgatggctc tccatctttg ctacacatgg ctgcaagtat   9240
ttacaaatac cagcagaact tctacaaacc acttacaggg aaaatgagtg cagatttta   9300 acactagtcc ctatgaaact atgacttgta gttttggaca cacagggtga attacttggg   9360
gttgattgta tttgaatttc taaccttatg taattctaga taccagacat tcttgttgtg   9420
caatgcttct ctccctttt attctcatga gaatgctggg ttgcagccgg ttggatccca   9480
taccttggga ccatgactga taactggagt ggagaaaatt cactgatctg gaaaggttga   9540
gctttagggt tcagagactt atttaaggta cacatgtgat tgtacccaat aaggaagtat   9600
attggcttta tataattgtt atgatcactt gttcaatgag taactataga attttacttt   9660
ttaagagtat gatcatagca tctacttgta ggtttgttga gtatgtttga caagcccaag   9720
atagatgctc atgttagacc cattaagaag ttggtgtagt gatggttatg gaaagcagta   9780
agatagaatt taggttctgt tctccttact ggagaaatga ctagcttact tgtcttcact   9840
ctctcttgtt tctctcaaaa ctttgtgaac cacctcagct gactataaat ttttgtacta   9900
gtatctccat aattttaaaa aagttgttca caagttgag tgtagtactt catctttgct    9960
ttttaatgca cttccaaaaa atgtaaatct gttctcgcat attaggaaca ttttgatttg  10020
```

-continued

```
ttgtttatttt ttagctttgc tttttataag taatttatac agaaggtaca ccatattcaa   10080
aagaagaaaa atgggctgtg aatttttgct gatgtactac tctcttcaaa gggaattgcc   10140
tatgttcagg catagaaatg caggcagtct gacatttagg tatgccatac agagtattga   10200
tatttttaat ttgctacttt taacattttg agatttgtca cagtttgttc tgtgggtggg   10260
taaaagtaat ggtaatttta attacagttg tcgtgcctca ttagccattg ctaaaacctg   10320
ccttaccaaa tcacttattt tcttgatgca gtgttaaatc tagcttctat gtccaggtta   10380
tacattaatg agaacattca cccatctctc aaatgggtta ttatagtatt ttctcctgaa   10440
atagatgatg cataaaaaaa agtaaaaaag cttcaatagg gataatgaaa gccagataac   10500
atagcatggt atatgagtta ttcctcccgt tttcttacc tgtctgcact aagaagggca   10560
cccattaaat accataatta ttagttgtgc tgcctctgaa gtagagcacc agaatgtgag   10620
agtaatacaa tgagaccaca cccagattct atccataaca tactgtcctg gtcttattaa   10680 ttttttaac ctgtttgttc tttagcact tttcctgctt ttgtttgaag tctcttgctt   10740
tgaagttata gaatttttat atttgccatt ggctgtaaag ttatctcagc tcttttataa   10800
cttttcatta tatttgcatt aaaaggatca ctttgagcac cctgtaatta attcagatga   10860
ttattagctt ttttgtttgt tctactgtgc actctcctat atacattata acagaagaaa   10920
aaaccatttc tacaaataca gtgtctgata gttcatcaaa tcagaatgag catcttaaaa   10980
agtgaattat taaaatatta attcatttac attcctattt taatgtacca aatgtaactg   11040
atgaaaagaa gaataccata aatgggtacc tttcaaaaat gaaggaaaaa aaaatctcac   11100
aactaaagat tcttaccata taaattattt attttagtaa ataattattt tagtacaaac   11160
agatacattt tagcaggaaa aaacacactt taaaccttgt tttatagatt ttatcttct   11220 tccaatctag ccactgaaat ggttttttct ccagtgaagt tatattatct acataagttg   11280 aattaaaac aaggttgtat tttaattttg cagttgtctg ccacattacg cttgtggaaa   11340
aacactggca gaaagcaaag ctaatagaca ttttgctgtt ggctcacctt attaatggct   11400
aagatttaat tatgtatttc tactgaaaag caaacttgaa aaagacgttt ggttactaac   11460
tgtgggaact aaaaattttt attattttt atttttatt ttttggtaga gtctcactct   11520
cttgcccagg ctggagtgca gtggcatgat cttggctcac tgcagcctcc tccttctggg   11580
ttcaagcgat tctcctgtct cagcctcccg agtagctggg attataggca ccagccacca   11640
tgcctggcta attttgcat ttttagtaga aacagcgttt cgccatgtag ctaggctgg   11700 tctcgaactc ctgacctcta gtgatccacc cccttctgct tcctaaagtg ctgggattac   11760
aggcatgagc catcggcctg gccaacttat ttactgttac aacttactta ctttgaaaca   11820
acttatttac tgttaaaaaa tgtggttctt atttcaaata agattttatg gacatcaact   11880
aattttttaa acatatattg taattttaaa acattttac caacattttt caagagcatg   11940
ggaaatctag ggtatggcat tttaaagtga ctttaaagac acttcttggg ttttgttgaa   12000
gtcagaatat tttaaaaat acaatgagtt taatttacta ctgacagatt ttctttaatt   12060
ttttttgcat tgttataatt agtcatgcct taatcctcgg ggttttggg aaactatatt   12120 taggggttaa aaacttagtt attgacattg taattttct cagtattggt aagaattcag   12180
gtgtttaagg aatggagttt acttgttttc tgttcacaaa cccattgtaa aagatataat   12240
gaatgtagat gaaggtgaaa tccgagatag gaagagaggt aaaatgctac ttttttttcc   12300
ttcacccaag gaaagccatt gaatactgaa tgggtcatgt tgtaatttaa ttgggtgtaa   12360
attataactt tgtaaatcat ttgcctactt agtgtatatc tctggttttt atgtaattca   12420
```

```
tctcccataa tatctcagtt tacactgaag taaataagca agcaggaata agtcctgcaa   12480
atagaggaag tagaaagtgc attcagaatg cattgctgaa attgtaaaac tgatcctaaa   12540
ttgaattagg tagagcagtt aatttagatt acaagaaatg caacaggaaa aaaatattac   12600
agttcttcct cttttttgga aaaaaaaaaa gaaagaaaag acaaataaat cacccttagt   12660
tagtgataat tccttgacat ctgtatgctc attttttaggg ccaaaaaata gtaggcttct   12720
ctttggaaat tgtagacgct ttctctcctt ccagttacac gcggtcacat caacatttga   12780
cacgtgggta ccgtgcacgt ggcagcagta tttacaaaca ccatcctagg attccagaga   12840
ctcttatgta acagtggaga gagtaagctt tgagtgtctg tgggcggagg aatcaacaca   12900
gtttaattca ttgtccggga gcccttgtct ggctctgata gggtcatgaa ccaaagatca   12960
aggtgtttag gtcaggatat tccctaacgc atggttttcc taccaaagcc tcaaaagctg   13020
tgcctaaata caagattaat cttttctttt cttcctttct tttttttttt tttttttgag   13080
acggagtttc gctcttgctg ccaaggttgg agtgcagtgg cgccgcgatc tcggctcact   13140
gcaacctccg cctcaccggt tcaagcgatt ctccagcctc agacacccaa gtagctggga   13200
ttataggcat gcgccaccac gcccggctaa ttttgtattt ttagtacaga cggggtttct   13260
ccatgttggt cagcctggtg ttgaactccc gacttaaggt gatccgcttg cttcggcccc   13320
ccaaagtgct gggattacag gcttgagcca ccgcgcccag ctaagattaa tcttttatg    13380 ccctgcagca acaactagt  catgccaaac cattttgtg  atttgggaa  acatgagcag   13440 atgatgcttt ggatctgatt ataattcaca gtgctcttgt aatttacgtg agatttgcat   13500
acctgcctcc cagcctcaca aaatgccttt aaaaaattac atcttggcca ggatggctca   13560
cgcctgtaat cccggcattt tgggaggcca aggcgggtgg caagagatcg agatcatcct   13620
ggccaacacg gtgaaaaccc gtctctgcta aaaatacaaa aattagctgg gcgtggtggc   13680
gggcgcctgt aatcccagct acttgggaga ctgtggcagg agaatcgctt gaccccggga   13740
ggcggaggtt gcagtgagcc gagatcgcgc cactgcactc cagcctggcg acagaacgag   13800
actccgtctc agaaaaaaaa aaaatcttga tatttgtatg catcttaaaa agcaagagaa   13860
ttcatgattg acttcccaaa ctaaacggtc tgaccagaaa acactcaaga aaactcttgg   13920
ttaatcatgc tccttagtat accattatac ctgcctctcc cctttcccca tcctctgtaa   13980
attctctcaa ccttctctca tttttaattt cataccaaga cctagagcta aaacaacaac   14040
aacaaagctt taagtctcta tatttaggga atgtgcctcc tatcccaaat tgattttag    14100 agcttttcat ttattttat caatacaaag caagttgaaa taaaaaaaaa ggcatcaaaa    14160
atttaaatgt ctaaccacgt atatttggta tatgtatact ggtgctatgt attagctgta   14220
agcagactgt tttgaatatt taaaatatga acagaatttg agttcttttt gtattgcatc   14280
taaggatcat ttgagatgga tgtcatcatt tatcatccaa aatagaagcc ttcttgccta   14340
acaaagaatt gtaattagat catcaaagat gaaatttata gtaattgaaa agttagctca   14400
tttgactgct tctttcatag actgtgtttt tgtaattaca ctacctttct aaagatagga   14460
aaaatcagag tctctgaaat gtaatactat aagtgaaata tgtatttttt aaaataaagg   14520
atcttttccc aagagctaaa ccaagcacca aatctgtttt tgggggtttt tttggtttgt   14580
tggtttgttt gtttgtttgt ttttgacaga gtctccctct gtcgcccagg ctggagtgaa   14640
gcggagcgat ctgggctcac cgcaacctcc gcctcctggg ttccagcaat tctctgcctc   14700
aggcttcgga gtagctggga ttacaggcac tcgccaccac gcccggctaa ttttgtatt    14760
```

```
tttagtagag gcggggtttt accatcttgg tcaggctggt tttgaactcc tgacctggtg    14820
atccactcgc ctcagcctcc caaagtgctg ggattacagg tgttttttct taagtaatac    14880
ttggtataag agaactttat atctggaata atttaaatat tatctgaccg aatctattat    14940
tcacatatag aaactcaggt tttagccatt taacatctaa agctgttctc atttagagga    15000
aattaccaaa agagtgactt atttaactaa caataaaatc taaggataga tatttttca     15060
ttctgttgca gagcaaaagc agccttctgg atatgaaaag atattacttc tttagtgttt    15120
attacttata atttattgta catttctgat acactgaatt aagatgcgat gagagtaggt    15180
tgtagatttt taaaagttct tatttgcgtg atttatctac ttgctttttt agtgtcggac    15240
tataaatgat gtatttctct caattatcct cggcctaaat agtaaaagct tgggtgaaat    15300
tacttatgag tatacttttc ctgcacagag cagagccatt actgaacact ctcgagcttt    15360
aacaaaaatc atcctatctt atattagaat attaatattt tccctctttc tcggacattt    15420
gtttcacagt aaatcatata tggatataag ctgcaagtgc tcagaatttg attaaggcta    15480
taagttaatt tctactaaaa aagggattca aatagaactt tcatttggct gtactgtagt    15540
ttcacttgaa ggggcaagca tgcaataaac attgacttat tcaatgcata ggctgtcttc    15600
ataagatga gactgagtga cagttgtctg tgtattataa aatatcagaa tggtagattg     15660
aatctgatgc ataccaagga gcaatgtgga aattttaggc tgttcgtctt ttttcagtta    15720
ctactaagtg tgtgtatgtg gtgtgtatgt gttttgaact tttcatattt aagctgaatc    15780
ctctttggta gaaatggtta aatagactat agtaaaagtt tctgtctata aatataaaat    15840
gaaaaaatac tgtatatcttg catttttccct aatatgttga aagtgcacag aatccttggg   15900
gtcttttgta taaactgttt ttatatggtt cctgtagaag acagctgagg caccaaacac    15960
acacacaaaa caaacagctt gcttggtgat gataacattc gtgcaaggga gttctctctt    16020
gcataggagt cccaggttac cctaatgcct tcccacatgg tcaaacacat ggagctttca    16080
tatttacaca cagctccaga attctgaagc ctgcagttgt ttatcagtgg gatacaggga    16140
gaaagagtgg tgtctatctt actaactgtt taatgacctg gatcatgaat actgatacag    16200
aataagaaag cactggcctg actgcagggg aaacatggta gatgcctaaa ggaggctttt    16260
ccctgcccca cactgtttat tttaaactat cattatcacc tgaaaggagc ttttcacttt    16320
gaacttaaaa tagtagcttt taaccctgac aagcaagtag gcactttagt attcaagaac    16380
tgaaggtgac aagccctgag gagtgttact ctctttcata accagctgaa ctcaaactct    16440
tttagaagct agtgtagtaa cttaaccatc tctaataatg ttgctgcatg ccttcataga    16500
aacagttgga gcaagagctg cattttcttt tttttaagtg tttattattt acattttatt    16560
tttgaaaaca tgccattcct attacatata gaaatacttc ccaaaatcac tgtttgtata    16620
gaactatttt gcttaacatt aggattctat tgaagagcct atatctgcaa taatacgggg    16680
agaaaatccc ctttttgtgtg atagattaat gataaagaga aagaaaaggt gagaagtaat    16740
tttgggaaat atgcaatgat aaactagtgg tatttattga actaaacacc agcagctgtg    16800
cttagcatgg ataattgcct aaaaggatga gaaaaaaaag taaaaatcag gagactataa    16860
atttttcagt gaagaataaa ttttctgtca caaattatga acattttaaa tatgtattttt   16920
aaacttttc ctacttgtaa caaattatca gactttttaa tctaccttttt tgagctttt     16980
catcttttc cctgaattat agatttaatt ctgtgtatgt atgtgtgtgt ttgaatatat     17040
ttttatattt tagatctaga tttgtaaact agagctgttt ctaactgctt ataagacatt    17100
gccacctgga ttgccaccac tttcactcca gtatttcaat aaacacttca tcaaaaacat    17160
```

-continued

```
agtttatttt caaacataga atcatggatt gctacaagct gaaaggactt tagagactca    17220
gtaaccccat tccttgcatt tacagatgag aaaatggagg catgggaaag taaagtcagt    17280
tgcctcaaat agcgtaacaa gctatgtata tttctaataa tagctactat tgattaagtt    17340
cttatgttgg gttaagtacc atgctaagca cttttccaaag attatctaat tcttatgtca    17400
tctatatttt tgttggtgct attactctcc tcactttact aaggaagaaa ccaagacatg    17460
gggttaaata acttccctat aaattttgaa ttatctttgg catcatctcc ctatttgcaa    17520
atctccattg tctctttgtt cgtaatcaat gtaaatcaac tcttaaacag ttggatgcca    17580
acaagcagtc tggtgtttgg agctcgaaag tttcgagaga gagagagaga gagagagaga    17640
gagagagaga gagagagaga gagtgtgtgt gtgtgtgtgt gtgtgtgtgt gtgtgttcca    17700
gctttgttga ggtataattg acaagtaaac agtccacaaa actgtacaca tttaagagat    17760
acagtgtgat gttttaatat acattgtgaa gtgattatta ctatcaggct aattcacatg    17820
tccatcacct ctcagtcatt ttttgtgttt acggtgagaa cacttaagag ctactcaaat    17880
gtagtcaagg ataccataca gtactaactg tagtcaccat gctgtacatt agatctccag    17940
aatgtattaa atattcatct ggcataactg aaactgtgta tcctttgaca aacctatttc    18000
ccctactacc cagcccatgg caaccaccat gttactctct gcgtttatga gttcgacttc    18060
tttagattcc acatataagt gagatcatgc aataggaaga tctaatttag catcctgact    18120
ttcctttttta ttagctgtgt atgtcatatt caggttgcct tagcatttgt gaatctgctt    18180
ctctacctgt aaaatgagaa caactaataa ttcttatctc atggattact gagaggatca    18240
gatgaagtaa cataaataaa acatccagca tgttacttgg caaaattgta gtgattgaat    18300
aaatatttgt ttattcttca agcatgtgtt gagcatctat gtatcaggca agaagagagc    18360
catcatcttt acccttctgg aatatacagg ctcataggaa ataatcaatg ctttgatctt    18420
ttttttaaagc ataatgagat gaaaattata ggactcatag actggtcagt tgaggaattt    18480
cccaggatgc ttccagcctc tgctcaaaag gtgtgaattc ccagttgcct gaataggcgc    18540
cagagttggc atagctttct cagtattggg acctgacagg gagattgcac aagtgtaaca    18600
gcacagcctc tgaagattgg ctcaagggg aagagatgaa ggattacttc catcccttt    18660
attgtttcaa tcaagatata tattatgagc tcatagtacc atcctttcat gatcatcctt    18720
tattgtcttt attagataca atgaaaagat acaaatttgt ccatagaaat attaaatgat    18780
agcaggcatg atttaaaaag tactaaggac tatagatatt actgttttc ctctatttg    18840
tatcatattt tcaggaagaa gagacaacat tttggcatac cttgcttaaa gatagatgat    18900
agccgggtgt ggtggctcag acctgtaatt ccagcacttt gggaggccga ggcgggcaga    18960
tcacctgagg tcaggagttt gaaaccaacc tggccaacgt agagaaaccc cgtctgtacc    19020
aaaaaataca aaaattagcc aggcgtggtg gtgggcgcct gtaattccag ccactcagga    19080
gactgaggca cgagaatcac ttgaacccag gaggcagagg ttgcagtgag ctgagatcgt    19140
gccattgcac tccagcctgg gtgacagagg gagacttcgt ctcccaaaaa ataaaaataa    19200
aaaataattg tcttggtgtg ctaatcagga gcttcctgtg agagtggaaa ttccttacat    19260
ggcagtgtca tgaaattta ggcccatgtg aaagatgttt ttgagtgtct caaaatagtt    19320
aacggtttaa aaatacatta tttatgtgtc agaaactgct ttcattgaaa ttgaagtttc    19380
tttgagaact aggatcatat catgtatatc tattgaattt cccacaacaa ttatcacgca    19440
agcaaatgaa tagcagaccc tcaataacac ttactgatga ttattgccat gtataagttg    19500
```

```
ggatactctt gagtacctttt ctaagtctgc atttagggaa atacagaaca caaaatgaaa   19560
tgtttgattg gttgcttagt ttccacagtg acttttcaaa atgtatagga gcatggtaac   19620 aaaactatttt taaatactac aatcttaagt atgcctttat tattcttacc cacaataatg   19680
cattgcttta aaaaattgtt tatcagtgtc agaccatacc tttctgagtc tctactatgt   19740
aagatgtgaa agttaatatt cttcaattcc agctactttt cttttcctgc cttctgtcaa   19800
ctcctgtatt ccatatcatt acttcttatt gctaaattta taatatttat attctggttt   19860
gcatctatag ttaattctct tgtgcttcat ttctcagtgc taattgaaaa agaaaacaca   19920
tcacttacaa tgccatgatt gtaataaata aaattcactg taacacctag cagtatggtt   19980
gaacatgtag aaaaggaaaa agtgatcctg tgacactaaa atttagcttg ttctaaggat   20040
gctactttaa gcattagggt aaaatggatt ccctttttgct aaattctttc agttcctcaa   20100
aattatgcca catttttgtt tctttcacat ttggactatag attttcctgt aagcattcaa   20160
tttttcttga aaattttaat tgcattttt tattcttgtt gacagaagaa acattttcat   20220
catatcacaa ttttttttca gatttcttaa ttataccatt tgatgaatga aatacacttt   20280
cttcttgaag tctgattttt ctgttctaat ttagagtttc ttctcatttt tctcctggct   20340
atgtctatta ttgcttagt ctcatgtctt tgtatttgat tattattttt ctttttacta   20400 ctgttttttct tcttacagaa aaaaaaagaa aaaaaaacag gggttttttac aaatattgtg   20460 ctgagtcttt acatgtccaa aatgcctttat attttttcctt atagtacatt cataaattat   20520
tgtgattaga accataaatt caaagtaatt ttctctcaga gcttgggaaa cattggtacg   20580
ttgttaccct tcatctagga ttgcttatga gatagatatc tgatgccagt ctgattctgt   20640
cttttttaga taactttttt ccctattcat atgtttatta ggatctttat cttttcactt   20700
ctgaaattcc tccagatatg gctctgttaa aatgtattct tctcagcact tgatgattct   20760
gtacaatctg gaaacaactg cctttatttta gcttaaggta cttttcttcc attgtacctt   20820
tgattatttc ttccttcttt ttttcacccct atctttatga aactcatgtt aatggtgcat   20880
tagaacttgt gaactgattt ttcttatttta ttaaattcca tcacatatttt ttcatctgtt   20940 tatctctgta tattttattt tctcaacttt tgatatttttt gttaattgaa atttaatttc   21000
caagaagtcc attttctatt ctctgattga ttctttttaa tggtagccta tttcgtggct   21060
caaatcatat aaaatgtatt aaatttttgtg ggaaaattag gcaaacaaag aaaattaaat   21120
tttacctaac tatatctaaa aacaatacaa ctaaacttaa gaaaagtgcg tatatgtgta   21180
cacatataca tatgcgtgta tatgtgtaca catatgctac atatacatgt atatgtagta   21240
tatgtacatg tagtatatgt gtgtatgtat gtatatacac atgtagtata tctatataca   21300
tgtatatgta caaagaaaaa atatgtatat aatagtttca ctgtacttta tttgctcccc   21360
ttttaaaaat aacagtgcta gagttcatga ctgactaatt ttcagaactt ggtgtgtatg   21420
gttgtttatt aagccctcaa taataatgct ttagtattac agtgcccagg catagtcagt   21480
gactgtgcta atagtcctag cagtagcagt tcatcctgta cagatctaag gtgtaactat   21540 tttcattttct gggcccttgg agattctttg gttgtcttca tatcttttac ctatcttgct   21600
gttcaataac aggtaataga aaaggagata aaacttaaat gtcatcattt cccactgctt   21660 aacagtctttt aaaaataaat gtgaaacccg taaggacgta atcttgccta gctttaagga   21720
atgaaggaaa cactagaaac aacagagaga aaaggaataa ctgatcctcc aacatgttct   21780
gttgactcta cctgtaaagt atattcagga tctgactact tcacaccatt tcaccaattt   21840
ccatctccat tcaaaccacc ttcatgtgtt actttgaaaa gtgcagtttc cctgtcatgg   21900
```

```
gtttccctgt ttctagcttt gctccccctt cttacctcac cgtgggtttt tacccaaaca   21960
aaaattcaag tgatcattta aaaattaagt caggtcatgc ctctcctctg cttaaaacca   22020
ttaatgggtc tctgtttcac tcagaatata agccaaagcc cttttcatga cccaccagtc   22080
ctcaagtgaa ttggctgcta tttgtgtttc tgattccatt tcttgccact attctccctc   22140
attctattct aatttccttg gttttcttgc tgtcctggca acaagaagag catccttttt   22200
cctccaggcc tttgcacttg ctgttccctc ttcctggagc acccttcctt cagagagcca   22260
caggtattgt ttctatcttt ccttctaatc tctccttgag tgttacttt tcagagataa   22320 attccctaac cattctatct aacagaactc tgactattga ccttgcttta ttttctctct   22380
ttttttttaa aatttattt ttttattccc ataggttatt ggggaacagg tggtatttgg   22440
ttacatgggt aagttcttta gtggtgattt gtgagatctt ggtgcaccta tcacccgagc   22500
agtatacact tcaccctatt cgtagtcttt tattcctcac ccccttccca ccctttccc   22560 ctgagtccct agagtccatt gtgtcattct tatgcctttg catcctcata gcgtagctcc   22620
cacttatgag tgagaacata tgatgtttgg ttttccatcc ctgagttact tcacttagaa   22680
taatagtctc cagtcttatc caggtcactg caaatgccat taattcattc cttttatgg   22740 ctgagtagta ttccatctta taaatatacc acagtttctt taactactca ccgattgacg   22800
agcatttggg ttggttccac attttttgcaa ttgcaaattg tgctgctata aatgtgtgtg   22860
caagtatctt tttcatataa tgactttttt cctctgggta gatacccagt agtgggattg   22920
ctggatcaaa tggtagttgt acttttagtt atttaaggaa tctccacact gttttccata   22980
gtggctgtac tagtttacat tcccaccagc agtgtagaag tgttctctgt tcaccatatc   23040
catgccaacg tctactattt tttgattttt tattgccgtt cttgcaggag taaagtattg   23100
cattgtggtt ttgatttgca tttccctgat cattagtgat attgaacatt ttctcatatg   23160
tttgttggtc atttgtatat cttcttttta aaattgtcta ttcatgtcct tagcccactt   23220
tttgatagga ttgtttgttt ttttccttgc taatttgttg gagttccttg tagattctag   23280
atattagtcc tttgccggat gcatagattg tgaagatttt ctcccactct gtgggttgtc   23340
tgtttacgct gctgactgtt cctattgctg tgcagaggct cttttgttta attaagtctc   23400
acctatttat ctttgttttt gttgcatttg cttttgggtt cttggtcatg aagtctttac   23460
ctaagccaat gtctagaagg gttttttctga tgttatcttc tagaattttt atagtttcag   23520
cacgtagatt taagttttg atccatcttg agttgatttt tatataaggt gagagatgag   23580 gatcagttt cattcttcta tatgtggctt accagctatc ccagcaccat tgttgaata   23640 gggtgtcctt tacctactaa tttatgtttt tgtttgcttt gtcaaaggtc agttggctgt   23700
aagtatgtgg gtttctttct tggttctcta tccccccatt ggtctctgta cctatttta   23760 taccagtacc atgctgtttt ggtgtctatg gccttctagt ataaagtcag gtaatgtgat   23820
tctgcccaat ttgttctttg tgcttagttt tgctttggct ctgtgggttc tttttttgttt   23880 tcatatgaat tttaaaattg ttttttcctaa ttctgtgaag aatgatggtg gtattttgat   23940
gggaattgca tagtttatca acccttggca aagtgtttct gcttttctta aacaattttt   24000
attgtctgct ttctccagta gatgtgagtt ctatgagatg aggaacattg tttgggtcac   24060
tgacatgtat tgtcagcata ccaaacagtg gctagcacat ggtgagcact caataaatat   24120
ttggtgaaag ttgcagtgaa tgaaaatggt ttctaaaatg gcaatgacta tagtcccagc   24180
tactctgaag gctgaggcag gaagattgcc tgagtctcaa aagtttgggg ttgtagtgca   24240
```

```
ctatgattgt gcctgtgaat agctgctgca ttgtagcctg gtcaacacag tgagaaccca    24300 tctcttttaaa aaaatggcaa tgaaataatc ttattttttac tgcttttctc tttaaggctg  24360
ccagtgttgt cttttctctg ctgatttatc ctcattggaa attgaagata gataaaatat    24420
ccattgatta tttataggtg aaattaggct tttggatcca tgaggaatag ctgagacaat    24480
cttccaggag cttctggagc cgaggaaaca ttggtcacta aaataccatt tatattggca    24540
actgtactct tttccgatgc tagtgtttca attacattgt gcatttaaaa ggctgttgcg    24600
gctacctcaa aatataaaca tgatgtgcga cactacttgt tagttttgaa caactgattt    24660
ataaatagac ttagggtgct caagcctcct gcaagatgag cactgcctgt gttcttcctt    24720
ctgcttcctt tatttcagct gtgtgtctac caacttcctc ctccttctac actaggagaa    24780
attgcactgt ttccaatatc tttaacatct gctatcatga tgagaaaata tcttttctgg    24840
atttgaaata ccttcttcat tctttttttt taaatggcgg aaataaattc atagtgtttt    24900
gagtgcagtt ttcttcctgc tgttattgct ggctcaaaat ccaggagcat ttcagtgtta    24960
tttctgagct ccatgatggg agttccattt ctgtttatt caaagtgtta tctccagtgt    25020
ctagcacagt gcctggcaca ttataagcct ataatgttta tctagtggat gtagaccaat    25080
actattaaag aattatcatt gcaaagattt agtggcatga aaaaatgata atgattaatg    25140
ctctactcca tgctaaggaa atgaagtgca aatcgttctt tattttctt ccaagtatag    25200 agaactttct gaaattaaag aagcattgat taataagttt taatatatgt tattgatcat    25260
aataatatgt aatcatataa ccaaataaga taacacaggc catcttttgt tctttaaaaa    25320
atgacaggaa gattagaata agagaaaaaa ttagaggtca aaacagtttt cttcaaacca    25380
gtagtgtaac ttactgagat atcttctgta atccttaaat tctgtattga tgctaccaag    25440
atgcaactct tgagctacaa ctgcctcttg ataaggatg ctggtccctg ctgccagtgt     25500
aatgtttgct catttacagt ggaatgtaca atatagtacc tgggatggtg aagaaggtga    25560
agcaacaaat ttaaaatagc tgtgggtaaa cctacagaaa cagactattc tctttcttcc    25620
agattgcatt attcattttc atatgcctgc ctttatctgc tttggaagcc tatttcctaa    25680
tcttccaaga tttatcatca ccttcatatg tccatagcat gcatttctca dacaggtaag    25740
atagaattgg tatatatttg gtatagcaaa aagtcaaggt tgtctttaga ttatatcctt    25800
ggtttttcat gtggtactgg ggagaaagcc tactgtttct tcatctataa aatgaaggac    25860
ctgggcaaga taacattctg tgaaatttca ctgaactttg agctcagcaa agtagggatg    25920
cgtgtgtgtg tgtctatttg caatgcatca cagaccttaa ataaatacag ttgacccttg    25980
aataacatgg aggttaagag caccaacccc ctgcactgtc aaaaatccac atgtaatttt    26040
tgactcccca aaaacttaac tactaatagc ctgctgttgt ctggaggccc tgctgataac    26100
acacacagtt gactaacaca tattttctat gatatgtatt gtgtactata ttcttacaat    26160
aaactaagct agagaaaaga aactgttatt aagaaaatcg taaggtaaag aaaatatatt    26220
tactatttat taaatggaag tagatcatca taaagatctt catcctttgt tgtcttcacc    26280
ttgagtatgc tgaagaagag gaggaaaagg atgggttggt cttgctgttc caggggtggc    26340
agaagtggaa gaaaattcac atataagcag tccatgcagt tcaaacctgt attttaaggt    26400
caacggtatt tgttacattg catttttgtaa gtgaccttgt taatttttttt caatgaaaaa    26460 aatagtgttc cattcaaatg cctgtatgtt tatgagaaac atttcagaac tatgaaagtt    26520
gaattcaagg tttcttgcag attgtttgta tactttctgt aatgtttgtc atataatgag    26580
aatactaatg gtcttacaac ttgaaactga ttaactgatt aactctttaa gcaacttaaa    26640
```

```
aagaaaatct tcagtgagg aaagagtatt catcagaagt attctagtag atgacatatt   26700
tttggtaatg aaattgatat gggcaattaa cagcttttc caagttggct atgctgctac   26760
tctcttatta tacaatgata ctattttca gagcagaaag caaattagtt ttatttttat   26820
aaaccaaatt ttaaatatcc ctttagagaa tagaaaatat gaaaagtat ttgcttctca    26880 gacctctcaa caatataaat tttcttctta agaggaaatt tattcttgca tgccaacaca   26940
aaggataaaa agtttaccta tccttagttt ctaagaggaa aatgtgcata aaatttccat   27000
ctgctgtgtg ccagttacca aaacgataag ttccaactca atcttggttg ggtgtggtgg   27060
ctcacgcctg tgatcccggc actttgggag gccgaggtgg gcagatcacg agctcaggag   27120
tttgagacca gcctggccaa tatggtgaaa cccgtctct actaaaaata caaaaaaaa    27180 aaaaaacaaa actagcccgg catggtggtg tgctcccgta gtcccagcta cttgggaggc   27240
tgaggcagga gaatcgattg aacccaggag gtggaggttg cagtgagcca agattgcacc   27300
actgcactcc agcctgggca aaagaggag actctctctc aaacaaacaa aaagactca   27360 atcttactaa aaactgcag agaagaatga gtcattttag tcaataaagg aataaagaa    27420 attctagttt tgaaaatgac ataatttgct acaagaatgc aaaggtgatg acatgaggaa   27480
aaaaggggtt tgctgatttg ttttctctac tactcagcaa atgcaggcca ggaacccatt   27540
tattcaaata tttattacat ggtaaattaa aacatttata aaattaggct catattctta   27600
gaattcctgt taacaaagtg acatataaac aagattataa tctaatggag attaatattg   27660
gttgagaaaa atcttgagac ttctttaaga cttcagttta ataaaatat gacttaggta   27720 gatatatgtg aggaaatata tattttaccc atgcatgcaa aaatgatgta tgtatttctt   27780
aaaagagtag gtagcaatga cttcaaagga ccatagctgt ccctatcaac atatatatta   27840
acaaaacaat tagaaacatg agcttagtat gctaattata tttctaccca aagcctcaat   27900
ttgttctata gctatactgt tcatatataa gtaaaatttt aggggtatca gagagagtta   27960 gaaagagca aatacatgta tgaatttgat aagcctatcc cttaatttga tagatcttaa   28020
aagatatttt atcactgcat tcttctaaag aaatgtattt gtacattgca aaacaaccct   28080
ttttgagaag tagactatga tcacagattt tcttgccact agtatttcct aagatttatt   28140
tggaatagaa gatcgatatt tttctgggat gacatatggt taaaaagtaa aaaacaaaac   28200
aaaacaaaaa actcttaaaa aacacaacaa gtaaaaagct gaatgaattg gaaaattaac   28260
gaatcttctt agatctgtca gaaaatgag attatagggc aaaccactgc atcaaatatt   28320
agagaagcag acaggtagat agaaagaatc acaacttagt ggggcaaaaa cctacaagga   28380 aaattttttgt gggaaccggt gccaggtagg aaaacatgaa ctgtaattga aaaattgttc   28440
agtgtgggcg gttgttcagt gtggcaagtc tgagggttaa aaactccagg aggactcact   28500
tacggaaggg cctgtacttt tgtgagttta acctccagga gtgttcacag tgactactgg   28560
agaaaattcc ctaaggggag aagaaaagga accatcttga aatatgtcag agcattttgt   28620
tggactcaag cctgctctca agtgaaacta ttttaccaga gcctaaactt tgggattttt   28680
ataagagtgt aacctcccaa agggaaggga aatacctaag ttcagccccc ttttagcttt   28740
ccacataggg aaaggaaaat atataactct ggacaactca aaccatcctg tccacgttag   28800
ggggcctagg ggaactgaga aaactggtga agttcatagt ccatgggtac agtttcacca   28860
aagagggaga ccaaattata aggctacaga atgcttccct ttcccacacc ttttactatc   28920
atattactaa aagcctattt gcagcagttt ctttactga gtatatcatg tctgtcattc    28980
```

```
aaccaaaaaa ttataaggca tgctaaaagg caggaaatgc agtttgaaga cactgaataa   29040
gcatcagaag cagagtcaaa tatggcagtg acattggaat tatcagacca gaaactttat   29100
aaaaaactat ggttaatatg gtgagggatt aaaaaaatga catacaagaa cagatggata   29160
atgtaaatat agagacggaa attttaggaa agaaccaaag agaaatgcca agtatcaagc   29220
atagtgtaca gaaatgatta aaatgtcttt gataggctca taagtagatt gaacatagcc   29280
gaggaaaaaa tctttgaagt taaggatatg ataataggaa cttcaaaact aaaatgcaaa   29340
gagaaaaaag actgtgaaaa aaacagaaga gattattcaa gaactgcagg agaactacaa   29400
aaggtataat gtacgtgcaa tgggcatact agaaaaagaa agaaaggatt agatgcaata   29460
tttgaagaaa tagtgtgtga aaatctcccc caattaatgt cagacaccaa actacttctc   29520
cagagagctc aaagaacacc aagcaggata aatgtcccaa aactactcat ggcatatta   29580 tattcaaact tcagaaaatc aaagattaaa aaaatatcga aagaatccag aaggaaaaaa   29640
cacctataga ggagcaaaaa taataaattt tatctgacat atcctcataa accatacaaa   29700
taagagagta gagtgagaca tttaagatgt tgaaagaaaa atccggcagt gtacgattct   29760
ggaccttgca aaattgtcct tcagaagtta agaaataaag tctgtcttaa agaaacaaaa   29820
atttcaggaa tttgttgcca gtggaccacc cttgcaaaaa atgtttaaag ttctttagag   29880
agaggtaaaa tgatacaggt tagaaactca gatccacata aggaaaataa aattagggat   29940
atagtagtat tccccaactt gataaagaaa atacacaaaa aacctacagt ttacatcata   30000
cttaattttt agaaactcaa agctttcctg ctaagatcaa gaacaagaca aaggtgtctc   30060
ctcttaccac tttgtttcct actggaagtg ctacctaatg caataagaca aaggaaagaa   30120
aatgaaaagc atacagattc cggaggaaga aatcaaactg tctttgttca cggatgacag   30180
ttgtttatat ggaatatcca aaggatcaga aaaagaaaa ctggaactaa taatgatta   30240 ttgtaaggtt acagaataca aacttaatat aaagaaagcc aatcactttc ctgtatacca   30300
gcaataaaca agtgtaattt gaattaaaaa cacattacca tttacattag cacccccaaga   30360 aatgaaatac ttttgtataa atctaacaga atatgtacat gatctatatg aagaaaacta   30420
caaaagtgta atgaaaaata ccagtgaact aaataatgaa gagatgttac atgttcattg   30480
tcaagatgtc agttcttccc aacttgatct atagattcag tgcaatgcca ttaaaaaaca   30540
cagcacgata ttttatggat atcaacaaaa ggattctaaa gtttatatgg agaggcaaaa   30600
gagcagaata gccaactcag tatttgagga gaacaacaaa gtcagaggac tgacactacc   30660 tggcttttaaa gcttactata aagctcgat aatcaatgta gtgggtactg gtgaaagaat   30720
attcaaatag accaatggaa tagaataaag agcccaaaca aacccatgta aatataatca   30780
aatgatcttt gacaagggag caaaggcaat acaatggagc aaagatggtc ttttcaacaa   30840
ataatgctgg aaaaactaca cattaacata caacaacaaa aattttttaa atccaaattg   30900
agtgtaaaca cagatcttat acccttgca aaaattaact tgaatcatag acctaaatgt   30960
aaaatgcaga actataaaac tcccagaaga taacacagga aaatcctag atgactttgg   31020 tatggcagtg gcatttttta gatacagctc caaggcacg atacatgaag gaatgattg   31080 acaagctgga cttaactaaa atttaaaact tctgctctgt gaaagacaat attaagaaa   31140 tgagaagaca agccacagat ggaaaaatta tttgcaaaag atacttctca taaggacta   31200 ttgttcacaa tgtgcaaaca actcttacaa ctcaacagtt tgaaaatgaa caactcaact   31260
taaaaaatga gcaaaaaacc tgaacagaca actcaccaaa gaagatacac aagtgtcaag   31320
aaagcatagg aaaagatgtt aaacatcata gtcattaggg tattgaaaat taaaacaaca   31380
```

```
atgagatacc gctacatacc tgttagaatg gctgaagtca gaacactgat gaaaccaagt   31440
gctggtgaga atgtggagca acaggaacct tcattcattg ctggtaagaa ttcaaaatgg   31500
catagtcact ttggaagaca gtttggcagt ttcttacaaa ataaacatac tcttcccata   31560
tgattcagca atagcgctcc ttggtatgga cttgaaaact tatgtcctgg ccgggcacag   31620
tagctcacgc ctgtaattgc agcactttgg gaggcccagg caggtggatc atttgaggtc   31680
aggagttcaa gaccagcctg gtgaaatccc atggtgaaac cccagctcta ctaaagatac   31740
aaaaaagtag ctgggtgtgg cagtgtgcgc ctgtaatctc agctactagg gaggctgagg   31800
caggagaatc acttgagccc aggaggcgga ggttgcagtg agctgagatc atgccattgc   31860
actccagcct gagtgacaga gcaaaactcc atctcaaaaa aaaaagcaaa acaaaaaca   31920 aacaaacaaa acttatctcc acataaaaac ctgcacacat tgtttaacag ctttacataa   31980
ttgccaaaac ttgggtgcaa tcaagatatc ctttaatatt tgagtggata aactgtggta   32040
catccagatg taagaatatt attcagcact aagaaatgag ctatcacatc ataaaacgac   32100
atggatgaaa cttaaatgca tattataaag tgaaagaagc taatccgaaa aggctaaata   32160
ctgtatgatt ccaactatat gacattccgg aaaagccaaa attatggaga cagtaaaaag   32220
agcagtgttt tccagaggga ggaatgtata ggcaaatttt tagtgcagtg aaatgaatct   32280
atgtaatact atagtggtgg atccatgtca ttatacattt gtccaaacac gtaggatgta   32340
accaccaata gtgaaccta atgtaaacta tggggtttgg gtatcaaaat gcatcaatgt   32400
aggtttatca gttgtaacaa atataccact ctggtatggg atgttgataa tggggaaggt   32460
tgtgggtctg tggggacagg ggtatatggg aactttctac tgtttactg tgaatcaatt   32520 ttactgtaaa gtttattaat gttaaaaaat ttaatgcaca tgtaccctaa aacttaaagt   32580
ataataataa taaaataaat ttaggcaatc tgaaaaaatg ttaataaaaa agaaaataaa   32640
ctagttgaat gtatcagttc attttcatac tgctataaag tactgcctga gactgagtaa   32700
tttataaagg aaagagattt aattgactca cagtttagca tggctgggga ggtctcagga   32760
aacttaacag tcatggcagg tgacttcaca aagtggcagg aaggagaaat gaacgcagaa   32820
gcaactacca aacacttata aaaccatcag atctcatgag aactcactcc ctatgatgag   32880
aacagcatgg gggcaactgc ccccatgatc caattacttc cacctggtct ctgccttgac   32940
acatgggtat tatggagatt atggggatta taattcaaga tgagatttgg gtggggacac   33000
aaagcctaac catatcagtg ataaaactat gtcttttctt ttatgggtg ctatagtgtt   33060 tcatttcaag ttgtcttttt gacctccatt ttccaatttc tggttaggaa aaataacttt   33120
gtctcctcct taattgaccc acaaccttgt ttgcaatgaa gaatcaacac aaatctttca   33180
ttaaaagaaa taggggaggt gatggggat atccatgagt gtccatgggc ataattcagt   33240
tgccttcatt caatgccaat gatactgcaa agcctacaag gcaaattcat gtacctacag   33300
acagactcca tccttttct caaactattc aagataaaaa atcttgtttc attttatgtg   33360
aggatttttt tcaccatcta tcctcaaaaa atgaaaaata tcctcttcat ttgggaaatg   33420
agtgcttata atagaaagta atttgtagtc agctgttaca cttagatgat ttgtgtcacc   33480
tctgacctgc tttctgataa tgcatgactt cattcatggc tctctaggtg acctgtgtac   33540
cctgacctgg cataaaccac tagagtatta agtcatttca gtggcacatg tttgagggaa   33600
gattgacatc ccactggaag actatctaca gtgagatcct ctaaagcagc tgcattccta   33660
gtgaggcatg attaagttta tcccactatt aggttctgga gtattacttg tcatgcccaa   33720
```

```
gaggaaagtt tttctagcat gcagagtatc tggtttttaa tggctactga gctgaaataa   33780
aatgtgccta ctaagggttg ttcatttgtc tgtctccctt ctttcactgt tttttttctt   33840
ggaggttaca gtagttatgc ctttctggtc agctggctgt tgacctatca tagaaatgac   33900
actttcacat cttcaagtgt aaggaattag atgttccagc cttcactttg tttctcatcc   33960
aaaatcaatg acaaaacttt cagtattgat ttctcatggc ctatgaacct gagtcaactt   34020
ggcataaagg acttttcaga caagcttctc taaatgcaga gtcagtggct tcttttttgcc  34080 aaactccact ttgctcagtg ataacattaa aatggtgatt tgattcattc ctagtctaaa   34140
aatacttcct catattccaa aatctcagtc attaatacat ggaggaaaat acaaattatt   34200
acatgcctgt gcttctcggc tgttgtagat agataaaata tatacaattg tgttctataa   34260
ttattgagtt cttttaagtt ttatctttt ttgttttacc aggaagcaaa attatgttta    34320
tttcagagct tatttactgc atttagaatc tcatgacact taaaaaacct ttctaaaacg   34380
taaatattct ccatgatctc catggtcaca aacagtattt cacgttctaa ttgatattgc   34440
cattttatca ttttttttt tttcttggag acagtctcac tctgttgccc aggctgggat    34500
gcagaagcac gatcttgcct cactgcaacc tccacctcct gagttcaagc gattctcctg   34560
cctcagcctc ccgggtagct agaattacag gcatgtgcca ccacacctgg ctaattctgt   34620
atttttagta gagacagggt ttcacgatgt tggccagact ggtcttgaac tcctgacctc   34680
aggtgatcca cccaccgcag cctcccaaag tgctggaatt acaggcgtga ggcactgcat   34740
ctggcccttt tatctttctt ttaactcaaa tcctcaaata tatccctcca tgtgaagttg   34800
ccttccctaa ttatgtactg tcctagttta atcttcattc cttgtttgcc tctataaaac   34860
caagtttaaa aatagtctct gattctgtaa atcatcactc ttatgctcat ttatatttct   34920
atctagaata ttttaaatcc tttgtaacaa agtttctact atgcagtcta cctttctcag   34980
ctacgatcta tatactcctt ggccatgtct tttgttattg tgtgtgtttg tctttgtgtg   35040
tgtctgtata gtagtggttt gtaaattctc catttagtca caatatgctt tttgaggatt   35100 ttcctttttcc tgggaatttc ttgatgattt ttattttgtc atgtgatgaa gaatgtatgt   35160
caaagcacca ctgcagaaat agtgcttttc tatttacttg cactcttcca tcttagaaga   35220
gctggtgata gacaaccgac tcttctttta tcttggtttc tacaacacag aggttgctaa   35280 gcgacttttaa tcccttttaa cacaggacaa tcaacaacaa attccttctt tctttagatt   35340
cagatatttc acttagaaaa tctagcaaat aaaaaatggt ttaaaacttc tttaaaatgt   35400
gtaattctgt acaatctcct acatctgtaa cccctgcccc aaatatttt tacttatgct    35460 atttcttgag cattatgata tgcttattca taggcaatca acttgtaagt agcaatagtg   35520
tagccccttc taggaaatcg aagatgtgaa aatccagttt aatgtgataa tgagttactt   35580
tgatgaaaaa tactatgtca caatttgtta taaaaatact catttggatt tctgattcac   35640
ttatattacc ctccaacctt aagtatgatt gaatttatag cttttttatac tactttcttt  35700 atttagggag gagtgtattt aaattctgtt atctcggtta ttacttgaaa gttcaacctc   35760
atactttcat ttttatataa ttttaatatt atgaaaatat tttatgtaat tttatgtata   35820
attcgaaaac attttaaat attgcatctt taaattttta tttcttttat caaattttcc    35880
ctatcatttg ttctctggct acaaccaaag ttaatagtta cattttttc cagtgacaaa    35940 tggtaatttg caaagacttg taacagttgc ttaatacttt tttatcccctt atttaagaat  36000 catgcaaaca accagagctg ataggcagca ggtgcacatg agtgtggctg tgctgatggt   36060
tactgaaaga tttccaaggt agctagtaat tctgctaccc taagccacta tagctccttc   36120
```

```
cccattactc cctgggtcta cccaccatcc tgcagctaga ataataaatg gcatgtaggt  36180
tcctctagga tcctcctcca gcactatgtc tcatgcctgg acatatgagc tgttaaatat  36240
tttgattatc actcctgtgt ggtaagggag acgtctactt gtcgtaactt gatgtttact  36300
aaactacttt taagattacc ttatgataaa agtagacact tgcaattttg cagaatgcat  36360
agtttgtttt taacaaacca ggtaaacata actgcagagt tttcctatac gttttgaaat  36420
ctttaaaaaa gtatttttta tttgcctttc tattagaaat agattagata aaatttcct  36480 tgtttcaatt tttagaatga acattagaga atattgttac tgaaggaatt ttttttaaaaa  36540 tagtgactga tcaaatgtca gcagctttat actatagtgt aaaattttat tttgtagttt  36600
gccatcccat taagcattag aatttttata attgatcctt tgatgtttat attcatgata  36660
ttaatgtaat gtcttttaaac cttagctcat ataggtcata tgacttaaag catccttaga  36720
tgaagatatt tgggctataa ataatttatg acataagtga tttaaaaatt cattctttcc  36780
atccattttg aagaaattgt aaggtagggt tcatgtatac ctaatactta tcccccaaa  36840 atacgaaaaa taaatcatt tttaaaatat ctgggttaat gctatagatt ggaagcagtt  36900
tttaaaaagc acttaaagtc taccagttta ttgatcctca atctgtggct gttttaaatg  36960
gatgcaatta gcagttcagt ctaagagaac catggtagta gactcattac tccccagaaa  37020 ccattcatc attttgtaat attaaattac taaatataag gaatagaata tatattgtaa  37080
aaattgcttt ggaatcaata ataagtattg tggctatcaa ttatagttat atattacaat  37140
gtaagggata tcctttata aacttaatat cacacaagta gacttagaat aattccatta  37200
atataatttt gcttgtgttt ttatacctat tcatttcaat aactctttt cctatatata  37260 tttttatct caaattcgat agtatctaaa tcatggaatc ataaaacctt aaagctgggt  37320
tggaacagaa ataatacaat ttaacatctt ataggctctc tagtcctcag tttccctaag  37380
tgatcggctc aagatcatga atttatggag gattagagtc agaattagaa cccaagatta  37440
atttatactt tgttatctct tctacagcct accccttag tttgcctgtg ggtttatgga  37500
agttacagga gagacattct gagattcagc taaaaaccta gctcccaata gaattattgc  37560
cctgtagtca gccgcgcaaa tacaatcaca aatacctgaa gttccttgtg tgaagaaaaa  37620
gaaaatgact attaaagcat caaaatcaat gcaagttacc tttctttgcc cctttcttcc  37680
cctttcactc ctttcttctc ctatactact tgaaatttct agcggggatc tctaaaatgc  37740
ctggatgtta ggaatggtaa gtctattgta gagaattata ttttctattt tagtggatga  37800
aaaataaacc ataccttaa gaggcttttc aaagttaaga ttttgagcac atccttcatt  37860
ggcccagtct ctgaccagtg aggtcaagta ttagccagtg tcagaatgtc gtgaaaagtt  37920
tgtgtttcag atgcagaatt tttttttgca ttttctgtgt gatgtttata gggtattttc  37980
ttctgaaatg ttttccatct tggtttttaa aaatatctat tattttaaaa aatattccct  38040
cataacttct ttttatttc ggaaactata taaattgatc tgataatcta tacacaatgc  38100
cttgtgaatt tatacctgta cctctcatgt tccagtgttt ggttcttaaa taatcacttt  38160
gtataatgga aatactatgt taaattgttt ataactggtg gttgatattt cagccttgtt  38220
tggctatcgt agttatataa agactgttaa ttagaaacaa cctcatatgg tgtatgcttg  38280
tttttatctt catggaattt gttctgcaaa cactgagttc tttactggga gtcaccactt  38340
tgtctatgtt aggaggagca ggaagtgaat acatttaagg tctttaatttt tcttcttaaa  38400 actttgacta ctgtagtggt ttttttaaagc attaacagga gaatagccat cactgccaag  38460
```

```
tagctgacat tctgaaatag cacttccctt taggcactgt acagttggaa tcatttactt    38520
gcagagaggt gtgtgtgtgt gtgtgtgtat ttatgtgtgt actcatgtgt ataagaatag    38580
gagaaacact ttgtgggcat atcctgctga ggtgagtaac gtgctgatta gtgaactcca    38640
gtctcatccc atttaaacct ggaggagaac cacatcaagc acagaagcag ccaaagcagc    38700
atttcaacag gaaggaaaca tctattactg gggctttgaa gaaacatgcc atgaaggtgt    38760
actaatatca caaagggaag ggaaggacta aattcagcat gataaacaaa gtcccttttt    38820
tgtaacggaa gtgtttgatg atgtttgatc aatggtggat ctatctcttg aaaggaaaat    38880
gcatttaaac cccaaatgga ggattcttat ataaggtgcc tagcttgtaa tgatatattc    38940
atgtttatag gtagagtgac tggtttttag agaagaggtt tttttttttc cttcatttt     39000 gaacgaaaac ttgtctgtct ctaggctttg aaatgtagaa ttatttacct ttccccaaaa    39060
tgaaatgttt cactgaatct cctacaagct tgtggaggcc atgaagcatg ttgaataaga    39120
gcacaggctc tggaggccct gccacccaca aagggtgtgc taaggtaaac aactgatagt    39180
attttgaaaa ttagatgact tagaatccat tcaataaatt ttagctatt ttattgtctt     39240 ttttttctaa atctatttgg aaaatattgc agataaagta gataaatacct ttctaaaaca   39300 cagtgagacc aggcgcagtg gctcatgcct gtaatcccag cactttcgga ggccgaggta    39360
tgcggatcac gaggtcagga gatcgagacc atcctggcta acacggtgaa atcccgtctc    39420
tactaaaaat acaaaaatta gccaggcgtg ggggcatgcg cctgtaatcc cagctactca    39480
ggaggctgag gcaggagaat ggcgtgaacc ggggaggcgg agcttgcagt gagccaagat    39540
cgcaccactg cactccagcc tgggctacag agcaagactc tgtctctaaa aataaaaaa    39600 taaaaataga acagtgaata gtttataaag ataaaataga ataggcttca atttagggaa    39660
caaaggaaaa tatgtttagg aatgatatta tgctcaaaat gattgcaact ttgatggtga    39720
agtgtatttt attcaattaa aaatgtagat atggctgggc gtggtggctc acacctgtaa    39780
tcccagcact ttggaaggtt gacgcaggtg gatcacttga ggttaggagt ttgagacctg    39840
cctgggcaac atagtgagac ctcatctcta caaaaaataa acaaaaaatg tgctgggtgt    39900
ggtggtacat gcctgtagtc ctagccactt gggagactga gatggaagga tagcttgagt    39960
ctgggaggtc agtgctgcag tgagccgaga tcgtgccact gcacttgagc ctgggtgaca    40020
gagcaagacc ctgtctcaag aaaacaaaca aaaaaacaaa aacaacagta gatatgtgtg    40080
tgggaatgag aacatttaaa tgtgctcatc ggcttagatt tttctttaac cccccttcatg   40140 gcccttatct taacctctgt cttcagcact accccttcata tgtttgttcc gttttatctt   40200
ctaagtgatt ttttttataac tctcaatgta tcatggcaga aggaaaactc agtgtataag   40260
ctgactgtat tttgcatttt cttttttttt tttttttttt tgagatggag tctcactctg    40320
tcacccaggc tggagtgcag tggtgcgatc tcagcttatt gcaacctccg cctcctggag    40380
gcgattctcc cgcctcagcc tcccagtag ctgggactac aggcttgcac caccatgcct     40440
ggataatttt tatattttta gtagagacgg ggtttcatca tgttgtctag gcaggtctca    40500
aactcctgac ctcaagtgat ccacccacct tggcctccca agtgctggg attgcaggca     40560 tgagccaccg cggcctggct tcatgatcca aaatagcatc attaagcttc tctttcaaaa    40620
catgtatata agcctgtgag tcatcactgt atttatcaga atattatcat attggagact    40680
ttgcaaagct gaacaaagcc agaattattg gctactgagg aactatattc tagcaagaga    40740
ctattctatt tgttggggat caccttcttttt tactaaaggg gactgttttg ggcatataaa  40800
actagaattc atggtttctc cttgatagtt tgccagcttg attcccagtc aaccagataa    40860
```

```
ctgctggtag tgacactcat gtcctccagg actcccaatc ttgtgccagc tcagagaggg    40920
aaatccccct agaactgctc acaccattcc aagaaccaca agcaccacct tggtatagtt    40980
aaaaatgtga taccaactca aattctgata aaaacaagtt ctataaagct taataaagtt    41040
atatttttta cttttttaagt tttgttttac tattttaaac agaaaacaga aggtaaaaac    41100
tcctctgcct tcctcagtat ttggtttgtc agttgctgaa ctcagattta agagtctaat    41160
catatacagg caataaccct cttctaatct taataatgtt tctttgatca tttctttaaa    41220
aagaaaaatg aaatagccta ttgactccaa ccctgacctc ctgtacttca cctgcctgat    41280
gaatatttat ttggaataca taagtttttt caaatgcatc atgtcaagaa tttgtcattt    41340
cagattcctt tctagaatta tctatttatc tcattagtag catcattctt tcagacaacc    41400
aaactcaaaa gctttatcac tataattgaa tttcttttt cttcttacat ttaaaatgtt    41460
actaaatgcc attcatttct ttatcagtaa tatttctgtt tgatcatttt atttcattta    41520
ttctgccacc ctctcattcc aactattgct tatacttgag tactgcaata agccaatatc    41580
ttgcatatga ttatttataa cacctaaatc ttctaccact tcacactcac tgggatggat    41640
ataattttta aaacatacaa taacaggtgt tagtgcggat atggaaaaat tggaaccctg    41700
acacattgct agtggaatgt aaaaaggtgc agccactttg caaaacagtt tggcagttca    41760
tcaaaagatt aagcatggaa ctaccataag acccagtagt ttcgctctta gggattccac    41820
tctcaagaga attgaaaaca tatgcccata caaaaactta taaacattgt atatccatgt    41880
ttgttgcagc attattcaca atagcctaaa ggtagaagca acccaaatgc ctacagatgg    41940
atgaatggat aaacagaatg tggtatagac atacaatgga ctattattca accttaaaga    42000
ggaagaaaat tctgacacat gctagaaaat aaatggatct tgtatacatt ctactaagtg    42060
gaataagcca atcacacaaa gaaaatatt atgattccac ttacatgagg tacttagaat    42120
agtcaaatta atagaggcat acagtagaat aatgattgcc aggggctggg aggaggagca    42180
aatgggaagt tattgtttaa tgagtataga atttctgttt aggaagatga aaaagttctg    42240
gagatgggtg gcagtgatgg ttgcacagca atgtgaatgt acttaatgcc acagaatagt    42300
atacttaaat atggtttgaa tggcaaactt tgttacatac atttatcac aattaaaaag    42360 tttgaaatga atatccaaag aagcattatt tatgaggcta aaagtggaag taacccaaaa    42420
gttcatcatt gatagctaaa ggaaacatgg catatcaaaa cagtgaaata ttagtcatac    42480
aaaggaataa agtacagaca catgctgcaa tacagatgca ccttaaaaac attcactaa    42540 gtgaaagaaa ccagacgtaa aaggccaaat tttgtatggt tttatatata taagtcgtt    42600 caaaatagga aaacccataa agactgaaag ttgattagtg gtcaccaagg cccgggggag    42660
gaatgaatga aaactggctc ctaatgggta ctgggttttt tggggcgagg gggacagagt    42720
gatgaaaata ttgtagaatt tgatagtaat gataggtgag agtggcataa ttttttttaa    42780
tatactaaaa cccactgact catatacttt acaaggatgt attttatggt atgtgaatta    42840
tatctcaaaa caccccttaa attttaacgt atggctttta tgatgccatg tttctaaaga    42900
agcaacgtgt cccagtctca gcttactatt tctaggcatg tgactttgag aaaaaattaa    42960
gagacctccc ttcttactct gtaaaatggg aataataata atgatgataa tgataataat    43020
aatgatctta ccagatttt ttgagtgtta aatgaggtaa catatgtagt gcatctagca    43080
tagtgtctgg catttaccaa gaaccccggg aacctgagct tcaactgctt ctgatactat    43140
tccagatact atttcaggat attccaatac tgtttccata tattcaggac aatggaccaa    43200
```

```
ctcctttagc cattttatca aaactctttta gattctgttt caaatcggtc tttccaaagt   43260
cttcttgtgc tcctttgtag acactcttca gtcagagaga gcttttaat  ctcctccaat   43320 ttgctgcagc tgtatctgtg cctcaaaaca acgctttctc cccattcctc ttttctctct   43380
gcccttggaa ctctgtggac ttctctcatg ttttaacct  actccctttt atcagtgcat   43440
gtcatctcca cttatttgta gcacccaata tttttactac atctttgacc aattaagtct   43500
tacttgggtt atgttttaa  agtaggtatc ttattaggtg gtcctttaa  agtatatgtc   43560 cagtctctcc agctaaatta aaaccttga  gcacagagac cacatgttat aatgttttac   43620
cttttccata gcacttagca tgttaccttg acatggcata tactgaatga atgcttgcta   43680
tttatgagtt tagttagtgc cacatctcat gaagtacagg gacttaatga ttctcaatcc   43740
tgacttcatc ttacagtcac ctggagaata aagtttcctc ttagctcaac aagtcagaat   43800
ctctgagcaa aatcctcaac ttcttaccta ggtgatactc ttgtaagcca cactgtgaac   43860
cactggattc aacagatgaa gtaatataag ccactggctc ttaagcctca ttgattattg   43920
cggtgaagat gtgaagacta aagatgcttt gggcatggca aagtgttcta cagatattag   43980
aattgttatt atggtacatt tgagagtgtc attgcttga  gaaagattct ctaagttttt   44040
taacagccac actgtaatgg aaatatccaa ttataggtat ccaaaacctt ttaaactctt   44100
tatatcaggt gtatataccc tgttcctttt tgctaactta aaaatgttca aactctgtct   44160
tctctaggct ggcaaacatt cagcagcaca ccctctcaag attgtttact tgcctttgct   44220
cctgttgagt tacaacgctt ggaagcagga gatgggctca gcagcagcca ataggacatg   44280
atccaggaag agcagtaagg gactgagctg ctggtaagac agtggagaca gttgacactt   44340
gtttgtcaag tatgaattta ttcctaatgt aatggtaatc tctctcccaa acttcaactt   44400
caagttaccc tgcaccctct caaatacttt tcttttattgt ctatgcttag gacacatgga   44460
ttagattgtt aagatttgtg aatttactaa agttgtgtac tgacttatgt atagctgtat   44520
ttttctggag aaagatagat ttttatcaat tctcaatgtc tatggagttt ttaaaaagag   44580
gtaaggatta ttcaaatgta actataaaca taagaaaatg tgatatctat aaccagttgt   44640
tagagtattt atcgcctcca ttttgcttca cttgtagcca cttcgtctca atcttgttaa   44700
ggaccaaata aatggtattt gtggttactt gctgatctga aaagtgagta cctcctgcac   44760
ctggctagtc agtcttgtga caatttggtg ccatagaact agcagagaac taaattatgg   44820
aatggcagat ctcaggagca gctatgtgat tttacatacg gtttgttttt aatggataga   44880
gacagagtct ggctatgttg cccaggctgc tctgaaactc ctgggttcaa gccatcatcc   44940
tgccttagcc tcttaaggag ctgggattac aggtgcatgc ccccaggccc agttcatatg   45000
attttctgaa aatacaaaag aaagagggag atacaaaata cttttttaat catgttctta   45060
taattatctt aataaaaatc aatttgctct gaatgccatg acctgctgag tgtcccaacc   45120
taagggttgt cagaccattt tctcatatat gcatgtatag aagtagggaa ctaatatatt   45180
tttgtctaaa atgtttaaga tgaagatgag aatgaattct acaatatata attttgcctg   45240
aactatataa gacagttaaa attatagaga cattgcagga gagactctgg attagataga   45300
aaaaaggaag aattaggctt ttttttttgtc tataatcctt ttagtaggta attcagcttc   45360
agtttcacta aatcttgttt atgcattcag cataacaaat cttctaataa gcctgtatag   45420
ctctaatctc tgccttactg cagacacctg aggatataag tatccactct gccacttgat   45480
acttctcaga gactgttctg gtgctgagaa atcctttcca gtgtgtcctc agttgaactc   45540
ccatgattcc tggatgttgc cattttcaag acacagggca agcgcatctg tctagattac   45600
```

```
ctctctacct tgggaattttt aagtcactct gtgagggaaa gagaactcag tatagtagta    45660
actctcagaa tgaaaatttt ccccttgcat gttaatattt ttagagtaat cattgtcact    45720
gaaaatagac ttcctctttc ccctctcatg ctggaaaatc ttaggtaatt atgaataaag    45780
cattctttac ttttccctc ctcccttgat gattgcttta cctcactctg tgagaactgt    45840
gactactcat tctgctcttg tcttttacat gagaactgag agcgcatttt taagatggaa    45900
ttttcctcct taatgaagtc ataacattag tcagaagatt ttctcttctt gaacgttaag    45960
cctgggtaag gaataaagtg cagaagttta tggaaaatta taagataact taaaaaaaaa    46020
acgaagacaa caaattaaaa tattagccat tgagggaaaa ggttttacag gtagctctct    46080
gaggagttct tccctcatat ctcctcaaaa atcttgttt gcatttaatt ttttacagtt     46140
ggataagctc agcccttgac atattttcaa tagcaaataa gcctagagtt tatttttagt    46200
acatttatta ggaatgtgtt cttgggaaaa ttatttaacc tctgtaagcc ctgctttaaa    46260
tggcaaagaa gaaagtaggt aataatagat aataacagga ttattttatg cattacctgt    46320
acattgccca acatatagta agttctcaat tttatattgg tatttgtttt attattaacc    46380
acttttatta atgttgcttt tagttttga aatatgaatt cattcaaaaa tatttcttga     46440
gcacctgcca aataccaggc actcttctag gaactagagt ggcattaatg agtaagaggc    46500
aaaaatctct tcccttgttg agcttagaat ccattagagt aagagacaga cacatacaaa    46560
ataaaatgta taatatagta aataccaaga agtgctaagt tttaaaaatg taaagcagaa    46620
aaaggaaatt gagtggcagg gttaggtagt aattgaagat atagtagtca agtaaggcag    46680
cttcaagaga agattatgtc ttaaataaaa atctgataaa gatataaaaa caagccatga    46740
agttatctga aggaattgca ggtagtggag aacagccaaa agacctggag tagtaaaagg    46800
ttttatgcag agtgatttaa aaagaatcac agtatcttat acatcagtaa atatttacac    46860
atacacttaa gtaagtgata tggacaagaa cttggaagt tgaatagcaa ggtccatctg     46920
gactataaca gaggaggctt cacaaaggaa ggtgacaggg catggcctgg atcctgaagg    46980
acaggaagaa ttgggatcga taacaaagaa tgacatccca gtggagagaa gtggagggaa    47040
aacagcatga aatggagtga aataagaatg ttggccttta gggcaggaat gggccaggca    47100
gagggcaagt gggaagcagg aaaaaggcga ccttgtataa agttcatgtt ggcaaataga    47160
gagaagatgg gaaagcaggg taaggccaaa tttagtaaaa tcctaaagtc aagctaaaga    47220
ttattgcatg ctatcctgaa aatattgggg aataattaga gcagatgagt agaaaggtga    47280
attcttgtat ttagctatat cattattttt acaaatttaa acaaataagg aaatggaggc    47340
agtagttgga gtaatttagg agataaattg aaaatggatt ttgttaagag agaagggaag    47400
atagatttta tatatttaa ggaaaaatca tgaggattta tttgctgact gcacgtaaga     47460
gataaaagag aggagtcaaa gatttctcta aaattttcaa aatgattaat tacgtgttgg    47520 tattaaaga aatagggaag ttgggacata tgagtttgaa ttcagcatga gtcagttaag     47580
acaatcagat gcagatattc ttaaggcaac taaagttcat ttgatatttg tcatataggc    47640
tgaattaagt ttctaagagc tgttttttact atgcattaaa tccgtgtaat actaacatag    47700
tacaaaagtt gtttgctatc caaattttgt atttttataa taagttggag agacagaaa     47760 tcaaaaaatt attgatttgg aaccattaga catcagctag tccaattagt tcattttgtg    47820
gaaggaaaaa ggataccccag agatgttaca tgacttata gccatgcctc tagctagtat    47880
ctaacttggt ctagcccagg tctccatact gagactctcc tcctgctaat aaaaaaataa    47940
```

```
taaaaaagta ttagtggttt gtattttgct ggcttgcttg tggagaatag gattagaagg    48000
tttgacttgc ctgttagcac tctcttgtag ccattttct  aattaacata cacattttac    48060
cctttctcat gaaacagatc taacttgttt agaagcttca gtcttcttga tttaattaat    48120
cactttctcc cacctttagt cattgttgaa gtttcctgat ttacaatgtt atctttttat    48180
cttttcagta gtataaggag gaatgatatt tctactgttg tactatttt  ctgtttatct    48240
ttcagaagaa aaatagcttt tcttattggc ccaaaaaacc atcaccctac aggaaataaa    48300
tcacactctt tgcttgattt tcctgatctg gctactgatt tctcttcaaa tttaagccaa    48360
tacttagact ttaagacttc attgttactt ccttacaggt cattcttatg aactaaaatc    48420
catagtcatt gttctagcaa gcctgagcag tttattcttt gagtcacagg attataaaag    48480
aaaaaataga ccttagagat cataatacag tgctcttcaa actgtactct tcaattttc    48540
tactacttat cagttgtttt ttattctaat aaaatataat tacctagcaa gtgagcagac    48600
atgtatttac agtagcttta caattcttta tacacttctt tactctctcc attacacatg    48660
ccacatggta tgatacaagt cataactcaa ctatgtgaaa gcaaaaccac tcttatacat    48720
ggtgtcttgc atatatatta aggcccagag tggtatcagt agtctctgtg tcccaagaga    48780
ctgaattaaa caagactgtt gaccttcttg tggcatttat ctgacaacct tggcaatccc    48840
taaattcaca aatagctgta tagcatttt  tgcatttaat gcatatccac atatgatgtg    48900
tcctttgatt ttagaacaag taaagcatgc taaaatagac tgcaccttat gaaagtcatt    48960
ttcactattc ttgtgtttca gtttcctcat caaaaggtga aatatcagct gcctctgttg    49020
atctcaggat cttttaagta gaaatggaag agtcttagtg aaaacagttt gtattctgaa    49080
agaaaattgc aatgtaaata caggcactaa aaacgtttat tcatctttac agatgttaat    49140
ctgaccagac attttctca  aaatgtgaaa atagtatgga ttttcttagc tcatttaata    49200
ttgaaagact agaaaaacaa gtaatgatgt tctagaagaa tctatgatca tataattaca    49260
gttgtccttc agtatctgtg ggagattggt tccaggaccc cccatggata tcaaaatctg    49320
tggatcctca agtctcttat ataaaatagt gcagtatttg cacatgattt acatataccc    49380
tcccatatac ttcgaatcat ctctcgatta tttataatac tacaatgtcc atgctatgta    49440
agtagttatt acactgtatt gtttagggaa tagtgacaag aaaattaatc tgtacatgtt    49500
cattacaaac acagcaatcc atttttttc  tgagtatttt gatctgtgat tgattgaatc    49560
cacagatgct ggaatccatg aatacccatg ggggctgac  tataatgttg tctatgtgcg    49620
tagcaatttt gtaattctca accaaggaca cgtatagtcc ttgaatcttg gtaggagtct    49680
tggggacttt tcttaaaata ttttgaccat cttctcaaga tcttgactcc taccccact    49740
tgtacacgtg cacatacttg tgcacactca cacacaatac ccttccttaa gtcctgctca    49800
ccagcttgct tcctattgca ttgagagcat tcaacctgta gaccaagaac ttctaccata    49860
tttttccacc tctacccaa  aacacagttt agacatatcc attctttca  ttcttcagag    49920
tcatctcacc acttccataa attatttcct aattgttccc tctgcctctg ttctttttt    49980
tttttctgat gatcagttca aagtacctct gtatgcccat tcttaagtgc aaatctgacc    50040
atctataccc cttcttaata tccttctctt tatggatacc catttcagac tttattaaag    50100
gagtggaagc ttcccctcc  ccacctcacc acttgaagtt tttgcaatta gaatggagtt    50160
tatttggtta atgcaaaaat agatgtgatg tagaattctt ggggacacct acttatcccc    50220
ttttcagagt ggccctgaat agctctgtga acccaggaat ctgaagaact cagtacagaa    50280
aaccatcagc ctacagaaag tagatcaaac tctatgcttg atattcctga tctggctcct    50340
```

```
ggttactctt caaattcctc cttactatat tgtcccttca gatttgtaaa tctttaccgt   50400
gacatcgtat tttacacact gaacctttgt accgctgttc ctctcctgat gaacttccct   50460
tttctcttaa ctacacagct cagatttctc ataagggaag cttcatattt gttgtggcac   50520
tgttgttcct caaacatcct acttactgta gtcatttgtt tatgcttgtc tcctttgcag   50580
attctgaaat tcctagggca aaggctgcat cttgtcttct tattactaat attttacaca   50640
gtatctggtt acatagtagg cattcaatca tacaatttaa aagaagaggt tgactttgtg   50700 atcttttttca tatgttttat ttccctctcc ccctactggc aacttcttcc tacttcttaa   50760
aatagataca gcacttgccc actaagtgga gggaagaggt gtgggagtcg agtagttgga   50820
acttcaagtg tcaaaacatg ataatctcat ttgcaaagtt acattatatc ggagcttgaa   50880
cctcagagat acttaattat aagcaacact tgtggaacat ttgatacctca catttttttc   50940 actaaagtat cctatcaaaa ttaaatgtgt tgcagttgag atttgtgagg ttttagctat   51000
ttagagactt tagggatatg tttagtgttc taattctaat agtattgatg aatataaatg   51060
tttcactgta gaaagagaag tttgagagct gttgtgaatg atatttgatg tctattaggt   51120
gataatttct gatgactaaa catgctcaag accttagtga gaaatacatg aatacagaaa   51180
atattttgaa aattatgaga agtttatcat tgattataga ttttcttatc cagcagtttt   51240
tggttgtgtt ctgtttttca ctgtcagaga agcagaaagt ggtcagtgga ctttagaatg   51300
taggctcttg taggaggcca tatgtttgag agtgctgtcc aggtgctttg tgatgtggct   51360
gagaatggat gcaggcttgc agggaaaaac taatactgta gatctctaga gagcatttta   51420
ggaaagactt ctaagcttta ggttccctga ccaaagagta aaaagtgatt cttaatatcc   51480
atagctatag aggaaagtaa atacacttcc cacatcaaat gtagaattaa atatttaggc   51540
atttcaagtg tatttcattt agaacaaaat aaaatcatat attcactaat gaaatataaa   51600
accagatggt ctctgaaagg ttttttccctt tactcacttt cagagtaagg caaggaagag   51660
tagttttgtt ttttaatttta tattttaatt gtcccttcct gtttttccaa aagttttatt   51720
ttttgaaagt gagtcacctt ttagacattt gaaaaattag aattactatg atgtttattt   51780
tattagtaag tcttcctaga gtagcaacgt agaaaagcat ctctgaatgc ctacatagta   51840
agtatttaat aaatgttttt tgggccaggt gaggtagctc actcctgtaa tcccagcaat   51900
ttgggaggcc gaggcgggtg gatcacctga ggtcaagagt ttgagaccag cctgaccagt   51960
atggtgaaac cccatctcta ctaaaaatgc aaaattagct gggggtggtg gtgcatgcct   52020
ataataccag ctactcggga ggctgaggca ggggaatcgc ttgaactcag gaggtggagg   52080
ttgcagtgag ccgagatcgt gccgttgcac tccagcctga gcaacaagag tgaaactctg   52140
tctcaataaa taaataaata aataaaatac ataaataaat gcttttttgat ttaacgaagg   52200 tgtcattgtc ctatgaaaag gaaaactatc aaaatatatt ttttaaaact tagctttttga   52260 taatgatatg gaagatattt ctcttaatta acctaagtca gaaactaaaa tatgttataa   52320
aatgctaaca tcaaatattt gagaccagtt aaaggagaca gaaggaagtt atggagaaag   52380
aagcagtagc cagaaaataa gggcaagaaa atgttttcta aatttatgag aatcagaatg   52440
tttacaaaat tgctattatt atcatctgga aaaaatatgc cttgtaggct gaaaaaatga   52500
acattccctt tccataccat gcaggaacct tctttactgc attcctaaga ggactagtct   52560
agcacctaat tggatacttg tggtaatatt tgggaactca ctgatctggt acatcagtgt   52620
gggagtcgag tagtcagaac ttcaagtgtc aaaacatgat agtctcattt gcgaagttac   52680
```

```
actatattag agcttgaacc tcagagatac ttaattataa ttaacacttg cagaacattt    52740
gatacttaca ttttttttc actaaagtgt cctaccaaaa ttaaatgtgt tgcagttgag     52800
agttgtgagg ttttagctat ttggaaactt tagggatatg tttagtgttc taattccaat    52860
agtattgatg aacataaatg ttttactgta gaaagagaag tttgagagca agttgagcaa    52920
gaatctgtca ctctaggtct tctactcttt attaaagaat gttggattca tttataactt    52980
actggtccct taaatattaa agtttggtgt ttggtatctt aaacatgatt acatccttat    53040
agggctctct tctaattgcc tggatactgc acatctatta atacagtctc aaagcacact    53100 tgctttttg atagtaagag cgtacgattt aatcacattg aagttagtcc gcaaaggttt     53160
ttgtcttttt ttcaggcaag cagctgatga atgaatctct actatccttc actttgtgac    53220
tgtgattttc taaataaatg ttggagattt taacttacaa tttattaatt ccatcttgt     53280 ttcttcaagt ccctccttta aggaaattta tggaaatctt tttccatacc atcaagtggc    53340
ttatttcttt ttaacttttt tccttaagtt caggagtaca cgtgcaggtt tgttgcatag    53400
gcaaccttgg gtcatgggag tttgttgtac aggttatttc atcacccagg tattaagcct    53460
agtacccatt agttatttt cctgatcctc tccctcctcc caccctccac cctctgatag     53520
gccccggtgt gtgttgttcc cctctgtgtc catatgtcct catcatttag ctcccactta    53580
taagtgagaa catgcagtat ttggttttct gttcctatgt tagtttgcta tggataatgg    53640
cctccagctc catccatgtc catgcaaaaa acatgatctt attctcttat atggctgcat    53700
gttattccat ggtgtatata taacacagtt tttttttatc cagtctatta ttggtgggca    53760
tttaggttga ttccatgtct ttgctattgt gaataggact gcagtgaaaa tatgtgtgca    53820
tgtgtcttta taatagaata attttttttt cctttggtat atacccagta gtggggttgc    53880
tgggttgaat agtatttctg tcttgaggtc tttgaggaat cgctacactg tcttccacaa    53940
tggttgaact aatttacatt cccaccaata gcatataagt gttccttttt ctccgcaacc    54000
tcactaacgt gttatttttt gacttttttaa taatagccgt cctgactggt gtgagatggt    54060
atctcattgt ggttttgatt tgcatttctc taatgatcag tgatgttgag ctttatttca    54120
tatgtttgtt ggccgcatgt atgtcttctt ttgtaaagtg tctgttcatg tcctttgccc    54180 acttttttcaa tggggatgtt tgtttgtttg tttgtttttc ctgtaaattt aagatcctta    54240
tagatgctgg atactattgt cagatacata aattgcaaaa ttttctctccc attctgtagg    54300 ttgtctgttt tctctgttga tagtttattt tgctatgaag aatgtcttta gtttaattag    54360
atcccatttg tgaattttg ctatgaactg gatctgtatat aagcatatgt ttaattttaa    54420
ctcccaggtc acactgtttt ttttgtttg ttttgttttt gttttgtttt tgttttttgt     54480
ttttttggag atggagtctc acgctgtcac cagtctggag tgtggtgata caatcttggc    54540
tcattgcaac ctccacattc cgggttcaag caattcttct gcctcagcct cctgagtagc    54600
tgggactaca ggcacacacc accatgccca gctaatttt gtatttttag taaagatggg     54660
gtttcaccat gttggccagg atggtctcta tctcttgact tcatgatctg cccgcctcag    54720
cctcccaaag tgctgggatt acaggcttga gccaccacac ctggcccag tcatacttt      54780 taatcaaaat gagaaaaaag attgacttca ctggagtgct tatgtcttgt tttatattca    54840
agttttaaat ttatgttctt gagattatta catcttgagt tacttgataa taccacggtt    54900
gaaatccatg ttgttgaatc cttcaacccc ttgaggactg agaattccct ttaattatct    54960
gtctgaatca ttaaatactt gtaaatcaag agttcaattt agaaatgtta tacttgatac    55020 atttttaaa gctggataaa ttaacctatt aaacaaaatt atctcttctt caaaaaaaag     55080
```

```
gcatcacttc ccccacaaat gtgtaattta ggaattgttt tctattggag tggttcacgc   55140
ttatatattt tagttgctct aatgcaaggt gtttcctaaa aagtttaagg aaagtataac   55200
tttattttca tgtatgatag taaataatac aatagggggt gcatttgtgc tatgcttgtt   55260
tttgttccca tttcagtgct caattactgt agcttctaat aaataaaatt atcagttgct   55320
aacatttaaa tcaaacagtt ccacaagtgg aagtattgct tatttgtgag agttgtgttt   55380
ttttaaactt aaccttactg aggggtttta aggactgcta attatagatt gtactaagca   55440
aagtataaag taatagaagg ttaccaagtt gaggctagaa ttcaattagt gccaatacag   55500
ttaaaatggt atcattaaca gaacatcttc atccaggacc tttttttttt tttttttttt   55560 tttttcaga cagggtttca ctcctgttgc ccagactgcg gtgcagtggc ctgattgagg    55620
ctcactgcag cctcaacttc ccaggctcag gtgatcctcc cacctcagct tccagagtag   55680
ctgagaccac aggggcatgc caccacccct ggctaatttt ttgtattttt tgtagagaca   55740
gggttttgcc atgttgccca ggctgttcgc aaactcctgg cctcaagcaa tccacctgcc   55800
tcggcttccc aaagtgctgg aattatggga atgagctgcc acacccagcc cctccggaat   55860
ctttagatta ccaacttctg tcttccaggt ttttatgtcc ttggaaattt atgcatattt   55920
ttagaggtaa gacccatcct catcttcttc ctaatccttg acatattgtg aacacagata   55980
tatatacaat taagtagttc cctgagttac aaatatactt aaatatactt taacttatta   56040
tagaaggctt acaaaaactg tggataaata acatatattt atcttagtta atgaataact   56100
gatgctgaaa ataatgtgaa tgtcaaatta gttctctttt tttctagccc tcacctttga   56160
aaagcctgag cctctgagat gtgagatgac tgctgtaaag tgaagcagcg aatttctaga   56220
ggctgggttc acgcttcagg tcctctaaat cctaggtcgc ttcccactac tacatactac   56280
cctaaaaaat ctgtaattcg caaatttatt ttttgatctt tttcataact tattaaattt   56340
ttattgaaca aatacaggaa acagttttaa attactcatt gctcttgaat acattggtga   56400
ttatttttct tctctgaaat tctgttttcc ttaaaggcag tcatttttg gtctcttcta    56460 aatgacactt agtattttta gtaacatcat aacttcagtg gccacagtga gccctcattt   56520
tgcaacatat gcctactttt catatctggc ttgccttttta ttattataa tttaatgaaa   56580 agaaagtacc actctttcca tagttttgta atagaattgc tgtcaacaaa gtagtggatg   56640
cactatgtta taaagatttc attgtgaaaa catgaaatgg ctgttaacta tacatcaggc   56700
aaaataaaaa caggaaatat aaacatttcc tggaacaggg cagagtatga gtaataaggt   56760
atcaaatata attggatacc tgaccaaata tttttaaatg tcttaagaaa tgtcactgga   56820
aagactggag tacttggatt tgtctcttat tcttattttg attcctaaca ctgtgcttgg   56880
cacatggtag gtaattaata aatgtgtgat ggatgaataa tgattgtcat tcaattagtg   56940
actaagagag ttggaaaggg ctatcaattt caaattggtt cctttaagac attttttacgt  57000 aagatttggg agaaaagtaa aagagcacca tatgattatg cttactaag agctgcttcc    57060 attcctacat tgaccatgtg gactcatatt tggcctatat aattacatta gaataaacaa   57120
agcaccaaaa gttggaaaag gaagtagtag taggagaggg ttttaagcta tgtatttact   57180
gggaaaaaaa gtcatgtttt ctttttttaaa aatgttctaa acagtactgt aatcacttgg  57240
gaattgaatg tgctttgtgt cagacaaagg tctttgtata caatacatta cattttgtat   57300
accaatacat tacattacac agaagggagt gcctggcttt gtatacaata cattacattt   57360
tgtataccaa tacattacat tacacagaag ggagtgcctg gctttgtata caatacatta   57420
```

```
cgttttgtat accaatacat tacattacac agaagggagt gcctggcttt gggaaacaca    57480
tctacctaaa ctcttaacat agcacaatgc tgccatacgg taggtaatac caagacaaat    57540
cagggccgtt attaacaacc ttgaggaaat gtcttgggaa atatttaaat aattttttgtt   57600 taattataat aaggaatcta cagcctctgt gaagtcatcc caaactcttc gaggcaaatt    57660
tagtctcctc ccacccctgt tttttaatgt ttctaaagga tgttatgtat aatctattag    57720
aaaactggcc aagtgcagtg gctcatgcct gtaatcgcag cactttggga ggccaaggcg    57780
ggtagattac ctgaggtcag gagtttgaga ccagcctagc caatatggcg aaaccctctc    57840
tactaaaaat acaaaaatta gccaggcgta gtggcaagtg cctgtaatcc cagctactca    57900
ggaggctgag gcaggagaat ctcttgaacc cgggaggcga ggttgcagtg agttgagttc    57960
gcgtcactgc attccagcct gggcgacgga gtgagactcc gtctcaaaaa acaaaaacaa    58020
accaaaaaaa aaaaaaatat atacacacac acacacacac acacacacac acacacatac    58080
atacatacat tagaaaacta attacattgt tttcttaaaa tgttttaagc atctctcttc    58140
ctcaaggaca agaatcttga atccttagtg catatgaggt acttaataga tatttaaatg    58200
aatagtgagc tactattgcc taaaaatatt agacatcatg taatatcagg cctacagttg    58260
atagaaaaag tattctcaac taagaataat ttaccaatgg agaaaactgt tagttttccc    58320 ttcttttttct ttgctttata aaatttaaat gacattaaga gttacgtttc ttggaaaatt   58380
gaaaagaata tctgtggcac aatgggctct gggtataatt gcaggataat ttgaaaagtt    58440
taaagaatat tttcaatagg tataagttta tttaggctct gtgtctcctc ttgagatgac    58500
tttagcagta tatatttccc tggaacacca tgcactctag gttttctaat ttattggttt    58560
aaaatacatg gcattttact acgtaaaatat tctctgtatc tgtaggtaca gcacctctgt   58620
gtacactaag ttagtgtatg tattttttta aaattgcctt agtttgcta ttcactagat     58680 tattttccaa ggaacctact cttagattta ttaagcctac tatatatatt ttgttattaa    58740
ctaattctct tatttttaaa aattacttt cctttctttg cttaaatttg ctttgttttc     58800
ctaaattagt gatttggaat acttaattgt ttttattttg ttttgttttg tcaataaaag    58860
agttttaaga ctctagttat actatagcta tagccaatgc attttgagag gtgcttacat    58920
attacaatta ttttcagaaa ttccttattt caaagctttg cttctctttga acaaagagtt   58980 atttaggaaa agaaaggaat aaaaatctca acttattctc cacttgacta gctttattat    59040
ttgcagtatt ctgttttta cttgttctaa tacttcttta tattttgttg tggaattatg     59100
tcacctaaca atattttcct taacttctta attttagcct gttttccaag ttaatcattt    59160
atctgttgtt tcaatgaata cctaagaaaa ttttctttgt caggataagg cacatgaggt    59220
ctaagattta tttctagaac agtaagcaaa tcatttctga aagtgtgttc ttctactatt    59280
aagtaacatg tttattttg tcttttagtt gaagtccccc ccaacccaat aggtactatt     59340
ctgatttgtt ctcctattca cacattcttg aaggagagct gatttatctg tacccacaaa    59400
attataatat aattttctca gagtattcaa acattgtct tttttatttt tcttttttt      59460 gagttttca ctcttgttgc ctaggctgga gtgcaatggc aggatctcag ctcactgcaa     59520
cctccgcctc ccggtttcaa gagattctcc tgcctcagcc tcccgagtag ctgggattat    59580
aggcatgcac caccactcct ggctaatttt tttctatttt tagtagagac ggagtttctc    59640
catgttggtc aggccggtct caaactccca acctcaggtg atccacctgc ttcagcctcc    59700
taaagtgcta ggattacagg cgtgagccac cacacccagc cgaaaacatt atcttaatgg    59760
agcatttaga acgttatcac tgacaaactt ttttctattg aaaatactgc ttaaaagatc    59820
```

```
aggtcatgcc caccccacaa cccacaccct ttgtatttct cttttacttg tcttggcctc   59880
tagttcagat ttatagtttg gtaatgtctg attttctttg ttagtgcttc agcccatctg   59940
gttggggaac agctctatcc cactgggacc tctcccttc ctcatgagtg acgccagggt   60000
cctgctgccc ataagcattc tgtttgctga gtttgtatat atttcctttc cccagcttcg   60060
ctgcctttgg ctgctttgtg attaagtaag acatacccat gtttcctaaa gcctccttcg   60120
cctttagtcc ttgatgctgg ggacctttttg gttgggaaga cagcttcctt atgtcagggt   60180
gagcctgcta cacaggtatg taactcagac agtgacctac tgttgagttt ctgtttagtg   60240
tttctttgtc tccctcaaat ggtacaaacg tggagggctt caactgcagt ctacctttgt   60300
cctgttagtt ttgtctatca cagcccatgc cctccaaata agagatgatg gagcagtctg   60360
cttattttct gtagcactcc acaactgact ttaaaagagg gactgggatt gggctcttag   60420
tgatgacttt taatgtggat tcatctgcat tttctctaga aattctttaa actctctgcc   60480
tctcagctgg cactattcca tggtatttta gtgctaatgg gggatctttt ctaatttttg   60540
tttttctttg actgtttaaa tcatttactg gaaagagggc ttagatatct gctcatatgc   60600
tcctgctagt ctacaagtcc tccagcctga ttttgttcat gaacatgatg gaaataagct   60660
tcttaaatgc ctttaatatt ggatactgct ttcaaggaaa tttaaatag caagcaggct   60720 ttcaagaaga gagaataaat tatcagccag tctcgcaaga acaaaaataa gccaagtcat   60780
ataaaacaag tttggagtaa acttgttttt acatttcaaa ttcgagttga actcttcaag   60840
tgaagcttca gagatataaa aaactttaac tgataaagat tccaaacatt aatatatgga   60900
aatgtatgag ctcactgaaa attttacata aattttacta gaagaggtga ctgaccagtt   60960
gcttttataa gattctcaaa aagatctcaa atcttaggga ctaatattgt aagtatacgg   61020
ggaaattaag acaaagattt actatcttgt gagttttttag tttggataat gaacttaatt   61080
tcacaagaaa ttgctttagc acaaacatga aaaccttaag catgagaact ctccttttga   61140
agtacaaagg gagactaaag tgaataactc aaactggaaa tgtagaaaat tgaatttgct   61200
atgatttgaa gtccttttcag aatagccaac agattttaaa caagagtttt attgcatagt   61260
ttctttggga tatacattga aggagaaagg aggagggagt tttaaaagac aagtggaaag   61320 cccttttctgc ttgttttggc tatggcttcc atttcagtgt ctgtatttaa gggatcataa   61380
aaggaactgg aaagactggt cacaatggca gctctgtacc tgtatgattt cggatgtgaa   61440
aagagtttag cgatttcctt gttaacctat actgctgtgg aagtcattca ttatgcagtt   61500
aggcattagc agaacaaata aagttcacag ctctaggaac caaatttaac tttatcactc   61560
ttctgattta gaatattttc atatgctttc atatgtccta cagacgataa gaagatagaa   61620
tcaatacttg gtgattgata ggttattttt taaaagggaa gaaagaatta aacatccatg   61680
gtttcttctt aagtaactgg ggggatgata gtatccctca caccaatggg gagtatagat   61740
gacaggtttg gagtgaaaga cagtgaattc cattttggat aagttgaatt tgaagtgcct   61800
atgggacata caggtacaga tgactaggag acaattgaaa atccaaattg tgaactctgc   61860
tgaagattag aagtacagat ctgagattaa attgctactt gagttcatgg gaataaaata   61920
ggtcattctg caaatggtta tctcaatatc ttcctggcca tctcttgggt caccttgcca   61980
acttttcatt ctctttacaa tctctaaatt ctcatgtttt taaggctctc atcttaggcc   62040
aacttatctt gggtcacctt gctaacttt cattctcttt acagtctcta aatttgtgct   62100
tttaaggccc cattctcaag ctggcttctc tgttttggtg ggaactggta gcaaacattc   62160
```

```
atttgtaaac aacccaaatg gctagcattg agcaggactc cccaacatac tcctctgaat    62220
tacattttga gttatctgaa ggatcaatat ctcaaactag gaaactgtag ctttctcatt    62280
tattttcatc atctaattat ttttcttgcc tttaagtata agggatagag acttgattga    62340
tttttatgta caacaagtta aaaaatttaa ttaggcgtct ttgccattta atcagtttat    62400
acttcttgaa tcttttccag tcatcaaaaa gttgctgagc atgcgcagct ttacttacta    62460
gcttatagca tgaagaagag taaaatagga gtggataaag gcacagtggt gagtagtcag    62520
tgtttccaat taatctcaaa gtttaggatt aatttagcgt gaattctgtt cttttgtgtc    62580
ttcctgcttt ttgacgtggt aacctgccat aacaaaagga aacagcagga aacttggtac    62640
caattaaaac agtcttcttc ccccaaagaa cgaactgtca gcaaacaatc tcaaattcaa    62700
agtgataagt gttttagagt gaaacaagga taaagagaca aggctattaa attttaacat    62760
ctgctggaac acaaagcgca tgccagtaga attaagtttg gcatttaata agatacaatt    62820
tgcacatcag aaatgaaata gatgcctcaa ggcatggtat atatatatat atatatatat    62880
atatatatat atatatatat atatatgttt gagcgagggg cacttctagc aaaactgaat    62940
acactggtat aaatgtctgc gtgaaaattt ttttatccat tcacttttgg tgtgtattcc    63000
agctgtgagt tattcaacca ggctcactaa gtttgagtct gattaataac gtttaaggtc    63060
acatctgatt aacagtattt gaagtttgaa tttgttctaa gatgactcaa gcgcaataac    63120
attttctata tcaaaatgaa tttccatcca aatagggagg aaatctgaaa tttcagttcc    63180
agtgttgact gagatgctct ggatgagcct ggactcagag ctcaccaact ttggatcttt    63240
atgttaagta gtcagtgggg ttgacttcta gactagagat caaaatgttc tacacctctt    63300
gatataggtc agtggctgat gtaatgtgct tccaacaact ttcttttaac taaaacagta    63360
catataccaa gttggtttgt cacaatggga acaaaacaga atctgacaa cagatttctc    63420
taattttttg tgtgtatgtt tctgaatggg ctaaaataca taattttact cttccttggt    63480
gaagatgctt ttataagagg acgtgtttaa gaaaattaag aaatgttgta ggtagccatg    63540
aaagaattat tttaaacaga attagtatag aggtgtgaag atctactgaa gggtgataag    63600
taagtgtgga agagatggtg ttcagcattg ggcttcagta tgaataggta gaagatgagc    63660
aaggcttaga gacaagaagt tcattcaata ggctgttgcg gttatccagc aatgagatgg    63720
tgacagcatg agccatggta gtaaaagtaa ggacatggat aatttgtggg ttctacagac    63780
aataagaaca tagaaccgat aggttatttt ttaaacggga agaaagaatt aaacatccat    63840
ggtttcttct taagtaactg cgtggatgat agtaccctc acactgatgg ggaatgtaga    63900
tgacaggttt ggagtgaaag aatgaattcc attttggata agtagagttt gaagtgccta    63960
tgggacatac aggtacagat gactaggaga cgattgaaaa tccaaattgt gaactctgct    64020
gaaggttaga agtatagatc tgagattgaa ttgctacttg agttcatggg aataaaatag    64080
gtcattcagt aaattgttat ctcaatatct tcctggccat ctcttgggtc accttgttga    64140
cttttcattc tctttacaat gtcaaaattc tggtgttttt aaggccccaa tctcaggctg    64200
gcttctccaa ctgtactctt acttgggatg atcttatcta gtcatggggc attaaatacc    64260
attggtaggt taacacagtt cacaattttc tccagcttag accccttgct gatttcctga    64320
cttgtacact caactgcctg cctaatatac ccactttaat gataatgtac atctcaaact    64380
gagcttattc gaaatagaag ccttaatttt tctgtcagtc atattgttcc catttaccca    64440
tcctaacaaa tagcaccatc atcaaccttt tagctcaaga caaaactcta ggcattatct    64500
tgctttcatt cctttcatgt actttctcac atctaatcca ttaccaagtt gttctgtttc    64560
```

```
tgccttcaaa atgtgtccta aatttatcca tttctctgcc actgctattc tctagttcag    64620
gacattctat cctttctctt gtattactgc ggtctctaaa cttcatgtat ctatgtttta    64680
tacttttaat tcattgtcta tacagctacc agagtgatct tttaaaggtc taaatcagtt    64740
catgtcactg ctttatatat aatgcaccta tggcttccca ctggatttaa ataataatct    64800
taacacttta ctcctccatg gcctttacat acttctagcc gcacctcaaa acactcctct    64860
tgttcactga gaactaacta gaccagtttc tcttctcctc agctatatca tgctaattta    64920
tgcttcagtg ccttttgtac ttttgttccc tctagctgaa tcattcttcc aggtcattct    64980
atcattggct ttttcattca gttcagatag atatcagcaa atcaagagag tctttcctta    65040
cctgctctat ctaaatagtc ctgttttagt cctctttatc tcatcactca gatttatttc    65100
cctcatagca ctcatcagtc tgaaattgtt tgtttatttg gctacttgtt tgtctagata    65160
aacttcactg gtgaaggaat ccagactatc ttgttcatcc ctacatccct agaacctaga    65220
acaatatgtt aaagataaat aaataaatag atgaaagaat gttgaagaga agagggtcca    65280
gtccagcccc ctgaggtgac cagcatttag ggaataagcc gaggcagagg agggccatta    65340
agaaggagca atgagagata gaggaaaaact aagaacaagg tgtccctaaa gtgagagtgt    65400
cctaacacag gtctaaatga aaggatagtt cagaagaggg cactgcagct ggctgaaaga    65460
gaacaagaaa ggctgtaagg tggaggtgaa ttttaattg agccgtgaaa gatagggaaa    65520
ttctgtatga aggagtaaat ggaggcatag aggcatagag gcagaagatg catgcctgtt    65580
tggggaatag tcatcccatt tgtctttcac atatctcatt taatacttct catttaatcc    65640
ttttagtgtt aatgttgtca ctagattaaa aaacaaaggc tccatcagga tcacacagta    65700
aacagaagaa tatggattta aatggagatc tatctgactg caaagactac ttactgtaac    65760
ttaagtcatt gagattcctt atggccacct catattcacc ctgcatataa cagtatgcca    65820
atgtaggaat gaggcgtgaa taagcagggt aacaatagaa acatattctc accttgatta    65880
ttcctttggt agcttcaagg gaaattgagt ttgaggataa agtaactctt cccatgtcag    65940
cactttatct gtcctgaaac atgagaaatt ccaaatgttc aagccatgca gtttttatct    66000
agtcagatgg ttgagaagtc caggttaccc atagttgtaa tgaatacctc ctctttatct    66060
tcttaatgtt ctgctttgcc aaatgatcta taaagattac tcagtgtacc tttcagattg    66120
aggtccagca gactttcaga acactacatt taattacaga aacccaacta ataaaataat    66180
aagctcatgt tagtttcagg tgttgatttg ttttttaatgt agtcaataat atttacatat    66240
aatgactggc aacttaacag agttataata gattattcac ctgtatttgc ctttatttgt    66300
gggtatacac acatatatac atgccttaaa ctagagtaaa atcatttatg catactaaat    66360
caaatttgag agtcccaaaa ttttcaaatt gtgtatggct ggtctatatt ttctaggact    66420
gtcctttctg gtttaaatga aattaaaaat tgaattaatg atattagtct cttttaattt    66480 tctattttt tcatgattaa aaaatattaa tttccagcca ggtgcggtag ctcacgcctg    66540
taatcccagc actttgggag gctgaggcgg gtggatcacc tgaagtcagg agttcaaaac    66600
cagcctggcc aacatggtga aacccctgtct ctactaaaaa tacaaaaact agccaggcat    66660
ggtggcacgt gcctgtagtc ccagatactt ggatggctga ggcaggagaa tcacttgaac    66720
ccaggaggcg gaggttgcag tgagctgaga ttgtgccact gcactctagc ctggtcgaca    66780
gagtgagaat ctgtctcaga ggaaaaaaaa aaattaattt tccccattcc cccacccacc    66840
caccaaaaga ctccattgga gttttatttt acaaatgcat ctgctcatct acttcttttt    66900
```

```
aagtgcataa actagttttta caagcttgag tttaaatctt aactcctcaa ttcttttttct    66960 gacatagaaa tatacaggtg cattatgaaa tagctaatag tgactatttt ctagggctgt    67020
aactcaatat ttataagcat aatgatataa cctgctgaag tttgacacgt cagtatagtt    67080
cttttgttat tctaagtcat aaaggcagaa tttggaaaaa ttcacagctt tcaaatatg    67140 cagaagagga aaaattgaga ggaagcatac taaaatttct ttagccaatt ttaatcaaat    67200
tgagtttgaa acttacagga ttatgcttca aagcttgtaa tgatcgtcaa aagtagcctt    67260
attcaaaatg acacactaat ttctaccaca tctgtattct tctcattgta agatgttaca    67320
tatacctatg cttgaccaaa tggacttcct gctattttaa gatatttttc tgtgttttaa    67380 gtcttctac aaattttctc aagcatttcc ctttacctag gatgttcttc tttcactgca    67440
agtgaagaca ttctaaaaat tcctaaagca cactaccaaa agcccttcat ttggatgacc    67500
caccttccta tgagtctcca tagttgcatg tctgatggca tttattttaa ctctatgatc    67560
tgcttctaaa ttagataaaa gctctcagag agaactatga ccaattgtca ttctgtttcc    67620
catggcacct agtacagtac tctgctcaca ggctcaataa gtaatgagtt gagctacgtt    67680
tttttaaggc agagtctccc tctgtcgccc agggtggagt acagtggtgc aatctctgct    67740
cactgcaacc tctgctgctg ggttcaagtg attctcctgt ctcagactcc cgagtagctg    67800
ggactatacc accatgccac catgcctggc taactttag tagaaacaag gtttcaccat    67860
gttggccagg ctggtctcca actcctggcc tcaagtgatc cacctgcctt ggcctcataa    67920
agtgctagga caaagtttg ccattgtcat gttacgatat atattggttt ttgtccatgg    67980
tttctggttc atagctccaa tatcccttt tacagtcttt tgttagaatg tgggtgtgt    68040 tggacctcgg ggcaggcctt agaaaacaga atctctcctg ccttcctttc acttgtcccc    68100
cgagggagat ttttttttt tttttttttt ttgagacaag acttccctgt gtcacccagg    68160
ctggagtgca gtggtgtgat catagctcac cgcagcctca gcctcctagg ttcaagcaat    68220
cctcccatct cagcctccca agtacctggg actacaggca catgccacca cacctggcat    68280
tttttttttt tttttttttt tgtagagag gtttcgccat gttgcccagt ctggcctcca    68340
gctcctgggc tcaagtgatc cacccacctt ggctcaaacc accacaccca accctgaggg    68400
agattctaat cttccccacc cttctgattt tgagtcttaa aacccagag aaggtcccac    68460 cctttgcact ggggaaagga atgctgatga tcatgaagcc tccataaaaa ctcaggagga    68520
ttgagtctgg ggagcttctg gatagctgaa ccagtggagg ttcctggaag gtggctcatc    68580
cagggaggac ttagaagctc cgtgcacttt ccttatactt caccctaagc atctcttcat    68640
ctgtatcctt tgataaacca gcaaatataa gtaagtgttt cttgagttat gtgagctgct    68700
tgaccaaacg tattgaaccc aaagagggtg ttgtgggaac cccaactcga agctggttgg    68760
tcagaagttc tggaggcctg gatttgtgac ttgtgtctgt ggcaggagca tcttgggaac    68820
tgagcgttta atctacgggg tctgacactg tctccgggaa ttaaattgga ggacacccag    68880
ctagtgtctg ctgcttgtta ttggggagaa accctcacac atttggtcac aagagagaag    68940
ttttctgttt tgaatattgt tgtgatgtga gagcagagga aaaatgcatt ttggagaggt    69000
tttttcctac acagccatag gcagtgataa gaatatgatg ctttttttcca gaaaatgcta    69060 catgagacct tttataaaa tctaattttc ttcaactgag tagcatttaa actaaaaaga    69120
ataggttatt tcagtgtctc tctgtaataa catcttacaa tcacttgtca gaccatgaaa    69180
taatgttcta gaaaatcagt gaaagagctt tttaaacttt gtgacatttg acttatattt    69240
attaccaaaa agcctgaatt attattcagc acattataat tttatttaaa atttaaatta    69300
```

```
gagatgaaat acttgtaaat gtttataaga ttggtagctg tgtgggcttc cagagttaga   69360
aatgcctctg agaaaagatt tagagttttg aaagtatttt gaaaaaagaa acagaaagga   69420
atacaacatt tttcccagca ctgcttcaat aatgcagtct tcagcatcat ctcaaagcaa   69480
taactgcagt acagatgaga tcagccagtt ttttttttccc ccttatctgc agtgatttta   69540
ccatctcttc atgctacatc ttaccacaaa gagaacattg aaacatggga aagagtttgc   69600
tttgatttca accagaatgc caactcattt ctggggttct aaaccataac cttttttagc   69660
agagcagtgt agaatttta tacgatacca taaatggtcg gcctgagtaa cattttaact   69720
gtaagtcaat acctttgaag agacatgtct gacaactcag agttctattt tctccatgtg   69780
tgactaaagt acctttttcta ttaagagatc aaccaccatt tccttctact ctttgttctc   69840
cccttaaata aagttaattc agcttcaaaa tattttatga tcttgattac taactgtggg   69900
tctttagaag acaatgtaaa acatttccat gctgtgaata ttagagctag tatacttgga   69960
gtttggctag tatttctggg ggaggtagaa gaggagacat agagtacaaa tgagtatttt   70020
taaagccacg ctgactaaaa caaaaggaat gttttataca tgtttatttc atagtacttc   70080
tttgaaacag gtcgggggga ggagagttaa aatattgctt tgaattttaa tcaaagttct   70140
ttcatggaat tgttggtgct tctggtaata acagttctat aatctttgtg agttaatctg   70200
aaatgctctt tttcttcatc gtaattcagt gcttgtctta actggtggac ttatttatg    70260
gtattatgtt tataagatgg caactaaaat cagatttttt atactcctaa aagatggata   70320
cgatagaggg gaagggggt aagctacaac ttttaggttg ttggtgatat ttgaagtgtt    70380
tattgcttct gatttacatt tatatattat attcaaatat aaactttaaa agtaatgatt   70440
tgccacaggt taaagcagaa catttatatg atatttccta gatgttttcc tctacaatcc   70500
tgttttttgtt ctatgaaaaa tgccataaac ttggatcatt cactaattaa tttgaagctg   70560
ttttcaaaca aaagctaat tcatctttta gcggatttag ttataatcgt gataacagat    70620
gtatagctaa gtctgttgga caaactgttg gtcacatcaa tcttaaatgc atcatacagc    70680
gtgatgtgaa tttatgatat ttcctaggta atgttaaggt tatatggaaa ttctcttgca   70740
ggtagttaag tcttattttg aattcaaatg ttattttcaa tacatacgtg gaagtgtatt    70800
ttttgtttgt cctaaatgtt tagatttttt gagtttacaa ttttttttgtg tgttctttct   70860
ttgttcttgc ccctccctgc attctctatg aagatacatg tcagcactat gcaacactaa    70920
aataacaatc aaccaaatta tatcctatga acagacctttt ctcttcattt caaaggcata   70980
acttggatgg tctgtttagc tcatggtgaa aaaaaaagt tatgattttg tatttgggca    71040
aagtacaggt gaagagcgtg aatcattaga acagcaatat aactggaaga agatagttta   71100
gttttttacaa gttaaatttg aagctaaagc aaaacttgca taggtatgtg tcctttgctc   71160
ttgaaaatga actcagaact ctacatctga gtggttttat gaatttatac tctcctagtc   71220
cacaggttct catcagtgcc tcaagatcta tgcacagatt aaaattacat aagatatcat   71280
atactacatc tgaattaggg ttttccaaag tatgctattc catggaaata ctgtttattc   71340
agggtgctcc ataaacaatg atcctgtgtt tcattatgtc caggaaatgc cacacagcac   71400
ctttccagac atcctatcat catattaaag actttgaggc catgcattaa agaaagtttt   71460
aaattagaaa aaaaataagt tttcttgctt gagcacagaa ctttattttt tctcaggctg   71520
gttctcctttt tttaaaatta cacgttaata tcccaaagaa ccagtcccat agatagatat    71580
cacatatgat aagaatctgt ttcaatggtg ttggtgtaca tgtgtgttca ggtacctaca    71640
```

-continued

```
cattaggaca catctctagt ttattaatac tgcacttata aagagacatg gtagagacat    71700
caagaagaca tcattttagg gtggacacca ttgcctagga cctgcttctt aatgtcaaaa    71760
attcagaaac ccaattttat ctctcccgca gagttgactc gagtgaagga aattgagttg    71820
ttttaattaa actcacatga gattgatgtt taaacaaaat tgtaagttta tcaattaata    71880
atcaagaatt ctgatttta atttcaaaa tattatttat gtccactgtc cagggtactt    71940
gctttaaggg cacccagtga ttcttgaaga tgaagagtct taggaatatt tattttctag    72000
acctcaatga agaaagcttt ttaatcatcc tgccccatag aagaatttat gttcctagtg    72060
atgtgatcat attggccaat ccagtgtttc ttttccaagg acagtactga taaggagcac    72120
caaatctacc tctttgtcct gaacagatca tctccatcta ttcatagttt ggctcagaag    72180
ttggacaagg ctgcattta tatctacttc ttcctcatgt cggctatgcc atgccgtttc    72240
gttcttttag cttgtttact tatgtgtaaa atgaggtaaa aattcaccc ttcaaaccga    72300 aagtggtctt cgtgatgagt tatttaattg aagccccagt agatatttat cattgccagt    72360
tttagagaat catagcattt tagaacacaa gatgacctta gatgtaatca tgttcattcc    72420
cctcgtatta taaattttta aaaattgaga tgtgggtgg ttgtgacttg ctcacaaacc    72480
cacatttaga accaaaactc agcattcttg ttctgactgt gtctatgtcc tgtaggtata    72540
tgtcttgtct tctcagttaa ataattaaag attcttaaag atagagacca tattttatgc    72600
aacttctgga tcccataaat tatgtttcca gaagaacctt ttgtaatgaa aaatatata    72660 taatgtctat attatatata tagtctatta ctatttgat aatctaaaac atgctatata    72720
attttaggcg atcttaacct atttatcaga gcttttcaga tcaaagaaaa ttagagtaat    72780
cttcatcatg tatgggaaca ttgatgtatt tttctgatga acacatggtt atatgatact    72840
cttttaaagc atctgtatta ctcttttcttc tgatagactg gttattttgt ttatgttatg    72900
aaataatgtt ggcagctttt cattagaact gatacatatt gaaatttctt aaattgatag    72960
ctcatggatg tgcagttggt ttaatggcat ctccattatt aatctttaag aagatcttca    73020
tcttactctc aaaataacc gtaatatcct acaaattaac taaaacatga tcattgctag    73080
ttgttccaaa ataggaagaa taaaaatgac cagattgtta tggtaaccag ttgattaaga    73140
ctagatcaat aggaaaacga atttattcaa gtctgtacaa aacttctcca aaacatagat    73200
ggcatgcctt tgaggcaat ggtagggaac aaaatatttt tgagaaggag cagatttag    73260 ggatacagta cagtacataa ttgccaaaat gcttgtgtta caaggattcc tggtacagag    73320
tttttaaata aaatgctagg tatgtcatgt ttgtttcaca ttaatattgt agagtccct    73380 ggggatgtga caatttagtt gaccaactct aatatagtta atttctacct tttgatagct    73440
ttgtggggtt ttgtttgttt gttttttgtt ttgccattct tgattttagg gctgaagata    73500
tgagacaatg tatcaaacag taaagaatta tgcattgatt aagatcatct tggtgaatta    73560 gatgttatt atataactcg acttaagac tttgttcaga tctcactatc ttaatgagat    73620
ttaccctcat tatatagtat ttaataggc aaccactcc cgatactctt gattcctcgt    73680
tagctgccct attattctt tgttttccc ttagcactca acattttctt accacaccac    73740
ataatttact ttcttattgt gtttattgtt tttctcctca ttagaatatc aggtccaaga    73800
agacaggagt atttatctct tttgttcagt ggtgtgttac tggtgactac tagagtgcct    73860
gacacataga atatgttcaa taatatttcg ttgcatgaaa gaatgaatac cttgacagat    73920
tatttttata actctaccag tgtcattata taactacact gaatgattat gagccctcct    73980
agaaattaca taaagttctt atatattatt agaacccatt tgttggcctt atgtaatggt    74040
```

```
tctattggaa aaatcatacc tccgtatata aaaatgaaag tattttttt ctacaattgc    74100 ccctcatata tactattata gtctccttca ccccattcag ccattaatgt cttcttgacc    74160
aggtaacata atttttacag caccttttgg ttattagaac aattttattt gtctttcaaa    74220
ctcagtccta ttcattttaa aactcccaac tcaagcctga gtcagtgttc ttctcccagc    74280
acaaacttaa acactggctc caacccttgg agttgaaagt aggggagcct cactcctgat    74340
acctcccctc cccctctacc gtgagcacca gtgcctagga gattgggcag gactgaggaa    74400
ggatgaaaag gagctcaggg ctccttaagc acctgaacaa gactggagga ctttggatgt    74460
tgctattttt ctgcctggca ttgactggct attggacgcc ctctgtgagg caggcatccg    74520
aatactggct ttcttgacat atatggagcg ttctttagag aggcctacaa gggctctcac    74580
tgcacagtac cctgatagga gagatctgtc cttatttctt ctatcaccat agctacttca    74640
gctttgcctg ctgagtccac cccacagtct ctttctgctg gggcatcctt gccctggaca    74700
gattcttaga gcatgaccaa gcctaaacaa cttctgcaat ttttctaagt acactttat    74760 ttaattgaaa gtttcaagca ttggataata taaatgtatc ctagacagtg ttccagtaag    74820
gacaaccagc tcacaattat ccattctaat aatgggagtc aactgaaata gaaaaatata    74880 gattttaaa ataatttatg agaaacaaat atttgtgaca cagtacattt ctaattatgt    74940
ttatctttat tattattatt atcgtttcct tcagtacaca ctagtttggt gagacttgga    75000
gaaaggccag gaataagccc aaattcaaaa aacaattcca ggattaacag ataagtggat    75060
aatagagaat tgacaaaaga tcatgctcat tttaccaata agaaactggt tggttaactt    75120
gggttgcaaa ctgaaagcag atttatacta aactggcagg tgtctccaga tcttaaatgc    75180
agatctctat ctctgagtta atctgcctct catcttcaat ggcattcctc tgaattttc    75240 tccctcaaat aatctatata ttattaaatt ttgtttatac tgccatttta agaaacagat    75300
tttaaaactt taaacatggg aattaaatag gccctactga ggattatgaa aaacctgaca    75360
aaacctccta tgcacatgat ttagattagg agcagtgcac acgctgtatg tgtatgtgca    75420
gctacttgtc caattaacac cttttcagaa atggaggaac tttctctgag ctttgaca      75480 tatttgtgtg ttcagcagtc cttttctttt tttttattt ttatttttt tattattata    75540 cttaagtttt tagggtacat gggcacaatg tgcaggttag ttacatatgt atacatgtgc    75600
catgctggtg cgctgcaccc actaactcgt catctagcat taggtgtatc tcccaatgct    75660
atccctcccc cgtccccca ccccacaaca gtccccagag tgtgatgttc cccttcctgt    75720
gtccatgtgt tctcattgtt caattcccac ctatgagtga gaatatgcgg tgtttggttt    75780
tttgttcttg tgatagttta ctgagaatga tgatttccaa tttcatccat gtccctacaa    75840
aggacatgaa ctcatcattt tttatggctg catagtattc catggtgtat atgtgccaca    75900
ttttcttaat ccagtctatc attgttggac attagggttg gttccaagtc tttgctattg    75960
tgaatagtgc cgcaataaac atacgtgtgc atgtgtcttt atagcagcat gatttatagt    76020
cctttgggta taaacccagt aatgggatgg ctcagtcaaa tggtatttct agttctagat    76080
ccctgaggaa tcgccacact gacttccaca atggttgaac tagtttacag tcccaccaac    76140
agcgtaaaag tgttcctatt tctccacatc ctctccagca cttgttgtgt cctcactttt    76200
taatgatcgc cattctaact ggtgtgagat gatatctcat tgtggttttg atttcattt    76260 ctctgatggc cagtgatggt gagcattttt tcatgtgtct tttggctgca taaatgtctt    76320
cttttgagaa gtgtctgttc atgtgcttcg cccactttt gatgggattg tttgttttt    76380
```

```
tcttgtaaat ttgtttgagt tctttgtaga ttctggatat tagcccttg tcagatgagt      76440 aggttgcgaa aattttctgc cattttgtgg gttgcctgtt cactctgatg gtagttcctt      76500
ttgctgtgca gaagctcttt agtttaatta gatcccattt gtcaattttg gcttttgttg      76560
ccattgcttt tggtgtttta gacatgaagt ccttgcccgt gcctatgtcg tgaatggtgt      76620
tgcctaggtt ttcttctagg gttttatgg ttttaggtct aacgtttaag tctttaatcc      76680
atcttgaatt gattttgta taaggtgtaa ggaagggatc cagtttcagc tttccacata      76740
tggctagcca gttttcccag caccatttat taaataggga atcctttccc catttcttgt      76800
ttttctcagg tttgtcaaag atcagatagt tgtagatatg tggccttatt tctgagggct      76860
ctgttctgtt ccattgatct atatctctgt tttggtacca gcaccaggac catgctcagc      76920 agtcctttt caagagatgt gaagtacatc ttcacagatt tttaaatatt tagatagaaa      76980
gttcttacag aatgagaaat aaaaagttag ctttgcctta aaatattaa ttcaccttat      77040 attctccata cttaatccat ataggaaaca ttatattcca ggtctaacat gtggcttgct      77100
tacattaatt ttgctgttga aaaatatatg ttttggatta tgttttaaa attttagctt      77160 taatatttaa atattaaata atgttaactt taaattaacg aagaatagtt tttaatttta      77220
taagaaatgc cctataaaaa acactttctt tacctcaaga gtgagacttg gcaaccatac      77280
caatattaca tagtaatttt aaagtcaaac gaaatggaga gaacttaata gatacagaag      77340
ataagaattt aaactaacat tttgctcggg attttagaac actatacaga gggaaattta      77400
gtagacaata atgaagtcca tagcattgca cacatcttga aataagtgta taattgacac      77460
aagctatgtc ccatgttgat aggaagaatc caaaatagtt ttggagaata atgccatcta      77520
tgcaggaggt gtggccatat acatcatctt tactcagtgt ttttcatgtc aataaatatt      77580
taattcctaa cactctgaat tactaataga ggtgaagcct gtcagtggaa gtgacagaga      77640
gatacacagt gattcccgta agtttgatcc tgaaacacag tgcctttagc agatatagtt      77700
cccataagca agcagtctga agtatttacc ctcagtaatc tgaatgtata aataaacagg      77760
attcatgatg gtagagtaat ttatatatac ttgtagtatt aggacatgca aaacttattt      77820
tatggaaaaa aataatttac taccttatag tatggcaact atacaaatct ataaattgac      77880
tcttttgtcc ccttgaaaaa aagctgacat aaaatttaaa tgatgtgtat ttttcttag      77940 agcaataaaa gatatacccc cacctagaaa agcaataaac caaaaaataa aacaaaaaca      78000
aaatcaagcc ctcttcacaa atttgagcat atctacagct ttatgtggtg agagatacag      78060
ctaccattct tgagtaatcc gaagagtcaa atggtatgga gcaaaattac agtcctaaat      78120
gcatattggt gaaatgagat gctgatccat ttgcacacta atgtgctatt tttaagtcat      78180
gcatcatagc atcttcaaag aggcctgtca taattatgat ggattagact gcagagtcag      78240
tcctagatgc agtaattgtt tcacagatgc tgccaatgcg actagaattt ataataaatt      78300
attttcagag aggcgggaga aggaacaaaa tcaaaggaaa actgctgtgg ctaaaacctg      78360
ttttggtctt aggaaaccaa aatgttagct agtagtcaaa aggccagtat tttcaactga      78420
gataaacatg cttcattaat acatgcctct gacatagaag ataaaggtta acataattga      78480
catatcagcc agtctctctc tctctctctc tctctctctc tctctctctc tctctgtctc      78540
gtagcttatg aaaatttatt ctggggcatt agctgaaatt attgagtggc catataattg      78600
ttgcatgttt ctatttatgt taaattgcct ggttataatt tgacctttag aatttctgaa      78660
aaaaatggtg gtatttatag taaatagaaa tattcttttt ggttccttgg aagcccatgc      78720
attacaaaga acattagatt attggaataa aaggatagac atacataata tgactagtgg      78780
```

```
gatctaaatt ataaccttt aaaattgtaa tttaattagt ctgtcattta ggcaaatgat    78840
aatttctaaa actgccttt tagacttaaa aaaataccaa agttcttata actttagcat    78900
tatgttttgt tcattcttaa agtttaattc actttgttgc cttttggta aacctatgaa    78960
gaaatctcat gctgcaccat atagtaaaaa atcgtgtgtg tgtgtgtgtg tgtgtgtgat    79020
ttgaataatg agctatgtgt tatattttga taagcaaaga taagtttata gtgaagcaga    79080
taaacatgcc atgtatttc ctaggttaag ggttcaataa tcagaagagc ttctacaact    79140
catttgcctt ctcactagtt tttttgaaat tgcgctctat gagttttta tgtggtgttc    79200
tctgtacttg ctgactactg atgcacattt ctccttaggt cactggttct cctccctcag    79260
caatgttgta ggtagctttg atgaacattc gttgtcagcc ttttaccttt gacttagtgt    79320
ttttctctca tactacggca agaagaaatg aagttaaatt ttacaagagt gacttgggtg    79380
gctgatatgc ccacattgac agggacaaga gctctagtct tccctctcc tgtattccca    79440
tggcacttca gtagtctcat tgcctcaaca taaccacagt tcagggcagt agaggatgtt    79500
tgcatctttg tgttagctcc atgccatggc aactgcactg agtgaggatt caactcagtg    79560
cagcaggact gaaaaaataa atgaactaat gtgtcttgag ctccaattct ctgagtgaca    79620
ttatcagggg agattcataa atcatcctca aatattctag agaaaaatca tcagcagtcc    79680
agcattgcaa agataatctg ggaaggtggc aaagaaggga tcagaataac tctgtggcag    79740
cttcaaattc catgtcctaa agtttacgt tttctttttt attctatccc aaaccacata    79800
aagaaatgat tgttggcaa aagacatgca aaatgcccctt aatcatctta ataattacag    79860
acctacagat acgtagccaa atacttgtt ttttaatcct aaaccttaaa aaaaaagctt    79920
aaattgttgg ctaaatgtga atttaataac aaaacttact cctttaatta tgcacttgtc    79980
ttagtattgt gtggtgggaa gagctttaga gagctgccag agtgcttagg cctagtccct    80040
gtgggagcct ctgtttttggt gcttcaccat gggcagattc ctcagttttc acatcttaa    80100
aatgagaaaa tggtactaga tccttgctgc tactctgaaa tgtttataca ttgttaggac    80160
cattgttaca tattattact tatatttgag tgtcaccta gaatttctta gccgtgtgat    80220
atggtttggt tgttggctcc tctaaatctc ctgttgaaat ataatcccca gtgttggagg    80280
tgggggcctg gtgggaagtg tttggattat tggggcagat ccctcatggc atggtgctgt    80340
cctcctgata gtgagttctc aagagatctg gttaagggtg tgtggcacgt cccctccct    80400
gtctccttcc ctccctctct ccttccctcc ctctgtcctt ccctccctct tcctccctct    80460
tcctctctct ttttctccca ctccagccat gttagatgcc tgctcccctt ttgctttctg    80520
ccatgattat aagttttgta aggcctcacc caaagcagat gccagtgctt gcctcctat    80580
acagcctgca gaaccatgag ccaattaaac ctatttcctt ataaattacc cagacagcta    80640
tttctttata gcaactcaaa aacagcctaa cataccttc aaaaggttaa aatgctattt    80700
agtcattcca gaagcaagat ctctttgtcc agaattctgg aaataaagat gccaaaataa    80760
tatggcatgt atttgatctc agggaattt catttttca aaaggaggaa aaaagagtaa    80820
tataattttt taatatttg gtagctctaa cagtgcttag aaccagttct caagagcaca    80880
ttgtgaaact ttcaggaatt gcatgagctg taggttgata acatgatgcc agctataacc    80940
cataagagca tctcctgagg aatatgttaa aaactgtatt cattcttaaa ttttaactaa    81000
atgcaatgag tgaagtattg acatcatgaa aatcatccct gggtaaacaa ttagtcactc    81060
caggttttcc caaaggttct tctgtctctg ttcttgtata taaacttcgt aaccagttta    81120
```

```
acaaccccaa aaaaggcctt aatttttgatt ggccagcatc ctcttaggaa agacattgcc    81180
atcctcttgt aaagttgctt ctcattctaa aataagaatt gtttccatct agggaatgat    81240
ttttataggt agaatcttat ttggcatgga ctcttttgca tacagtgaat tacaatgtgt    81300
agaccttcaa tagcaaggtg tttgaatatt tagttgcaca atagagcagt atcttaatat    81360
tgtataccat attaattttg tgttctctgg tgtaagaaaa aatagaagga tgtttaattt    81420
caactaaaaa atcaatcatg ataattcaaa atatttctga tgagtcattt ataagagcag    81480
atatgaatta aaattatatt tttgttctta gtctctgaga agcaaaaatc acacaaataa    81540
tctccatagc aaaaatttat atttatctga aaaacagttt aactttgaaa aacttttctt    81600
tgcaatcatt taaattcata aaaaaaattc attaactcta ctttcactga atagcaggtg    81660
aatagcaggt caatatctac aaaaattcat ctttgaagat tttttatct tacgcaaaaa    81720 ttattgactt catgtagact ttttatgcaa gcttgaaaac actgtgtaaa tgaccccata    81780
aaaactacag catgaaagct ttttcagtat ttctacaatg agcaaatgc ataggtctca    81840 tttccttctc ttttattaag caaaataata ctttatcaac atcagtatgc aagcactaag    81900
agcttgaaag agtactgtgc aagtgggtta ctggatcata atattccagg gtatgtatat    81960
aaaaagtgtg atttagcaca tattaaagta aaagaaaata ttgcattttt ctccttctaa    82020
aatggcagtt tattagttta aatttcctga aataagattt aaagaccaat aacaaatttt    82080
cctcattcta acatataact ttcctgccct tcttgtgaaa aagttaacca ttaaacttt    82140 cacacaaatg gttgtataaa ggacttgctg tcacagacaa aatagttctg tataatgttt    82200
aaaaatggcc attgtgttta aaactccata ttgaaataca tttcttttt agtcaccttc    82260 atttcttagt agctattatt atactcaaag gatttgccct tgacacttta aagaatgtcc    82320
aaaattatgt ggaatggatt ataataaaag ataatatatt aaatgcttaa aatatttat    82380 accttagaaa gtagaaaaac atgtattatg tacagatcct acaaatttta tataatttat    82440
cataaatgta cacatgtata tacatgtaaa taccttttga ttgctctgta tatgaattgg    82500
tgttttacag ttaccaaaag aaaagtgcct ttttttggta gtatctggac aggtaattga    82560
ctttcttcct gcaggattta tttagattta tgtctatgct ccttaatttt tgaaaagtga    82620
tagtgtcctg attttggaga agcctctcat atcaaagact acaaatcaat tttcatgatt    82680 ttaaaccta aagtttcttt attaggtgtt attgatgatt aaaagccatt gtctcaccca    82740
aattttctac ttgttcaata gaaacataat gtaagccaca tggaatttta catttctag    82800 tactcacatt aaaacaagtg aaaaagaaac aaattgatga tacgtttgat ttaacccaat    82860
acatttaaaa tagttcaaca tgtattaaat attttttgag tattttgtg ttttttaac    82920 actaaatctt tgaaatccaa actaaatgtt ttcatagata ccacatctca atttggacta    82980
gacacatttt aagggctcaa tagctatatg tgactagtca ctgttggatg atgtatatct    83040
agaccatctc ttaatgtatg gaaggaagta aatctagcag aaataaaaac atcactttgt    83100
tttctttgtc caatatgagt tataacttta tttttttgag acagagtctc gctctgttgc    83160
caggctggag tgcagtggcg cgatctcggc tcactgcaac ctccgcctcc tgggttcaaa    83220
tgattctcct gcctcagcct cccaagtaac tgggactaca ggcatgcgcc accatgccca    83280 gctactttt gtatttttag tagtggcggt gtttgaccac gttggccaag atggtctcga    83340
tctcttgacc tcgtgatctg cctgcctcag cctcccaaag tgctgggact acaggcgtga    83400
gccaccgtgc ctggccttt atttatttta ttaagtaata cacatgcttg gaagttattt    83460
aaaaaaaaaa aaaaggaata gttaaaagta atcccccctcc cagtgctttt ctccagctgc    83520
```

```
cccattcctt ttcctggagg caaattatta tggccagttc attatatatt ctccagagat   83580 gattttttt tattttacaa aggtataggt tgtagcattt ttatataaac tgttgtgtag    83640
cttcctttat tccatttaat tactgggaga tacttccatc tgaaaatata gagatactaa   83700
ttttaatagc tacatggtat tatattgtgt ggctgtacca taaattattt aacataaccc   83760
ttattgatgt aggttgtttc taaccttta ttactgcaaa agattgtgcc tacatcattt    83820
aatgtatata tgagcatatt tgtcagatat atatatatat attttttgag acagtgtctc   83880
actctgtcac ccaggctgga gtgcagcatc acaatctcac ctcactgcag tgtccacctc   83940
ctgggttcag gtgattcttc ttcctcagcc tcccaagtaa ctgggattac aggtgcctac   84000
caccatgccc tgctaatttt tgtatctttt taggagagac gggatttcac catgttggcc   84060
aggttggtct agaactcctg gcctcaggtg atccactggc cttagcttcc caaagtgctg   84120
ggattatagg cgtgagctac cacacccagc ctgtcagata aattcttaaa agggtcaagg   84180
aaagtgtttc tgaaattta tacatattgc caaattgtca tcctacatga tatttgtggc    84240
agttttgact ctcaaaagcc acatgagaga gtatctgttt tcccacatgc ttgccaaaca   84300
tagtatagta tcaagcttac tgatcttcac taattggaga agagaaaaaa actgtacctt   84360
gttgcagttt taatttgcat ttcttttat gagcaatagt agatatcttc ttaaatactt    84420
aagagccatt cacatttcat tttctatgaa ctgtccatgt cccttgtcca ttttttagta   84480
tgtggttatt catttatttg taggcgtcct atatgttaag aaaagtttta tacaacttt     84540 aactcttttt acatgtttat tttggcacat ataaatttta gcaaactttc ccatctttta   84600
tgacttctag attttgtttc acaaaaaaag agcttagcca gtcattagat tttttaagt     84660 tttctcagat tgttttaac ttttgggggg gttttatttc ctgtattcaa atattaaatt     84720
catctagaat ttatcttaaa gtgtaaggga atgatcccac tttatcattt tttcaggaga   84780
ttacccagtt gttctaatat caagtatgtc tttgaaatcc catccttatc ttgtagcata   84840
tttctgtggt ttgggtctat ttttgaacat tctgttttat tccattgatc atattaatat   84900
tatatgtgca aacacaaact attttaagta tagtagcttt gttgcttta aatatctttt     84960 aatttggcta ctaggcccca tacaattctt tttcagaata ttcctggcta cccaatttgt   85020 ttattttttcc aaatgaactt tggagtcaac ttccttaatt cctcaaaata ttctgcaagt   85080
acttttagta agagtatatt aagtgaataa tttgacaact atctaagaac atattatagc   85140
ttttcccttg ttttgttttt gtacttatat attagtatag ttttaaagtt atattaaaat   85200
aggtcttcca cattttaaaa acttattcct agtgtattaa tttcttctat tataactaca   85260 gtatttatt ccagtaaaac ttctgactgg ttgatgctct tataaatcaa ggctataaat    85320
ttttcttcag ctactttgct gaattctcac aaactgtaac cattttttac ttgattctct   85380
aggttgacca gtatataatc tttttatctg taaacaataa ctttagcgtt gctttcaaca   85440
tctatattct tattctatttt cattttcctt gtttatcaag aaatagctgt tttaatagag   85500 ttgttttcg cccaaaaaga aaatagtctt tcttttcta cttatatctt taaaataaat     85560
gtaatgagaa agactgtggg aaaataaagc agacaccta tacaatggat taatttttt     85620 agtgccattt cttctggctt tctctattat tgggactctg aaatcttcgt tagtactact   85680
ctcaaaaatg ttcgaatgaa tgcaatcaga ttcaagggta caagtgcagg ttatataggt   85740
gaattgcatg cctggggggt ttggtgtaca gactattttg tcacccaggt aataagcgta   85800
gtacttaata ggtagttttt tgatcctctc ccttctccca tcctcaaagt atccctgctg   85860
```

|  |  |  |  |  |  |
|---|---|---|---|---|---|
| tctgttgttc | cccctctttg | tgtccatgtg | ttcttgctgt | ttagctgcca | cttaagagaa | 85920 |
| catgtggtat | ttttctgttc | ctttgttagt | ttgtttagga | taatggcctc | cagctccatc | 85980 |
| catgttgctg | cacagaacac | gattttgtgt | ttctttatgg | ctgtgtagta | ttccatggtg | 86040 |
| tatatgtaac | actttcttta | tccagtctac | tacttacgga | catttaggtt | gattccatgt | 86100 |
| cttcgctatc | attaatagtg | ctgtgatgaa | catacgtgtg | caatatgcct | ttatggtaga | 86160 |
| atgatttata | tccctttggg | taatatgccg | aataatggga | ttgctcggtc | agatggcaat | 86220 |
| tctaagtcct | ctgaaattac | cgcactgctt | tccacaacag | ctgaactagt | ttacattccc | 86280 |
| acaagcaata | aggggataag | tgttcccttt | tctctgcagg | aatgattaat | tcttttagag | 86340 |
| agtcaaagat | ggaatcctag | ggaagatgat | atctgaggca | ggtttagagt | cattgggcaa | 86400 |
| ataaggggat | taagaaggca | ttctaggcag | acagaaaacc | aaaggcatga | agctctgaaa | 86460 |
| cagcttacta | tgtttggata | tttataagct | gttgttattg | ttggagtata | aactgtaaga | 86520 |
| gagagtagga | ggacagaaaa | aacagcctgt | atgcgggggg | aagaaaacat | ttaaacagaa | 86580 |
| attctcaaaa | gatttgggca | gccagcccct | ctagagaaaa | acatagaatc | acctagaaag | 86640 |
| ggttttcat | aaagtacact | tttcatcacc | cctattctgt | cacctggaat | attgataaca | 86700 |
| ctgaagggag | tgtgccttat | ctctcaggtg | tatttggatg | aaatagtttg | agaaccatgc | 86760 |
| aggcaagttt | aagccagtgt | gttaaagaga | atatgacatc | agatttgcat | tttacaatct | 86820 |
| tcctttttgat | aacaaggga | accttaaagg | gctggagggg | aagggcagac | ggggctaggg | 86880 |
| gaggagaacc | cttttaaaaa | gctactgcag | gtggggtgcg | gtggctcaca | cctgtaatcc | 86940 |
| cagcactttg | ggaggccaag | gcaggcagat | cacctgaggt | caggagttca | agaccagcct | 87000 |
| ggccaacata | gtaaaacccc | atctctacta | aaaatacaaa | aattagctag | gcatggtagc | 87060 |
| aggcacctgt | aatctcagct | acttgggagg | ctgaggcagg | agaattgctt | gaacctggga | 87120 |
| ggcagaggtt | gcagtgagcc | aagattgtgc | cgctgcactc | cagcctgggc | aagagagtga | 87180 |
| gactccatct | caaaaaaaaa | aaaaaaaaag | ctactgcagt | agatcaggag | gaggcacagt | 87240 |
| gataaagaga | agatctgagc | tatgaagtgg | cagtcaagat | gattaaagga | atatatagga | 87300 |
| agtacagttg | atagaactta | gcaagtgatt | aggtaaatga | agtgctagag | aaaataaagg | 87360 |
| ggatatttt | caattgtttt | tagcattttg | gcaaaaaatt | atttaggaat | gaaattgatg | 87420 |
| ctagtaacta | agagtatgaa | cttcccacat | tagctggtaa | ttttgatcac | ccttgttctc | 87480 |
| catgaccata | aatattttag | agttgctatg | aagacaagaa | tgtttatttc | ctgagtagct | 87540 |
| gtcagttgtc | actatgaaac | atgaaaataa | atatcagttt | gctatgtcta | ggtattccga | 87600 |
| tatttatcca | caattattcc | ttaagatata | ttagtatttt | tatagataga | tagatagata | 87660 |
| gatagaaata | aacacatttt | aattttttgtt | tccatgctct | ttagaattca | actgagggc | 87720 |
| agccttgtgg | atggccccga | agcaagcctg | atggaacagg | atagaaccaa | ccatgttgag | 87780 |
| ggcaacagac | taagtccatt | cctgatacca | tcacctccca | tttgccagac | agaacctctg | 87840 |
| gctacaaagc | tccagaatgg | aagcccactg | cctgagagag | ctcatccaga | agtaaatgga | 87900 |
| gacaccaagt | ggcactcttt | caaaagttat | tatgaatac | cctgtatgaa | gggaagccag | 87960 |
| aatagtcgtg | tgagtcctga | ctttacacaa | gaaagtagag | ggtattccaa | gtgtttgcaa | 88020 |
| aatggaggaa | taaaacgcac | agttagtgaa | ccttctctct | ctgggctcct | tcagatcaag | 88080 |
| aaattgaaac | aagaccaaaa | ggctaatgga | gaaagacgta | acttcggggt | aagccaagaa | 88140 |
| agaaatccag | gtgaaagcag | tcaaccaaat | gtctccgatt | tgagtgataa | gaaagaatct | 88200 |
| gtgagttctg | tagcccaaga | aaatgcagtt | aaagatttca | ccagttttc | aacacataac | 88260 |

```
tgcagtgggc ctgaaaatcc agagcttcag attctgaatg agcaggaggg gaaaagtgct    88320
aattaccatg acaagaacat tgtattactt aaaaacaagg cagtgctaat gcctaatggt    88380
gctacagttt ctgcctcttc cgtggaacac acacatggtg aactcctgga aaaacactg     88440 tctcaatatt atccagattg tgtttccatt gcggtgcaga aaaccacatc tcacataaat    88500
gccattaaca gtcaggctac taatgagttg tcctgtgaga tcactcaccc atcgcatacc    88560
tcagggcaga tcaattccgc acagacctct aactctgagc tgcctccaaa gccagctgca    88620
gtggtgagtg aggcctgtga tgctgatgat gctgataatg ccagtaaaact agctgcaatg    88680 ctaaatacct gttcctttca gaaaccagaa caactacaac aacaaaaatc agttttttgag   88740 atatgcccat ctcctgcaga aaataacatc cagggaacca caaagctagc gtctggtgaa    88800
gaattctgtt caggttccag cagcaatttg caagctcctg gtggcagctc tgaacggtat    88860
ttaaaacaaa atgaaatgaa tggtgcttac ttcaagcaaa gctcagtgtt cactaaggat    88920
tccttttctg ccactaccac accaccacca ccatcacaat tgcttctttc tcccctcct    88980 cctcttccac aggttcctca gcttccttca gaaggaaaaa gcactctgaa tggtggagtt    89040
ttagaagaac accaccacta ccccaaccaa agtaacacaa cacttttaag ggaagtgaaa    89100
atagagggta aacctgaggc accaccttcc cagagtccta atccatctac acatgtatgc    89160
agcccttctc cgatgctttc tgaaaggcct cagaataatt gtgtgaacag gaatgacata    89220
cagactgcag ggacaatgac tgttccattg tgttctgaga aaacaagacc aatgtcagaa    89280
cacctcaagc ataacccacc aattttttggt agcagtggag agctacagga caactgccag    89340
cagttgatga gaaacaaaga gcaagagatt ctgaagggtc gagacaagga gcaaacacga    89400
gatcttgtgc ccccaacaca gcactatctg aaaccaggat ggattgaatt gaaggcccct    89460
cgttttcacc aagcggaatc ccatctaaaa cgtaatgagg catcactgcc atcaattctt    89520
cagtatcaac ccaatctctc caatcaaatg acctccaaac aatacactgg aaattccaac    89580
atgcctgggg ggctcccaag gcaagcttac acccagaaaa caacacagct ggagcacaag    89640
tcacaaatgt accaagttga aatgaatcaa gggcagtccc aaggtacagt ggaccaacat    89700
ctccagttcc aaaaaccctc acaccaggtg cacttctcca aaacagacca tttaccaaaa    89760
gctcatgtgc agtcactgtg tggcactaga tttcattttc aacaaagagc agattcccaa    89820
actgaaaaac ttatgtcccc agtgttgaaa cagcacttga tcaacaggc ttcagagact     89880 gagccatttt caaactcaca cctttttgcaa cataagcctc ataaacaggc agcacaaaca    89940
caaccatccc agagttcaca tctccctcaa aaccagcaac agcagcaaaa attacaaata    90000
aagaataaag aggaaatact ccagactttt cctcacccc aaagcaacaa tgatcagcaa     90060
agagaaggat cattctttgg ccagactaaa gtggaagaat gttttcatgg tgaaaatcag    90120
tattcaaaat caagcgagtt cgagactcat aatgtccaaa tgggactgga ggaagtacag    90180
aatataaatc gtagaaattc cccttatagt cagaccatga atcaagtgc atgcaaaata     90240 caggtttctt gttcaaacaa tacacaccta gtttcagaga ataaagaaca gactacacat    90300
cctgaacttt ttgcaggaaa caagacccaa aacttgcatc acatgcaata tttttccaaat    90360 aatgtgatcc caaagcaaga tcttcttcac aggtgctttc aagaacagga gcagaagtca    90420
caacaagctt cagttctaca gggatataaa aatagaaacc aagatatgtc tggtcaacaa    90480
gctgcgcaac ttgctcagca aaggtacttg atacataacc atgcaaatgt ttttcctgtg    90540
cctgaccagg gaggaagtca cactcagacc cctcccccaga aggacactca aaagcatgct    90600
```

```
gctctaaggt ggcatctctt acagaagcaa gaacagcagc aaacacagca accccaaact    90660
gagtcttgcc atagtcagat gcacaggcca attaaggtgg aacctggatg caagccacat    90720
gcctgtatgc acacagcacc accagaaaac aaaacatgga aaaggtaac taagcaagag     90780 aatccacctg caagctgtga taatgtgcag caaaagagca tcattgagac catggagcag    90840
catctgaagc agtttcacgc caagtcgtta tttgaccata aggctcttac tctcaaatca    90900
cagaagcaag taaagttga aatgtcaggg ccagtcacag ttttgactag acaaaccact     90960
gctgcagaac ttgatagcca caccccagct ttagagcagc aaacaacttc ttcagaaaag    91020
acaccaacca aagaacagc tgcttctgtt ctcaataatt ttatagagtc accttccaaa     91080
ttactagata ctcctataaa aaatttattg gatacacctg tcaagactca atatgatttc    91140
ccatcttgca gatgtgtagg taagtgccag aaatgtactg agacacatgg cgtttatcca    91200
gaattagcaa atttatcttc agatatggga ttttccttct tttttaaat cttgagtctg     91260 gcagcaattt gtaaaggctc ataaaaatct gaagcttaca ttttttgtca agttaccgat    91320
gcttgtgtct tgtgaaagag aacttcactt acatgcagtt tttccaaaag aattaaataa    91380
tcgtgcatgt ttattttcc ctctcttcag atcctgtaaa atttgaatgt atctgtttta     91440
gatcaattcg cctatttagc tctttgtata ttatctcctg gagagacagc taggcagcaa    91500
aaaaacaatc tattaaaatg agaaaataac gaccataggc agtctaatgt acgaacttta    91560
aatatttttt aattcaaggt aaaatatatt agtttcacaa gatttctggc taataggaa     91620 attattatct tcagtcttca tgagttgggg gaaatgataa tgctgacact cttagtgctc    91680
ctaaagtttc cttttctcca tttatacatt tggaatgttg tgatttatat tcatttgat    91740 tcccttttct ctaaaatttc atcttttga ttaaaaata tgatacaggc atacctcaga     91800
gatattgtgg gtttggctcc ataccacaat aaaatgaata ttacaataaa gcaagttgta    91860 aggactttt ggtttctcac tgtatgtaaa agttatttat atactatact gtaacatact     91920
aagtgtgcaa tagcattgtg tctaaaaaat atatacttta aaaataattt attgttaaaa    91980
aaatgccaac aattatctgg gcctttagtg agtgctaatc tttttgctgg tggagggtcg    92040
tgcttcagta ttgatcgctg tggactgatc atggtggtag ttgctgaagg ttgctgggat    92100
ggctgtgtgt gtggcaattt cttaaaataa gacaacagtg aagtgctgta tcaattgatt    92160
tttccattca caaagatttt ctctgtagca tgcaatgctg tttgatagca tttaacccac    92220
agcagaattt cttttgaaaat tggactcagt cctctcaaac tgtgctgctg ctttatcaac    92280 taagttttg taattttctg aatcctttgt tgtcatttca gcagtttaca gcatcttcat     92340
tggaagtata ttccatctca aacattcttt gttcatccat aagaagcaac ttcttatcaa    92400
gttttttcat gacattgcag taactcagcc ccatcttcag gctctacttc taattctggt    92460
tctcttgcta catctccctc atctgcagtg acctctccac ggaagtcttg aactcctcaa    92520
agtaatccat gagggttgga atcaacttct aaactcctgt taatgttgat atattgaccc    92580
cctcccatga attatgaatg ttcttaataa cttctaaatg gtgataccatt tccagaaggc    92640 tttcaatgta ctttgcccgg atccatcaga agactatctt ggcagctgta gactaacaat    92700
atatttctta aatgataaga cttgaaagtc aaaagtactc cttaatccat aggctgcaga    92760
atcaatgttg tattaacagg cacgaaaaca gcattaatct tgtgcatctc catcggagct    92820
cttgggtgac taggtgcctt gagcagtaat attttgaaag gaggttttgg ttttgttttt    92880 tgttttttt ttttgttttt tagcagtaag tctcaacact gggcttaaaa tattcagtaa     92940
actatgttgt aaaaagatgt gttatcatcc agactttgtt gttccattac tctacacaag    93000
```

```
cagggtacac ttagcataat tcttaagggc cttggaattt tcagaatggt aaatgagtat   93060
gggcttcaac ttaaaatcat caactgcatt agcctgtaac aagagagtca gcctgtcctt   93120
tgaagcaagg cattgacttc tatctatgaa agtcttagat ggcaccttgt ttcaatagta   93180
ggctgtttag tacagccacc ttcatcagtg atcttagcta gatcttctgc ataacttgct   93240
gcagcttcta catcagcact tgctgcctca ccttgtcctt ttatgttata gagacagctg   93300
cgcttcttaa actttataaa ccaacttctg ctagcttcca acttctcttc tgcagcttcc   93360
tcattctctt catagaactg aagggagtca aggccttgct ctggattaag ctttggctta   93420
aggaatgttg tggctgacgt gatcttctat ccagaccact aaagcgctct ccatatcagc   93480
aataaggccg ttttgctttc ttacctttca tgtgttcact ggagtaattt ccttcaagaa   93540
ttttcccttt acattcacaa cttggctaac tggcatgcaa ggcctagctt tcagcctgtc   93600
ttggcttttg acatgccttc ctcacttagc tcgtcatatc tagcttttga tttaaagtgg   93660
caggcataca actcttcctt tcacttgaac acttagaggc cactgtaggg ttattaattg   93720
gcctaatttc aatattgttg tgttttaggg aatagagagg cccagggaga gggagagagc   93780
ccaaacggct ggttgataga gcaggcagaa tgcacacaac atttatcaga ttatgtttgc   93840
accatttacc agattatggg tacggtttgt ggcaccccc aaaaattaga atagtaacat   93900
caaagatcac tgatcacaga tcgccataac ataataata ataaacttta aaatactgtg   93960
agaattacca aaatgtgata cagagacatg aagtgagcac atgctgttga aaaaaatgac   94020
actgatagac atacttaaca cgtgggattg ccacaaacct tcagtttgta aaagtcacag   94080
taactgtgac tcacaaaaga acaaagcaca ataaaacgag gtatgcctgt atttttaaaa   94140
aaagcttttt gttaaaattc aggatatgta ataggtctgt aggaatagtg aaatatttt   94200 gctgatggat gtagatatat acgtggatag agatgaagat cttaattata gctatgcagc   94260
atagatttag tcaaagacat ttgaaaagac aaatgttaaa ttagtgtggc taatgaccta   94320
cccgtgccat gttttccctc ttgcaatgag ataccccaca ctgtgtagaa ggatggaggg   94380
aggactccta ctgtccctct ttgcgtgtgg ttattaagtt gcctcactgg gctaaaacac   94440
cacacatctc atagataata tttggtaagt tgtaatcgtc ttcactcttc tcttatcacc   94500 caccctatc ttcccacttt tccatctttg ttggtttgca acagccccctt cttttttgcct   94560 gactctccag gattttctct catcataaat tgttctaaag tacatactaa tatgggtctg   94620
gattgactat tcttatttgc aaaacagcaa ttaaatgtta tagggaagta ggaagaaaaa   94680
ggggtatcct tgacaataaa ccaagcaata ttctggggt gggatagagc aggaaatttt   94740 attttaatc ttttaaaatc caagtaatag gtaggcttcc agttagcttt aaatgttttt   94800
tttttccagc tcaaaaaatt ggattgtagt tgatactaca tataatacat tctaattccc   94860
tcactgtatt ctttgtttag tttcatttat ttggtttaaa ataatttttt atcccatatc   94920
tgaaatgtaa tatatttta tccaacaacc agcatgtaca tatacttaat tatgtggcac   94980
attttctaat agatcagtcc atcaatctac tcattttaaa gaaaaaaaaa ttttaaagtc   95040
acttttagag cccttaatgt gtagttgggg gttaagcttt gtggatgtag cctttatatt   95100
tagtataatt gaggtctaaa ataataatct tctattatct caacagagca aattattgaa   95160
aaagatgaag gtccttttta tacccatcta ggagcaggtc ctaatgtggc agctattaga   95220
gaaatcatgg aagaaggta attaacgcaa aggcacaggg cagattaacg tttatccttt   95280
tgtatatgtc agaattttc cagccttcac acacaaagca gtaaacaatt gtaaattgag   95340
```

-continued

```
taattattag taggcttagc tattctaggg ttgccaacac tacacactgt gctattcacc    95400
agagagtcac aatatttgac aggactaata gtctgctagc tggcacaggc tgcccacttt    95460
gcgatggatg ccagaaaacc caggcatgaa caggaatcgg ccagccaggc tgccagccac    95520
aaggtactgg cacaggctcc aacgagaggt cccactctgg ctttcccacc tgataataaa    95580
gtgtcaaagc agaaagactg gtaaagtgtg gtataagaaa agaaccactg aattaaattc    95640
acctagtgtt gcaaatgagt acttatctct aagttttctt ttaccataaa agagagcaa     95700
gtgtgatatg ttgaatagaa agagaaacat actatttaca gctgccttttt ttttttttt    95760
tcgctatcaa tcacaggtat acaagtactt gcctttactc ctgcatgtag aagactctta    95820
tgagcgagat aatgcagaga aggcctttca tataaattta tacagctctg agctgttctt    95880
cttctagggt gccttttcat taagaggtag gcagtattat tattaaagta cttaggatac    95940
attgggcag ctaggacata ttcagtatca ttcttgctcc atttccaaat tattcatttc     96000
taaattagca tgtagaagtt cactaaataa tcatctagtg gcctggcaga aatagtgaat    96060
ttccctaagt gccttttttt tgttgttttt ttgttttgtt ttttaaacaa gcagtaggtg    96120
gtgctttggt cataagggaa gatatagtct atttctagga ctattccata ttttccatgt    96180
ggctggatac taactatttg ccagcctcct tttctaaatt gtgagacatt cttggaggaa    96240
cagttctaac taaaatctat tatgactccc caagttttaa aatagctaaa tttagtaagg    96300
gaaaaaatag tttatgtttt agaagactga acttagcaaa ctaacctgaa ttttgtgctt    96360
tgtgaaattt tatatcgaaa tgagctttcc cattttcacc cacatgtaat ttacaaaata    96420
gttcattaca attatctgta cattttgata ttgaggaaaa acaaggctta aaaaccatta    96480
tccagtttgc ttggcgtaga cctgtttaaa aaataataaa ccgttcattt ctcaggatgt    96540
ggtcatagaa taaagttatg ctcaaatgtt caaatatttt gattgcctct tgaattcatt    96600
tgctaattgt atgtgtgtgt gtttctgtgg gtttctttaa ggtttggaca aagggtaaa     96660
gctattagga ttgaaagagt catctatact ggtaaagaag gcaaaagttc tcagggatgt    96720
cctattgcta agtgggtaag tgtgacttga taaagccttt ggtcttaaat cttgggcatt    96780
ttgatttgta aatctgaccc tgagaattgg gttacccaga tcaaagactc atgccagtta    96840
aaaagaacat tacctgtatt ttttatcatg tgttatctct taagaagagg cagattagtt    96900
ctaaaatcaa caaattgtat ttaattgaaa taatttagtg atgaggaaga ggtccattct    96960
agtgcctgct aaatgtataa tccttcttag aatgtgaagt tgtccttaaa cttttaaata    97020
ccttcagtta atctttatat tgtcatttat gaaaaccttg aactaagact tatgtatctt    97080
tcatctagct ctggttttaa tgcaggtagc atttaattgt ccccactgta ctgggtatag    97140
tctgctaaac attaaggagt agttttgcat ctctccttgt tctgatacta gggtcaaagc    97200
ccactttta tagatgggca gcaaaaggca cattggacat gctgataaat gttgccctaa     97260
ttgtgatcta aacatgataa aatatacata cataagtgcc cttatctgct gcaagtgacc    97320
cttgtttgt tttggttggg gtgggggtg tttgggatgg aatggtgatc cacgcaggtg      97380
gttcgcagaa gcagcagtga agagaagcta ctgtgtttgg tgcgggagcg agctggccac    97440
acctgtgagg ctgcagtgat tgtgattctc atcctggtgt gggaaggaat cccgctgtct    97500
ctggctgaca aactctactc ggagcttacc gagacgctga ggaaatacgg cacgctcacc    97560
aatcgccggt gtgccttgaa tgaagagtaa gtgaagccca gggcctctcc cctctttgcg    97620
gccactgata ggaaagccca atctttggtt gaaaggaaga gagttcagcg tgcacttta     97680
catttataaa atgggcatca aaatgcctgt ttggcagtca tgcgataaga agttgtattt    97740
```

```
gctaatgtga ataacttgag atgatttcat tatctgaatt gtacagttta gccattaatt   97800
aggagcagtc agagtgtctg taaccacatg gcctcagtta taccataaac ttgaaattgt   97860
ttatgtgctc acatgctaca agtgacggct cctgtgtgcc tggccactat attagtatgt   97920
attgactcca cttccatgtt gcagtatctg aaacagaaag taagtctaat gagaaacttt   97980
gggattccca ggtcaaatac cttccatatg tatgtagcaa aaacaaaata caaagcctag   98040
aagttctgta gaaatagaac tgattttttac tttcattcaa actattcatt atttccacaa   98100
tagtaatcaa aactgcttct acttttactg ctgctaaatg atcagcaaat tactggatat   98160
ggatatatat tattttccag gaatataaga atttagaata gaactgcaag agtatgcact   98220
taaatatatt tagtgcatcc agttgctaat gttttgtttt aaacaccatc cactttgcat   98280
gaagtctaaa ccttcagttg gaaaaagcct cattttttaat attcctctac tgtgctgata   98340
atcctgtata aacactaaaag aatagatgaa tgttcacggt gctacacaga aatgtttttt   98400
tttttttttt tttttttttt gagatggagt ttcgctcttg ttgcccaggc tggagtgcaa   98460
tggcgcgatc ttggttcacc gcgacctcca cctcccaggt tcaagagatt ctcctgcctc   98520
agcctcccta gtagctggga ttacaggcat gtgccaccac acccggctaa ttttgtattt   98580
ttagtagaga cagggtttct ccatgttggt caggctggtc tcgaactccc gacctcaggt   98640
gattgcccac ctcggcctcc caaagtgcct tacaggcatg agccgccgcg cctggccaga   98700
aatcttacaa gttattttgc ccacgattgg ttttaaaata atttttaattt tgcactattt   98760 cctttagtgt cttttttctct gcatccacca aactatagaa tcatttgctg agcttataag   98820
aaatgctcat actgctcatt gcaacagcta gccaaatttg tcctttgctg tttaaaactc   98880
taactagcat ggttttacta aatttatgtt aacacagttt ctctctctgg ttgtggggga   98940
gacaaatcaa ttataaataa tctctttaga aaagttactc tttctatatg aaagtgtgac   99000
ttgactttct atgataatta tgatccaaaa attttatggt gtgtacctga ccactttttac   99060 aaatgattaa ttggaaggta gaaattgctg attcataaca tgtaacttat aaacttatga   99120
tggactactt taagcataaa ttttttttttt tttttaaga cagagtttca ctctgtcacc   99180
caggctggag tgcaatggtg cgatctcggc tcactgcaac ctccatctcc tgggttcaag   99240
caattctcct gcctcagcct cccgaatagc tgggattaca ggcatgcact accacaccca   99300
gctaattttg tattttttagt agagacaggg tttctccatg ttgatcaggc tggtctggaa   99360
ctcctgacct cgggtgatcc gcccgcctcg gcctcccaga gtgctgggat tacaggcatg   99420
agccactgtg cccagcctga aatattttt taatctaccc tgactcctct tgctctttct   99480
gaagaaaaat ttttaaaaat gtatgtaggt gcctttaatt agaaaaaaaa ttaaaaatta   99540
aggcaacttg tgctcatatt ggtaatagca tttctttcaa gaactcagta atactgcatt   99600
gtctttaaag cataatatct cttagacttg acggtttgag attctaaatc actgaagaac   99660
ctcttgtgaa aatgatagtt ttaaaatttc ttttcaaaaa tagtcctatt gcaaaatgtt   99720
tgattttctt gaagtttcct ggaaactata tttcattcat tgtaatgaat ttaattttca   99780
ttaacataga tctctaatat ttttctcagc tcaccacaac ctccacctcc cgggttcaag   99840
tgattctcat gccacagcct cccgagtagc tagaattaca ggcacccacc cggctcattt   99900
ttgtattttt agtagagaca gggtttcacc atgttggcca gattgatctc gaactcctgg   99960
cttcaggtaa cccacccacc ctggcctccc aaagtgctgg gattacaggt gtaggccacc  100020
atgcccagcc agcttttcca taattcttat aaatgccaat gcctgaaatg gaatctgaca  100080
```

```
tataaaaaat tacatgaaga actttatta ttttgcattt gaaaaccatg aaaaatagtt   100140
ggaccagagt ctcagaaagc ttgtagtttg ttagtttaac tgctctaaat gtcaggcaga   100200
tacaaaacta ttaaaagaca tgcttcaaat atgaagacaa tttaaaagca cagctgtaca   100260
cttttgcttt ttgtctagtt tcaaggtaaa gatgaataat catttagata atgcttaagc   100320
tatgcttatg catacttaga gcaattctcc aaaataaaaa attttaatac ttaaatacat   100380
gattaaaata gacacgtatc caatgtcaat acagacttta ctcagaaata gcttttgaag   100440
tttcttctac cccataaata gattttattt tatggctggc agaaatgaaa attacaactt   100500
tttgccaaga acagagaata gaataatctc aaattggggc tgcggactca gttttatgtt   100560
caaagctgtg tgaacctcat cactgagttc ttacaaatcc ctgtgtccac atgctccaaa   100620
ccacccactg tgagttcaga aaagaactct gagtgcatct ttcagtagga aagtaaaaac   100680
tgattttac  atttcctttg agccaaacca gctgtttctt ctttaaagat ttccctttga    100740
gatttccatt ttatgactaa gtctaaccag tatttttttg gcaagtaaga gttgtgggag   100800
tgtatctgtc atcataagga aatcaaagcc agaaatgcct tctgccatgg tgggtgatgt   100860
taaacatttc aaggaacttt atattataaa aattgtcaaa cataaaagga aaagtgcaat   100920
ataatgaatt ccatggaccc atcacacagc atcaatattc atcaacattt tatcaatatt   100980
ttttcatata ttttccccac atccactccc actagtgttt gaaagcagaa gacagataac   101040
ttaccatctt acctgttaac atttcaggat gtatttctaa caggtaaaga ctttatcatt   101100
taatatttag actgtgtttg ttcaaattat ctgattagat tctatttcag aaaacacaca   101160
cataaacaaa aatgataatg agaaaaagaa agcccttcca catgattgac acttctgagt   101220
agtgtgatcc cagttcatgt ccattgtctg ggatagctat taaataaaac ttcctctcat   101280
aaaattctct ccatttagaa gataaaattct gtgattcaca agcctctttt tatttataat   101340
agcccttccc ctttctttat gaatttgaat ttgttttta aagaaactgt gattttctct   101400
gtaaaattcc ccacattctg gatttggccg atttcatctt ggttcttttg tttacttta   101460
cctattcctc tatccccagt atcttctgtg gactggtagt ttgactggtt cttttctttt   101520
tctttttttt tttttttttt tttttttgag acaggctctc gctctgtcgc ttaggctgga   101580
gtgcagtggc ccaatctcag ctcactgcaa cctccacctc ccaggttcaa gctattctca   101640
tgcctcagcc tcctgagtaa ctgggactgc aagcatgtgc cacctcatcc tgctgatttt   101700
tgtacttta  gtagagacgg ggtttcgcca tgttggccag gctggtctgg aactcctggc   101760
ctcaagtgat ccgcccacct tggcctccca aagtgctggg attacaggca tgagctatca   101820
cgcccagctg attttaagt aatataagta tgtgtgcatg tatagtatac attggcaaaa    101880
acacttcata agtagtgcta aaatcatctt atttatatac atcaggagac acataatgtc   101940
tgtttgtttc ccatttagt gatattaaga gtgtttagca tgtttagttg tcagcctgat    102000
ccatcattat gttcttcatc aaactttcac cagatagttt cacatcaatt gatgatcatt   102060
gcctgtttct attatttgt tttcaagttg acagttttct ctcacttgat gttgtgtaaa    102120
tttagttata taaagttaaa ttattttgct attttttcta tgctgtatac atttgaataa   102180
ctgacctaat ttttactta  aaaatatttt acaattagaa gtccaaatag taatcaaag    102240
gttaagaatt tttgcagaaa tctgttatat agatgacatt ttaatatttg ccctttatat   102300
catttaccat gagccaaatt tcaagtcata ttaaaatgac tgtcatgtgc taattctaac   102360
aatatttgaa agaccctat  caaaataaat atacctttta gtagccactt tattagaaaa   102420
tcaactttaa gttattcccc catgtttttt tctaattgag atataattca cataccataa   102480
```

```
aatttaccct tttaaagtat acaattcagt tgtttcagta cattcacaaa gctatgcaaa  102540
tgtcacctct acctagtttc agaacgtttt catcattccc agaaggaaac cctgtattta  102600
ttaggcagtc acttcccctt ctccccttct tccttcctct aagtggcaac cacaaataaa  102660
cattcagttt ctctggattt acctattctg ggcattttgt attagtgaaa tcatgtattt  102720
ggcctttctc tctggcttct ttcatgtacc tcaatgtttt caagtctcat tcattttatt  102780
aaaaaaaaaa agtaccttt  ttcttttct  tttttttttt  tttgtccacg tatatattca  102840
caccacattt tttgagacag agtctcgctc tgttgcccag gctagggtgc aatggtgcaa  102900
cctcagctca ctgcaacctc tgtctcccgg gttcaagtga ttctcatgcc tcagccccca  102960
agtagttggg attacagttg tgcaccacca cacccagcta attttgtat  ttttagtaga  103020 gacagggttt caccatgttg gctaggctgg tctcaaactc agcctcaagt gatccttcta  103080
ccttagcctc ctaaagtgct gggattacaa gcatgagcca ctgtgcccag ccacattttc  103140
tttttccatt tattagttaa ttgacatttg gatcgtttct acttttggc  gattataaat  103200 tatgctgcaa tgaacatcgg tgtacaagtt tttgtgtgaa catgttttca gttaccttgg  103260
gatatacacc taggagtgac attgttagta atatggtaac tttatgttta acttttgaa   103320 gaactgccaa actgttttcc aaagtagctt tatgctttta catttctgcc aacaatgtat  103380
gaaggttcca gtgtatctcc acatcctcaa gaaaatgtta ttgtcttttt aattgtaacc  103440
atccaagtgg gtatgaagtt tatctcgtga ttttgatttg cattttccta atggctgata  103500
ttgggcatct tttcacgtgt gtattgacca tgtattttt  tgagaaaagt ctacttatat  103560
gtttttaatt gtattatttt tagagttgta agaatatgtt atgttgatac ttgaactttg  103620
tcaaatgcct ggtttgcaga tattttctcc tatcccacag gttgtcgctt cactttgata  103680
atgtccttaa agtacaaaag ttttaaattg attttgatga aactcaattt cttttaatt   103740 ggcagcttgt gcatttgggg tcatatttaa gaaatcattg cctcattcaa gatctgaaag  103800
atttacacct atgctttctt ctcagagtat tataacttta gttcttacat ttagattttt  103860
aattaatgtt gagttaattt gatggtgaga gataagagtc caacttcatt cctttgcaag  103920
tagctgtcca gttttctcag caccatttgt taaaagactt ttttttttca attaactgac  103980
caagatgtat gggtttattt ctggactctt aattctgtta atctgcatga cttttcttat  104040
gccagtacca cactgtgctg attcctgtag ttttgtagta aattttgaaa tcaagacagg  104100
taagtcttcc aactttgtac ttttgcctac catgtttctt gggtttccat atgcatttta  104160
agatcagctt ctccgtttcc tttctggatt tttttttttt tttttttttt tttttttttg  104220
gtggagctgg agtcttacta tattacccaa gctggttttg aactcctggc taaagagatc  104280
ctccctccta ggcttcccag agagctgggg ttacaggcat gagccaccac atccaacccc  104340
cttctgggac tttgactggg gttctgttga atctgttggt caatttggag agtattgata  104400
tcttaacatt aaagcttcca atttatgaac acaggctatt tttccattta ttcttaaatt  104460
tctttcagta atgttttgga tgaaacatgt acaaagtcct gcacttttta ttttttttaa  104520
gacagagtct tgctctgctg cccagtccag agtgcagtgc tgccatctca gctcactgca  104580
acctccacct ccgggttcaa gtgattctcc tgcctcagct ggaactacag gtgcgcgcca  104640
ccatgcctgg ctaattgttt tgtgtttttg gtggagacag ggtttcacca tgttggccag  104700
gctggtctca aacacctggc ctcaagtgac ctgactgcct tggcctccca aagtactggg  104760
attacaggca tgagccacca cgcctggcct gtacttctgt taaaattttt tctatgtatt  104820
```

```
tttttttatcc tattgcaaaa tcaaatttttt tgttgataat atatggtcat aaatttcatt    104880
tttatatatt ggtctcatat cctaccaact tgctgaacta gcttattagc actaactttt    104940
tttggtagat tccttaggat ttgctgcata caagattatg tcatctacaa gtagagatag    105000
ttttgtttct tcacttccaa tctgggtggc tttatgtttt tttcttgcct gattacccag    105060
ttagaacttc cagaaaatgt caggtacaat taacaactgc aaacatcctt gtcttattca    105120
ttttagaaag aaattttttag ttttttcacca ttaagtatga tactagttgt aggttttgtt    105180
taaaaaaaga ctgtgtcaag ttcagaagtt cccttctgtt gctagtttgt tgaataattt    105240
tatcacgaaa gggtgttgaa cttttctcaa atgctgtggc tacatctaat gaaatgatca    105300
tgcgttcttc tcctttattc tattaatatg gtatattata ttgattcatt tttatacatt    105360
agattaacat tatatttctg gaataaatcc cacttggcct cagtgtgtat tactttttat    105420
atattgctgg agtctgtttg caggtatttc attgaggact ttcgcatctc tgttgataag    105480
gtatactgat ctttagttct cttgtgtatt ctttggtttt ggtgtcagag taattctgag    105540
ttcacaaaat gcattgggaa atgttccctt ctctatcttt tggaagagtt tacaaaggat    105600
tggtttaact ctttttttaaa tgtttgagga aattctctac ccctgggctt tcctttgtgg    105660 gaattttttaa acatttttaa aatagattat ttttaaagca attttagggt aaaagcacat    105720
tgaatgaaag gcacagagct tccttaagta catgctgccc ctgtatgtgc atagcctccc    105780
tcattatcaa catcctttac cagaatggta catttgttgc agtcaatgaa cctgcattga    105840
caattgtcga tgaaagttca tagtttagag ttcacctttg gtgttatgta ttctgtgagt    105900
ctggatccat gtttaatgat actcattcac cattacagta tcattcagag taatttcact    105960
gccttaaaag tcctctgtac cctacctatt tttctctcct accccactaa cccttagcaa    106020
ccaatgatct ttttatctca ataattttgc ctattccaga atgtcatata gttggaatga    106080
tacagtatat ggagcctttt cagactggtt tttgtcactt agtaataagc ttttaaattt    106140
tccaccatgt catgatcgtt catttctttt cagcattgaa taatattcca ttgtctggtt    106200
tatcacagtt gatttatcca ttcacatagt gaaagacatc ttagttgctt ccaagttttg    106260
acaattatga ataaagctgt tataaaagta tgtaggtttt tgtgtggaca aaagttttca    106320
gctcctttga gtaaataaca cagagcacag tagcttgatt gacagtaaga gtaagaaata    106380
ttttttctca gtctgtgtct tatttttttca ttcacttgac agtgccattt gcagaacaaa    106440
cagaaagttt taatttttaat gaagtctagg ttatcagtta attcatgaat aatgttttg    106500 gtattgtatc taaaaagtca acaccaaggt catctatatg ttctgtgtta tcttccagaa    106560
attttatagt tctgcatttt acatttaggg ctgtgaccca ttttgcatta attttgcaaa    106620
agctataaag actatgtata gattcacttg tttgcatgtg gagttgtcca gttgttcccg    106680
taccatttct taaagactat ctttgcttta ttgtattacc tttgctactt tgtcaaagat    106740
cagttgatta taattaagtg gtctgttct ggactcttta ttctgttcca ttgatatatt    106800
tgtctagact ttcaccaata ccacactatc ttgttaactt aggctttaga gtaagtcttg    106860
caatcatgta gtgtcagtcc tctgacattg tttttctcct tcagtattga gttggctatt    106920
cttttgccta ttactaagta aaaaaagcag tctgaaaagg ctatatatac agtcatttat    106980
tggtcttttg cctcttgata taaactttaa aattactttg tcagtatcct caaaatcttg    107040
caggaatttt gatagattgc actgcatttc tagattgagt tagaaatact gccatcttga    107100
caatacacat cttcctatcc atgaacatgg aacatctctt tcttggatat ccttcattag    107160
aattttgcat tttccccata tagaccatgt acatattaga tttatacata aatatttcat    107220
```

```
ttgggggggt gctaatggta atgtattttt atctcagatt ctgcttgtac attgctggta  107280
tgcagaaaag tgatcaactt ttgtatatta aacttgtttc ctgcaaccat gttatataat  107340
cactttagat ccagtttttt tttttttggt cattctttca tattttctag gtgatcatgt  107400
catctagcaa agacaacttc tttctaatct gtatacettt tattttcttg tcttaatgta  107460
ttagctagca tttccagtat gatgttgaaa ggcattggtg agaggcaaca tacttgcctt  107520
gttcctgatc tcagcaggaa atcttcaatt ttatgttagc tctatggttt tgtagatatt  107580
ctttatttac attaaatatg ttagctgtat ggttttgtat atattcttta tcaggttcag  107640
gtagttcccc tcttttccta gtttactgag aggcttttga aaatcattaa tcagtgttgg  107700
attttgtaaa tactttttt ccacctattg atattaccat atgattttc tttagcttat  107760 taacgaaatg gattacatta attgattttc aaattttgaa ctagactggc atacctggag  107820
caaatcccac atggttgtga tacattattt atgaatgcat tcatggtcat ggttgctatt  107880
agtctgtagt tatcttttat tgtaaagact ttggtgttgg tattaaggta atgctgccct  107940
catagaataa gttatgaagt attttctctg cttctgtctt aattgagatt gtagagaatt  108000
catataattt cttccttaaa actttggtag aaatcagaat gaaccatctg tgtctggtac  108060
tttgttttga aaagttattg ctgattcaat ttctttcata gatataggcc tatttagatt  108120
attattttgc ataaatattg gtagttgtgt ccttcaagga attggtccat ttcaccttga  108180
ttattaaatg tgtgggcaca tttgttcata atatttcttt attatccttt gttttgaga  108240 cagggtctca ctctggttgc ccaggctgga gtgcagtagt atgatctcag ctcactgcag  108300
ccttgacttc ctgggctcaa gtgatttacc cacctcagcc tcccaagtag ctcggactac  108360
aggcacatgc caccatgcct ggctaatttt tttattatta ttagagatgg agttttccta  108420
tgttgcccag tgtggtcttg aactcctgga ctcaagcaat ctgcctgcct cagcctccaa  108480
agagtgatgg gattgcaggc atgagccatc acacctagcc tgatggcaga actttttagg  108540
aacaatagaa tggtatatgg cattttcaaa aattgttttc ccctcctcct atggaagcat  108600 gaagggatt ttctctagta ttcattgtga gaacctcatc tggctcctga atgtagaaaa  108660
ctcacaaaac tgtgaggaac ctattatgac tggatgcctt tggagttgtt cacactgaac  108720
ctccagcaat tcatcaatta tatttcagat tttcctatcc caacactggt tcctacagag  108780
gtttctgctc cagtaagctg taattctttt tatccatctg cttccttggt tgtgagggca  108840
gtgattttcc ctgtgacctc atttctctga cagatctaag tagtcttgat tacatcttt  108900 aacctgttgt aggtatattc agattttcta tttcttcttc agtcaatttt agtagttgt  108960 gtttttctag aagtttgttc tctagctctg ctttagctcc atccaataaa atatgagtat  109020
gtcgagtttt catttacaac aaggtatttt ctaatttcta tcatgttttt ttgattcctg  109080
actgtatagg agtatatttt tacctattac ccaaatttgc ttgttattca tgtataattt  109140
tatcagaaaa cacactttgc acaattttg cagtgttaca tttatttaga cttgttttat  109200
aacttgacat acagtccatc ctggagaatg tttcacgtgt gcttgagaag aatgtgtata  109260
ttcagctgtt ggtgggtggc atgtttttata gatgtctgtt agacctagtt ggtttatagt  109320
gttttttaca acttctgttt tcttttttaat cttctatcta cttttagcca ttattgaaag  109380
tggattagta aattatctat ttattccttt aattctgcca tttttttgctt catgtatttt  109440 ggtgctctgt tgcttattac atgtatgttt acatttgtta catcatttta atggcttgaa  109500 cttttttatta taaaatgtgt atatcttgta gatatcgtat agttaaatct ttttaaaaat  109560
```

```
tgatattgct agtctttgcc ttttaattt tcaatttata tacatttaac ataattattg   109620
ataaggtagg atttgtctgc cattttgtct gtatcttgtc ttttttttgtg ttcaatagat   109680
attttctagt gtactgtttt aattcccttg tcttttacta aattttttga tgttcttaat   109740
ggtttccctg gggattacaa ctaacttata acagctagtc tgaagtaata ccaatttcat   109800
tacaatataa ggaaactttg ttcccatata gctacattcc ctcttttac tctgtgctat   109860
tatacaaatt acattttatt ttatgcccat taacacagat tatgttttt cttttaaatc   109920
agattgatat tgtcatttaa atcaaatatg agaaaaatag ttacaaaaaa atacatatat   109980
gatttcatat ttacctatgt aattatcttt actggtgctc tttaagttct taggtgtatt   110040
tgaggtactg tctagtgtcc tttcctttca gcctgaagta tacatttagt atttttttgta   110100
ggacatgcct gaaaacaata aactcttatt tatcagagaa tgtcctaatt tattatataa   110160
tacatttctg aaagatagtt ttgcaaaata cagaattctt ggttggcagt cttttttcttg   110220
tggttctatg tcattctact gccttctggt cttcattgtt tctgatcaga gatcagctat   110280
taatcttatt gggaatcctg catacatgat aatcatacag ttttcatgat tttcttgtgt   110340
tggctttcag cagtttggtt atgatgttta tatgtatgca tatctttggg tttatgttac   110400
atggagttag ttgagcttct tggacatgta gattgatgtt gttcatcaaa tttgagaagt   110460
tttcggccat tatttttcaa atattcttcc tattctttat tcttcatcct ctactttggg   110520
gacctgcatt atgtctatgt tggtatgctt tatggtcttc cacagatctc tgaggttctg   110580
tttatgtttt cattttttcag actgaataat ctcaattgac ttatcttcaa gtccctttt   110640
cccctccttt tcaactctgc tattgaaccc ctctaatttt tactgcagtt attacactttt   110700
cagctttaga attctatta ataatatctt tttcttgagt ttatctcatg tatttaataa   110760
aatgctgtag tcttacttta gttatttaaa tacagttttc tttcattatt tgggcataca   110820
tgaaatagct gacttaaagt ctttgtccag tggcctaaca tctggacttt tcaggaata   110880
gcctctattg actactttat aggggccata cttttgtttct gtttctctta attgtttaga   110940
cattttaaac taatgtaatg gctgagagca gtggctcgtg cctgtaatcc cagcacgttg   111000
agaggccaaa gcaggagcat cacttaagcc caggagttca agactagcct gggcagcata   111060
gtgagaccct gtctctacaa aaataaaaat aaataaaata atataatctg gtaaatctga   111120
aaatcagatt ctaccccctg cccagaatat gttactgttt ctggtggttg ttgtttattt   111180
cttttttaact actcctataa agtttgtatt gtttctcata gatagccatc gaagtctttg   111240
cttggttaac ttagaggtca gctaaggatt agacagaatt ccttaggtgc ctgagatcaa   111300
taagtcagtc tttgacaaag gggtctgtat gtgtgttggg gcatgcattc aacactcagc   111360
caggctattt gcagctctgg attagccttt attccctgct tgtgcagagt ctcaaggtta   111420
gactgtggtg agagtttagg gctttctgag gtcttttgtg ggccctacag ttgcatgtgg   111480
ctttctaaat tcccaggaat atattttcaa agcctcctgt ggatcatctc atttcccagg   111540
taatttactt ttaagctttt ttagttatct tatgttttgc tccagttatt agctacacct   111600
gagtcagtga caatattcaa cagctgccta tgattatttg acaaatgcct ctgtggaaaa   111660
ggtggttcac actaggtgaa ctccaagtta gataaagtaa agataaccct actagtggga   111720
tcttccagga aactaccaaa caggtcaaat aatgtaaggt ctctgtgaat gggactttag   111780
agtatatcca accagtctag agtatatcca accaatctgg cctcctctag tggcagcctg   111840
gctgctgctt ttcataataa atgtgggctg ttttgatttg aaggctacca tagagctgtg   111900
gggaaagtta aaataccaca gagctcactc ttctcactga aatcctgtct ttttttccct   111960
```

```
tgaacaaatt ctccctatat tgctgcaagc tttttgctaa tttccagatc tgaaaaagct    112020
gattctgaca atatttatca gtactttat tgcttttatg gaggataaaa ttttcagaga     112080
tccttattct gccattttg ctgacatgtg taaagtgatc atttctaatt gtaaaattcc     112140
ttttgcattt attagctgga atactttaca ggacttttcc tcatcaaccg ttagttacca   112200
tttaatatag tttgtaagaa tgatagaata aatgcatggc aagaatcttt acttctcaaa   112260
tttcagagat tttgatggga aattatattt agagatcaca atcagtgtct agatgtgctc   112320
cctgctatgg aggtgtcatt acttttaggc ttttttaatg ggcaaataca tgaagtaatt   112380 atttttaga aagaaaatct gagattaact caaatcatta attcatactg attttccta    112440 ttcatagttg acagagtatt attatctttt gttctgcttc tcttgtacac tgaaattctt   112500 ggttttgat attaacaatt atttacttat atcacaatat acatacatta atttaaaaat    112560
aatttacagt gctacctgaa tatttttct tgtaagttgt tttatctctc tttgcttact    112620
tgtatgtttg tttattgtca ttagaatgta tcaaactagg gctataaagc tgtaatacta   112680
tattttagcc agaaactagg acctagcact caaatgccca tcaatggtag aataattcat   112740
cacattttta taagatggaa tatggtactc aatgaaaatg aataaagtac aactacatgc   112800
agtgatttgg atggatatcc caaacataat ggaaaaagca cacacaaata agcttatatt   112860
atataattcc atatacctat gtatatatca agtataaaag taggcaaaac aagctactga   112920
tggtggcaca cacctatagt tccagctatt tgggaggctg aggcgggaag atcacttgag   112980
cccagaagtt caggttcaac ctgagcaaca tagcaagacc ccatctgtaa aaagaaagc    113040 attattaaca taaaatagg cagaactact atattcttag agaagttact gttagggaga    113100
cagacagtga gtgactgaaa ggcaaaatga ggggaaattc caggggatag taaatatttt   113160
gtttcttagt gtgggttcta cttaactggg tattttccat ttgtaaactg taaaattatg   113220
tgcacttttc tgtatgtgta ttacattgca ataaaattgt ttaaaagtca attgaaatag   113280
ttctgtgtgt ggttatgcca cagcttaata cagagttaga ttagacttct tttcaaactc   113340
attttgcata tagacaccta taatatcagc tgcacagcct atataatgct atccatagca   113400
atgaatttgg tcttttgatt tttcaggaga acttgcgcct gtcaggggct ggatccagaa   113460
acctgtggtg cctccttctc ttttggttgt tcatggagca tgtactacaa tggatgtaag   113520
tttgccagaa gcaagatccc aaggaagttt aagctgcttg gggatgaccc aaaagaggtt   113580
tgtttacttc ctgatgtata atcgctttat ttttcataga gaattcatta gcttagatga   113640
agtgaacaat atgacatatc ttggtaagct cttattaatc aaagttttc ccaaactgta    113700 gatacacact atttttaag ttggcataat aatcatatta tgccaaaata atagataaaa    113760
tttgagcaac aaaaacttcc tctttggtct tttatgttaa ttccaaagtt ttaaaggggt   113820
gtcacttcat tgttaaaact aaatgagaat tggtgatgtt tttcatattt tgactctgaa   113880
ttatggaagt tacataagta ctacattcag aaaagaccat ttttagtcac atttatgtgc   113940
aatgagattc aaataattta aagtcactgt aatgaatgca tttaataaag tcactgtaat   114000
gaatgcattt aagtaactaa aacatttaga ttttaatata actctgtaat ggaaataaat   114060
ggacactaat ttctcactga agtcattggt ttttgtcttg tctgtagaat acgtatttct   114120
tataatttgc aaattgataa atttaacaac ttttgggtgg catgtagtct agagtataga   114180
tacttcttga cttatgagga gactacattc ctataaatcc gttgtaaaat gaaaatccat   114240
ttaatacccc caataaaccc atcctaaagt aaaaaaaaaa cgaagccatt ataggtcagg   114300
```

```
gactgtctcc gtactaattg aatgatgaga aaacctcagt atatttagca tttagctatg  114360
accacatttt cagtcattct atacacttac aattatcttt tgaatttcga atacaattaa  114420
aatatttcca tactatagat attataacat tgatgagtcc ctttaaatga agaatttgtt  114480
aaccttatta agctttcact tactattata gtcacagtta ataaagcaag tgcaaaaact  114540
cctgaaatca cagtataagt tttttaaagg atgttttcaa taattaaagt ttacttaaat  114600
gtgcgagaca tcatttcata agacaagaat atgaatatta ataacttaat gaaaagtact  114660
gattttgctt gctgtcattt taattttcta cagataactt ttttttttaac cactgtttta  114720
tcaagtgata aatgtttatc actttcacga ggtttcatgt aaaccaaatc cagaggatac  114780
caagtaactt attgcctctg ttgggtagga gagctctgtt cagaaacctc ctcaccttct  114840
aaaatttaca tctctgccag gtggttatgt ctcacaactt ttttttttta gagaaatatc  114900
aatctgaaat gaagacttct aagtataaat ggagcagcta aatatgatca cctaccattt  114960
tttaacagta tattacttgg aaaatctgtt cttcatgagc agggcaggtg ggggtgtaac  115020
tgagcatttc cccttttcaag taaattctgc aaaggttttc atgtatcctg cattctagtt  115080
ctgaagcatt ttatccatat ttgaagtgtc cagtaaattt tagttgctct atggagagat  115140
cattccaaat tatttaaata ctatctttat aaacataaaa tgtaaagatt agaaatagac  115200
aaattaagct aaagaagttc ttttaatagt tcatcttcct tggtagctaa aaaatgtgac  115260
ctctttaaga ccatacggct taattcccct aaccctactc ctggcacagg cttgtgtgta  115320
taaaatgcaa aatatctgca tgcagttaga aaatcaatct tatgaaaaaa acaaatagct  115380
agatatttac tagcacatat gaaattaaat gatagtcatg ttttaaagat gctttattta  115440
gtaataaagg caccatatat tgtgtttggg attcaaaatg taaggggaat aatctaactg  115500
atagtctctt ttacatagag aaaatggact tagaatttaa tatgtagaat tattcactt  115560
atacaggaag agaaactgga gtctcatttg caaaacctgt ccactcttat ggcaccaaca  115620
tataagaaac ttgcacctga tgcatataat aatcaggtaa gtttaaataa tcattggcag  115680
caattgtaac aacttacttg ttactaatga cctatgtcca aaaatatttt tgaaacaatg  115740
atttttaaat attattctaa cttttcctct taattgttga aaccactgca gtgttcagtt  115800
tcgagtatat aaaaattata ccatacaaaa gtacattttt tttgtctttt agctgtaaag  115860
acatgcgctt ctaaaagtca caggctgttc tatctactaa tcttgttctc atatgaataa  115920
ttttgtttct gtaaacagac tatggagatt acatcaaaat tatgtggccc aagctatagg  115980
ttctaactac ctattttac tgcaagtcta aagtataaa tgagtattca taagaattta  116040
tagacttaca aatattcaca taaagctatg catatactaa cattgtaagt atatatattt  116100
cggtccagat gtgtcagatt ttgctgatct tcctttttg tttgacctg acttcataca  116160
ccaagcaaaa acatttttt tttctatttt acatgtgtat tctaaactat agctagttaa  116220
gacaggtaga tgatttggtc agaaatctct catcatgaag gcaaaaaact aaaatcttca  116280
ctgtttcagt aacatcaaca acaaaagcat taagtgaaag tctattacaa actaaacact  116340
gtgtttagtc actgggaaca taaaggtgag cagtgccatc tctgtctgtc tttaagaatt  116400
ccgtctttgc tgggtacggt ggctcacacc tttaatccca cactttggg aggccaaggc  116460
aggtggatca cctgaggtca ggagttctag accagcctga tcaacatgga gaaaccctgt  116520
ctctactaaa aatacaaaat tagctgggtg tggtggcagg cacctgtaat cccagctact  116580
cggaaggcta aggcaggaga atagcttgaa cctgggaggt ggaggttgca gtgagccgaa  116640
gtcaaaccat tgcactccag cctaggcaac aagagcgaaa ctccatctca aaaaaaaaaa  116700
```

```
aaaattcatc tttaactggg tgcggtagtt tatgcctgta atcccagcta cccaggagac   116760
caggagtctg aggctgcggt gagccatgat tgcatcactg tgctccatcc tgggtgacaa   116820
agatgaccca gattctaaaa aaaaagcaaa aacaaaaga attccttctt tagtggagac   116880
agagacatat aaaataaata gcaattttag aattacacag ttccagctgg aatagaagaa   116940
tgtgcacatt tctaaaaaaa tttaaaaaca aacccaaaa gtagactaga tgtcacaagc   117000
agccttagac gctaaataaa gatctttgaa ctttattctg taggtaacca ttgggctgtt   117060
tcaagtgtgt gttggggatg aagggtaaa gtgatgtaat tcgtattttg aaaaatttac   117120
ttaaaagcca gtaagggaa atataactta aatctatgta agattagaga gagaagaaag   117180
ctattgcaat cattgggcaa gagattttaa ggacctaaag aaatggcagg aattaagtat   117240
gtacactaac taaggtggag cttagagaac ttggtgacta gatgtatgga tgagaaaaga   117300
atttggagat acaacaaatt tccagtttgg acaggtagtt ctattaacta gtatcagaaa   117360
ttggtaagaa atagtaagtt ttgggatggg agaagagatat caaaattttg gacatgctag   117420
gcttctaggt taattagatg gagaatcagg agaaaaattc aggctagcac tgtagatttg   117480
agagtcagaa tgctggcagg acttaaagtt gaatacatag gaatgaaagg aggttttcaa   117540
agtagagatt ataagagga caaagggctg atgatgggat tctggagcca tcaatcattt   117600
taggcatgag tggaggaaga gaagccaatg aagtaagaac tggggagggg agtagaagaa   117660
atgtagtagg aaaagtgaaa gagggagatg gatggatgga ggaaagctgg aatgatgaga   117720
agacacccag agcagagtat acaggagcaa taggtatggg gctctgggat gggtgctctg   117780
tcatttactt gataatatta aagactctcg tgggattaga ttagtttaca cagcagacat   117840
ggacaaggga ctaatcctaa aatgatttag ctactcttct tttccactgt ggactttaac   117900
gtcccaaaca tttttttttt ttttttggttc gaacaataga ggcaaattaa acgatggtct   117960
atttgtaagt tattttatgt caaattatgt ttttagaaat gtgtatgaat atctatgaaa   118020 agttttaaa cactattaat agttggatta atactgttat tttgtttagc tagtatcaca   118080
aagtataagg agtgctttga tactgtcgta aaagtttaat tctcagcaag aacttctgaa   118140
ataaatcaag ctataaaaat aaataaatga atgagtctat gttgctagat ttaaagttgg   118200 gtcatttctct attaaatgaa ttttaataag gtgctgttaa tcaaatggct ttacttgagg   118260
cagaataaca aagcattgat gttctttttg ctcccttgat tcttattatg gaccgtctca   118320
tacttgaaac tattttatac atttcctaaa acttaagtac ccaaaatatg aagccatcaa   118380
atatgttcaa gttttaatat ttatatatga aaatgtgttg atgtaatgtc tagataaatt   118440
aagtcaatta atagttgtaa atggatgaga tgcttctgaa tggataaaat atttttatat   118500
tgcatggtag gtactattgg taatattcat ccatgtatgt taatatgctt tagagatcaa   118560
aataatagcc atgtgatgtt tccacacagt acacgggaag accatttgat gttatagatg   118620
ctgtcataaa acctactatt tgatctttac ctcctttccc caactgagtg tcgtatctct   118680
atttctcaca tctgaatatt cttccttgct ttattccttg atttcatgaa gtcttattgc   118740
taaagtttag ttggctctcc acagcatctc ttctgtcagt cccatggaat tagagcttca   118800
gttttctcaa cttaaatgtc ctttcttcgt gtctatccag tagacatata tttggctctg   118860
tcttttctat gcctgcctta caatttaaca gtagacctga aatagcaggt gtcaatctca   118920
aaatcgtgtg ctatttatca tacatgaaga tgacatttta gacaaatgct tctaagagag   118980
ctttctatga agatggaaat attctctatt tatgctgttc agtgtaatag gcactagcca   119040
```

```
catgtggtta ttatttaaca gttgatacgt ggctagtgta attgagttta aattaatgta   119100
aaaattaaca caaacagcca catgtggata atggttacca tagtgaacag cacaacctta   119160
gaccatgaga aagttatgca tttagaattg tcttccagac atttagatgg atttccagta   119220
attcattcac aaaatcctgc atggtatttt ttaggagatg gcataagtgt aatttctagc   119280
tgattgtata tctgtttttg ttcaagaaac agaataaagc taactagacc acagcatgaa   119340
ctgaacggcc acaaagcaca catctatgtt aaagagtagt tggtaccttc attttccttt   119400
ggccaaagtt ttatgaggtt agatagacaa atacatatat gaatccaaca gtaaataata   119460
tgaagccacc acaaactttt atcctaatgc aagttcatct tctagccatg atggagtaaa   119520
cagagactac atatgccgtt acacatttaa gaaaaaactg acaaaatata tgaaacaatg   119580
gtttttagac atagaataag aaattcaaga gacagtggca ccagagagaa aggaagtaaa   119640
aaggtgaacc tataaatacc ccagtttact tcctgaagag agtattaggc tccagtgtag   119700
ccagtaggaa cccaaacaca cccagcctta tctctgtatt aaggagacaa agttcaaaat   119760
ttggagaggc caaggtgacg agagttcact attcagaata tcagagagga gagagtgtta   119820
ttgagaaaag ctccagagac ctgcagaggg ttctgatcca gtcttcagct gagtattaaa   119880
cagcacatgc atgtgaaaaa actgccaagg ctaggtaggg aaagaaccat cagaagagc   119940 aggcagaata atcccttgat ctcacacagg acctggaata gttcttgatc ataccagcca   120000
gacggagaag acttcataat actattcata attgtattgc cttggtagta gaagtaaatt   120060
tggcagttct gacctcatct aaaaatgctt aaaatgaaaa catagaaggg ccaaactgat   120120
tctaagtaat ttaactgcat cacagtacaa aaattaaaaa aaaaatctac caacaaggta   120180
aaatttatag tctagcattc catcagaaaa tacaaggcat acaaagaaaa aagaaaatat   120240 aaccttact ggggaacagg cagaaatcaa tcaataaaaa tagtcccaga actgacatat   120300
gtgatacaat atgtaaataa gttcattaaa atggctatca tatttcatat gttaaaatgc   120360
cagaggaaag catgagagtg ataaggaaag atcagaagat attaaaatac ctacaatga   120420 ccttctagaa gtgaaaaata tatctctaga ttaaaaatac actaggcgga attaacagat   120480
taaggaactt gaagacatag taatagaaat ttttcagtat aaagaaaaaa ctgaaaaaaa   120540
tgaatatata aaagacctat tagccaatat tgttacacta atatatgtgt aattggagta   120600
ccagaaggag gtgggagaca gaaaaatatt taaagaaaca atggccaaat ttttttcaga   120660
tttgttcaaa actgtgaacc cacagatctc agcagctcag caaaccccag attaaaaaac   120720 aaaagacataa aaaaagacta tcaaaaattt ataatcaact tgcttacaat ctgtgataaa   120780
gagaaactca gaaaggcaaa tggagaaaaa aggacatatt acactaggtg ggaaaaaata   120840
agacaggaga cttcattcag aaaaaggcaa gagagaagat gtaagagaaa catctttaac   120900
atactaaaag aaaaaagact ctccacccag aaatatataa ccaatgaaaa caactctcaa   120960
aaaagacagc aaaataaaga atattttttc agacatacat acaaaagctg aaagaattca   121020
ccaccaacaa actagcactt taaaaatgtt aaacgaaatc cttcaggaag aaagaacatg   121080
ataccagaca gaaatccaga tcaacataat gaaatgaaca gtatcaaaaa tagtaaacat   121140
ggttaaaaga cttttaaaaa aatgataact tgctatctta aaaatatatt aacaatgtat   121200
tatgaggttt ataacacgta gaagtagcac agaggctgag gaattgaaag tatattattg   121260
taaagtactt atacgatatg tggactgggt atattacttg gctgtaaact gtgagacgtt   121320
agagtacact gtgtacctta aaccactaaa aaaaaaaaa aaagtatata gctaatcagc   121380
cagtaaagac agaaaaatga aatcaatcca aaaatgtttt taaaaatata taggaccaaa   121440
```

```
aaaagataaa tataaaaata aaacaaatag caagatggtt tatttaaacc caactgtatc   121500
aacaaccaca ttaaatgtaa atggttttaa cacccctaat tataaggcag agcttgtgat   121560
attgaaaaaa aagcaaaaac caagaaaacc actttaaata taaagataca aataaattaa   121620
aaagatattt ttaacataaa aaatgatgtt gaaaagacat aacaggaaaa aatatgatta   121680
ttgcagtagg tacagaaaaa ccatttgata atattcaaca ttcataaaag gaaactttct   121740
caacctatta aatacataaa tggaaagcca aaagctaatg ctatacttag tggtgaaaga   121800
ctaatacttg acccctaaga taaggaacaa gacaacaatg tccatttttta accaactgct   121860 tctattcaac atcaaactgt aaattttaga aagtgcagta aggcaataaa taaagcagtc   121920
aagattgggt aggaaaaaat aaaactgtac ttatttgcag atgacatgtt tgtctacata   121980
agaagtctca aaaaatctac cagaaaatga aattaatata tgaatttagc aaagttgtga   122040
aatacaaaat tcaagtgtat ttttatatac tagcaataaa taaatcaaaa taaaccatta   122100
aaatagcatc aaaatataaa attcttagac atacatttga caaaaatgta taagattata   122160
tactggaaac taaaacattg ctgagataaa ttatagaaaa cttcagtaac tggagagata   122220
cactatgtta atggatcaaa agactaaata ttattaagat gtcagttctc cccaaactaa   122280
tcaatatgtt caatacatga tgtttcaaaa ccccagcagg ttttttgaaa gaattggaca   122340
agatggctgt aaaatatata tacttggaaa tgcaaaggac ttggaatagt caaataaat   122400 tttaaaataa gggcagaatt tgagactata tattgcatgg ttttcagatt tactgaaatc   122460
tataattgct actgtctgtc aagacagttt gatattgccc aggcgcagtg gctcacgcct   122520
gtaattccag cactttcgga ggccgaggtg ggtggatcac ttgaggccag gagttttgag   122580
accagcctgg ccaacatggc aaaactctat ctctaataaa aatacaaaaa attactgggg   122640
catggtggcg cgtgcttata gtcccagctg cttgggaggt tgaggcctga gaatcgcttg   122700
aatccaggag gcagaggttg cagtgagccc agatcgtgcc actgcactcc agcctgggtg   122760
acagagtggg actctgtctc aataaataaa taaaatttt aaaaagtttg atattgacat   122820
acctacatac acaccattat acacaagtgg atcagaatag agaatcctta agtagaccca   122880
acatatataa tatggtcaat tgattttaa caaagatgat tcaattggga agggataacc   122940
attttatcca gtagtatctg aacagttgga aagccataag ggaaaaaagg taatcttgac   123000 ccttaattc acaccattta taaaaattaa ctccaaataa atccatttat atgaaattct   123060
agaaaatgaa aatctgtagt gatagattag tagttgtctg agaacaaagc aggaagcatg   123120
aattatacag gggcatgagg aaattttaa gagtaatgaa tatgtacttt attttggttg   123180
tgacaaatat atatcaaaac tcaaatagca tactttatgg cctcaataac actataaaat   123240 aaaaattta ccatgtcaag atatttgctc tattttgtgt cattccattt tgtttctgga   123300
tatatattta agttcaaaac attttttaa agttctaaat ggtctaaata ctagtgagtt   123360
ttcggtgtaa gagtaaaact aactactttc gcattcacac acacttttat ttttcagatt   123420
gaatatgaac acagagcacc agagtgccgt ctgggtctga aggaaggccg tccattctca   123480
ggggtcactg catgtttgga cttctgtgct catgcccaca gagacttgca caacatgcag   123540
aatggcagca cattggtaag ttgggctgag gacagcttag cagctgttga gtctgttctc   123600
acactgctaa taaagacata tgcaagactg ggtaatttat aaaggaaaga gatttaattg   123660
actcacagtt ccacatggct gtggaggcct cacaatcata gctgaaggca aatgaggagc   123720
aaagtcacat cttacatggc ggcaggcaag agaacatgtg caggggaact cccctttata   123780
```

```
aaatcatcag atctcatgag acttactctc ctgagaacag catgggaaag atctgccccc   123840
atgattcaat tacctcccac tgggtccttc ccaaaacaca tgggaatttt gggagctaca   123900
attcaagatg agatttaggt agggacacag ccagaccata tcagcagcat ctcatgttga   123960
ggagcagaac actggaattt agtagcattc ggttagagta atatgttgtc tgcaggtttc   124020
actggacagc aatattttca tgaatgaatt cctgttgcaa agtgacctgc tttggcataa   124080
ctagcactct catgataggt tggcacatta gtttcctgtc aattgtgttg acaagcacat   124140
gagaatcatg gaaatccttg gtgttaatct aaaccagtga ctatgcattg ccagttacag   124200
ttaacttcca ggaaaatctc aaaattcagt gccagttacc tggtagattg taatcagtta   124260
agcaaaaagc caaatacaag ccattcacct tacagagaga gaagcatatt caccttacag   124320
agagagaagc ataaatgaga aacacatcat cattgtcaca gtaactgtgg taacctattg   124380
taaaagattc acagtgcaaa agagcctgac tacatattac agtgggtaaa atggatcggt   124440
cttgtaattg gaggcagtgg tgaggggaaa atagatacat gttatatata tatatatata   124500
tatatatgtt ctataccaac aaagggttca gggtataatt ttgcatgtaa aggggtgacc   124560
cagagtagag ataagaaaca aaatattctg ttgaaaaaac tatgaatcaa tcaacctaat   124620
gaattatcaa catggatgta ggtgtagttg aagaagatgg tcagtgagaa tatggaaaca   124680
gatatcagga attaaagtca tattctaggg cagaaaagca ttcatggagg tattagatga   124740
tagctgaagt aatttgaaga agctggtgtg aagttttttgt tgagaagcag agaagatatt   124800
aatttaatgt tctagatcag agattggaaa actcttctct ataaagggca agatggtaaa   124860
tattttaggg actgcaggcc ataggatt tctgtcacat tgtttggtgg ggtttttttg   124920
tttattttgt tttttaaaaa ctccttgaaa atgtaaaaac cattcttagt ttactggcca   124980
tacaaacaca agctgtgagg cacattagcc gtaggttctg gtttcctaac ttctgatcca   125040
gaagaacaaa cacaaggcct accaaccacc ccaacatcta aaatcatcac taatcatgta   125100
ctcagcacct gctcattatt aggaggctat gctagtttct gaaaagcaga agtagtaaat   125160
gataactggg gctatagtgc atcctaatat aaccatgttt cattccagga aggtgacaga   125220
gagtaagatg atgagaagga tgtttagaat caagaagaat ttgcctctga tagagcatgg   125280
gttctgtgaa gtaaaatgga aaggagcact agataagaac tgaatagggt taaatatgta   125340
tgggaaaagt aacaaggtgc tcagagacat gaatttgaag acttctgtgc agaaagtgac   125400
aggctcatta ataccatctc atgttgaagt tatttctaaa gtcagtccat tgtgatcaca   125460
tttctctcaa gaatatcttc taatttatt ttagatcaca ttagatcaca ttgtctccat   125520
tgatcaaaaa cactaaatac taaaaagtta gtatttaaaa accacaaata atctttttacc   125580 aaagctagtg taattgtagt aactaaagca aaaagtacca tttaattatc aaagcaacag   125640
aggtagcttt cctccctcca cccccttaccc ttttcagagt acccacttat atggtcatat   125700
ttcagaaaag aaatgaagaa aagagaaagt taggtttgac agagtacaaa ggaggagaga   125760
caagagagtg aaaatagtat taagttgcat attacctgta tcagccaaat ctttaccttt   125820
tcatttttta tattttact tcagttatct tatggaaatt tcttaaacag agagagttag   125880
gtgtcaggta tgtgaaaaga catgaaattt gtgttcagaa gtatgagatg aggcaaatgt   125940
gatactacca aaaacagagg aagtcatttc gtagaaaaaa ctttagcct gttttgaag   126000 aggcttcaca tctagcacat ctatttttga agtgtgaaaa gcaagagagt gcttcatttt   126060
gggggagtgt tgcttcttcc catagacaga aacatatgtg aagaacaagg gtcaccacag   126120
ctaactgttc ctgatagact cagagaaagg gtgggtgggc aatgtcaatt tgtcttatct   126180
```

```
ccctgtacca ttttgttgct attttcatta ataacaggta ggatggtttt atggtaatat    126240
atatgtcact gatctggatc aactaggcca ccaacacaaa tctgaatact gagaggagaa    126300
agatacacac acacacacac gttttctttg ggacctgtag ttgaggctgt aatgtcttac    126360
ttccctacca ggtatgcact ctcactagag aagacaatcg agaatttgga ggaaaacctg    126420
aggatgagca gcttcacgtt ctgcctttat acaaagtctc tgacgtggat gagtttggga    126480
gtgtggaagc tcaggaggag aaaaaacgga gtggtgccat tcaggtactg agttcttttc    126540
ggcgaaaagt caggatgtta gcagagccag tcaagacttg ccgacaaagg aaactagaag    126600
ccaagaaagc tgcagctgaa aagctttcct ccctggagaa cagctcaaat aaaaatgaaa    126660
aggaaaagtc agccccatca cgtacaaaac aaactgaaaa cgcaagccag gctaaacagt    126720
tggcaggtaa atttaatgta aagcatttgt agataaatgt gttgtgtggt atattaaaaa    126780
tgaaaattat tttggttttg cccccatcaa cttgtaagtt ctggggtaca catgcaggat    126840
gtgcaggttt gttatacagg taaacatgtg ccatggtgat ttgctgcaca gatcaaccca    126900
ttacctaggt attaagccca gcatcttcct gatgcacccc taccaatagg cgccagtgtg    126960
tgttgtcccc actcccccac catgtgtcca tgtgctctta ttgtaaaatg aacattgtta    127020
attttggaaa gttatatcaa tcatggtctt agttctgtgc cagagtcttc tctaaagtag    127080
caagggccag gctttgttct cagagatggt aatgagatat tgcaccatca acatggaaaa    127140
catggaaaag tctggatttt attctataat aaacagcaac ttttttttaac aggtaagtga    127200 tacgatgaaa ttcattgtaa tttggcagta ggccaaatta gtagaggagc taatagtttg    127260
gagataaaca cagtaaacca gaactgaggt aacaagacct tgaattttgt tggttagtag    127320
caaagatata gcaaaatgat gcaaatgagc tcttccaaaa tgggaaaaag aaaatacatt    127380
ggtgacaaaa cactggaatg aaagagaaga aaagtttaaa gatgaccca aagttttaaa     127440 cctaaactta acctactgtt ttaggtttct aaaacagtac tatttattga ataagtaag     127500 tttgaaaata tgattgagag agagagaggg gagaatgaaa cattttcct tagacatgtt     127560 gagtctgtgg tttaggaggg gttctacatg tagattatgc tacaaaactt ttacccatca    127620
aaatagatta cagctgtagt aataacaata gaacattatt catgaatact aagttattgt    127680
ctttccatag cctcctgctt tatgtctgca gtttgtaaaa agaaaaaaaa tccaaaattt    127740
gggatggtat tggcctggcc attaacaaaa gcaaaccagt ttgcttaaaa ctagccatct    127800
ttgctgcttc atgaagtcaa atttctctac tgattcattt ccaagctcag aggaactaag    127860
ttaaataatt tagaatatgc taaagatgct tgataagtgt ttattgactg gttgacttaa    127920
cactaagtaa atactgttca cttaggttag ctgtgaaata taattagata gaaccttgtc    127980
tctgctccct tttaactggc ttctgcaggt aataatccct tctgttctca gaactgccat    128040
tgcagtttca tctatttgtt cttaactcat atgactttt aaagtgaggt caaaacagaa     128100
gtatgacttt taaagtttc atttacaaag ctgaaagttt cttaaagtg ttatctacaa      128160 ctgtgttaac ttcctttctg gaaagcctgc ttataaagta gcacttgttg attatataag    128220 atgcttttg tgtttaaata cgtgtcattc tttttttttca caacattccc gaatcttaca    128280
taataaatct tattttaatt atttagcaaa ttccattgca tgccaggcaa tgaagaagta    128340
agtaaaataa aacatttcc ttcccattta ggaatttact taccagtggg ggtgaagaga     128400
gggctaaaaa cataactata atacattgtg agtattgctt tatcagatct atctttgcag    128460
ttgagtatta caaaagcact agaagatgag gtcaaagcgg tcccttgagg aagggatgac    128520
```

```
tacaccaagg aaggataggg agagagggag gaaaagggag gcacttcaag cagaggcatg   128580
ttcagaagtt ccaaagaaca ttttgctctc aatggaatgg ctttggatgt ttattacatt   128640
ttttttttca ctaagttttg tatttctaat gccttagaca aaaaattgtg ctggacaatg   128700
atcagaaccc tgactttgct cttatctttg cttaatgggt gtcgtatatc actagtggag   128760
tttcttacct acatttaagt atcctcacta gccttcataa aataatcatc aacatcaaag   128820
atacctgttt ctgttctctc ttaccctgtc cacagaactt ttgcgacttt caggaccagt   128880
catgcagcag tcccagcagc cccagcctct acagaagcag ccaccacagc cccagcagca   128940
gcagagaccc cagcagcagc agccacatca ccctcagaca gagtctgtca actcttattc   129000
tgcttctgga tccaccaatc catacatgag acggcccaat ccagttagtc cttatccaaa   129060
ctcttcacac acttcagata tctatggaag caccagccct atgaacttct attccacctc   129120
atctcaagct gcaggttcat atttgaattc ttctaatccc atgaaccctt accctgggct   129180
tttgaatcag aatacccaat atccatcata tcaatgcaat ggaaacctat cagtggacaa   129240
ctgctcccca tatctggggt cctattctcc ccagtctcag ccgatggatc tgtataggta   129300
tccaagccaa gaccctctgt ctaagctcag tctaccaccc atccatacac tttaccagcc   129360
aaggtttgga aatagccaga gttttacatc taaatactta ggttatggaa accaaaatat   129420
gcagggagat ggtttcagca gttgtaccat tagaccaaat gtacatcatg tagggaaatt   129480
gcctccttat cccactcatg agatggatgg ccacttcatg ggagccacct ctagattacc   129540
acccaatctg agcaatccaa acatggacta taaaaatggt gaacatcatt caccttctca   129600
cataatccat aactacagtg cagctccggg catgttcaac agctctcttc atgccctgca   129660
tctccaaaac aaggagaatg acatgctttc ccacacagct aatgggttat caaagatgct   129720
tccagctctt aaccatgata gaactgcttg tgtccaagga ggcttacaca aattaagtga   129780
tgctaatggt caggaaaagc agccattggc actagtccag ggtgtggctt ctggtgcaga   129840
ggacaacgat gaggtctggt cagacagcga gcagagcttt ctggatcctg acattggggg   129900
agtggccgtg gctccaactc atgggtcaat tctcattgag tgtgcaaagc gtgagctgca   129960
tgccacaacc cctttaaaga atcccaatag gaatcacccc accaggatct ccctcgtctt   130020
ttaccagcat aagagcatga atgagccaaa acatggcttg gctctttggg aagccaaaat   130080
ggctgaaaaa gcccgtgaga aagaggaaga gtgtgaaaag tatggcccag actatgtgcc   130140
tcagaaatcc catggcaaaa aagtgaaacg ggagcctgct gagccacatg aaacttcaga   130200
gcccacttac ctgcgtttca tcaagtctct tgccgaaagg accatgtccg tgaccacaga   130260
ctccacagta actacatctc catatgcctt cactcgggtc acagggcctt acaacagata   130320
tatatgatat cacccccttt tgttggttac ctcacttgaa aagaccacaa ccaacctgtc   130380
agtagtatag ttctcatgac gtgggcagtg gggaaaggtc acagtattca tgacaaatgt   130440
ggtgggaaaa acctcagctc accagcaaca aaagaggtta tcttaccata gcacttaatt   130500
ttcactggct cccaagtggt cacagatggc atctaggaaa agaccaaagc attctatgca   130560
aaaagaaggt ggggaagaaa gtgttccgca atttacattt ttaaacactg gttctattat   130620
tggacgagat gatatgtaaa tgtgatcccc ccccccgct tacaactcta cacatctgtg   130680
accactttta ataatatcaa gtttgcatag tcatggaaca caaatcaaac aagtactgta   130740
gtattacagt gacaggaatc ttaaaatacc atctggtgct gaatatatga tgtactgaaa   130800
tactggaatt atggcttttt gaatgcagt ttttactgta atcttaactt ttatttatca   130860
aaatagctac aggaaacatg aatagcagga aaacactgaa tttgtttgga tgttctaaga   130920
```

```
aatggtgcta agaaaatggt gtctttaata gctaaaaatt taatgccttt atatcatcaa  130980
gatgctatca gtgtactcca gtgcccttga ataataggg tacctttca ttcaagtttt    131040
tatcataatt acctattctt acacaagctt agtttttaaa atgtggacat tttaaaggcc   131100
tctggatttt gctcatccag tgaagtcctt gtaggacaat aaacgtatat atgtacatat   131160
atacacaaac atgtatatgt gcacacacat gtatatgtat aaatatttta aatggtgttt   131220
tagaagcact ttgtctacct aagctttgac aacttgaaca atgctaaggt actgagatgt   131280
ttaaaaaaca agtttacttt cattttagaa tgcaaagttg attttttaa  ggaaacaaag   131340
aaagctttta aaatatttt  gctttagcc  atgcatctgc tgatgagcaa ttgtgtccat   131400
ttttaacaca gccagttaaa tccaccatgg ggcttactgg attcaaggga atacgttagt   131460
ccacaaaaca tgttttctgg tgctcatctc acatgctata ctgtaaaaca gttttataca   131520
aaattgtatg acaagttcat tgctcaaaaa tgtacagttt taagaatttt ctattaactg   131580
caggtaataa ttagctgcat gctgcagact caacaaagct agttcactga agcctatgct   131640
attttatgga tcataggctc ttcagagaac tgaatggcag tctgcctttg tgttgataat   131700
tatgtacatt gtgacgttgt catttcttag cttaagtgtc ctctttaaca agaggattga   131760
gcagactgat gcctgcataa gatgaataaa cagggttagt tccatgtgaa tctgtcagtt   131820
aaaaagaaac aaaaacaggc agctggtttg ctgtggtggt tttaaatcat taatttgtat   131880
aaagaagtga aagagttgta tagtaaatta aattgtaaac aaaacttttt taatgcaatg   131940
ctttagtatt ttagtactgt aaaaaaatta aatatataca tatatatata tatatatata   132000
tatatatata tgagtttgaa gcagaattca catcatgatg gtgctactca gcctgctaca   132060
aatatatcat aatgtgagct aagaattcat taaatgtttg agtgatgttc ctacttgtca   132120
tatacctcaa cactagtttg gcaataggat attgaactga gagtgaaagc attgtgtacc   132180
atcatttttt tccaagtcct ttttttatt gttaaaaaaa aaagcatacc ttttttcaat    132240
acttgatttc ttagcaagta aacttgaac  ttcaacctt  tgttctaaa  aattcaggga   132300
tatttcagct catgctctcc ctatgccaac atgtcacctg tgtttatgta aaattgttgt   132360
aggtaataa  atatattctt tgtcagggat taacccttt  tattttgaat cccttctatt   132420
ttacttgt                                                           132428
```

<210> SEQ ID NO 2
<211> LENGTH: 2002
<212> TYPE: PRT
<213> ORGANISM: Homo sapiens

<400> SEQUENCE: 2

```
Met Glu Gln Asp Arg Thr Asn His Val Glu Gly Asn Arg Leu Ser Pro
1               5                   10                  15

Phe Leu Ile Pro Ser Pro Pro Ile Cys Gln Thr Glu Pro Leu Ala Thr
            20                  25                  30

Lys Leu Gln Asn Gly Ser Pro Leu Pro Glu Arg Ala His Pro Glu Val
        35                  40                  45

Asn Gly Asp Thr Lys Trp His Ser Phe Lys Ser Tyr Tyr Gly Ile Pro
    50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95
```

```
Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Asp Ala Asp Asn Ala
290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
    370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Ser Gln Ser Pro Asn
    450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510

Lys His Asn Pro Pro Ile Phe Gly Ser Ser Gly Glu Leu Gln Asp Asn
```

```
                515                 520                 525
Cys Gln Gln Leu Met Arg Asn Lys Glu Gln Glu Ile Leu Lys Gly Arg
    530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
                580                 585                 590

Gln Pro Asn Leu Ser Asn Gln Met Thr Ser Lys Gln Tyr Thr Gly Asn
    595                 600                 605

Ser Asn Met Pro Gly Gly Leu Pro Arg Gln Ala Tyr Thr Gln Lys Thr
    610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                645                 650                 655

Ser His Gln Val His Phe Ser Lys Thr Asp His Leu Pro Lys Ala His
                660                 665                 670

Val Gln Ser Leu Cys Gly Thr Arg Phe His Phe Gln Gln Arg Ala Asp
    675                 680                 685

Ser Gln Thr Glu Lys Leu Met Ser Pro Val Leu Lys Gln His Leu Asn
    690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735

His Leu Pro Gln Asn Gln Gln Gln Lys Leu Gln Ile Lys Asn
                740                 745                 750

Lys Glu Glu Ile Leu Gln Thr Phe Pro His Pro Gln Ser Asn Asn Asp
    755                 760                 765

Gln Gln Arg Glu Gly Ser Phe Phe Gly Gln Thr Lys Val Glu Glu Cys
    770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
                820                 825                 830

Ser Cys Ser Asn Asn Thr His Leu Val Ser Glu Asn Lys Glu Gln Thr
    835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
                900                 905                 910

Gln Leu Ala Gln Gln Arg Tyr Leu Ile His Asn His Ala Asn Val Phe
    915                 920                 925

Pro Val Pro Asp Gln Gly Gly Ser His Thr Gln Thr Pro Pro Gln Lys
    930                 935                 940
```

-continued

```
Asp Thr Gln Lys His Ala Ala Leu Arg Trp His Leu Leu Gln Lys Gln
945                 950                 955                 960

Glu Gln Gln Gln Thr Gln Pro Gln Thr Glu Ser Cys His Ser Gln
            965                 970                 975

Met His Arg Pro Ile Lys Val Glu Pro Gly Cys Lys Pro His Ala Cys
            980                 985                 990

Met His Thr Ala Pro Pro Glu Asn Lys Thr Trp Lys Lys Val Thr Lys
        995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050

Val Lys Val Glu Met Ser Gly Pro Val Thr Val Leu Thr Arg Gln
    1055                1060                1065

Thr Thr Ala Ala Glu Leu Asp Ser His Thr Pro Ala Leu Glu Gln
    1070                1075                1080

Gln Thr Thr Ser Ser Glu Lys Thr Pro Thr Lys Arg Thr Ala Ala
    1085                1090                1095

Ser Val Leu Asn Asn Phe Ile Glu Ser Pro Ser Lys Leu Leu Asp
    1100                1105                1110

Thr Pro Ile Lys Asn Leu Leu Asp Thr Pro Val Lys Thr Gln Tyr
    1115                1120                1125

Asp Phe Pro Ser Cys Arg Cys Val Glu Gln Ile Ile Glu Lys Asp
    1130                1135                1140

Glu Gly Pro Phe Tyr Thr His Leu Gly Ala Gly Pro Asn Val Ala
    1145                1150                1155

Ala Ile Arg Glu Ile Met Glu Glu Arg Phe Gly Gln Lys Gly Lys
    1160                1165                1170

Ala Ile Arg Ile Glu Arg Val Ile Tyr Thr Gly Lys Glu Gly Lys
    1175                1180                1185

Ser Ser Gln Gly Cys Pro Ile Ala Lys Trp Val Val Arg Arg Ser
    1190                1195                1200

Ser Ser Glu Glu Lys Leu Leu Cys Leu Val Arg Glu Arg Ala Gly
    1205                1210                1215

His Thr Cys Glu Ala Ala Val Ile Val Ile Leu Ile Leu Val Trp
    1220                1225                1230

Glu Gly Ile Pro Leu Ser Leu Ala Asp Lys Leu Tyr Ser Glu Leu
    1235                1240                1245

Thr Glu Thr Leu Arg Lys Tyr Gly Thr Leu Thr Asn Arg Arg Cys
    1250                1255                1260

Ala Leu Asn Glu Glu Arg Thr Cys Ala Cys Gln Gly Leu Asp Pro
    1265                1270                1275

Glu Thr Cys Gly Ala Ser Phe Ser Phe Gly Cys Ser Trp Ser Met
    1280                1285                1290

Tyr Tyr Asn Gly Cys Lys Phe Ala Arg Ser Lys Ile Pro Arg Lys
    1295                1300                1305

Phe Lys Leu Leu Gly Asp Asp Pro Lys Glu Glu Lys Leu Glu
    1310                1315                1320

Ser His Leu Gln Asn Leu Ser Thr Leu Met Ala Pro Thr Tyr Lys
    1325                1330                1335
```

```
Lys Leu Ala Pro Asp Ala Tyr Asn Asn Gln Ile Glu Tyr Glu His
    1340                1345                1350

Arg Ala Pro Glu Cys Arg Leu Gly Leu Lys Glu Gly Arg Pro Phe
    1355                1360                1365

Ser Gly Val Thr Ala Cys Leu Asp Phe Cys Ala His Ala His Arg
    1370                1375                1380

Asp Leu His Asn Met Gln Asn Gly Ser Thr Leu Val Cys Thr Leu
    1385                1390                1395

Thr Arg Glu Asp Asn Arg Glu Phe Gly Gly Lys Pro Glu Asp Glu
    1400                1405                1410

Gln Leu His Val Leu Pro Leu Tyr Lys Val Ser Asp Val Asp Glu
    1415                1420                1425

Phe Gly Ser Val Glu Ala Gln Glu Glu Lys Lys Arg Ser Gly Ala
    1430                1435                1440

Ile Gln Val Leu Ser Ser Phe Arg Arg Lys Val Arg Met Leu Ala
    1445                1450                1455

Glu Pro Val Lys Thr Cys Arg Gln Arg Lys Leu Glu Ala Lys Lys
    1460                1465                1470

Ala Ala Ala Glu Lys Leu Ser Ser Leu Glu Asn Ser Ser Asn Lys
    1475                1480                1485

Asn Glu Lys Glu Lys Ser Ala Pro Ser Arg Thr Lys Gln Thr Glu
    1490                1495                1500

Asn Ala Ser Gln Ala Lys Gln Leu Ala Glu Leu Leu Arg Leu Ser
    1505                1510                1515

Gly Pro Val Met Gln Gln Ser Gln Gln Pro Gln Pro Leu Gln Lys
    1520                1525                1530

Gln Pro Pro Gln Pro Gln Gln Gln Arg Pro Gln Gln Gln
    1535                1540                1545

Pro His His Pro Gln Thr Glu Ser Val Asn Ser Tyr Ser Ala Ser
    1550                1555                1560

Gly Ser Thr Asn Pro Tyr Met Arg Arg Pro Asn Pro Val Ser Pro
    1565                1570                1575

Tyr Pro Asn Ser Ser His Thr Ser Asp Ile Tyr Gly Ser Thr Ser
    1580                1585                1590

Pro Met Asn Phe Tyr Ser Thr Ser Ser Gln Ala Ala Gly Ser Tyr
    1595                1600                1605

Leu Asn Ser Ser Asn Pro Met Asn Pro Tyr Pro Gly Leu Leu Asn
    1610                1615                1620

Gln Asn Thr Gln Tyr Pro Ser Tyr Gln Cys Asn Gly Asn Leu Ser
    1625                1630                1635

Val Asp Asn Cys Ser Pro Tyr Leu Gly Ser Tyr Ser Pro Gln Ser
    1640                1645                1650

Gln Pro Met Asp Leu Tyr Arg Tyr Pro Ser Gln Asp Pro Leu Ser
    1655                1660                1665

Lys Leu Ser Leu Pro Pro Ile His Thr Leu Tyr Gln Pro Arg Phe
    1670                1675                1680

Gly Asn Ser Gln Ser Phe Thr Ser Lys Tyr Leu Gly Tyr Gly Asn
    1685                1690                1695

Gln Asn Met Gln Gly Asp Gly Phe Ser Ser Cys Thr Ile Arg Pro
    1700                1705                1710

Asn Val His His Val Gly Lys Leu Pro Pro Tyr Pro Thr His Glu
    1715                1720                1725

Met Asp Gly His Phe Met Gly Ala Thr Ser Arg Leu Pro Pro Asn
```

```
                        1730                1735                1740
Leu Ser  Asn Pro Asn Met Asp  Tyr Lys Asn Gly Glu  His His Ser
    1745                 1750                 1755

Pro Ser  His Ile Ile His Asn  Tyr Ser Ala Ala Pro  Gly Met Phe
    1760                 1765                 1770

Asn Ser  Ser Leu His Ala Leu  His Leu Gln Asn Lys  Glu Asn Asp
    1775                 1780                 1785

Met Leu  Ser His Thr Ala Asn  Gly Leu Ser Lys Met  Leu Pro Ala
    1790                 1795                 1800

Leu Asn  His Asp Arg Thr Ala  Cys Val Gln Gly Gly  Leu His Lys
    1805                 1810                 1815

Leu Ser  Asp Ala Asn Gly Gln  Glu Lys Gln Pro Leu  Ala Leu Val
    1820                 1825                 1830

Gln Gly  Val Ala Ser Gly Ala  Glu Asp Asn Asp Glu  Val Trp Ser
    1835                 1840                 1845

Asp Ser  Glu Gln Ser Phe Leu  Asp Pro Asp Ile Gly  Gly Val Ala
    1850                 1855                 1860

Val Ala  Pro Thr His Gly Ser  Ile Leu Ile Glu Cys  Ala Lys Arg
    1865                 1870                 1875

Glu Leu  His Ala Thr Thr Pro  Leu Lys Asn Pro Asn  Arg Asn His
    1880                 1885                 1890

Pro Thr  Arg Ile Ser Leu Val  Phe Tyr Gln His Lys  Ser Met Asn
    1895                 1900                 1905

Glu Pro  Lys His Gly Leu Ala  Leu Trp Glu Ala Lys  Met Ala Glu
    1910                 1915                 1920

Lys Ala  Arg Glu Lys Glu Glu  Cys Glu Lys Tyr Gly  Pro Asp
    1925                 1930                 1935

Tyr Val  Pro Gln Lys Ser His  Gly Lys Lys Val Lys  Arg Glu Pro
    1940                 1945                 1950

Ala Glu  Pro His Glu Thr Ser  Glu Pro Thr Tyr Leu  Arg Phe Ile
    1955                 1960                 1965

Lys Ser  Leu Ala Glu Arg Thr  Met Ser Val Thr Thr  Asp Ser Thr
    1970                 1975                 1980

Val Thr  Thr Ser Pro Tyr Ala  Phe Thr Arg Val Thr  Gly Pro Tyr
    1985                 1990                 1995

Asn Arg  Tyr Ile
    2000

<210> SEQ ID NO 3
<211> LENGTH: 311
<212> TYPE: PRT
<213> ORGANISM: Homo sapiens

<400> SEQUENCE: 3

Arg Cys Val Glu Gln Ile Ile Glu Lys Asp Glu Gly Pro Phe Tyr Thr
1               5                   10                  15

His Leu Gly Ala Gly Pro Asn Val Ala Ala Ile Arg Glu Ile Met Glu
                20                  25                  30

Glu Arg Phe Gly Gln Lys Gly Lys Ala Ile Arg Ile Glu Arg Val Ile
            35                  40                  45

Tyr Thr Gly Lys Glu Gly Lys Ser Ser Gln Gly Cys Pro Ile Ala Lys
        50                  55                  60

Trp Val Val Arg Arg Ser Ser Ser Glu Glu Lys Leu Leu Cys Leu Val
65                  70                  75                  80
```

-continued

Arg Glu Arg Ala Gly His Thr Cys Glu Ala Val Ile Val Ile Leu
                85                  90                  95

Ile Leu Val Trp Glu Gly Ile Pro Leu Ser Leu Ala Asp Lys Leu Tyr
            100                 105                 110

Ser Glu Leu Thr Glu Thr Leu Arg Lys Tyr Gly Thr Leu Thr Asn Arg
            115                 120                 125

Arg Cys Ala Leu Asn Glu Glu Arg Thr Cys Ala Cys Gln Gly Leu Asp
            130                 135                 140

Pro Glu Thr Cys Gly Ala Ser Phe Ser Phe Gly Cys Ser Trp Ser Met
145                 150                 155                 160

Tyr Tyr Asn Gly Cys Lys Phe Ala Arg Ser Lys Ile Pro Arg Lys Phe
                165                 170                 175

Lys Leu Leu Gly Asp Asp Pro Lys Glu Glu Lys Leu Glu Ser His
            180                 185                 190

Leu Gln Asn Leu Ser Thr Leu Met Ala Pro Thr Tyr Lys Lys Leu Ala
            195                 200                 205

Pro Asp Ala Tyr Asn Asn Gln Ile Glu Tyr Glu His Arg Ala Pro Glu
            210                 215                 220

Cys Arg Leu Gly Leu Lys Glu Gly Arg Pro Phe Ser Gly Val Thr Ala
225                 230                 235                 240

Cys Leu Asp Phe Cys Ala His Ala His Arg Asp Leu His Asn Met Gln
                245                 250                 255

Asn Gly Ser Thr Leu Val Cys Thr Leu Thr Arg Glu Asp Asn Arg Glu
            260                 265                 270

Phe Gly Gly Lys Pro Glu Asp Glu Gln Leu His Val Leu Pro Leu Tyr
            275                 280                 285

Lys Val Ser Asp Val Asp Glu Phe Gly Ser Val Glu Ala Gln Glu Glu
            290                 295                 300

Lys Lys Arg Ser Gly Ala Ile
305                 310

<210> SEQ ID NO 4
<211> LENGTH: 80
<212> TYPE: PRT
<213> ORGANISM: Homo sapiens

<400> SEQUENCE: 4

Asn Asp Glu Val Trp Ser Asp Ser Glu Gln Ser Phe Leu Asp Pro Asp
1               5                   10                  15

Ile Gly Gly Val Ala Val Ala Pro Thr His Gly Ser Ile Leu Ile Glu
            20                  25                  30

Cys Ala Lys Arg Glu Leu His Ala Thr Thr Pro Leu Lys Asn Pro Asn
            35                  40                  45

Arg Asn His Pro Thr Arg Ile Ser Leu Val Phe Tyr Gln His Lys Ser
            50                  55                  60

Met Asn Glu Pro Lys His Gly Leu Ala Leu Trp Glu Ala Lys Met Ala
65                  70                  75                  80

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
tgaacttccc acattagctg gt                                           22

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gaaactgtag caccattagg catt                                           24

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
caaaaggcta atggagaaag acgta                                          25

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
gcagaaaagg aatccttagt gaaca                                          25

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gccagtaaac tagctgcaat gctaa                                          25

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
tgcctcatta cgttttagat ggg                                            23

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gaccaatgtc agaacacctc aa                                             22

<210> SEQ ID NO 12
<211> LENGTH: 26
<212> TYPE: DNA
<213> ORGANISM: Artificial sequence
<220> FEATURE:

```
<223> OTHER INFORMATION: Primer

<400> SEQUENCE: 12
ttgattttga atactgattt tcacca                                          26

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ttgcaacata agcctcataa acag                                            24

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
attggcctgt gcatctgact at                                              22

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
gcaacttgct cagcaaaggt act                                             23

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgctgccaga ctcaagattt aaaa                                            24

<210> SEQ ID NO 17
<211> LENGTH: 34
<212> TYPE: DNA
<213> ORGANISM: Artificial sequence
<220> FEATURE:
<223> OTHER INFORMATION: Primer

<400> SEQUENCE: 17
atactacata taatacattc taattccctc actg                                 34

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
tgtttactgc tttgtgtgtg aagg                                            24
```

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
catttctcag gatgtggtca tagaat                                         26

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
cccaattctc agggtcagat tta                                            23

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
agacttatgt atctttcatc tagctctgg                                      29

<210> SEQ ID NO 22
<211> LENGTH: 25
<212> TYPE: DNA
<213> ORGANISM: Artificial sequence
<220> FEATURE:
<223> OTHER INFORMATION: Primer

<400> SEQUENCE: 22
actctcttcc tttcaaccaa agatt                                          25

<210> SEQ ID NO 23
<211> LENGTH: 27
<212> TYPE: DNA
<213> ORGANISM: Artificial sequence
<220> FEATURE:
<223> OTHER INFORMATION: Primer

<400> SEQUENCE: 23
atgccacagc ttaatacaga gttagat                                        27

<210> SEQ ID NO 24
<211> LENGTH: 30
<212> TYPE: DNA
<213> ORGANISM: Artificial sequence
<220> FEATURE:
<223> OTHER INFORMATION: Primer

<400> SEQUENCE: 24
tgtcatattg ttcacttcat ctaagctaat                                     30

<210> SEQ ID NO 25
<211> LENGTH: 28
<212> TYPE: DNA
<213> ORGANISM: Artificial sequence
<220> FEATURE:
<223> OTHER INFORMATION: Primer

<400> SEQUENCE: 25
gatgctttat ttagtaataa aggcacca                               28

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
ttcaacaatt aagaggaaaa gttagaataa tattt                       35

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
tgtcattcca ttttgtttct ggata                                  25

<210> SEQ ID NO 28
<211> LENGTH: 26
<212> TYPE: DNA
<213> ORGANISM: Artificial sequence
<220> FEATURE:
<223> OTHER INFORMATION: Primer

<400> SEQUENCE: 28
aaattaccca gtcttgcata tgtctt                                 26

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
ctggatcaac taggccacca ac                                     22

<210> SEQ ID NO 30
<211> LENGTH: 33
<212> TYPE: DNA
<213> ORGANISM: Artificial sequence
<220> FEATURE:
<223> OTHER INFORMATION: Primer

<400> SEQUENCE: 30
ccaaaattaa caatgttcat tttacaataa gag                         33

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
gctcttatct ttgcttaatg ggtgt                                  25

<210> SEQ ID NO 32
<211> LENGTH: 27

```
<212> TYPE: DNA
<213> ORGANISM: Artificial sequence
<220> FEATURE:
<223> OTHER INFORMATION: Primer

<400> SEQUENCE: 32
tgtacatttg gtctaatggt acaactg                                              27

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
aatggaaacc tatcagtgga caac                                                 24

<210> SEQ ID NO 34
<211> LENGTH: 26
<212> TYPE: DNA
<213> ORGANISM: Artificial sequence
<220> FEATURE:
<223> OTHER INFORMATION: Primer

<400> SEQUENCE: 34
tatatatctg ttgtaaggcc ctgtga                                               26

<210> SEQ ID NO 35
<211> LENGTH: 23
<212> TYPE: DNA
<213> ORGANISM: Artificial sequence
<220> FEATURE:
<223> OTHER INFORMATION: Primer

<400> SEQUENCE: 35
cagagctttc tggatcctga cat                                                  23

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
gcccacgtca tgagaactat actac                                                25

<210> SEQ ID NO 37
<211> LENGTH: 28
<212> TYPE: DNA
<213> ORGANISM: Artificial sequence
<220> FEATURE:
<223> OTHER INFORMATION: Primer

<400> SEQUENCE: 37
tctaagctca gtctaccacc catccata                                             28

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
```
tgctcgctgt ctgaccagac ctcat                                         25

<210> SEQ ID NO 39
<211> LENGTH: 6869
<212> TYPE: DNA
<213> ORGANISM: Homo sapiens

<400> SEQUENCE: 39

| | | | | | |
|---|---|---|---|---|---|
| ccgtgccatc | ccaacctccc | acctcgcccc | caaccttcgc | gcttgctctg | cttcttctcc | 60 |
| caggggtgga | gacccgccga | ggtccccggg | gttcccgagg | gctgcaccct | tccccgcgct | 120 |
| cgccagccct | ggccccctact | ccgcgctggt | ccgggcgcac | cactcccccc | gcgccactgc | 180 |
| acggcgtgag | ggcagcccag | gtctccactg | cgcgccccgc | tgtacggccc | caggtgccgc | 240 |
| cggcctttgt | gctggacgcc | cggtgcgggg | ggctaattcc | ctgggagccg | gggctgaggg | 300 |
| ccccagggcg | gcggcgcagg | ccggggcgga | gcggaggag | gccggggcgg | agcaggagga | 360 |
| ggcccgggcg | gaggaggaga | gccggcggta | gcggcagtgg | cagcggcgag | agcttgggcg | 420 |
| gccgccgccg | cctcctcgcg | agcgccgcgc | gcccgggtcc | cgctcgcatg | caagtcacgt | 480 |
| ccgcccccctc | ggcgcggccg | ccccgagacg | ccggccccgc | tgagtgatga | aacagacgt | 540 |
| caaactgcct | tatgaatatt | gatgcggagg | ctaggctgct | ttcgtagaga | agcagaagga | 600 |
| agcaagatgg | ctgcccttta | ggatttgtta | gaaaggagac | ccgactgcaa | ctgctggatt | 660 |
| gctgcaaggc | tgagggacga | gaacgaggct | ggcaaacatt | cagcagcaca | ccctctcaag | 720 |
| attgtttact | tgcctttgct | cctgttgagt | tacaacgctt | ggaagcagga | gatgggctca | 780 |
| gcagcagcca | ataggacatg | atccaggaag | agcaaattca | actagagggc | agccttgtgg | 840 |
| atggccccga | agcaagcctg | atggaacagg | atagaaccaa | ccatgttgag | ggcaacagac | 900 |
| taagtccatt | cctgatacca | tcacctccca | tttgccagac | agaacctctg | gctacaaagc | 960 |
| tccagaatgg | aagcccactg | cctgagagag | ctcatccaga | agtaaatgga | gacaccaagt | 1020 |
| ggcactcttt | caaaagttat | tatggaatac | cctgtatgaa | gggaagccag | aatagtcgtg | 1080 |
| tgagtcctga | ctttacacaa | gaaagtagag | ggtattccaa | gtgtttgcaa | aatggaggaa | 1140 |
| taaaacgcac | agttagtgaa | ccttctctct | ctgggctcct | tcagatcaag | aaattgaaac | 1200 |
| aagaccaaaa | ggctaatgga | gaaagacgta | acttcggggt | aagccaagaa | agaaatccag | 1260 |
| gtgaaagcag | tcaaccaaat | gtctccgatt | tgagtgataa | gaaagaatct | gtgagttctg | 1320 |
| tagcccaaga | aaatgcagtt | aaagatttca | ccagtttttc | aacacataac | tgcagtgggc | 1380 |
| ctgaaaatcc | agagcttcag | attctgaatg | agcaggaggg | gaaagtgct | aattaccatg | 1440 |
| acaagaacat | tgtattactt | aaaaacaagg | cagtgctaat | gcctaatggt | gctacagttt | 1500 |
| ctgcctcttc | cgtggaacac | acacatggtg | aactcctgga | aaaaacactg | tctcaatatt | 1560 |
| atccagattg | tgtttccatt | gcggtgcaga | aaaccacatc | tcacataaat | gccattaaca | 1620 |
| gtcaggctac | taatgagttg | tcctgtgaga | tcactcaccc | atcgcatacc | tcagggcaga | 1680 |
| tcaattccgc | acagacctct | aactctgagc | tgcctccaaa | gccagctgca | gtggtgagtg | 1740 |
| aggcctgtga | tgctgatgat | gctgataatg | ccagtaaact | agctgcaatg | ctaaatacct | 1800 |
| gttcctttca | gaaaccagaa | caactacaac | aacaaaaatc | agttttttgag | atatgcccat | 1860 |
| ctcctgcaga | aaataacatc | cagggaacca | caaagctagc | gtctggtgaa | gaattctgtt | 1920 |
| caggttccag | cagcaatttg | caagctcctg | gtgcagctc | tgaacggtat | ttaaaacaaa | 1980 |
| atgaaatgaa | tggtgcttac | ttcaagcaaa | gctcagtgtt | cactaaggat | tccttttctg | 2040 |
| ccactaccac | accaccacca | ccatcacaat | tgcttctttc | tccccctcct | cctcttccac | 2100 |

```
aggttcctca gcttccttca gaaggaaaaa gcactctgaa tggtggagtt ttagaagaac    2160
accaccacta ccccaaccaa agtaacacaa cacttttaag ggaagtgaaa atagagggta    2220
aacctgaggc accaccttcc cagagtccta atccatctac acatgtatgc agcccttctc    2280
cgatgctttc tgaaaggcct cagaataatt gtgtgaacag gaatgacata cagactgcag    2340
ggacaatgac tgttccattg tgttctgaga aaacaagacc aatgtcagaa cacctcaagc    2400
ataacccacc aattttttggt agcagtggag agctacagga caactgccag cagttgatga    2460
gaaacaaaga gcaagagatt ctgaagggtc gagacaagga gcaaacacga gatcttgtgc    2520
ccccaacaca gcactatctg aaaccaggat ggattgaatt gaaggcccct cgttttcacc    2580
aagcggaatc ccatctaaaa cgtaatgagg catcactgcc atcaattctt cagtatcaac    2640
ccaatctctc caatcaaatg acctccaaac aatacactgg aaattccaac atgcctgggg    2700
ggctcccaag gcaagcttac acccagaaaa caacacagct ggagcacaag tcacaaatgt    2760
accaagttga aatgaatcaa gggcagtccc aaggtacagt ggaccaacat ctccagttcc    2820
aaaaaccctc acaccaggtg cacttctcca aaacagacca tttaccaaaa gctcatgtgc    2880
agtcactgtg tggcactaga tttcattttc aacaaagagc agattcccaa actgaaaaac    2940
ttatgtcccc agtgttgaaa cagcacttga atcaacaggc ttcagagact gagccatttt    3000
caaactcaca ccttttgcaa cataagcctc ataaacaggc agcacaaaca caaccatccc    3060
agagttcaca tctccctcaa aaccagcaac agcagcaaaa attacaaata aagaataaag    3120
aggaaatact ccagactttt cctcaccccc aaagcaacaa tgatcagcaa agagaaggat    3180
cattctttgg ccagactaaa gtggaagaat gttttcatgg tgaaaatcag tattcaaaat    3240
caagcgagtt cgagactcat aatgtccaaa tgggactgga ggaagtacag aatataaatc    3300
gtagaaattc cccttatagt cagaccatga aatcaagtgc atgcaaaata caggtttctt    3360
gttcaaacaa tacacaccta gtttcagaga ataaagaaca gactacacat cctgaacttt    3420
ttgcaggaaa caagacccaa aacttgcatc acatgcaata ttttccaaat aatgtgatcc    3480
caaagcaaga tcttcttcac aggtgctttc aagaacagga gcagaagtca caacaagctt    3540
cagttctaca gggatataaa aatagaaacc aagatatgtc tggtcaacaa gctgcgcaac    3600
ttgctcagca aaggtacttg atacataacc atgcaaatgt ttttcctgtg cctgaccagg    3660
gaggaagtca cactcagacc cctcccccaga aggacactca aaagcatgct gctctaaggt    3720
ggcatctctt acagaagcaa gaacagcagc aaacacagca accccaaact gagtcttgcc    3780
atagtcagat gcacaggcca attaaggtgg aacctggatg caagccacat gcctgtatgc    3840
acacagcacc accagaaaac aaaacatgga aaaggtaac taagcaagag aatccacctg    3900
caagctgtga taatgtgcag caaaagagca tcattgagac catggagcag catctgaagc    3960
agtttcacgc caagtcgtta tttgaccata aggctcttac tctcaaatca cagaagcaag    4020
taaaagttga aatgtcaggg ccagtcacag ttttgactag acaaaccact gctgcagaac    4080
ttgatagcca cacccagct ttagagcagc aaacaacttc ttcagaaaag acaccaacca    4140
aaagaacagc tgcttctgtt ctcaataatt ttatagagtc accttccaaa ttactagata    4200
ctcctataaa aaatttattg gatacacctg tcaagactca atatgatttc ccatcttgca    4260
gatgtgtaga gcaaattatt gaaaaagatg aaggtccttt ttatacccat ctaggagcag    4320
gtcctaatgt ggcagctatt agagaaatca tggaagaaag gtttggacag aagggtaaag    4380
ctattaggat tgaaagagtc atctatactg gtaaagaagg caaagttct cagggatgtc    4440
```

```
ctattgctaa gtgggtggtt cgcagaagca gcagtgaaga gaagctactg tgtttggtgc    4500
gggagcgagc tggccacacc tgtgaggctg cagtgattgt gattctcatc ctggtgtggg    4560
aaggaatccc gctgtctctg gctgacaaac tctactcgga gcttaccgag acgctgagga    4620
aatacggcac gctcaccaat cgccggtgtg ccttgaatga agagagaact tgcgcctgtc    4680
aggggctgga tccagaaacc tgtggtgcct ccttctcttt tggttgttca tggagcatgt    4740
actacaatgg atgtaagttt gccagaagca agatcccaag gaagtttaag ctgcttgggg    4800
atgacccaaa agaggaagag aaactggagt ctcatttgca aaacctgtcc actcttatgg    4860
caccaacata aagaaactt gcacctgatg catataataa tcagattgaa tatgaacaca     4920
gagcaccaga gtgccgtctg ggtctgaagg aaggccgtcc attctcaggg gtcactgcat    4980
gtttggactt ctgtgctcat gcccacagag acttgcacaa catgcagaat ggcagcacat    5040
tggtatgcac tctcactaga gaagacaatc gagaatttgg aggaaaacct gaggatgagc    5100
agcttcacgt tctgccttta tacaaagtct ctgacgtgga tgagtttggg agtgtggaag    5160
ctcaggagga gaaaaaacgg agtggtgcca ttcaggtact gagttcttt cggcgaaaag     5220 tcaggatgtt agcagagcca gtcaagactt gccgacaaag gaaactagaa gccaagaaag    5280
ctgcagctga aaagctttcc tccctggaga acagctcaaa taaaaatgaa aaggaaaagt    5340
cagccccatc acgtacaaaa caaactgaaa acgcaagcca ggctaaacag ttggcagaac    5400
ttttgcgact ttcaggacca gtcatgcagc agtcccagca gccccagcct ctacagaagc    5460
agccaccaca gccccagcag cagcagagac cccagcagca gcagccacat caccctcaga    5520
cagagtctgt caactcttat tctgcttctg gatccaccaa tccatacatg agacggccca    5580
atccagttag tccttatcca aactcttcac acacttcaga tatctatgga agcaccagcc    5640
ctatgaactt ctattccacc tcatctcaag ctgcaggttc atatttgaat tcttctaatc    5700
ccatgaaccc ttaccctggg cttttgaatc agaatacccca atatccatca tatcaatgca    5760
atggaaacct atcagtggac aactgctccc catatctggg ttcctattct ccccagtctc    5820
agccgatgga tctgtatagg tatccaagcc aagaccctct gtctaagctc agtctaccac    5880
ccatccatac actttaccag ccaaggtttg gaaatagcca gagttttaca tctaaatact    5940
taggttatgg aaaccaaaat atgcagggag atggtttcag cagttgtacc attagaccaa    6000
atgtacatca tgtagggaaa ttgcctcctt atcccactca tgagatggat ggccacttca    6060
tgggagccac ctctagatta ccacccaatc tgagcaatcc aaacatggac tataaaaatg    6120
gtgaacatca ttcaccttct cacataatcc ataactacag tgcagctccg ggcatgttca    6180
acagctctct tcatgccctg catctccaaa acaaggagaa tgcatgcttt cccacacag    6240 ctaatgggtt atcaaagatg cttccagctc ttaaccatga tagaactgct tgtgtccaag    6300
gaggcttaca caaattaagt gatgctaatg gtcaggaaaa agcagccattg gcactagtcc    6360 agggtgtggc ttctggtgca gaggacaacg atgaggtctg gtcagacagc gagcagagct    6420
ttctggatcc tgacattggg ggagtggccg tggctccaac tcatgggtca attctcattg    6480
agtgtgcaaa gcgtgagctg catgccacaa ccccttaaa gaatcccaat aggaatcacc     6540
ccaccaggat ctccctcgtc ttttaccagc ataagagcat gaatgagcca aacatggct     6600 tggctctttg ggaagccaaa atggctgaaa aagcccgtga aaagaggaa gagtgtgaaa     6660 agtatggccc agactatgtg cctcagaaat cccatggcaa aaaagtgaaa cgggagcctg    6720
ctgagccaca tgaaacttca gagcccactt acctgcgttt catcaagtct cttgccgaaa    6780
```

```
ggaccatgtc cgtgaccaca gactccacag taactacatc tccatatgcc ttcactcggg    6840
tcacagggcc ttacaacaga tatatatga                                      6869
```